United States Patent
Ban et al.

(10) Patent No.: US 10,934,309 B2
(45) Date of Patent: Mar. 2, 2021

(54) TRICYCLIC QUINONE DERIVATIVE

(71) Applicant: Boston Biomedical, Inc., Cambridge, MA (US)

(72) Inventors: Hitoshi Ban, Osaka (JP); Seiji Kamioka, Osaka (JP); Shoukou Ri, Osaka (JP); Tomoyuki Furuta, Osaka (JP); Hiroyuki Kitano, Osaka (JP); Chiang Jia Li, Cambridge, MA (US)

(73) Assignee: Sumitomo Dainippon Pharma Oncology, Inc., Cambridge, MA (US)

( * ) Notice: Subject to any disclaimer, the term of this patent is extended or adjusted under 35 U.S.C. 154(b) by 0 days.

(21) Appl. No.: 16/233,816

(22) Filed: Dec. 27, 2018

(65) Prior Publication Data

US 2019/0241583 A1     Aug. 8, 2019

Related U.S. Application Data

(63) Continuation of application No. 16/054,875, filed on Aug. 3, 2018, now abandoned, which is a continuation of application No. 15/300,917, filed as application No. PCT/JP2015/001814 on Mar. 30, 2015, now abandoned.

(30) Foreign Application Priority Data

Mar. 31, 2014 (JP) .................. 2014-072398

(51) Int. Cl.
| | | |
|---|---|---|
| C07D 495/04 | (2006.01) | |
| A61K 31/381 | (2006.01) | |
| A61K 31/4355 | (2006.01) | |
| A61K 31/4365 | (2006.01) | |
| A61K 31/5377 | (2006.01) | |
| C07D 491/048 | (2006.01) | |
| C07D 471/04 | (2006.01) | |

(52) U.S. Cl.
CPC .......... *C07D 495/04* (2013.01); *A61K 31/381* (2013.01); *A61K 31/4355* (2013.01); *A61K 31/4365* (2013.01); *A61K 31/5377* (2013.01); *C07D 471/04* (2013.01); *C07D 491/048* (2013.01)

(58) Field of Classification Search
CPC .................................................. C07D 495/04
USPC .......................................................... 549/44
See application file for complete search history.

(56) References Cited

U.S. PATENT DOCUMENTS

| | | | |
|---|---|---|---|
| 4,778,805 A | 10/1988 | Adams et al. | |
| 5,166,315 A | 11/1992 | Summerton et al. | |
| 6,174,913 B1 | 1/2001 | Lee et al. | |
| 6,337,346 B1 | 1/2002 | Lee et al. | |
| 6,734,203 B2 | 5/2004 | Matsuhisa et al. | |
| 8,217,176 B2 | 7/2012 | Oguro | |
| 2003/0114508 A1 | 6/2003 | Matsuhisa et al. | |
| 2006/0142271 A1 | 6/2006 | Muller et al. | |
| 2009/0227561 A1 | 9/2009 | Fujii et al. | |
| 2011/0003788 A1 | 1/2011 | Fujii et al. | |
| 2017/0015677 A1 | 1/2017 | Ban et al. | |

FOREIGN PATENT DOCUMENTS

| | | |
|---|---|---|
| AR | 70479 A1 | 4/2010 |
| AU | 4548899 A | 12/1999 |
| AU | 3228601 A | 8/2001 |
| AU | 2009217982 A1 | 9/2009 |
| CA | 2395717 A1 | 8/2001 |
| CA | 2716773 A1 | 9/2009 |
| CN | 1322206 A | 11/2001 |
| CN | 1400969 A | 3/2003 |

(Continued)

OTHER PUBLICATIONS

Venkatesh, J. Pharm. Sci. 89, 145-54 (2000) (p. 146, left column).*
Yanni, Collection of Czechoslovak Chemical Communications (1991), 56(3), 706-11.*
Zuloaga, Journal of the Chemical Society, Perkin Transactions 2: Physical Organic Chemistry (1995), (5), 939-43.*
Campiglia, Organic & Biomolecular Chemistry (2010), 8(3), 622-627.*

(Continued)

*Primary Examiner* — Nizal S Chandrakumar
(74) *Attorney, Agent, or Firm* — Fish & Richardson P.C.

(57) ABSTRACT

This invention provides a compound represented by formula (1) or a pharmaceutically acceptable salt thereof. Specifically, the present invention provides a compound represented by formula (1) or a pharmaceutically acceptable salt thereof [Therein, A is O, S, or N—$R^6$; ring G is a 5-membered or 6-membered aromatic ring, etc., including 1-3 heteroatoms selected from O, S and N as constituent atoms; $R^1$ and $R^2$ are each independently a hydrogen atom, a halogen atom, or an optionally-substituted $C_{1-6}$ alkyl carbonyl group, etc.; $R^3$, $R^4$ and $R^5$ are each independently a hydrogen atom, a halogen atom, or an optionally-substituted $C_{1-6}$ alkyl carbonyl group, etc.; and $R^6$ is a hydrogen atom or an optionally-substituted $C_{1-6}$ alkyl group, etc.].

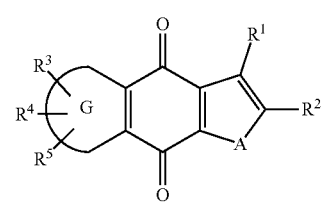

(1)

1 Claim, No Drawings

(56) References Cited

FOREIGN PATENT DOCUMENTS

| | | | |
|---|---|---|---|
| CN | 102015705 | A | 4/2011 |
| DE | 69913697 | T2 | 8/2004 |
| DE | 60111498 | T2 | 5/2006 |
| DK | 1256576 | T3 | 10/2005 |
| EP | 1093456 | A2 | 4/2001 |
| EP | 1256576 | A1 | 11/2002 |
| EP | 2247588 | A2 | 11/2010 |
| EP | 3127907 | A1 | 2/2017 |
| ES | 2243441 | T3 | 12/2005 |
| IL | 207735 | A | 12/2014 |
| JP | 63196576 | A | 8/1988 |
| JP | 1121284 | A | 1/1999 |
| JP | 2002517397 | A | 6/2002 |
| JP | 3397320 | B2 | 4/2003 |
| JP | 2011513199 | A | 4/2011 |
| JP | 2011098978 | A | 5/2011 |
| JP | 4719317 | B2 | 7/2011 |
| KR | 1020100137482 | A | 12/2010 |
| TW | 238165 | B | 8/2005 |
| WO | WO-1999062909 | A2 | 12/1999 |
| WO | WO-0160803 | A1 | 8/2001 |
| WO | WO-2001060803 | A1 | 8/2001 |
| WO | WO-2004026253 | A2 | 4/2004 |
| WO | WO-2009107850 | A2 | 9/2009 |
| WO | WO-2015151490 | A1 | 10/2015 |

OTHER PUBLICATIONS

Venugopalan, European Journal of Medicinal Chemistry (1989), 24(6), 611-14.*
Dorwald F. A. Side Reactions in Organic Synthesis, 2005, Wiley: VCH, Weinheim p. IX of Preface p. 1-15.*
File Registry on STN, RN 859218-71-6, entered STN: Aug. 9, 2005, 2 pgs.
File Registry on STN, RN 167705-94-4, entered STN: Sep. 15, 1995, 1 pg.
"U.S. Appl. No. 15/300,917, Advisory Action dated Jul. 12, 2018", 3 pgs.
"U.S. Appl. No. 15/300,917, Examiner Interview Summary dated May 8, 2017", 2 pgs.
"U.S. Appl. No. 15/300,917, Final Office Action dated May 4, 2018", 38 pgs.
"U.S. Appl. No. 15/300,917, Non Final Office Action dated Jun. 20, 2017", 12 pgs.
"U.S. Appl. No. 15/300,917, Non Final Office Action dated Nov. 30, 2017", 50 pgs.
"U.S. Appl. No. 15/300,917, Preliminary Amendment filed Sep. 30, 2016", 44 pgs.
"U.S. Appl. No. 15/300,917, Response filed Apr. 26, 2017 to Restriction Requirement dated Feb. 28, 2017", 3 pgs.
"U.S. Appl. No. 15/300,917, Response filed Jun. 28, 2018 to Final Office Action dated May 4, 2018", 34 pgs.
"U.S. Appl. No. 15/300,917, Response filed Sep. 20, 2017 to Non Final Office Action dated Jun. 20, 2017", 5 pgs.
"U.S. Appl. No. 15/300,917, Restriction Requirement dated Feb. 28, 2017", 9 pgs.
"European Application Serial No. 15772788.4, Extended European Search Report dated Mar. 7, 2018", 16 pgs.
"European Application Serial No. 15772788.4, Invitation Pursuant to Rule 63(1) EPC dated Jul. 28, 2017", 4 pgs.
"European Application Serial No. 15772788.4, Partial European Search Report dated Nov. 22, 2017", 7 pgs.
"European Application Serial No. 15772788.4, Response filed Oct. 1, 2018 to Extended European Search Report dated Mar. 7, 2018", 49 pgs.
"European Application Serial No. 15772788.4, Response filed Oct. 6, 2017 to Invitation Pursuant to Rule 63(1) EPC dated Jul. 28, 2017", 1 pgs.
"Furo[3,2-G]Quinoline-4,9-Dione, 2-(1-Methylethyl)-(CA Index Name)", Database Registry, (Sep. 15, 1995), 1 page.

"International Application Serial No. PCT/JP2015/001814, International Preliminary Report on Patentability dated Oct. 13, 2016", 9 pgs.
"International Application Serial No. PCT/JP2015/001814, International Search Report dated May 26, 2015", 5 pgs.
"International Application Serial No. PCT/JP2015/001814, Written Opinion dated May 26, 2015", 7 pgs.
"Japanese Application Serial No. 2016-511381, Examiners Decision of Final Refusal dated Oct. 4, 2019", W/ English Translation, 6 pgs.
"Japanese Application Serial No. 2016-511381, Office Action dated Mar. 19, 2019", w/ English translation, 10 pgs.
"Japanese Application Serial No. 2016-511381, Response filed Sep. 10, 2019 to Office Action dated Mar. 19, 2019", w/English Claims, 81 pgs.
"Thieno[2,3-F]Benzofuran-6-Carboxylic Acid,4,8-Dihydro-4,8-Dioxo-2,7-Diphenyl-, Ethyl Ester (CA Index Name)", Database Registry, (Aug. 9, 2005), 1 page.
Aeschi, Y, et al., "Directed Metalation Cascade to Access Highly Functionalized Thieno[2,3-f] benzofuran and Exploration as Building Blocks for Organic Electronics", Organic Letters, 15(21) particularly, compounds 5 to 8 (Scheme 2), (2013), 5586-5589.
Barret, Roland, et al., "Hetero Diels-Alder Reaction with Indoloquinones", Chemical & Pharmaceutical Bulletin, 46(3), (1998), 548-550.
Cherkaoui, "Tetrahedron", (1996), 9499-9508.
Diaz, et al., "Furanonaphthoquinones from *Tabebuia ochracea* ssp. neochrysanta", J. Nat. Prod. 59, (1996), 423-424.
Hayashi, Toshimitsu, et al., "Antitumor agents. 89. Psychorubrin, a new cytotoxic naphthoquinone from Psychotria rubra and its structure-activity relationships", Journal of Medicinal Chemistry, vol. 30, No. 11, (1987), 2005-2008.
Hirai, et al., "Furanonaphthoquinone Analogs Possessing Preferential Antitumor Activity Compared to Normal Cells", Cancer Detection and Prevention. 23.6, (1999), 539-550.
Hisahiro, Hagiwara, et al., "Domino Michael O alkylation reaction one pot synthesis of 2 4 diacylhydrofuran derivatives and its application to antitumor naphthofuran synthesis", J. Chem. Soc Perkin Trans 1, (2001), 2946-2957.
Hisahiro, Hagiwara, et al., "Tandem nucleophilic reaction leading to hydrofurans application to one pot synthesis of antitumor naphthofuran natural product", Heterocycles vol. 51 No. 3, (1999), 4 pages.
Jackson, Yvette A., et al., "Synthesis of a thiophene analogue of kuanoniamine A", A, J. Chem. Soc., Perkin Trans. particularly, compound 8 (Scheme 3), vol. 1, No. 18, (Jan. 2001), 2237-2239.
Junko, Koyama, et al., "Correlation between Cytotoxic Activities and Reduction Potentials of Heterocyclic Quinones", Molecules, vol. 15, No. 9, XP055424360, DOI: 10.3390/molecules15096559 figure 1; table 1; compounds 4,6-8 , (Sep. 20, 2010), 6559-6569.
Kenneth, O Eyong, et al., "Semisynthesis and antitumoral activity of 2-acetylfuranonaphthoquinone and other naphthoquinone derivatives from lapachol", Bioorganic & Medicinal Chemistry Letters, (2008), 5387-5390.
Kobayashi, et al., "One-Pot Synthesis of Naphtho[2,3-b]furan-4,9-diones by Sequential Coupling/Ring Closure Reactions", Tetrahedron Letters, vol. 38, No. 5, (1997), 837-840.
Koyoma, et al., "Micellar electrokinetic chromatography (MEKC) separation of furanonaphthoquinones from Tabebuia impetiginosa", Chem. Pharm. Bull (Tokyo), 48(6), (Jun. 2000), 873-875.
Muller, Klaus, et al., "Potential Antipsoriatic Agents: Lapacho Compounds as Potent Inhibitors of HaCaT Cell Growth", J Nat Prod 62, (1999), 1134-1136.
No Author, "International Research Congress on Natural Product as Medicinal Agents", Journal of Medicinal Plant Research, vol. 39, Planta Med, (Jul. 1980).
Ogawa, et al., "Cytotoxic Activity toward KB Cells of 2-Substituted Naptho[2,3-b]furan-4,9 diones and Their Related Compounds", Bioscience Biotechnology and Biochemistry. 70.4, (2006), 1009-1012.
Peraza-Sanchez, Sergio R, et al., "Cytotoxic Constituents of the Roots of Ekmanianthe longiflora", Journal of Natural Products, vol. 63, No. 4, (2000), 492-495.

(56) References Cited

OTHER PUBLICATIONS

Perez-Sacau, et al., "Synthesis and Pharmacophore Modeling of Naphthoquinone Derivatives with Cytotoxic Activity in Human Promyelocytic Leukemia HL-60 Cell Line", J. Med. Chem. 50, (2007), 696-706.

Periera, et al., "Invasion-associated MMP-2 and MMP-9 are up-regulated intracellularly in concert with apoptosis linked to melanoma cell detachment", Clinical and Experimental Metastasis, 22, (2005), 285-295.

Rao, et al., "Plant anticancer agents. XII. isolation and structure elucidation of new cytotoxic quinones from Tabebuia cassinoides", Journal of Natural Products, 45(5), (1982), 600-604.

Rieber, et al., "Relationship of Mcl-1 isoforms, ratio p21WAF1/cyclin A, and Jun kinase phosphorylation to apoptosis in human breast carcinomas", Biochemical and Biophysical Research Communications 297, (2002), 943-949.

Ryu, Chung-Kyu, et al., "Synthesis and antifungal activity of 1H-pyrrolo(3.2-g]quinoline-4.9-diones and 4,9-dioxo-4-9-dihydro-1H-benzo[f]indoles", Bioorganic & Medicinal Chemistry Letters, 19(1), (2009), 146-148.

Sanchez, "International Electronic Conferences on Synthetic Organic Chemistry", (2001), 1-30.

Seo, Ji-Min, et al., "JM91, a newly synthesized indoledione derivative, inhibits rat aortic vascular smooth muscle cells proliferation and cell cycle progression through inhibition of ERKl/2 and Akt activations", Biochemical Pharmacology 75(6), (2008), 1331-1340.

Seo, Ji-Min, et al., "YSK2821, a newly synthesized indoledione derivative, inhibits cell proliferation and cell cycle progression via the cell cycle-related proteins by regulating phosphatidylinositol-3 kinase cascade in vascular smooth muscle cells", European Journal of Pharmacology, 586(1-3), (2008), 74-81.

Shanab, Karem, et al., "Synthesis and antiproliferative activity of new cytotoxic azanaphthoquinone pyrrolo-annelated derivatives: Part II", Bioorganic & Medicinal Chemistry Letters vol. 21, No. 10, (2011), 3117-3121.

Sheng, "", CN 103265559 STN Abstract Accession No. 2013:1330613, (Aug. 2013).

Simamura, et al., "Furanonaphthoquinones Cause Apoptosis of Cancer Cells by Inducing the Production of Reactive Oxygen Species by the Mitochondrial Voltage-Dependent Anion Channel", Cancer Biology & Therapy 5:11, (Nov. 2006), 1523-1529.

Solorzano, et al., "Decreased glycolytic metabolism accelerates apoptosis in response to 2-acetyl furanonaphthoquinone in K1735 melanoma irrespective of bcl-2 overexpression", Cancer Bio. Ther, vol. 4, No. 3, (Mar. 2005), 329-335.

Suh, M E, "Comparison of QSAR Methods (CoMFA, CoMSIA, HQSAR) of Anticancer 1-N-Substituted Imidazoquinoline-4,9-dione Derivatives", Bull Korean Chem. Soc., 23(3), (2002), 417-422.

Suh, M E, et al., "Cytotoxic Effects of Pyridino [2,3-f]indole-4,9-diones on Human Tumor Cell Lines", Biol. Pharm. Bull., 23(3), (Mar. 1, 2000), 354-355.

Suh, M E, "The 3-D QSAR Study of Anticancer 1-N-substituted Imidazo- and Pyrrolo-quinoline-4,9-dione Derivatives by CoMFA and CoMSIA", Bioorganic & Medicinal Chemistry, vol. 9, No. 11, (2001), 2987-2991.

Suh, MYUNG_EUN, et al., "Synthesis of 1N-alkyl-2-amino-3-ethoxycarbonylpyridino[2,3-f]indole-4,9-dione derivatives (I)", STN Document No. 128:88804, 41 (5), (1997), 2 pgs.

Takano, et al., "Tumor-specific cytotoxicity and type of cell death induced by naphtho[2,3-b]furan-4,9-diones and related compounds in human tumor cell lines: relationship to electronic structure", Anticancer Research, 29, (2009), 455-464.

Valderrama, J A, et al., "Diels-Alder Reactions of 1-Dimethylamino-1-AZA-1,3-Dienes With Benzo[b]Thiophene-4,7-Quinones", Heterocyclic Communications 9 (2), particularly, compound 11, (2003), 175-180.

Yanni, "", Journal of the Indian Chemical Society, (1990), 777-9.

Yong, Rok Lee, et al., "Ceric Ammonium Nitrate (CAN)-Mediated Oxidative Cycloaddition of 1,3-Dicarbonyls to Conjugated Compounds. Efficient Synthesis of Dihydrofurans, Dihydrofurocoumarins, Dihydrofuroquinolinones, Dihydrofurophenalenones, and Furonaphthoquinone Natural Products", Tetrahedron 56, (2000), 8845-8853.

Yoon, Yeo Pyo, et al., "Preparation of indoledione derivatives for inhibiting hyper-proliferation of vascular smooth muscle cell", Accession No. 2009:161540, Document No. 150:259971, (2009), 3 pgs.

* cited by examiner

TRICYCLIC QUINONE DERIVATIVE

TECHNICAL FIELD

The present invention relates to novel tricyclic quinone derivatives useful as medicament or a pharmacologically acceptable salt thereof. More particularly, the invention relates to pharmaceutical compositions comprising a novel tricyclic quinone derivative or a pharmacologically acceptable salt thereof. The invention relates to therapeutic agents comprising a novel tricyclic quinone derivative comprising the compound, or a pharmacologically acceptable salt thereof.

BACKGROUND ART

Cancer develops when abnormality in gene occurs by an action of radiation, ultra violet rays, carcinogen, virus, or the like. The number of deaths by cancer increases year by year, and cancer is currently the top cause of death in Japan. As means for such cancer therapy, antitumor agents, surgical operation, radiotherapy, immunotherapy, and the like are performed. However, among these, the therapeutic use of an antitumor agent is the most important as an internally therapeutic means. Major antitumor agents act on any of metabolism, DNA synthesis, RNA synthesis, or protein synthesis of a nucleic acid precursor. However, such metabolic processes occur in not only cancer cells, but also normal cells. Therefore, many antitumor agents act on not only on cancer cells, but also on normal cells, and consequently any types of side effects develop.

In recent years, a new type of antitumor agent, called molecular targeting agent, has been introduced. This molecular targeting agent is a pharmaceutical agent designed to target a molecule specifically expressed in each cancer. Therefore, it is believed that a molecular targeting agent has higher specificity to cancer cells than conventional antitumor agents, and has fewer side effects. However, with regard to molecular targeting agents, although previous side effects are reduced, there are problems that new side effects are exhibited and alternatives of pharmaceutical agents are limited. Although the aforementioned antitumor agents were clinically used for the purpose of cancer therapy and prolonging the life of a cancer patients, there are still a number of unsolved problems including problems of side effects and the like as described above. Accordingly, it is recognized that the development of a novel antitumor agent is an important topic in the future.

In recent studies, the existence of cancer stem cells (CSC) having replication competence has been revealed, the CSC is closely related to the malignant transformation of cancer. In nearly all of major types of cancer in human, such as breast cancer, colon cancer, lung cancer, hematological malignancy, and the like, CSCs are identified. A CSC and a normal cancer cell differentiated from the CSC are significantly different in biological characteristics. A CSC is shown to be important in continuous proliferation of malignant tumor, metastasis and recurrence of cancer, and its resistance to an antitumor agent. Although Conventional therapy that targets normal cancer cells accounting for most part of tumor lumps can reduce the size of a tumor, as long as a CSC is also targeted at the same time, a meaningful survival effect cannot be expected. Therefore, targeting a CSC is very promising as a new method to treat a cancer (Non Patent Literature 1). One of the characteristics of CSCs is to have replication competence. Reliable methods established as a method of measuring replication competence of a cell include measurement of cancer cell sphere-forming ability in non-adhesion state in the absence of serum (Non Patent Literature 2). A compound that inhibits not only the proliferation of a non-CSC cancer cell, but also cancer cell sphere-forming ability is possibly very useful as a novel antitumor agent.

(1) Non Patent Literature 2 describes the following compounds as quinone derivatives isolated from the extract of a plant of the *Tabebuia* genus in the Bignoniaceae family.

[Chemical formula 1]

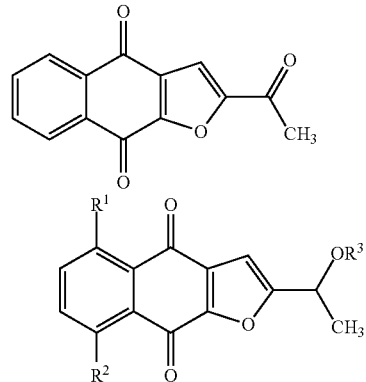

[wherein $R^1$, $R^2$, and $R^3$ are hydrogen atoms; $R^1$ and $R^3$ are H, $R^2$ is a hydroxyl group; $R^1$ is a hydroxyl group, $R^2$ and $R^3$ and hydrogen atoms; $R^1$ and $R^2$ and hydrogen atoms, and $R^3$ is $COCH_3$; or $R^1$ and $R^2$ are hydrogen atoms, $R^3$ is COC $(CF_3)(OCH_3)C_6H_5$.] It also discloses that these compounds have antitumor activity.

(2) Patent Literature 1 describes the following compound having antitumor activity and cancer cell sphere-forming ability.

[Chemical formula 2]

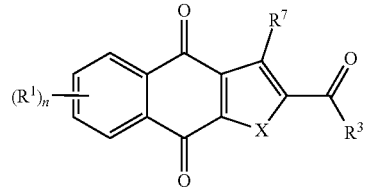

[wherein X is O or S, $R^1$ is a hydrogen atom, a halogen atom, a cyano group, a nitro group, a trifluoromethyl group, a trifluoromethoxy group, an optionally substituted alkyl group, or the like, $R^3$ is a hydrogen atom, a cyano group, an optionally substituted alkyl group, or the like, $R^7$ is a hydrogen atom, a halogen atom, a cyano group, a nitro group, an optionally substituted alkyl group, or the like, n is 1 to 4, with the proviso that when $R^3$ is not an amino group, $R^7$ is not a hydrogen atom and at least one of $R^1$ and $R^7$ is a halogen atom, or an optionally substituted aryl group.]

Patent Literature 2 describes the following compound having antitumor activity.

[Chemical formula 3]

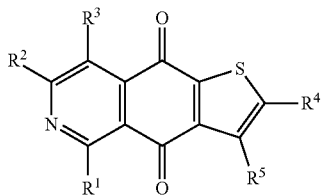

[wherein $R^1$, $R^2$, $R^3$, $R^4$, and $R^5$ are the same as or different from one another, and are a hydrogen atom, an alkyl group, an alkenyl group, an aryl group, or a substituent having a nitrogen atom, an oxygen atom, a sulfur atom, a phosphorus atom, or a halogen atom.]

Patent Literature 3 describes the following compound having antifungal activity.

[Chemical formula 4]

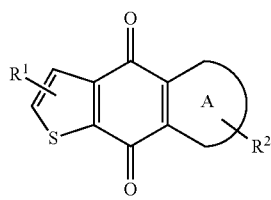

[wherein $R^1$ is a nitro group, an amino group, a cyano group, an alkyl group, a halogen atom, or the like, $R^2$ is a hydrogen atom, a halogen atom, a short-chain alkyl group, a substituted aryl group, a methacrylate group, or the like, and the ring A is pyridine, isoxazole, or aryl.]

Non Patent Literature 3 describes the following compounds having antitumor activity.

[Chemical formula 5]

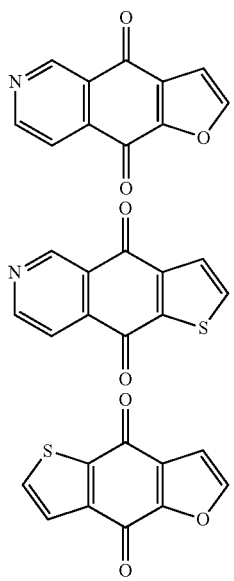

However, None of Non Patent Literatures 5 and 6 and Patent Literatures 1-3 describes any specific compound represented by formula (1) of the present invention.

CITATION LIST

Patent Literature

[Patent Literature 1]: International Publication No. 2009/036059 pamphlet
[Patent Literature 2]: Japanese Laid-Open Publication No. 2002-284684
[Patent Literature 3]: Chinese Patent Publication No. 103265559

Non Patent Literature

[Non Patent Literature 1]: Ponti et al. Cancer Res 65(13): 5506-11. 2005
[Non Patent Literature 2]: Rao et al. J Nat Prod 45(5):600-4. 1982
[Non Patent Literature 3]: Koyama et al. Molecules 15(9): 6559-69. 2010

SUMMARY OF INVENTION

Technical Problem

The problem of the present invention is to provide significantly useful compound as a novel antitumor agent by providing a compound that is targeted to CSC, which is important in continuous proliferation of a malignant tumor, metastasis and recurrence of cancer, and its resistance to an antitumor agent, and the compound inhibits not only the proliferation of non-CSC cancer cell but also cancer cell sphere-forming ability.

Solution to Problem

The present inventors focused on quinone derivatives, and intensively studied with regard to their antitumor activities to find that a compound represented by the following formula (1) or a pharmacologically acceptable salt thereof (hereinafter also referred to as "the present compound") has excellent effects on the inhibition of the proliferation of a cancer cell and cancer cell sphere-forming ability, and is significantly useful as a novel antitumor agent. The present inventors finally reached the completion of the present invention.

Specifically, the present invention is as described below.
Item 1: A compound represented by formula (1) or a pharmacologically acceptable salt thereof:

[Chemical formula 6]

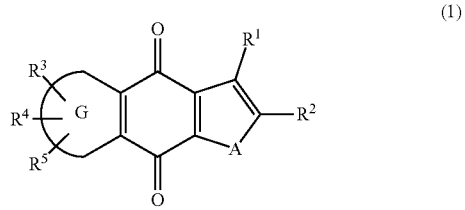

(1)

wherein

A is O, S, or N—R$^6$;

the ring G is a 5- or 6-membered aromatic ring that contains one to three heteroatoms consisting of O, S, and N as constituent atoms;

R$^1$ is each independently a hydrogen atom, a halogen atom, a cyano group, an optionally substituted 3- to 8-membered cyclic amino group, an optionally substituted C$_{1-6}$ alkyl group (with the proviso that an unsubstituted methyl group, and a C$_{1-6}$ alkyl group substituted with one dimethyl amino group or one chlorine atom are excluded), an optionally substituted C$_{3-10}$ cycloalkyl group, an optionally substituted C$_{1-6}$ alkenyl group, an optionally substituted C$_{1-6}$ alkynyl group, an optionally substituted C$_{6-10}$ aryl group, an optionally substituted 5- to 12-membered monocyclic or polycyclic heterocyclic group, an optionally substituted C$_{1-6}$ alkylcarbonyl group, an optionally substituted C$_{3-10}$ cycloalkylcarbonyl group, an optionally substituted C$_{6-10}$ arylcarbonyl group, an optionally substituted 5- to 12-membered monocyclic or polycyclic heterocyclylcarbonyl group, a carboxyl group, an optionally substituted C$_{3-10}$ cycloalkyloxycarbonyl group, an optionally substituted C$_{6-10}$ aryloxycarbonyl group, an optionally substituted 5- to 12-membered monocyclic or polycyclic heterocyclyloxycarbonyl group, an optionally substituted aminocarbonyl group, an optionally substituted 3- to 8-membered cyclic aminocarbonyl group, an optionally substituted C$_{1-6}$ alkylthio group, an optionally substituted C$_{3-10}$ cycloalkylthio group, an optionally substituted C$_{6-10}$ arylthio group, an optionally substituted 5- to 12-membered monocyclic or polycyclic heterocyclylthio group, a sulfinate group, an optionally substituted C$_{1-6}$ alkylsulfinyl group, an optionally substituted C$_{3-10}$ cycloalkylsulfinyl group, an optionally substituted C$_{6-10}$ arylsulfinyl group, an optionally substituted 5- to 12-membered monocyclic or polycyclic heterocyclylsulfinyl group, an optionally substituted aminosulfinyl group, an optionally substituted 3- to 8-membered cyclic aminosulfinyl group, a sulfonate group, an optionally substituted C$_{1-6}$ alkylsulfonyl group, an optionally substituted C$_{3-10}$ cycloalkylsulfonyl group, an optionally substituted C$_{6-10}$ arylsulfonyl group, an optionally substituted 5- to 12-membered monocyclic or polycyclic heterocyclylsulfonyl group, an optionally substituted aminosulfonyl group, or an optionally substituted 3- to 8-membered cyclic aminosulfonyl group;

R$^2$ is each independently a hydrogen atom, a halogen atom, a cyano group, a substituted amino group, an optionally substituted 3- to 8-membered cyclic amino group, an optionally substituted C$_{1-6}$ alkyl group (with the proviso that an unsubstituted methyl group is excluded), an optionally substituted C$_{3-10}$ cycloalkyl group, an optionally substituted C$_{1-6}$ alkenyl group, an optionally substituted C$_{1-6}$ alkynyl group, an optionally substituted C$_{6-10}$ aryl group, an optionally substituted 5- to 12-membered monocyclic or polycyclic heterocyclic group, an optionally substituted C$_{1-6}$ alkylcarbonyl group, an optionally substituted C$_{3-10}$ cycloalkylcarbonyl group, an optionally substituted C$_{6-10}$ arylcarbonyl group, an optionally substituted 5- to 12-membered monocyclic or polycyclic heterocyclylcarbonyl group, a carboxyl group, an optionally substituted C$_{3-10}$ cycloalkyloxycarbonyl group, an optionally substituted C$_{6-10}$ aryloxycarbonyl group, an optionally substituted 5- to 12-membered monocyclic or polycyclic heterocyclyloxycarbonyl group, an optionally substituted aminocarbonyl group, an optionally substituted 3- to 8-membered cyclic aminocarbonyl group, an optionally substituted C$_{1-6}$ alkylthio group, an optionally substituted C$_{3-10}$ cycloalkylthio group, an optionally substituted C$_{6-10}$ arylthio group, an optionally substituted 5- to 12-membered monocyclic or polycyclic heterocyclylthio group, a sulfinate group, an optionally substituted C$_{1-6}$ alkylsulfinyl group, an optionally substituted C$_{3-10}$ cycloalkylsulfinyl group, an optionally substituted C$_{6-10}$ arylsulfinyl group, an optionally substituted 5- to 12-membered monocyclic or polycyclic heterocyclylsulfinyl group, an optionally substituted aminosulfinyl group, an optionally substituted 3- to 8-membered cyclic aminosulfinyl group, a sulfonate group, an optionally substituted C$_{1-6}$ alkylsulfonyl group, an optionally substituted C$_{3-10}$ cycloalkylsulfonyl group, an optionally substituted C$_{6-10}$ arylsulfonyl group, an optionally substituted 5- to 12-membered monocyclic or polycyclic heterocyclylsulfonyl group, an optionally substituted aminosulfonyl group, or an optionally substituted 3- to 8-membered cyclic aminosulfonyl group;

R$^3$, R$^4$, or R$^5$ is each independently a hydrogen atom, a halogen atom, a cyano group, a hydroxyl group, an optionally substituted amino group, an optionally substituted C$_{1-6}$ alkyl group, an optionally substituted C$_{3-10}$ cycloalkyl group, an optionally substituted C$_{1-6}$ alkenyl group, an optionally substituted C$_{1-6}$ alkynyl group, an optionally substituted C$_{1-6}$ alkoxy group, an optionally substituted C$_{6-10}$ aryl group, an optionally substituted 5- to 12-membered monocyclic or polycyclic heterocyclic group, an optionally substituted C$_{1-6}$ alkylcarbonyl group, an optionally substituted C$_{3-10}$ cycloalkylcarbonyl group, an optionally substituted C$_{6-10}$ arylcarbonyl group, an optionally substituted 5- to 12-membered monocyclic or polycyclic heterocyclylcarbonyl group, a carboxyl group, an optionally substituted C$_{1-6}$ alkoxycarbonyl group, an optionally substituted C$_{3-10}$ cycloalkyloxycarbonyl group, an optionally substituted C$_{6-10}$ aryloxycarbonyl group, an optionally substituted 5- to 12-membered monocyclic or polycyclic heterocyclyloxycarbonyl group, an optionally substituted aminocarbonyl group, an optionally substituted C$_{1-6}$ alkylthio group, an optionally substituted C$_{3-10}$ cycloalkylthio group, an optionally substituted C$_{6-10}$ arylthio group, an optionally substituted 5- to 12-membered monocyclic or polycyclic heterocyclylthio group, a sulfinate group, an optionally substituted C$_{1-6}$ alkylsulfinyl group, an optionally substituted C$_{3-10}$ cycloalkylsulfinyl group, an optionally substituted C$_{6-10}$ arylsulfinyl group, an optionally substituted 5- to 12-membered monocyclic or polycyclic heterocyclylsulfinyl group, an optionally substituted aminosulfinyl group, a sulfonate group, an optionally substituted C$_{1-6}$ alkylsulfonyl group, an optionally substituted C$_{3-10}$ cycloalkylsulfonyl group, an optionally substituted C$_{6-10}$ arylsulfonyl group, an optionally substituted 5- to 12-membered monocyclic or polycyclic heterocyclylsulfonyl group, or an optionally substituted aminosulfonyl group;

R$^6$ is a hydrogen atom, an optionally substituted C$_{1-6}$ alkyl group, an optionally substituted C$_{3-10}$ cycloalkyl group, an optionally substituted C$_{6-10}$ aryl group, an optionally substituted 5- to 12-membered monocyclic or polycyclic heterocyclic group, an optionally substituted C$_{1-6}$ alkylcarbonyl group, an optionally substituted C$_{3-10}$ cycloalkylcarbonyl group, an optionally substituted C$_{6-10}$ arylcarbonyl group, an optionally substituted 5- to 12-membered monocyclic or polycyclic heterocyclylcarbonyl group, an optionally substituted C$_{1-6}$ alkoxycarbonyl group, an optionally substituted C$_{3-10}$ cycloalkyloxycarbonyl group, an optionally substituted C$_{6-10}$ aryloxycarbonyl group, an optionally substituted 5- to 12-membered monocyclic or polycyclic heterocyclyloxycarbonyl group, an optionally substituted C$_{1-6}$ alkylsulfinyl group, an optionally substituted C$_{3-10}$ cycloalkylsulfinyl group, an optionally substituted C$_{6-10}$ arylsulfinyl group, an optionally substituted 5- to 12-membered monocyclic or polycyclic heterocyclylsulfinyl group, an optionally substituted $C_{1-6}$ alkylsulfonyl group, an optionally substituted $C_{3-10}$ cycloalkylsulfonyl group, an optionally substituted $C_{6-10}$ arylsulfonyl group, or an optionally substituted 5- to 12-membered monocyclic or polycyclic heterocyclylsulfonyl group; with the proviso that in the formula (1), a compound in which $R^1$ and $R^2$ are both hydrogen atoms, a compound in which when A is O, the ring G is a furan ring or an imidazole ring, a compound in which when A is S, the ring G is a thiophene ring or an imidazole ring, a compound in which when A is N—$R^6$, the ring G is a pyrrole ring, a pyrazole ring, or an imidazole ring, 2-isopropylfuro[3,2-g]quinoline-4,9-dione, and ethyl 4,8-dioxo-2,7-diphenyl-4,8-dihydrothieno[2,3-f]benzofuran-6-carboxylate are excluded.

Item 2: The compound according to item 1 or a pharmacologically acceptable salt thereof, wherein A is S.

Item 3: The compound according to item 1 or a pharmacologically acceptable salt thereof, wherein A is O.

Item 4: The compound according to item 1 or a pharmacologically acceptable salt thereof, wherein A is N—$R^6$.

Item 5: The compound according to any one of items 1-4 or a pharmacologically acceptable salt thereof, wherein the ring G is of any formula selected from the group consisting of the following formulas (a) to (l):

[Chemical formula 7]

(a)
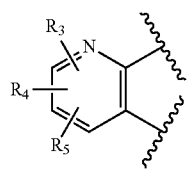

(b)
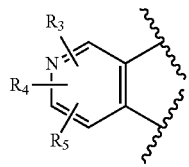

(c)
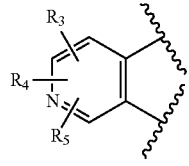

(d)
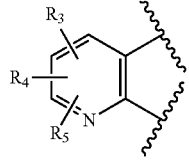

(e)
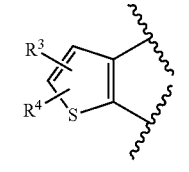

(f)
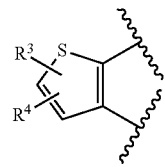

(g)
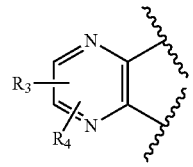

(h)
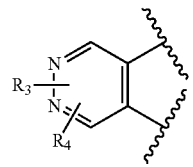

(i)
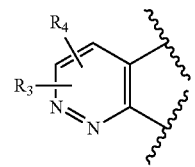

(j)
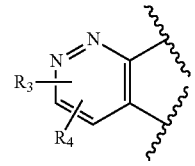

(k)
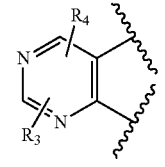

(l)
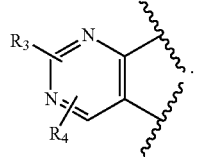

Item 6: The compound according to item 5 or a pharmacologically acceptable salt thereof, wherein the ring G is of any formula selected from the group consisting of the following formulas (a) to (h):

[Chemical formula 8]

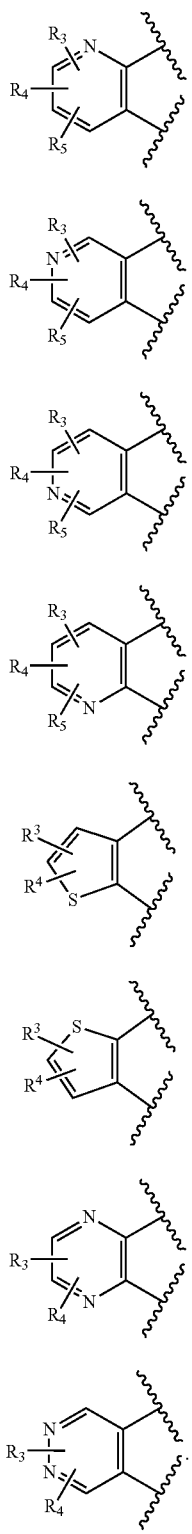

Item 7: The compound according to item 6 or a pharmacologically acceptable salt thereof, wherein the ring G is of any formula selected from the group consisting of the following formulas (a) to (f):

[Chemical formula 9]

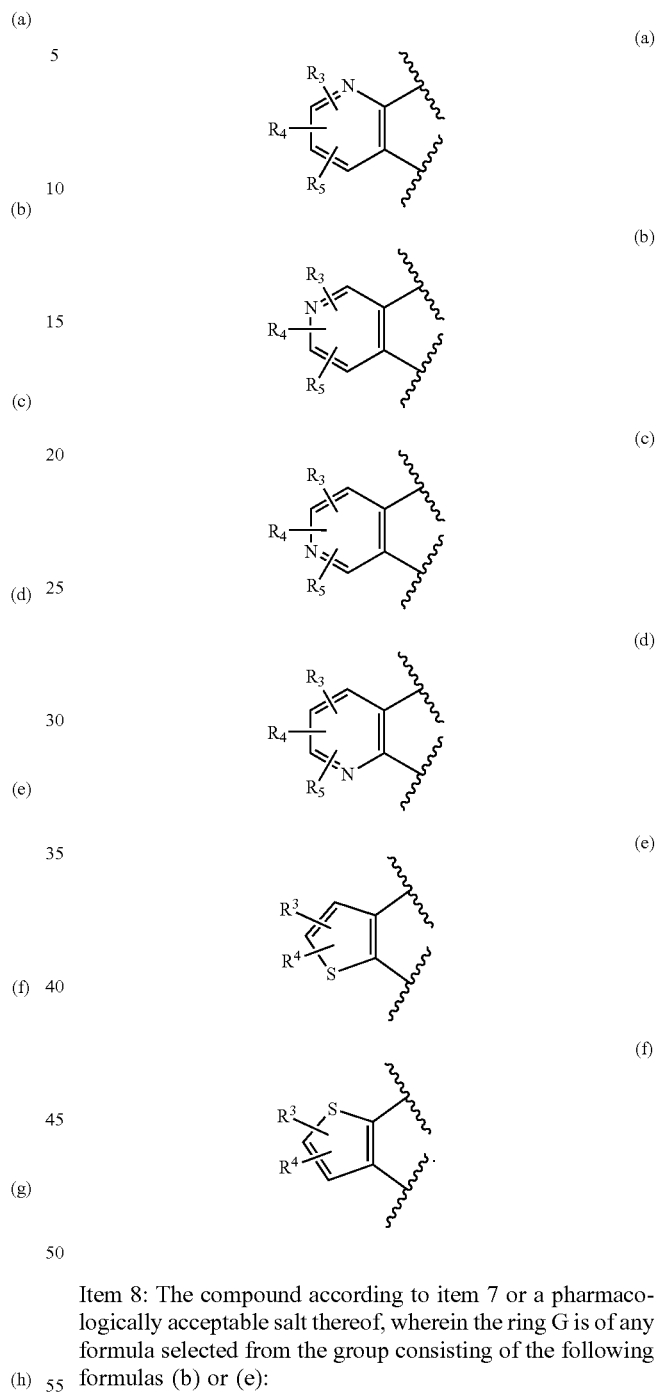

Item 8: The compound according to item 7 or a pharmacologically acceptable salt thereof, wherein the ring G is of any formula selected from the group consisting of the following formulas (b) or (e):

[Chemical formula 10]

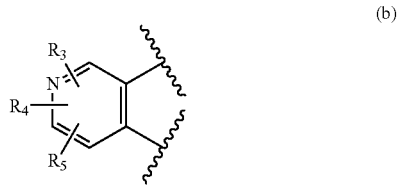

-continued (e) 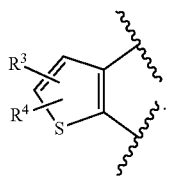

Item 9: The compound according to any one of items 1-8 or a pharmacologically acceptable salt thereof, wherein $R^1$ is a group selected from the group consisting of:
1: a hydrogen atom;
2: a cyano group;
3: a $C_{1-6}$ alkyl group (wherein the alkyl is optionally substituted with one to three groups selected from the group consisting of a fluorine atom, hydroxy, $C_{1-6}$ alkoxy, $C_{3-10}$ cycloalkyl, $C_{6-10}$ aryl, and 3- to 8-membered cyclic amino);
4: a $C_{1-6}$ alkylcarbonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle (which is optionally substituted with one to three $C_{1-6}$ alkyl));
5: a $C_{6-10}$ aryl group (wherein the aryl is optionally substituted one to three groups selected from a halogen atom, hydroxy, $C_{1-6}$ alkyl, and $C_{1-6}$ alkoxy);
6: a 5- to 12-membered monocyclic or polycyclic heterocyclic group (wherein the heterocycle is optionally substituted with one to three groups selected from the group consisting of a halogen atom, hydroxy, $C_{1-6}$ alkyl, and $C_{1-6}$ alkoxy);
7: a carboxyl group;
8: an aminocarbonyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, or $C_{1-6}$ alkoxy), and
(d) a 5- to 12-membered monocyclic or polycyclic heterocycle (wherein the heterocycle is optionally substituted with one to three groups selected from a halogen atom, hydroxy, $C_{1-6}$ alkyl, or $C_{1-6}$ alkoxy)); and
9: a 3- to 8-membered cyclic aminocarbonyl group (wherein the cyclic amino is optionally substituted with one to three $C_{1-6}$ alkyl).
Item 10: The compound according to item 9 or a pharmacologically acceptable salt thereof, wherein $R^1$ is a hydrogen atom or a $C_{1-6}$ alkylcarbonyl group (wherein the alkyl is optionally substituted with 3- to 8-membered cyclic amino).
Item 11: The compound according to any one of items 1-10 or a pharmacologically acceptable salt thereof, wherein $R^2$ is a group selected from the group consisting of:
1: a hydrogen atom;
2: a halogen atom;
3: a cyano group;
4: an amino group (wherein the amino is substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{1-6}$ alkylcarbonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(c) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(d) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(e) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
5: a 3- to 8-membered cyclic amino group (wherein the cyclic amino is optionally substituted with one to three $C_{1-6}$ alkyl);
6: a $C_{1-6}$ alkyl group (wherein the alkyl is optionally substituted with one to three groups selected from the group consisting of
(a) a halogen atom,
(b) hydroxy,
(c) amino (wherein the amino is optionally substituted with one or two groups selected from the group consisting of
(i) $C_{1-6}$ alkyl (wherein the alkyl is optionally substituted with one to three groups selected from the group consisting of a halogen atom, hydroxy, $C_{1-4}$ alkoxy, an aminocarbonyl group (wherein the amino is optionally substituted with one to three $C_{1-6}$ alkyl), $C_{6-10}$ aryl, and a 5- to 12-membered monocyclic or polycyclic heterocycle (which is optionally substituted with one to three $C_{1-6}$ alkyl))),
(ii) $C_{3-8}$ cycloalkyl (wherein the cycloalkyl is optionally substituted with one to three groups selected from the group consisting of a halogen atom, hydroxy, $C_{1-6}$ alkyl, or $C_{1-6}$ alkoxy),
(iii) $C_{1-6}$ alkylcarbonyl (wherein the alkyl is optionally substituted with one to three groups selected from a halogen atom, hydroxy, $C_{1-4}$ alkoxy, $C_{6-10}$ aryl, or a 5- to 12-membered monocyclic or polycyclic heterocycle (which is optionally substituted with one to three $C_{1-6}$ alkyl)),
(iv) $C_{1-6}$ alkoxycarbonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(v) $C_{1-6}$ alkylsulfinyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), (vi) $C_{1-6}$ alkylsulfonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(vii) aminocarbonyl (wherein the amino is optionally substituted with one or two $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl))),
(viii) 3- to 8-membered cyclic amino (wherein the cyclic amino is optionally substituted with one to three $C_{1-6}$ alkyl), and
(ix) $C_{3-10}$ cycloalkylcarbonyl,
(d) 3- to 8-membered cyclic amino (wherein the cyclic amino is optionally substituted with one to three $C_{1-6}$ alkylcarbonyl),
(e) $C_{1-6}$ alkoxy (wherein the alkoxy is optionally substituted with one to three $C_{6-10}$ aryl),
(f) $C_{3-10}$ cycloalkyl,
(g) $C_{6-10}$ aryl, and
(h) a 5- to 12-membered monocyclic or polycyclic heterocycle);
7: a $C_{3-10}$ cycloalkyl group (wherein the cycloalkyl is optionally substituted with one to three groups selected from the group consisting of a halogen atom, hydroxy, $C_{1-6}$ alkyl, and $C_{1-6}$ alkoxy);
8: a $C_{1-6}$ alkenyl group (the alkenyl is optionally substituted with one to three groups selected from $C_{1-6}$ alkyl and $C_{1-6}$ alkoxycarbonyl groups);
9: a $C_{1-6}$ alkynyl group (the alkynyl is optionally substituted with one to three groups selected from $C_{1-6}$ alkyl and $C_{1-6}$ alkoxycarbonyl groups);
10: a $C_{6-10}$ aryl group (wherein the aryl is optionally substituted with one to three groups selected from the group consisting of a halogen atom, hydroxy, $C_{1-6}$ alkyl, and $C_{1-6}$ alkoxy);
11: a 5- to 12-membered monocyclic or polycyclic heterocyclic group (wherein the heterocycle is optionally substituted with one to three groups selected from a halogen atom, hydroxy, $C_{1-6}$ alkyl, and $C_{1-6}$ alkoxy);
12: a $C_{3-10}$ cycloalkyloxy group (wherein the cycloalkyl is optionally substituted with one to three groups selected from the group consisting of a halogen atom, hydroxy, $C_{1-6}$ alkyl, and $C_{1-6}$ alkoxy);
13: a $C_{6-10}$ aryloxy group (wherein the aryl is optionally substituted with one to three groups selected from the group consisting of a halogen atom, hydroxy, $C_{1-6}$ alkyl, and $C_{1-6}$ alkoxy);
14: a 5- to 12-membered monocyclic or polycyclic heterocyclyloxy group (wherein the heterocycle is optionally substituted with one to three groups selected from the group consisting of a halogen atom, hydroxy, $C_{1-6}$ alkyl, and $C_{1-6}$ alkoxy);
15: a carboxyl group;
16: a $C_{1-6}$ alkylcarbonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
17: a $C_{3-10}$ cycloalkylcarbonyl group (wherein the cycloalkyl is optionally substituted with one to three groups selected from the group consisting of a halogen atom, hydroxy, $C_{1-6}$ alkyl, and $C_{1-6}$ alkoxy);
18: a $C_{6-10}$ arylcarbonyl group (wherein the aryl is optionally substituted with one to three groups selected from the group consisting of a halogen atom, hydroxy, $C_{1-6}$ alkyl, and $C_{1-6}$ alkoxy);
19: a 5- to 12-membered monocyclic or polycyclic heterocyclylcarbonyl group (wherein the heterocycle is optionally substituted with one to three groups selected from the group consisting of a halogen atom, hydroxy, $C_{1-6}$ alkyl, and $C_{1-6}$ alkoxy);
20: a $C_{3-10}$ cycloalkyloxycarbonyl group (wherein the cycloalkyl is optionally substituted with one to three groups selected from the group consisting of a halogen atom, hydroxy, $C_{1-6}$ alkyl, and $C_{1-6}$ alkoxy);
21: a $C_{6-10}$ aryloxycarbonyl group (wherein the aryl is optionally substituted with one to three groups selected from the group consisting of a halogen atom, hydroxy, $C_{1-6}$ alkyl, and $C_{1-6}$ alkoxy);
22: a 5- to 12-membered monocyclic or polycyclic heterocyclyloxycarbonyl group (wherein the heterocycle is optionally substituted with one to three groups selected from the group consisting of a halogen atom, hydroxy, $C_{1-6}$ alkyl, and $C_{1-6}$ alkoxy);
23: an aminocarbonyl group (wherein the amino is optionally substituted with one or two groups selected from
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
24: a 3- to 8-membered cyclic aminocarbonyl group (wherein the cyclic amino is optionally substituted with one to three $C_{1-6}$ alkyl);
25: a $C_{1-6}$ alkylthio group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
26: a $C_{3-10}$ cycloalkylthio group (wherein the cycloalkyl is optionally substituted with one to three groups selected from the group consisting of a halogen atom, hydroxy, $C_{1-6}$ alkyl, and $C_{1-6}$ alkoxy);
27: a $C_{6-10}$ arylthio group (wherein the aryl is optionally substituted with one to three groups selected from the group consisting of a halogen atom, hydroxy, $C_{1-6}$ alkyl, and $C_{1-6}$ alkoxy);
28: a 5- to 12-membered monocyclic or polycyclic heterocyclylthio group (wherein the heterocycle is optionally substituted with one to three groups selected from the group consisting of a halogen atom, hydroxy, $C_{1-6}$ alkyl, and $C_{1-6}$ alkoxy);

29: a sulfinate group;
30: a $C_{1-6}$ alkylsulfinyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
31: a $C_{3-10}$ cycloalkylsulfinyl group (wherein the cycloalkyl is optionally substituted with one to three groups selected from the group consisting of a halogen atom, hydroxy, $C_{1-6}$ alkyl, and $C_{1-6}$ alkoxy);
32: a $C_{6-10}$ arylsulfinyl group (wherein the aryl is optionally substituted with one to three groups selected from the group consisting of a halogen atom, hydroxy, $C_{1-6}$ alkyl, and $C_{1-6}$ alkoxy);
33: a 5- to 12-membered monocyclic or polycyclic heterocyclylsulfinyl group (wherein the heterocycle is optionally substituted with one to three groups selected from the group consisting of a halogen atom, hydroxy, $C_{1-6}$ alkyl, and $C_{1-6}$ alkoxy);
34: an aminosulfinyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
35: a 3- to 8-membered cyclic aminosulfinyl group (wherein the cyclic amino is optionally substituted with one to three $C_{1-6}$ alkyl);
36: a sulfonate group;
37: a $C_{1-6}$ alkylsulfonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
38: a $C_{3-10}$ cycloalkylsulfonyl group (wherein the cycloalkyl is optionally substituted with one to three groups selected from the group consisting of a halogen atom, hydroxy, $C_{1-6}$ alkyl, and $C_{1-6}$ alkoxy);
39: a $C_{6-10}$ arylsulfonyl group (wherein the aryl is optionally substituted with one to three groups selected from the group consisting of a halogen atom, hydroxy, $C_{1-6}$ alkyl, and $C_{1-6}$ alkoxy);
40: a 5- to 12-membered monocyclic or polycyclic heterocyclylsulfonyl group (wherein the heterocycle is optionally substituted with one to three groups selected from the group consisting of a halogen atom, hydroxy, $C_{1-6}$ alkyl, and $C_{1-6}$ alkoxy);
41: an aminosulfonyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy)); and
42: a 3- to 8-membered cyclic aminosulfinyl group (wherein the cyclic amino is optionally substituted with one to three $C_{1-6}$ alkyl).

Item 12: The compound according to any one of items 1-11 or a pharmacologically acceptable salt thereof, wherein $R^2$ is a group selected from the group consisting of:
1: a hydrogen atom;
2: a halogen atom;
3: a cyano group;
4: an amino group (wherein the amino is substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{1-6}$ alkylcarbonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(c) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(d) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(e) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
5: a 3- to 8-membered cyclic amino group (wherein the cyclic amino is optionally substituted with one to three $C_{1-6}$ alkyl);
6: a $C_{1-6}$ alkyl group (wherein the alkyl is optionally substituted with one to three groups selected from the group consisting of
(a) a halogen atom,
(b) hydroxy,
(c) amino (wherein the amino is optionally substituted with one or two groups selected from the group consisting of
(i) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), (ii) $C_{3-8}$ cycloalkyl (wherein the cycloalkyl is optionally substituted with one to three groups selected from the group consisting of a halogen atom, hydroxy, $C_{1-6}$ alkyl, or $C_{1-6}$ alkoxy), (iii) $C_{1-6}$ alkylcarbonyl (wherein the alkyl is optionally substituted with one to three groups selected from a halogen atom, hydroxy, $C_{1-4}$ alkoxy, $C_{6-10}$ aryl, or a 5- to 12-membered monocyclic or polycyclic heterocycle (which is optionally substituted with one to three $C_{1-6}$ alkyl)), (iv) $C_{1-6}$ alkoxycarbonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), (v) $C_{1-6}$ alkylsulfinyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), (vi) $C_{1-6}$ alkylsulfonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), (vii) aminocarbonyl (wherein the amino is optionally substituted with one or two $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl))), and (viii) 3- to 8-membered cyclic amino (wherein the cyclic amino is optionally substituted with one to three $C_{1-6}$ alkyl)), (d) 3- to 8-membered cyclic amino, (e) $C_{1-6}$ alkoxy, (f) $C_{3-10}$ cycloalkyl, (g) $C_{6-10}$ aryl, and (h) a 5- to 12-membered monocyclic or polycyclic heterocycle);

7: a $C_{3-10}$ cycloalkyl group (wherein the cycloalkyl is optionally substituted with one to three groups selected from the group consisting of a halogen atom, hydroxy, $C_{1-6}$ alkyl, and $C_{1-6}$ alkoxy);

8: a $C_{6-10}$ aryl group (wherein the aryl is optionally substituted with one to three groups selected from the group consisting of a halogen atom, hydroxy, $C_{1-6}$ alkyl, and $C_{1-6}$ alkoxy);

9: a 5- to 12-membered monocyclic or polycyclic heterocyclic group (wherein the heterocycle is optionally substituted with one to three groups selected from a halogen atom, hydroxy, $C_{1-6}$ alkyl, and $C_{1-6}$ alkoxy);

10: a $C_{3-10}$ cycloalkyloxy group (wherein the cycloalkyl is optionally substituted with one to three groups selected from the group consisting of a halogen atom, hydroxy, $C_{1-6}$ alkyl, and $C_{1-6}$ alkoxy);

11: a $C_{6-10}$ aryloxy group (wherein the aryl is optionally substituted with one to three groups selected from the group consisting of a halogen atom, hydroxy, $C_{1-6}$ alkyl, and $C_{1-6}$ alkoxy);

12: a 5- to 12-membered monocyclic or polycyclic heterocyclyloxy group (wherein the heterocycle is optionally substituted with one to three groups selected from the group consisting of a halogen atom, hydroxy, $C_{1-6}$ alkyl, and $C_{1-6}$ alkoxy);

13: a carboxyl group;

14: a $C_{1-6}$ alkylcarbonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);

15: a $C_{3-10}$ cycloalkylcarbonyl group (wherein the cycloalkyl is optionally substituted with one to three groups selected from the group consisting of a halogen atom, hydroxy, $C_{1-6}$ alkyl, and $C_{1-6}$ alkoxy);

16: a $C_{6-10}$ arylcarbonyl group (wherein the aryl is optionally substituted with one to three groups selected from the group consisting of a halogen atom, hydroxy, $C_{1-6}$ alkyl, and $C_{1-6}$ alkoxy);

17: a 5- to 12-membered monocyclic or polycyclic heterocyclylcarbonyl group (wherein the heterocycle is optionally substituted with one to three groups selected from the group consisting of a halogen atom, hydroxy, $C_{1-6}$ alkyl, and $C_{1-6}$ alkoxy);

18: a $C_{3-10}$ cycloalkyloxycarbonyl group (wherein the cycloalkyl is optionally substituted with one to three groups selected from the group consisting of a halogen atom, hydroxy, $C_{1-6}$ alkyl, and $C_{1-6}$ alkoxy);

19: a $C_{6-10}$ aryloxycarbonyl group (wherein the aryl is optionally substituted with one to three groups selected from the group consisting of a halogen atom, hydroxy, $C_{1-6}$ alkyl, and $C_{1-6}$ alkoxy);

20: a 5- to 12-membered monocyclic or polycyclic heterocyclyloxycarbonyl group (wherein the heterocycle is optionally substituted with one to three groups selected from the group consisting of a halogen atom, hydroxy, $C_{1-6}$ alkyl, and $C_{1-6}$ alkoxy);

21: an aminocarbonyl group (wherein the amino is optionally substituted with one or two groups selected from (a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), (b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy), (c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and (d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));

22: a 3- to 8-membered cyclic aminocarbonyl group (wherein the cyclic amino is optionally substituted with one to three $C_{1-6}$ alkyl);

23: a $C_{1-6}$ alkylthio group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);

24: a $C_{3-10}$ cycloalkylthio group (wherein the cycloalkyl is optionally substituted with one to three groups selected from the group consisting of a halogen atom, hydroxy, $C_{1-6}$ alkyl, and $C_{1-6}$ alkoxy);

25: a $C_{6-10}$ arylthio group (wherein the aryl is optionally substituted with one to three groups selected from the group consisting of a halogen atom, hydroxy, $C_{1-6}$ alkyl, and $C_{1-6}$ alkoxy);
26: a 5- to 12-membered monocyclic or polycyclic heterocyclylthio group (wherein the heterocycle is optionally substituted with one to three groups selected from the group consisting of a halogen atom, hydroxy, $C_{1-6}$ alkyl, and $C_{1-6}$ alkoxy);
27: a sulfinate group;
28: a $C_{1-6}$ alkylsulfinyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
29: a $C_{3-10}$ cycloalkylsulfinyl group (wherein the cycloalkyl is optionally substituted with one to three groups selected from the group consisting of a halogen atom, hydroxy, $C_{1-6}$ alkyl, and $C_{1-6}$ alkoxy);
30: a $C_{6-10}$ arylsulfinyl group (wherein the aryl is optionally substituted with one to three groups selected from the group consisting of a halogen atom, hydroxy, $C_{1-6}$ alkyl, and $C_{1-6}$ alkoxy);
31: a 5- to 12-membered monocyclic or polycyclic heterocyclylsulfinyl group (wherein the heterocycle is optionally substituted with one to three groups selected from the group consisting of a halogen atom, hydroxy, $C_{1-6}$ alkyl, and $C_{1-6}$ alkoxy);
32: an aminosulfinyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
33: a 3- to 8-membered cyclic aminosulfinyl group (wherein the cyclic amino is optionally substituted with one to three $C_{1-6}$ alkyl);
34: a sulfonate group;
35: a $C_{1-6}$ alkylsulfonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
36: a $C_{3-10}$ cycloalkylsulfonyl group (wherein the cycloalkyl is optionally substituted with one to three groups selected from the group consisting of a halogen atom, hydroxy, $C_{1-6}$ alkyl, and $C_{1-6}$ alkoxy);
37: a $C_{6-10}$ arylsulfonyl group (wherein the aryl is optionally substituted with one to three groups selected from the group consisting of a halogen atom, hydroxy, $C_{1-6}$ alkyl, and $C_{1-6}$ alkoxy);
38: a 5- to 12-membered monocyclic or polycyclic heterocyclylsulfonyl group (wherein the heterocycle is optionally substituted with one to three groups selected from the group consisting of a halogen atom, hydroxy, $C_{1-6}$ alkyl, and $C_{1-6}$ alkoxy);
39: an aminosulfonyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy)); and
40: a 3- to 8-membered cyclic aminosulfinyl group (wherein the cyclic amino is optionally substituted with one to three $C_{1-6}$ alkyl).
Item 13: The compound according to any one of items 1-11 or a pharmacologically acceptable salt thereof, wherein $R^2$ is a group selected from the group consisting of:
1: a hydrogen atom;
2: a halogen atom;
3: a cyano group;
4: an amino group (wherein the amino is optionally substituted with one to three $C_{1-6}$ alkyl groups);
5: a 3- to 8-membered cyclic amino group (wherein the cyclic amino is optionally substituted with one to three $C_{1-6}$ alkyl);
6: a $C_{1-6}$ alkyl group (wherein the alkyl is optionally substituted with one to three groups selected from the group consisting of
(a) a halogen atom,
(b) hydroxy,
(c) amino (wherein the amino is optionally substituted with one or two groups selected from the group consisting of
(i) $C_{1-6}$ alkyl (wherein the alkyl is optionally substituted with one to three groups selected from the group consisting of a halogen atom, hydroxy, and $C_{1-4}$ alkoxy),
(ii) $C_{3-8}$ cycloalkyl,
(iii) $C_{1-6}$ alkylcarbonyl,
(iv) $C_{1-6}$ alkoxycarbonyl, and
(v) $C_{1-6}$ alkylsulfonyl),
(d) 3- to 8-membered cyclic amino,
(e) $C_{1-6}$ alkoxy,
(f) $C_{3-10}$ cycloalkyl,
(g) phenyl, and
(h) a 5- to 6-membered monocyclic or polycyclic heterocycle);
7: a $C_{1-6}$ alkenyl group (wherein the alkenyl is optionally substituted with one to three groups selected from $C_{1-6}$ alkyl and $C_{1-6}$ alkoxycarbonyl groups);
8: a $C_{1-6}$ alkynyl group (wherein the alkynyl is optionally substituted with one to three groups selected from $C_{1-6}$ alkyl and $C_{1-6}$ alkoxycarbonyl groups);
9: a 5- to 12-membered monocyclic or polycyclic heterocyclic group;

10: a $C_{1-6}$ alkylcarbonyl group (wherein the alkyl is optionally substituted with one to three groups selected from the group consisting of a halogen atom, hydroxy, amino (which is optionally substituted with one or two $C_{1-6}$ alkyl groups), $C_{1-4}$ alkoxy, $C_{3-8}$ cycloalkyl, phenyl, and a 5- to 6-membered monocyclic heterocycle (which is optionally substituted with one to three $C_{1-6}$ alkyl));
11: an aminocarbonyl group (wherein the amino is
(a) $C_{1-6}$ alkyl (wherein the alkyl is optionally substituted with one to three groups selected from the group consisting of a halogen atom, hydroxy, $C_{1-4}$ alkoxy, phenyl, and a 5- to 6-membered monocyclic heterocycle (which is optionally substituted with one to three $C_{1-4}$ alkyl)),
(b) $C_{3-8}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) phenyl (wherein the aryl is optionally substituted with one to three groups selected from the group consisting of a halogen atom, hydroxy, $C_{1-6}$ alkyl, and $C_{1-6}$ alkoxy), and
(d) a 5- to 6-membered monocyclic heterocycle (wherein the heterocycle is optionally substituted with one to three groups selected from the group consisting of a halogen atom, hydroxy, $C_{1-6}$ alkyl, and $C_{1-6}$ alkoxy)); and
12: a 3- to 8-membered cyclic aminocarbonyl group (wherein the cyclic amino is optionally substituted with one to three $C_{1-6}$ alkyl).
Item 14: The compound according to item 13 or a pharmacologically acceptable salt thereof, wherein $R^2$ is a group selected from the group consisting of:
1: a $C_{1-6}$ alkyl group (wherein the alkyl is optionally substituted with one to three groups selected from the group consisting of a halogen atom, hydroxy, amino (which is optionally substituted with one or two $C_{1-6}$ alkyl groups), $C_{1-4}$ alkoxy, $C_{3-8}$ cycloalkyl, phenyl, and a 5- to 6-membered monocyclic heterocycle);
2: a $C_{1-6}$ alkylcarbonyl group (wherein the alkyl is optionally substituted with one to three groups selected from the group consisting of a halogen atom, hydroxy, amino (which is optionally substituted with one or two $C_{1-6}$ alkyl groups), $C_{1-4}$ alkoxy, $C_{3-8}$ cycloalkyl, phenyl, and a 5- to 6-membered monocyclic heterocycle (which is optionally substituted with one to three $C_{1-6}$ alkyl));
3: an aminocarbonyl group (wherein the amino is optionally substituted with one or two groups selected from
(a) $C_{1-6}$ alkyl (wherein the alkyl is optionally substituted with one to three groups selected from the group consisting of a halogen atom, hydroxy, $C_{1-4}$ alkoxy, phenyl, and a 5- to 6-membered monocyclic heterocycle (which is optionally substituted with one to three $C_{1-4}$ alkyl)),
(b) $C_{3-8}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) phenyl (wherein the aryl is optionally substituted with one to three groups selected from the group consisting of a halogen atom, hydroxy, $C_{1-6}$ alkyl, and $C_{1-6}$ alkoxy), and
(d) a 5- to 6-membered monocyclic heterocycle (wherein the heterocycle is optionally substituted with one to three groups selected from the group consisting of a halogen atom, hydroxy, $C_{1-6}$ alkyl, and $C_{1-6}$ alkoxy)); and
4: a 3- to 8-membered cyclic aminocarbonyl group (wherein the cyclic amino is optionally substituted with one to three $C_{1-6}$ alkyl).
Item 15: The compound according to any one of items 1-14 or a pharmacologically acceptable salt thereof, wherein $R^3$, $R^4$, or $R^5$ is each independently a group selected from the group consisting of:
1: a hydrogen atom;
2: a halogen atom;
3: a cyano group;
4: a hydroxyl group;
5: an amino group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{1-6}$ alkylcarbonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(c) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(d) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(e) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
6: a 3- to 8-membered cyclic amino group (wherein the cyclic amino is optionally substituted with one to three $C_{1-6}$ alkyl);
7: a $C_{1-6}$ alkyl group (wherein the alkyl is optionally substituted with one to three groups selected from a halogen atom, hydroxy, amino (which is optionally substituted with one or two $C_{1-6}$ alkyl), $C_{1-6}$ alkoxy, $C_{3-10}$ cycloalkyl, $C_{6-10}$ aryl, and a 5- to 12-membered monocyclic or polycyclic heterocycle);
8: a $C_{3-10}$ cycloalkyl group (wherein the cycloalkyl is optionally substituted with one to three groups selected from the group consisting of a halogen atom, hydroxy, $C_{1-6}$ alkyl, and $C_{1-6}$ alkoxy);
9: a $C_{6-10}$ aryl group (wherein the aryl is optionally substituted with one to three groups selected from the group consisting of a halogen atom, hydroxy, $C_{1-6}$ alkyl, and $C_{1-6}$ alkoxy);
10: a 5- to 12-membered monocyclic or polycyclic heterocyclic group (wherein the heterocycle is optionally substituted with one to three groups selected from the group consisting of a halogen atom, hydroxy, $C_{1-6}$ alkyl, and $C_{1-6}$ alkoxy);
11: a $C_{1-6}$ alkoxy group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
12: a $C_{3-10}$ cycloalkyloxy group (wherein the cycloalkyl is optionally substituted with one to three groups selected from the group consisting of a halogen atom, hydroxy, $C_{1-6}$ alkyl, and $C_{1-6}$ alkoxy);

13: a $C_{6-10}$ aryloxy group (wherein the aryl is optionally substituted with one to three groups selected from the group consisting of a halogen atom, hydroxy, $C_{1-6}$ alkyl, and $C_{1-6}$ alkoxy);

14: a 5- to 12-membered monocyclic or polycyclic heterocyclyloxy group (wherein the heterocycle is optionally substituted with one to three groups selected from the group consisting of a halogen atom, hydroxy, $C_{1-6}$ alkyl, and $C_{1-6}$ alkoxy);

15: a carboxyl group;

16: a $C_{1-6}$ alkylcarbonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);

17: a $C_{3-10}$ cycloalkylcarbonyl group (wherein the cycloalkyl is optionally substituted with one to three groups selected from the group consisting of a halogen atom, hydroxy, $C_{1-6}$ alkyl, and $C_{1-6}$ alkoxy);

18: a $C_{6-10}$ arylcarbonyl group (wherein the aryl is optionally substituted with one to three groups selected from the group consisting of a halogen atom, hydroxy, $C_{1-6}$ alkyl, and $C_{1-6}$ alkoxy);

19: a 5- to 12-membered monocyclic or polycyclic heterocyclylcarbonyl group (wherein the heterocycle is optionally substituted with one to three groups selected from the group consisting of a halogen atom, hydroxy, $C_{1-6}$ alkyl, and $C_{1-6}$ alkoxy);

20: a $C_{1-6}$ alkoxycarbonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);

21: a $C_{3-10}$ cycloalkyloxycarbonyl group (wherein the cycloalkyl is optionally substituted with one to three groups selected from the group consisting of a halogen atom, hydroxy, $C_{1-6}$ alkyl, and $C_{1-6}$ alkoxy);

22: a $C_{6-10}$ aryloxycarbonyl group (wherein the aryl is optionally substituted with one to three groups selected from the group consisting of a halogen atom, hydroxy, $C_{1-6}$ alkyl, and $C_{1-6}$ alkoxy);

23: a 5- to 12-membered monocyclic or polycyclic heterocyclyloxycarbonyl group (wherein the heterocycle is optionally substituted with one to three groups selected from the group consisting of a halogen atom, hydroxy, $C_{1-6}$ alkyl, and $C_{1-6}$ alkoxy);

24: an aminocarbonyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));

25: a 3- to 8-membered cyclic aminocarbonyl group (wherein the cyclic amino is optionally substituted with one to three $C_{1-6}$ alkyl);

26: a $C_{1-6}$ alkylthio group (wherein the alkyl is optionally substituted with one to three groups selected from the group consisting of a halogen atom, hydroxy, amino (which is optionally substituted with one or two $C_{1-6}$ alkyl), $C_{1-6}$ alkoxy, $C_{3-10}$ cycloalkyl, $C_{6-10}$ aryl, and a 5- to 12-membered monocyclic or polycyclic heterocycle);

27: a $C_{3-10}$ cycloalkylthio group (wherein the cycloalkyl is optionally substituted with one to three groups selected from the group consisting of a halogen atom, hydroxy, $C_{1-6}$ alkyl, and $C_{1-6}$ alkoxy);

28: a $C_{6-10}$ arylthio group (wherein the aryl is optionally substituted with one to three groups selected from the group consisting of a halogen atom, hydroxy, $C_{1-6}$ alkyl, and $C_{1-6}$ alkoxy);

29: a 5- to 12-membered monocyclic or polycyclic heterocyclylthio group (wherein the heterocycle is optionally substituted with one to three groups selected from the group consisting of a halogen atom, hydroxy, $C_{1-6}$ alkyl, and $C_{1-6}$ alkoxy);

30: a sulfinate group;

31: a $C_{1-6}$ alkylsulfinyl group (wherein the alkyl is optionally substituted with one to three groups selected from the group consisting of a halogen atom, hydroxy, amino (which is optionally substituted with one or two $C_{1-6}$ alkyl), $C_{1-6}$ alkoxy, $C_{3-10}$ cycloalkyl, $C_{6-10}$ aryl, and a 5- to 12-membered monocyclic or polycyclic heterocycle);

32: a $C_{3-10}$ cycloalkylsulfinyl group (wherein the cycloalkyl is optionally substituted with one to three groups selected from the group consisting of a halogen atom, hydroxy, $C_{1-6}$ alkyl, and $C_{1-6}$ alkoxy);

33: a $C_{6-10}$ arylsulfinyl group (wherein the aryl is optionally substituted with one to three groups selected from the group consisting of a halogen atom, hydroxy, $C_{1-6}$ alkyl, and $C_{1-6}$ alkoxy);

34: a 5- to 12-membered monocyclic or polycyclic heterocyclylsulfinyl group (wherein the heterocycle is optionally substituted with one to three groups selected from the group consisting of a halogen atom, hydroxy, $C_{1-6}$ alkyl, and $C_{1-6}$ alkoxy);

35: an aminosulfinyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));

36: a 3- to 8-membered cyclic aminosulfinyl group (wherein the cyclic amino is optionally substituted with one to three $C_{1-6}$ alkyl);

37: a sulfonate group;
38: a $C_{1-6}$ alkylsulfonyl group (wherein the alkyl is optionally substituted with one to three groups selected from the group consisting of a halogen atom, hydroxy, amino (which is optionally substituted with one or two $C_{1-6}$ alkyl), $C_{1-6}$ alkoxy, $C_{3-10}$ cycloalkyl, $C_{6-10}$ aryl, and a 5- to 12-membered monocyclic or polycyclic heterocycle);
39: a $C_{3-10}$ cycloalkylsulfonyl group (wherein the cycloalkyl is optionally substituted with one to three groups selected from the group consisting of a halogen atom, hydroxy, $C_{1-6}$ alkyl, and $C_{1-6}$ alkoxy);
40: a $C_{6-10}$ arylsulfonyl group (wherein the aryl is optionally substituted with one to three groups selected from the group consisting of a halogen atom, hydroxy, $C_{1-6}$ alkyl, and $C_{1-6}$ alkoxy);
41: a 5- to 12-membered monocyclic or polycyclic heterocyclylsulfonyl group (wherein the heterocycle is optionally substituted with one to three groups selected from the group consisting of a halogen atom, hydroxy, $C_{1-6}$ alkyl, and $C_{1-6}$ alkoxy);
42: an aminosulfonyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy)); and
43: a 3- to 8-membered cyclic aminosulfonyl group (wherein the cyclic amino is optionally substituted with one to three $C_{1-6}$ alkyl).
Item 16: The compound according to item 15 or a pharmacologically acceptable salt thereof, wherein $R^3$, $R^4$, or $R^5$ is each independently a group selected from the group consisting of:
1: a hydrogen atom;
2: a halogen atom;
3: a cyano group;
4: a hydroxyl group;
5: an amino group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{1-6}$ alkylcarbonyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(c) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(d) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(e) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
6: a 3- to 8-membered cyclic amino group (wherein the cyclic amino is optionally substituted with one to three $C_{1-6}$ alkyl);
7: a $C_{1-6}$ alkyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
8: a $C_{1-6}$ alkoxy group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
9: a $C_{1-6}$ alkylcarbonyl group (wherein the alkyl is optionally substituted with one to three groups selected from the group consisting of a halogen atom, hydroxy, amino (which is optionally substituted with one or two $C_{1-6}$ alkyl groups), $C_{1-6}$ alkoxy, $C_{3-10}$ cycloalkyl, $C_{6-10}$ aryl, and a 5- to 12-membered monocyclic or polycyclic heterocycle);
10: an aminocarbonyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)),
(b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy),
(c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and
(d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy));
11: a 3- to 8-membered cyclic aminocarbonyl group (wherein the cyclic amino is optionally substituted with one to three $C_{1-6}$ alkyl);
12: a $C_{1-6}$ alkylsulfonyl group (wherein the alkyl is optionally substituted with one to three groups selected from the group consisting of a halogen atom, hydroxy, amino (which is optionally substituted with one or two $C_{1-6}$ alkyl), $C_{1-6}$ alkoxy, $C_{3-10}$ cycloalkyl, $C_{6-10}$ aryl, and a 5- to 12-membered monocyclic or polycyclic heterocycle);
13: an aminosulfonyl group (wherein the amino is optionally substituted with one or two groups selected from the group consisting of
(a) $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), (b) $C_{3-10}$ cycloalkyl (wherein the cycloalkyl is optionally substituted with one to three groups selected from the group consisting of a halogen atom, hydroxy, $C_{1-6}$ alkyl, and $C_{1-6}$ alkoxy), (c) $C_{6-10}$ aryl (wherein the aryl is optionally substituted with one to three groups selected from the group consisting of a halogen atom, hydroxy, $C_{1-6}$ alkyl, and $C_{1-6}$ alkoxy), and (d) a 5- to 12-membered monocyclic or polycyclic heterocycle (wherein the heterocycle is optionally substituted with one to three groups selected from the group consisting of a halogen atom, hydroxy, $C_{1-6}$ alkyl, and $C_{1-6}$ alkoxy)); and 14: a 3- to 8-membered cyclic aminosulfonyl group (wherein the cyclic amino is optionally substituted with one to three $C_{1-6}$ alkyl).

Item 17: The compound according to item 16 or a pharmacologically acceptable salt thereof, wherein $R^3$, $R^4$, or $R^5$ is all hydrogen atoms.

Item 18: The compound according to any one of item 1 or 4-17 or a pharmacologically acceptable salt thereof, wherein $R^6$ is a group selected from the group consisting of:

1: a hydrogen atom;

2: a $C_{1-6}$ alkyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl));

3: a $C_{3-10}$ cycloalkyl group (wherein the cycloalkyl is optionally substituted with one to three groups selected from the group consisting of a halogen atom, hydroxy, $C_{1-6}$ alkyl, and $C_{1-6}$ alkoxy);

4: a $C_{1-6}$ alkylcarbonyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl));

5: a $C_{3-10}$ cycloalkylcarbonyl group;

6: a $C_{6-10}$ arylcarbonyl group;

7: a 5- to 12-membered monocyclic or polycyclic heterocyclylcarbonyl group;

8: a $C_{1-6}$ alkoxycarbonyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl));

9: a $C_{3-10}$ cycloalkyloxycarbonyl group (wherein the cycloalkyl is optionally substituted with one to three groups selected from the group consisting of a halogen atom, hydroxy, $C_{1-6}$ alkyl, and $C_{1-6}$ alkoxy);

10: a $C_{6-10}$ aryloxycarbonyl group (wherein the aryl is optionally substituted with one to three groups selected from the group consisting of a halogen atom, hydroxy, $C_{1-6}$ alkyl, and $C_{1-6}$ alkoxy);

11: a 5- to 12-membered monocyclic or polycyclic heterocyclyloxycarbonyl group (wherein the heterocycle is optionally substituted with one to three groups selected from the group consisting of a halogen atom, hydroxy, $C_{1-6}$ alkyl, and $C_{1-6}$ alkoxy);

12: a $C_{1-6}$ alkylsulfinyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl));

13: a $C_{3-10}$ cycloalkylsulfinyl group (wherein the cycloalkyl is optionally substituted with one to three groups selected from the group consisting of a halogen atom, hydroxy, $C_{1-6}$ alkyl, and $C_{1-6}$ alkoxy);

14: a $C_{6-10}$ arylsulfinyl group (wherein the aryl is optionally substituted with one to three groups selected from the group consisting of a halogen atom, hydroxy, $C_{1-6}$ alkyl, and $C_{1-6}$ alkoxy);

15: a 5- to 12-membered monocyclic or polycyclic heterocyclylsulfinyl group (wherein the heterocycle is optionally substituted with one to three groups selected from the group consisting of a halogen atom, hydroxy, $C_{1-6}$ alkyl, and $C_{1-6}$ alkoxy);

16: a $C_{1-6}$ alkylsulfonyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl));

17: a $C_{3-10}$ cycloalkylsulfonyl group (wherein the cycloalkyl is optionally substituted with one to three groups selected from the group consisting of a halogen atom, hydroxy, $C_{1-6}$ alkyl, and $C_{1-6}$ alkoxy);

18: a $C_{6-10}$ arylsulfonyl group (wherein the aryl is optionally substituted with one to three groups selected from the group consisting of a halogen atom, hydroxy, $C_{1-6}$ alkyl, and $C_{1-6}$ alkoxy);

19: a 5- to 12-membered monocyclic or polycyclic heterocyclylsulfonyl group (wherein the heterocycle is optionally substituted with one to three groups selected from the group consisting of a halogen atom, hydroxy, $C_{1-6}$ alkyl, and $C_{1-6}$ alkoxy);

20: a $C_{6-10}$ aryl group (wherein the aryl is optionally substituted with one to three groups selected from the group consisting of a halogen atom, hydroxy, $C_{1-6}$ alkyl, and $C_{1-6}$ alkoxy); and 21: a 5- to 12-membered monocyclic or polycyclic heterocyclic group (wherein the heterocycle is optionally substituted with one to three groups selected from the group consisting of a halogen atom, hydroxy, $C_{1-6}$ alkyl, and $C_{1-6}$ alkoxy).

Item 19: The compound according to item 18 or a pharmacologically acceptable salt thereof, wherein $R^6$ is a group selected from the group consisting of:

1: a hydrogen atom;

2: a $C_{1-6}$ alkyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl));

3: a $C_{1-6}$ alkylcarbonyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl)); and 4: a $C_{1-6}$ alkylsulfonyl group (wherein the alkyl is optionally substituted with one to three groups selected from the group consisting of a halogen atom, $C_{1-6}$ alkoxy, $C_{6-10}$ aryl, and a 5- to 6-membered monocyclic heterocycle (which is optionally substituted with one to three $C_{1-4}$ alkyl)).

Item 20: The compound according to item 19 or a pharmacologically acceptable salt thereof, wherein Re is a hydrogen atom.

Item 21: The compound according to items 1-20 or a pharmacologically acceptable salt thereof, wherein $R^2$ is a group selected from the group consisting of:

1: a $C_{1-6}$ alkyl group (wherein the alkyl is optionally substituted with one to three groups selected from the group consisting of a halogen atom, hydroxy, amino (which is optionally substituted with one or two $C_{1-6}$ alkyl groups), $C_{1-4}$ alkoxy, $C_{3-8}$ cycloalkyl, and a 5- to 6-membered monocyclic heterocycle);

2: a $C_{1-6}$ alkylcarbonyl group;

3: an aminocarbonyl group (wherein the amino is optionally substituted with one to three $C_{1-6}$ alkyl groups (wherein the alkyl is optionally substituted with one to three halogen atoms)); and 4: a 3- to 8-membered cyclic aminocarbonyl group (wherein the cyclic amino is optionally substituted with one to three $C_{1-6}$ alkyl)

Item 22: The compound according to item 1 or a pharmacologically acceptable salt thereof, wherein A is O or S;

the ring G is either one selected from the group consisting of the following formula (b) or (e):

[Chemical formula 11]

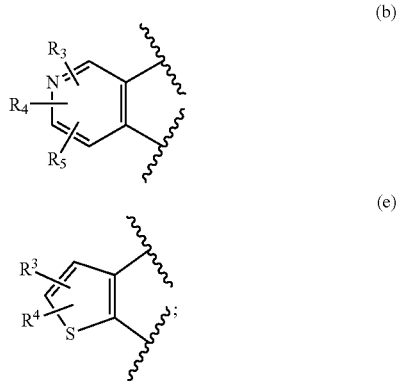

$R^1$ is a hydrogen atom; and $R^2$ is a group selected from the group consisting of:

1: a $C_{1-6}$ alkyl group (wherein the alkyl is optionally substituted with one to three groups selected from the group consisting of a halogen atom, hydroxy, amino (which is optionally substituted with one or two $C_{1-6}$ alkyl groups), $C_{1-4}$ alkoxy, $C_{3-8}$ cycloalkyl, and a 5- to 6-membered monocyclic heterocycle);

2: a $C_{1-6}$ alkylcarbonyl group;

3: an aminocarbonyl group (wherein the amino is optionally substituted with one to three $C_{1-6}$ alkyl groups (wherein the alkyl is optionally substituted with one to three halogen atoms)); and 4: a 3- to 8-membered cyclic aminocarbonyl group (wherein the cyclic amino is optionally substituted with one to three $C_{1-6}$ alkyl).

$R^3$, $R^4$, and $R^{s5}$ are hydrogen atoms.

Item 23: The compound according to item 1 or a pharmaceutically acceptable salt thereof, wherein the compound is selected from the following compounds:

2-acetylthieno[2,3-g]quinoline-4,9-dione;
2-acetylthieno[2,3-g]isoquinoline-4,9-dione;
2-(1-hydroxyethyl)thieno[2,3-g]isoquinoline-4,9-dione;
2-(2-hydroxypropan-2-yl)thieno[2,3-g]isoquinoline-4,9-dione;
2-[cyclopropyl(hydroxy)methyl]thieno[2,3-g]isoquinoline-4,9-dione;
N,N-dimethyl-4,9-dioxo-4,9-dihydrothieno[2,3-g]isoquinoline-2-carboxyamide;
2-(morpholin-4-ylcarbonyl)thieno[2,3-g]isoquinoline-4,9-dione;
N-(2,2-difluoroethyl)-4,9-dioxo-4,9-dihydrothieno[2,3-g]isoquinoline-2-carboxyamide;
2-{[ethyl(2-methoxyethyl)amino]methyl}thieno[2,3-g]isoquinoline-4,9-dione;
2-{[(2,2-difluoroethyl)amino]methyl}thieno[2,3-g]isoquinoline-4,9-dione;
2-[(4-acetylpiperazin-1-yl)methyl]thieno[2,3-g]isoquinoline-4,9-dione;
4,9-dioxo-4,9-dihydrothieno[2,3-g]isoquinoline-2-carbonitrile;
2-(1-fluoroethyl)thieno[2,3-g]isoquinoline-4,9-dione;
2-(3-ethyl-1,2,4-oxadiazol-5-yl)thieno[2,3-g]isoquinoline-4,9-dione;
2-acetylthieno[3,2-g]isoquinoline-4,9-dione;
N-(2,2-difluoroethyl)-4,9-dioxo-4,9-dihydrofuro[2,3-g]isoquinoline-2-carboxamide;
2-(1-hydroxyethyl)furo[3,2-g]isoquinoline-4,9-dione;
2-acetylthieno[3,2-f][1]benzofuran-4,8-dione; and
2-(morpholin-4-ylcarbonyl)thieno[3,2-f][1]benzofuran-4,8-dione.

Item 24: A pharmaceutical composition comprising a compound according to any one of items 1-23 or a pharmacologically acceptable salt thereof.

Item 25: An anticancer agent comprising a compound according to any one of items 1-23 or a pharmacologically acceptable salt thereof as an active ingredient.

Item 26: The anticancer agent according to item 25, wherein the cancer is at least one cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder•bile duct cancer, hepatoma, pancreatic cancer, colon cancer, rectal cancer, chorioepithelioma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

Item 27: A method for treating a cancer, characterized by administering a therapeutically effective amount of a compound according to any one of items 1-23 or a pharmacologically acceptable salt thereof to a patient in need of the treatment.

Item 28: The method for treating according to item 27, wherein the cancer is at least one cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder•bile duct cancer, hepatoma, pancreatic cancer, colon cancer, rectal cancer, chorioepithelioma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

Item 29: The use of a compound according to any one of items 1-23 or a pharmacologically acceptable salt thereof for the manufacture of a therapeutic agent for cancer.

Item 30: The use of a compound according to item 29 or a pharmacologically acceptable salt thereof, wherein the cancer is at least one cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder•bile duct cancer, hepatoma, pancreatic cancer, colon cancer, rectal cancer, chorioepithelioma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

Item 31: A compound according to any one of items 1-23 or a pharmacologically acceptable salt thereof for use in treating cancer.

Item 32: The compound according to item 31 or a pharmacologically acceptable salt thereof, wherein the cancer is at least one cancer selected from the group consisting of acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder•bile duct cancer, hepatoma, pancreatic cancer, colon cancer, rectal cancer, chorioepithelioma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma.

Item 33: A method of producing a compound represented by formula (1) or a pharmacologically acceptable salt thereof:

[Chemical formula 13]

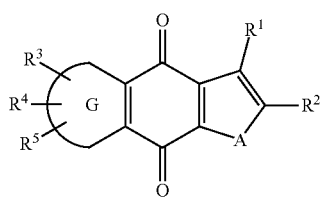

(1)

wherein A, $R^1$, $R^2$, $R^3$, $R^4$, and $R^5$ are defined as in above item 1, wherein the method is characterized by comprising a step of mixing a compound represented by formula (2) or a salt thereof:

[Chemical formula 12]

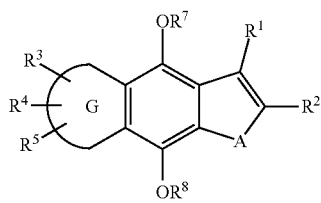

(2)

wherein A, $R^1$, $R^2$, $R^3$, $R^4$, and $R^5$ are defined as in above item 1; $R^7$ and $R^8$ are each $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), with an oxidant.

Item 34: A method of producing a compound represented by formula (1) or a pharmacologically acceptable salt thereof:

[Chemical formula 15]

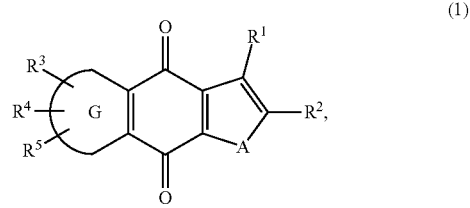

(1)

wherein A, $R^1$, $R^2$, $R^3$, $R^4$, and $R^5$ are defined as in above item 1, and wherein the method is characterized by comprising a step of mixing a compound represented by formula (2) or a salt thereof:

[Chemical formula 14]

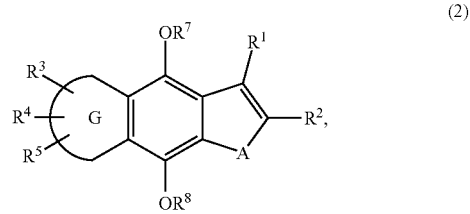

(2)

wherein A, $R^1$, $R^2$, $R^3$, $R^4$, and $R^5$ are defined as in above item 1, or $R^1$ and $R^2$ are optionally substituted alkoxycarbonyl groups, and $R^7$ and $R^8$ are each $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)), with an oxidant.

Item 35: A compound represented by the following formula (2) or a salt thereof:

[Chemical formula 16]

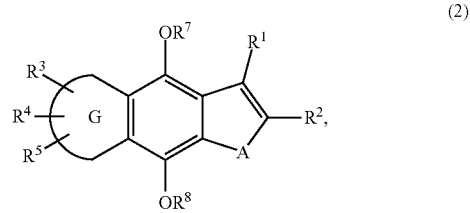

(2)

wherein A, $R^1$, $R^2$, $R^3$, $R^4$, and $R^5$ are defined as in above item 1, and $R^7$ and $R^8$ are each $C_{1-6}$ alkyl (wherein the alkyl is optionally substituted with one to three groups selected from the group consisting of a halogen atom, hydroxy, $C_{1-4}$ alkoxy, $C_{6-10}$ aryl, and a 5- to 12-membered monocyclic or polycyclic heterocycle (which is optionally substituted with one to three $C_{1-6}$ alkyl)).

Moreover, it will be understood that the characteristics of the above-described embodiments of the present invention can be used alone or in combination. Accordingly, in the present invention, it is intended that in addition to the clarified combinations, the above-mentioned one or more characteristics can be further combined and provided.

Advantageous Effects of Invention

The compounds represented by the formula (1) or the pharmacologically acceptable salts thereof (also referred to as the present compound(s)) exhibit strong inhibitory effects on proliferation of a cancer cell and cancer cell sphere-forming ability, and these compounds are useful, for example, as medicament to be effective in prevention and/or treatment of cancer.

DESCRIPTION OF EMBODIMENTS

The present invention is described below in more detail.

In the present specification, the number of substituents of a group defined by "an optionally substituted" or "substituted" is not particularly limited if it is substitutable, and is one or plural. In addition, unless otherwise indicated, the description for each group is also applied when the group is one part of or a substituent on other groups.

In the present specification, examples of "halogen atom" include a fluorine atom, a chlorine atom, a bromine atom, and an iodine atom. Preferably, it is a fluorine atom or a chlorine atom.

A "$C_{1-6}$ alkyl group" means a linear or branched, saturated hydrocarbon group of which the carbon number is one to six. Preferably, it includes a "$C_{1-4}$ alkyl group" and the like. Specific examples of the "$C_{1-6}$ alkyl group" include, for example, methyl, ethyl, propyl, 1-methylethyl, butyl, 2-methylpropyl, 1-methylpropyl, 1,1-dimethylethyl, pentyl, 3-methylbutyl, 2-methylbutyl, 2,2-dimethylpropyl, 1-ethylpropyl, 1,1-dimethylpropyl, hexyl, 4-methylpentyl, 3-methylpentyl, 2-methylpentyl, 1-methylpentyl, and the like. Specific examples of the "$C_{1-4}$ alkyl group" include those having a carbon number from 1 to 4 that are exemplified in the specific examples of "$C_{1-10}$ alkyl group". In the specification, for example, $C_{1-6}$ represents that the carbon number is one to six, $C_{1-4}$ represents that the carbon number is one to four, or $C_6$ represents that the carbon number is six. The same applies to cases of other numbers.

A "$C_{2-6}$ alkenyl group" means a linear or branched, unsaturated hydrocarbon group that has two to six carbons and contains one to three double bonds. Specific examples of "$C_{2-6}$ alkenyl group" include, for example, vinyl, propenyl, methylpropenyl, butenyl, methylbutenyl, pentenyl, hexenyl, and the like.

A "$C_{2-6}$ alkynyl group" means a linear or branched, unsaturated hydrocarbon group that has two to six carbons and contains one triple bond. Specific examples of "$C_{2-6}$ alkynyl group" include, for example, propynyl, methylpropynyl, butynyl, methylbutynyl, pentynyl, hexynyl, and the like.

A "$C_{3-10}$ cycloalkyl group" means a cyclic saturated hydrocarbon group of which the carbon number is three to ten, and also includes those having a partially crosslinked structure. Preferably, it includes a "$C_{3-7}$ cycloalkyl group" and the like. Specific examples of "$C_{3-10}$ cycloalkyl group" include, for example, cyclopropyl, cyclobutyl, cyclopentyl, cyclohexyl, cycloheptyl, cyclooctyl, cyclononyl, cyclodecyl, adamantyl, and the like. Specific examples of "$C_{3-7}$ cycloalkyl group" include, for example, cyclopropyl, cyclobutyl, cyclopentyl, cyclohexyl, cycloheptyl, and the like. The "$C_{3-10}$ cycloalkyl group" also encompasses a compound fused to an aromatic ring. Specific examples thereof include, for example, groups represented by the following:

[Chemical formula 17]

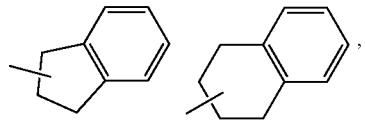

and the like.

A "$C_{1-6}$ alkoxy group" refers to a "$C_{1-6}$ alkyloxy group" and the "$C_{1-6}$ alkyl" moiety in a "$C_{1-6}$ alkoxy group" is defined the same as the above-described "$C_{1-6}$ alkyl". The "$C_{1-6}$ alkoxy group" includes, preferably, a "$C_{1-4}$ alkoxy group" and the like. Examples of "$C_{1-6}$ alkoxy group" include, for example, methoxy, ethoxy, propoxy, 1-methylethoxy, butoxy, 2-methylpropoxy, 1-methylpropoxy, 1,1-dimethylethoxy, pentyloxy, 3-methylbutoxy, 2-methylbutoxy, 2,2-dimethylpropoxy, 1-ethylpropoxy, 1,1-dimethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, and the like.

The "$C_{3-10}$ cycloalkyl" moiety in a "$C_{3-10}$ cycloalkyloxy group" is defined the same as the above described "$C_{3-10}$ cycloalkyl group". Preferably, it is a "$C_{3-7}$ cycloalkyloxy group" and the like. Examples of "$C_{3-10}$ cycloalkyloxy group" include, for example, cyclopropoxy, cyclobutoxy, cyclopentyloxy, cyclohexyloxy, cycloheptyloxy, and the like.

The "$C_{1-6}$ alkyl" moiety in a "$C_{1-6}$ alkylcarbonyl group" is defined the same as the above-described "$C_{1-6}$ alkyl group". The "$C_{1-6}$ alkylcarbonyl group" includes, preferably, a "$C_{1-4}$ alkylcarbonyl group" and the like. Specific examples of "$C_{1-6}$ alkylcarbonyl group" include, for example, methylcarbonyl, ethylcarbonyl, propylcarbonyl, 1-methylethylcarbonyl, butylcarbonyl, 2-methylpropylcarbonyl, 1-methylpropylcarbonyl, 1,1-dimethylethylcarbonyl, and the like.

The "$C_{3-10}$ cycloalkyl" moiety in a "$C_{3-10}$ cycloalkylcarbonyl group" is defined the same as the above described "$C_{3-10}$ cycloalkyl group". Preferably, it is a "$C_{3-7}$ cycloalkylcarbonyl group" and the like. Specific examples of "$C_{3-10}$ cycloalkylcarbonyl group" include, for example, cyclopropylcarbonyl, cyclobutylcarbonyl, cyclopentylcarbonyl, cyclohexylcarbonyl, cycloheptylcarbonyl, and the like.

The "$C_{1-6}$ alkylcarbonyl" moiety in a "$C_{1-6}$ alkylcarbonyloxy group" is defined the same as the above-described "$C_{1-6}$ alkylcarbonyl group". The "$C_{1-6}$ alkylcarbonyloxy group" includes, preferably, a "$C_{1-4}$ alkylcarbonyloxy group" and the like. Specific examples of "$C_{1-6}$ alkylcarbonyloxy group" include methylcarbonyloxy, ethylcarbonyloxy, propylcarbonyloxy, 1-methylethylcarbonyloxy, butylcarbonyloxy, 2-methylpropylcarbonyloxy, 1-methylpropylcarbonyloxy, 1,1-dimethylethylcarbonyloxy, and the like.

The "$C_{1-6}$ alkylcarbonyl" moiety in a "$C_{1-6}$ alkylcarbonylamino group" is defined the same as the above-described "$C_{1-6}$ alkylcarbonyl group". Specific examples of "$C_{1-6}$ alkylcarbonylamino group" include, for example, methylcarbonylamino, ethylcarbonylamino, and the like.

The "$C_{1-6}$ alkyl" moiety in a "$C_{1-6}$ alkylthio group" is defined the same as the above-described "$C_{1-6}$ alkyl group".

The "C$_{1-6}$ alkylthio group" includes, preferably, "C$_{1-4}$ alkylthio group" and the like. Specific examples of "C$_{1-6}$ alkylthio group" include, for example, methylthio, ethylthio, propylthio, 1-methylethylthio, butylthio, 2-methylpropylthio, 1-methylpropylthio, 1,1-dimethylethylthio, and the like.

The "C$_{3-10}$ cycloalkyl" moiety in a "C$_{3-10}$ cycloalkylthio group" is defined the same as the above-described "C$_{3-10}$ cycloalkyl group". Preferably, it is a "C$_{3-7}$ cycloalkylthio group" and the like. Specific examples of "C$_{3-10}$ cycloalkylthio group" include, for example, cyclopropylthio, cyclobutylthio, cyclopentylthio, cyclohexylthio, cycloheptylthio, and the like.

The "C$_{1-6}$ alkyl" moiety in a "C$_{1-6}$ alkylsulfinyl group" is defined the same as the above-described "C$_{1-6}$ alkyl group". The "C$_{1-6}$ alkylsulfinyl group" includes, preferably, "C$_{1-4}$ alkylsulfinyl group" and the like. Specific examples of "C$_{1-6}$ alkylsulfinyl group" include, for example, methylsulfinyl, ethylsulfinyl, propylsulfinyl, 1-methylethylsulfinyl, butylsulfinyl, 2-methylpropylsulfinyl, 1-methylpropylsulfinyl, 1,1-dimethylethylsulfinyl, and the like.

The "C$_{3-10}$ cycloalkyl" moiety in a "C$_{3-10}$ cycloalkylsulfinyl group" is defined the same as the above-described "C$_{3-10}$ cycloalkyl group". Preferably, it is a "C$_{3-7}$ cycloalkylsulfinyl group" and the like. Specific examples of "C$_{3-10}$ cycloalkylsulfinyl group" include, for example, cyclopropylsulfinyl, cyclobutylsulfinyl, cyclopentylsulfinyl, cyclohexylsulfinyl, cycloheptylsulfinyl, and the like.

The "C$_{1-6}$ alkyl" moiety in a "C$_{1-6}$ alkylsulfonyl group" is defined the same as the above-described "C$_{1-6}$ alkyl group". Preferably, it includes a "C$_{1-4}$ alkylsulfonyl group" and the like. Specific examples of "C$_{1-6}$ alkylsulfonyl group" include, for example, methylsulfonyl, ethylsulfonyl, propylsulfonyl, isopropylsulfonyl, butylsulfonyl, pentylsulfonyl, hexylsulfonyl, and the like.

The "C$_{3-10}$ cycloalkyl" moiety in a "C$_{3-10}$ cycloalkylsulfonyl group" is defined the same as the above-described "C$_{3-10}$ cycloalkyl group". Preferably, it is a "C$_{3-7}$ cycloalkylsulfonyl group" and the like. Specific examples of "C$_{3-10}$ cycloalkylsulfonyl group" include, for example, cyclopropylsulfonyl, cyclobutylsulfonyl, cyclopentylsulfonyl, cyclohexylsulfonyl, cycloheptylsulfonyl, and the like.

The "C$_{1-6}$ alkoxy" moiety in a "C$_{1-6}$ alkoxycarbonyl group" is defined the same as the above-described "C$_{1-6}$ alkoxy group". Specific examples of "C$_{1-6}$ alkoxycarbonyl group" include, for example, methoxycarbonyl, ethoxycarbonyl, and the like. In the relevant field, although an "alkoxycarbonyl group" may be referred to as an "alkyloxycarbonyl group", the two are synonymous.

The "C$_{3-10}$ cycloalkyl" moiety in a "C$_{3-10}$ cycloalkyloxycarbonyl group" is defined the same as the above-described "C$_{3-10}$ cycloalkyl group". Preferably, it is a "C$_{3-7}$ cycloalkyloxycarbonyl group" and the like. Specific examples of "C$_{3-10}$ cycloalkyloxycarbonyl group" include, for example, cyclopropyloxycarbonyl, cyclobutyloxycarbonyl, cyclopentyloxycarbonyl, cyclohexyloxycarbonyl, cycloheptyloxycarbonyl, and the like.

A "C$_{6-10}$ aryl group" means an aromatic hydrocarbon of which the carbon number is six to ten. Specific examples of "C$_{6-10}$ aryl group" include, for example, phenyl, 1-naphthyl, 2-naphthyl, and the like. Particularly preferably, it includes a phenyl group. The "C$_{6-10}$ aryl group" also encompasses a 8- to 14-membered polycyclic group in which an aromatic ring and a C$_{4-6}$ cycloalkyl are ring-fused, or 9- to 14-membered polycyclic group in which an aromatic ring is fused to, for example, 5- to 6-membered heterocyclic group having one to three atoms that are identical or different and are selected from a nitrogen atom, an oxygen atom, or a sulfur atom. Specific examples thereof include, for example, groups represented by the following:

[Chemical formula 18]

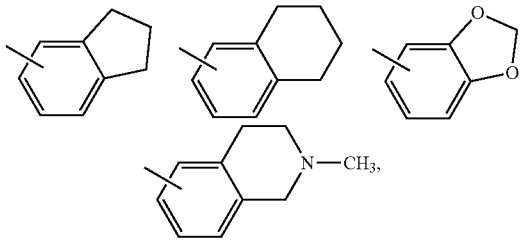

and the like.

Examples of "heterocyclic group" include 3- to 10-membered heterocyclic group having one to three atoms that are identical or different and are selected from a nitrogen atom, an oxygen atom, or a sulfur atom, and the like. Preferably, it is a 4- to 7-membered group, more preferably, a 5- or 6-membered group. All the aforementioned nitrogen atom, oxygen atom, and sulfur atom are atoms constituting a ring. The heterocyclic group may be any of saturated, partially unsaturated, or unsaturated heterocyclic groups, and a saturated heterocyclic group is more preferred. Specific examples of "heterocyclic group" include epoxy, aziridine, azetidine, pyranyl, tetrahydrofuryl, pyrrolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxooxazolidinyl, dioxooxazolidinyl, dioxothiazolidinyl, tetrahydrofuranyl, tetrahydropyridinyl, oxetanyl, tetrahydropyranyl, and the like. It is noted that the group encompasses heterocyclic groups having a bridge structure. In the group, a bond on the "group" cannot be from a nitrogen atom constituting a ring. That is, the group does not encompass the concept of, for example, a 1-pyrrolidino group and the like.

The aforementioned "heterocyclic group" may form a fused ring with a 6-membered aromatic hydrocarbon or a 6-membered heteroaryl. Examples thereof include a bicyclic "heterocycle" having eleven or twelve ring-constituting atoms, wherein the foregoing 5- or 6-membered "heterocyclic ring" is fused to a 6-membered aromatic hydrocarbon or a 6-membered heteroaryl. Examples of the 6-membered aromatic hydrocarbon include benzene and the like. Examples of a 6-membered unsaturated heterocyclic group include pyridine, pyrimidine, pyridazine, and the like. Specific examples of the fused ring include dihydroindolyl, dihydroisoindolyl, dihydropurinyl, dihydrothiazolopyrimidinyl, dihydrobenzodioxanyl, isoindolyl, indazolyl, pyrrolidinyl, tetrahydroquinolinyl, decahydroquinolinyl, tetrahydroisoquinolinyl, decahydroisoquinolinyl, tetrahydronaphthyridinyl, tetrahydropyridoazepinyl, and the like.

Examples of a "saturated heterocyclic group" include a 5- to 10-membered monocyclic or polycyclic group and the like. The group contains one or more (e.g., one to four) heteroatoms that are identical or different and are selected from a nitrogen atom, a sulfur atom, or an oxygen atom. Preferably, examples thereof include a 5- or 6-membered monocyclic heteroaryl group, and the like. Specific examples of a "heteroaryl group" include, for example, pyrrolyl, thienyl, benzothienyl, benzofuranyl, benzoxazolyl, benzothiazolyl, furyl, oxazolyl, thiazolyl, isoxazolyl, isothiazolyl, oxadiazolyl, benzisoxazolyl, benzisothiazolyl, imidazolyl, pyrazolyl, pyridyl, pyrazyl, pyrimidyl, pyridazyl, quinolyl, isoquinolyl, triazolyl, triazinyl, tetrazolyl, indolyl, imidazo[1,2-a]pyridyl, pyrazolo[1,5-a]pyridyl, [1,2,4]triazolo[1,5-a]pyridyl, benzimidazolyl, quinoxalyl, cinnolyl, quinazolyl, indazolyl, naphthyridyl, quinolinolyl, isoquinolinolyl, and the like.

The "heterocycle" moiety in a "heterocyclyloxy group" is defined the same as the above-described "heterocyclic group". It is preferably 4- to 7-membered, and more preferably 5- or 6-membered. Specific examples thereof include a 4-pyranyloxy group and the like.

The "heterocycle" moiety in a "heterocyclylthio group" is defined the same as the above-described "heterocyclic group". It is preferably 4- to 7-membered, and more preferably 5- or 6-membered. Specific examples thereof include a 4-pyranylthio group and the like.

The "heterocycle" moiety in a "heterocyclyloxycarbonyl group" is defined the same as the above-described "heterocyclic group". It is preferably 4- to 7-membered, and more preferably 5- or 6-membered. Specific examples thereof include a pyranyloxycarbonyl group and the like.

The "heterocycle" moiety in a "heterocyclylsulfinyl group" is defined the same as the above-described "heterocyclic group". It is preferably 4- to 7-membered, and more preferably 5- or 6-membered. Specific examples thereof include a pyranylsulfinyl group and the like.

The "heterocycle" moiety in a "heterocyclylsulfonyl group" is defined the same as the above-described "heterocyclic group". It is preferably 4- to 7-membered, and more preferably 5- or 6-membered. Specific examples thereof include a pyranylsulfonyl group and the like.

The "$C_{6-10}$ aryl" moiety in a "$C_{6-10}$ aryloxy group" is defined the same as the above-described "$C_{6-10}$ aryl group". It preferably includes a "$C_6$ aryloxy group" (phenoxy group). Specific groups thereof include, for example, phenoxy, 1-naphthoxy, 2-naphthoxy, and the like.

The "$C_{6-10}$ aryl" moiety in a "$C_{6-10}$ arylthio group" is defined the same as the above-described "$C_{6-10}$ aryl group". It includes preferably a "$C_6$ arylthio group". Specific examples thereof include, for example, phenylthio, 1-naphthylthio, 2-naphthylthio, and the like.

A "$C_{6-10}$ arylcarbonyl group" means a group having the above-described "$C_{6-10}$ aryl group" bound with a carbonyl group. The "$C_{6-10}$ aryl" moiety is defined the same as the above-described "$C_{6-10}$ aryl group". It preferably includes a "$C_6$ arylcarbonyl group" (a phenylcarbonyl group). Specific examples of the "$C_{6-10}$ arylcarbonyl group" include, for example, benzoyl, 1-naphthoyl, 2-naphthoyl, and the like.

The "$C_{6-10}$ aryl" moiety in a "$C_{6-10}$ arylsulfinyl group" is defined the same as the above-described "$C_{6-10}$ aryl group". It preferably includes a "$C_6$ arylsulfinyl group". Specific examples thereof include, for example, phenylsulfinyl, 1-naphthylsulfinyl, 2-naphthylsulfinyl, and the like.

The "$C_{6-10}$ aryl" moiety in a "$C_{6-10}$ arylsulfonyl group" is defined the same as the above-described "$C_{6-10}$ aryl group". It preferably includes a "$C_6$ arylsulfonyl group". Specific examples thereof include, for example, phenylsulfonyl, 1-naphthylsulfonyl, 2-naphthylsulfonyl, and the like.

A "$C_{6-10}$ aryloxycarbonyl group" means a group having the above-described "$C_{6-10}$ aryloxy group" bound to a carbonyl group. It preferably includes a "$C_6$ aryloxycarbonyl group" (a phenyloxycarbonyl group). Specific examples of the "$C_{6-10}$ aryloxycarbonyl group" include, for example, phenoxycarbonyl, 1-naphthoxycarbonyl, 2-naphthoxycarbonyl, and the like.

Examples of "an optionally substituted amino group" include amino, mono- or di-substituted amino.

Examples of the "mono- or di-substituted amino" include "$C_{1-6}$ alkyl", "$C_{3-10}$ cycloalkyl", "$C_{3-10}$ cycloalkyl $C_{1-4}$ alkyl", "$C_{3-7}$ cycloalkyl $C_{1-4}$ alkoxycarbonyl", "$C_{1-4}$ alkylcarbonyl", "$C_{1-4}$ alkoxycarbonyl", "a 4- to 7-membered saturated heterocycle", "4- to 7-membered saturated heterocyclyl $C_{1-4}$ alkyl", "4- to 7-membered saturated heterocyclyl carbonyl", "4- to 7-membered saturated heterocyclyloxycarbonyl", "4- to 7-membered saturated heterocyclyl $C_{1-4}$ alkylcarbonyl", "$C_{6-10}$ aryl", "$C_{7-14}$ aralkyl", "$C_{6-10}$ arylcarbonyl", "$C_{6-10}$ aryloxycarbonyl", "5- or 6-membered monocyclic heteroaryl", "5- or 6-membered monocyclic heteroaryl $C_{1-4}$ alkyl", and the like.

Specific examples of the "mono-substituted amino" include, for example, "mono-$C_{1-6}$ alkylamino" (e.g., methylamino, ethylamino, propylamino, 1-methylethylamino, butylamino, 2-methylpropylamino, 1-methylpropylamino, 1,1-dimethylethylamino, and the like);

"$C_{3-8}$ cycloalkylamino" (e.g., cyclopropylamino, cyclobutylamino, cyclopentylamino, cyclohexylamino, cycloheptylamino, and the like);

"($C_{3-8}$ cycloalkyl$C_{1-4}$ alkyl)amino" (e.g., cyclopropylmethylamino, cyclobutylmethylamino, cyclopentylmethylamino, cyclohexylmethylamino, cycloheptylmethylamino, and the like);

"($C_{3-8}$ cycloalkyl$C_{1-4}$ alkoxycarbonyl)amino" (e.g., cyclopropoxycarbonylamino, cyclobutoxycarbonylamino, cyclopentoxycarbonylamino, cyclohexyloxycarbonylamino, cycloheptyloxycarbonylamino, and the like);

"($C_{1-4}$ alkylcarbonyl)amino" (e.g., methylcarbonylamino, ethylcarbonylamino, propylcarbonylamino, 1-methylpropylcarbonylamino, 2-methylpropylcarbonylamino, butylcarbonylamino, 2,2-dimethylethylcarbonylamino, and the like);

"($C_{1-4}$ alkoxycarbonyl)amino" (e.g., methoxycarbonylamino, ethoxycarbonylamino, propoxycarbonylamino, 1-methylpropoxycarbonylamino, 2-methylpropoxycarbonylamino, butoxycarbonylamino, 2,2-dimethylethoxycarbonylamino, and the like);

"$C_{5-10}$ arylamino" (e.g., phenylamino, 1-naphthylamino, 2-naphthylamino, and the like);

"$C_{7-14}$ aralkylamino" (e.g., benzylamino, 1-naphthylmethylamino, 2-naphthylmethylamino, and the like);

"$C_{6-10}$ arylcarbonylamino" (e.g., phenylcarbonylamino, 1-naphthylcarbonylamino, 2-naphthylcarbonylamino, and the like);

"$C_{6-10}$ aryloxycarbonylamino" (e.g., phenoxycarbonylamino, 1-naphthoxycarbonylamino, 2-naphthoxycarbonylamino, and the like);

"3- to 8-membered saturated heterocyclyl-amino" (e.g., tetrahydropyranylamino, tetrahydropyridinylamino, pyrrolidinylamino, oxopyrrolidinylamino, tetrahydrofuranylamino, piperidinylamino, and the like);

"(3- to 8-membered saturated heterocyclyl $C_{1-4}$ alkyl) amino" (e.g., tetrahydropyranylmethylamino, tetrahydropyridinylmethylamino, pyrrolidinylmethylamino, oxopyrrolidinylmethylamino, tetrahydrofuranylmethylamino, piperidinylmethylamino, piperazinylmethylamino, morpholinylmethylamino, and the like);

"3- to 8-membered saturated heterocyclyl carbonylamino" (e.g., tetrahydropyranylcarbonylamino, tetrahydropyridinylcarbonylamino, pyrrolidinylcarbonylamino, oxopyrrolidinylcarbonylamino, tetrahydrofuranylcarbonylamino, piperidinylcarbonylamino, and the like);

"3- to 8-membered saturated heterocyclyloxycarbonylamino" (e.g., tetrahydropyranyloxycarbonylamino, tetrahydropyridinyloxycarbonylamino, pyrrolidinyloxycarbonylamino, oxopyrrolidinyloxycarbonylamino, tetrahydrofuranyloxycarbonylamino, piperidinyloxycarbonylamino, and the like);

"(5- or 6-membered monocyclic heteroaryl)amino" (e.g., pyrrolylamino, thienylamino, furylamino, oxazolylamino, thiazolylamino, isoxazolylamino, isothiazolylamino, imidazolylamino, pyrazolylamino, triazolylamino, oxadiazolylamino, thiadiazolylamino, tetrazolylamino, pyridylamino, pyrazylamino, pyrimidylamino, pyridazylamino, triazinylamino, and the like);

"(5- or 6-membered monocyclic heteroaryl $C_{1-4}$ alkyl) amino" (e.g., pyrrolylmethylamino, thienylmethylamino, furylmethylamino, oxazolylmethylamino, thiazolylmethylamino, isoxazolylmethylamino, isothiazolylmethylamino, imidazolylmethylamino, pyrazolylmethylamino, triazolylmethylamino, oxadiazolylmethylamino, thiadiazolylmethylamino, tetrazolylmethylamino, pyridylmethylamino, pyrazylmethylamino, pyrimidylmethylamino, pyridazylmethylamino, triazinylmethylamino, and the like); and the like.

Specific examples of the "di-substituted amino" include, for example,

"di-$C_{1-6}$ alkylamino" (e.g., dimethylamino, diethylamino, dipropylamino, di-1-methylethylamino, dibutylamino, di-2-methylpropylamino, di-1-methylpropylamino, di-1,1-dimethylethylamino, and the like);

"N—($C_{1-6}$ alkyl)-N—($C_{3-10}$ cycloalkyl)amino" (e.g., methylcyclopropylamino, methylcyclobutylamino, methylcyclopentylamino, methylcyclohexylamino, methylcycloheptylamino, and the like);

"N—($C_{1-6}$ alkyl)-N-(4- to 7-membered saturated heterocyclyl)amino" (e.g., methyltetrahydropyranylamino, methyltetrahydropyridinylamino, methylpyrrolidinylamino, methyloxopyrrolidinylamino, methyltetrahydrofuranylamino, methylpiperidinylamino, and the like); and the like.

Examples of the "3- to 8-membered cyclic amino" include 3- to 8-membered monocyclic cyclic amino having one to three heteroatoms that are identical or different and are selected from a nitrogen atom, an oxygen atom, or a sulfur atom. It is preferably a 5- to 6-membered monocyclic cyclic amino group. In the "3- to 8-membered cyclic amino", a bond on the "group" will be from a nitrogen atom constituting a ring. Specific examples of the "3- to 8-membered cyclic amino" include, for example, azetidino, pyrrolidino, imidazolidino, oxazolidino, thiazolidino, piperazino, piperidino, morpholino, thiomorpholino, azepano, oxoazepano, and the like. It is noted that the group encompasses cyclic amino of which the ring contains a partially unsaturated bond.

The "3- to 8-membered cyclic amino" or "5- or 6-membered cyclic amino" may form a fused ring with $C_{3-6}$ cycloalkyl, 6-membered aromatic hydrocarbon, or a 5- or 6-membered heterocycle. Specific examples of cyclic amino forming such a fused ring include "groups" represented by the following:

[Chemical formula 19]

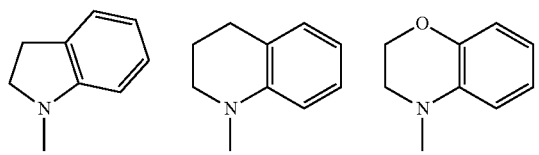

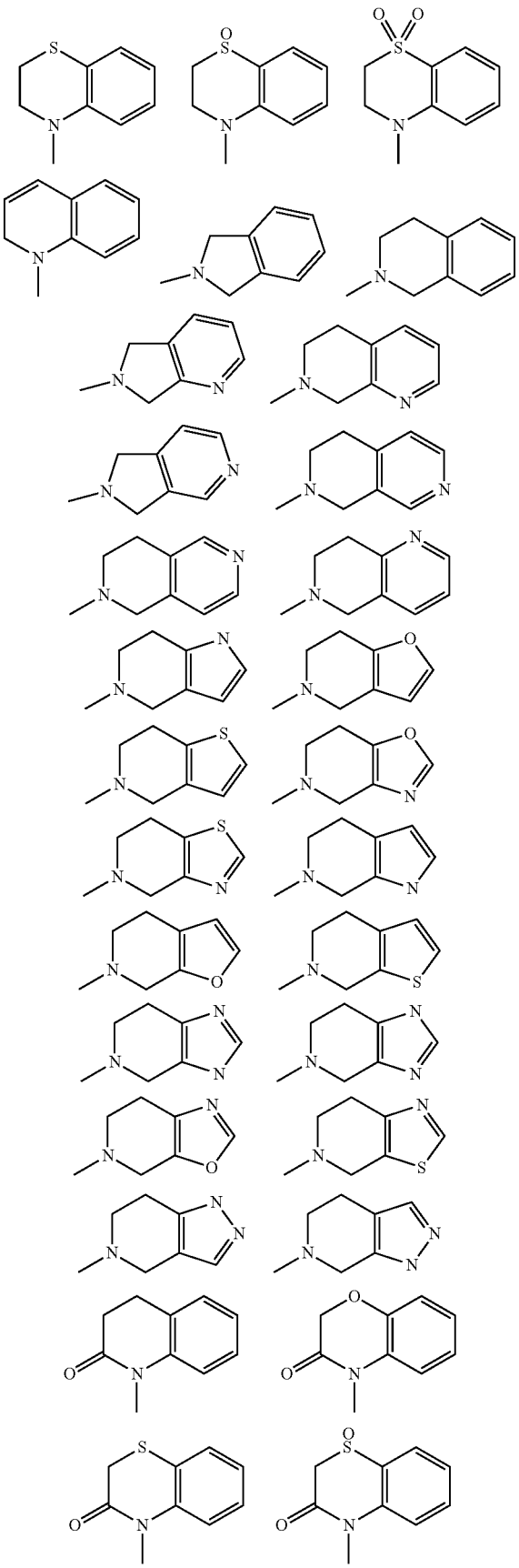

-continued

-continued

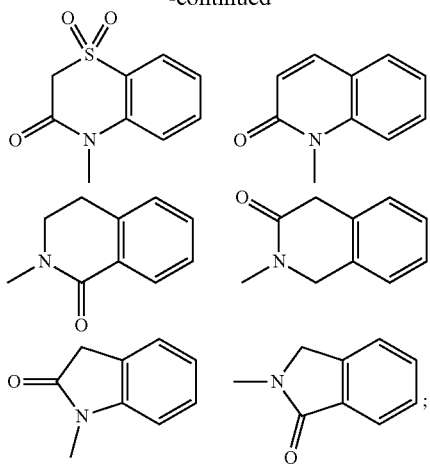

and the like.

An "aminocarbonyl group" means a group having the above-described "amino group" bound to a carbonyl group. In this regard, the "amino" means an unsubstituted amino group, a mono-substituted amino group, a di-substituted amino group, or 3- to 8-membered cyclic amino.

An "aminosulfinyl group" means a group having the above-described "amino group" bound to a sulfinyl group. In this regard, the "amino" means an unsubstituted amino group, a mono-substituted amino group, a di-substituted amino group, or 3- to 8-membered cyclic amino.

An "aminosulfonyl group" means a group having the above-described "amino group" bound to a carbonyl group. In this regard, the "amino" is an unsubstituted amino group, a mono-substituted amino group, a di-substituted amino group, or 3- to 8-membered cyclic amino.

The "aminocarbonyl" moiety in an "aminocarbonyloxy group" is defined the same as the above-described "aminocarbonyl group".

A "$C_{1-6}$ alkylaminocarbonyl group" means a group that is the above-described "mono- or di-substituted amino" in which the amino group substituted with one or two $C_{1-6}$ alkyl is bound to a carbonyl group.

The "$C_{1-6}$ alkylaminocarbonyl" moiety of a "$C_{1-6}$ alkylaminocarbonylamino group" is defined the same as the above-described "$C_{1-6}$ alkylaminocarbonyl group".

Examples of a substituent of "an optionally substituted $C_{1-6}$ alkyl group" include:
(a) a halogen atom;
(b) a cyano group;
(c) a hydroxy group;
(d) a formyl group;
(e) a $C_{1-6}$ alkylcarbonyl group;
(f) a $C_{1-6}$ alkylcarbonyloxy group;
(g) a carboxy group;
(h) amino (wherein the amino is optionally substituted with one or two groups that are identical or different and are selected from the group consisting of
(h1) $C_{1-6}$ alkyl (wherein the alkyl is optionally substituted with
(h11) hydroxy,
(h12) cyano,
(h13) a halogen atom,
(h14) amino (wherein the amino is optionally substituted with one or two $C_{1-6}$ alkyl groups or $C_{1-6}$ alkylcarbonyl groups that are identical or different),
(h15) $C_{1-6}$ alkoxy,
(h16) 5- or 6-membered monocyclic heteroaryl,
(h17) a 4- to 7-membered saturated heterocycle, or
(h18) a $C_{3-10}$ cycloalkylcarbonyl)
(h2) $C_{3-10}$ cycloalkyl (wherein the ring is optionally substituted with $C_{1-6}$ alkyl),
(h3) $C_{3-10}$ cycloalkyl $C_{1-4}$ alkyl,
(h4) a 4- to 7-membered saturated heterocycle (wherein the ring is optionally substituted with a halogen atom or $C_{1-6}$ alkyl),
(h5) a 4- to 7-membered saturated heterocyclyl-$C_{1-4}$ alkyl,
(h6) $C_{6-10}$ aryl (wherein the ring is optionally substituted with a halogen atom or $C_{1-6}$ alkyl),
(h7) $C_{7-14}$ aralkyl (wherein the ring is optionally substituted with a halogen atom, $C_{1-6}$ alkyl, or $C_{1-6}$ alkoxy),
(h8) a 5- or 6-membered monocyclic heteroaryl (wherein the ring is optionally substituted with a halogen atom or $C_{1-6}$ alkyl), and
(h9) 5- or 6-membered monocyclic heteroaryl $C_{1-4}$ alkyl);
(i) $C_{1-6}$ alkoxy (wherein the group is optionally substituted with
(i1) hydroxy,
(i2) $C_{1-6}$ alkoxy (wherein the group is optionally substituted with one to three fluorine atoms),
(i3) $C_{3-10}$ cycloalkyl,
(i4) 4- to 7-membered cyclic amino (wherein the group is optionally substituted with
(i41) hydroxy,
(i42) cyano,
(i43) one to four fluorine atoms,
(i44) $C_{1-6}$ alkyl (wherein the alkyl is optionally substituted with one to three fluorine atoms or $C_{1-6}$ alkoxy)
(i45) $C_{1-6}$ alkoxy (wherein the alkoxy is optionally substituted with one to three $C_{6-10}$ aryl),
(i46) formyl,
(i47) $C_{1-6}$ alkylcarbonyl,
(i48) $C_{1-6}$ alkylsulfonyl, or
(i49) oxo),
(i5) a 4- to 7-membered saturated heterocycle (wherein the heterocycle is optionally substituted with a group selected from the above-described (i41)-(i49)),
(i6) 5- or 6-membered monocyclic heteroaryl (wherein the ring is optionally substituted with a halogen atom or $C_{1-6}$ alkyl),
(i7) $C_{6-10}$ aryl (wherein the group is optionally substituted with a halogen atom, $C_{1-4}$ alkyl, or $C_{1-4}$ alkoxy),
(i8) $C_{1-6}$ alkylcarbonylamino,
(i9) amino (wherein the amino is optionally substituted with one or two groups that are identical or different and are selected from the group consisting of $C_{1-6}$ alkyl (wherein the group is optionally substituted with hydroxy), $C_{3-10}$ cycloalkyl, and $C_{3-10}$ cycloalkyl $C_{1-4}$ alkyl),
(i10) mono- or di-$C_{1-6}$ alkylaminocarbonyl,
(i11) a halogen atom, or
(i12) $C_{7-14}$ aralkyloxy);
(j) a $C_{3-10}$ cycloalkyloxy group (wherein the ring is optionally substituted with $C_{1-6}$ alkyl);
(k) an oxo group;
(l) 5- or 6-membered monocyclic heteroaryl group (wherein the group is optionally substituted with a halogen atom or $C_{1-6}$ alkyl);
(m) a 4- to 7-membered saturated heterocycle (wherein the heterocycle is optionally substituted with a group selected from the above-described (i41)-(i49));
(n) an optionally substituted aminocarbonyl group;
(o) an optionally substituted aminosulfonyl group;
(p) an optionally substituted aminocarbonyloxy group;
(q) a $C_{7-14}$ aralkyloxy group;

(r) a 5- or 6-membered monocyclic heteroaryloxy group (wherein the ring is optionally substituted with a halogen atom or $C_{1-6}$ alkyl);
(s) a 4- to 7-membered saturated heterocyclyloxy group (wherein the ring is optionally substituted with $C_{1-6}$ alkyl optionally substituted with one to three halogen atoms);
(t) a $C_{1-6}$ alkylsulfonyl group;
(u) a $C_{1-6}$ alkoxycarbonyl group;
(v) a $C_{1-6}$ alkylsulfonyloxy group;
(w) a $C_{1-6}$ alkoxycarbonylamino group;
(x) a $C_{1-6}$ alkylcarbonylamino group (wherein the group is optionally substituted with
(x1) hydroxy,
(x2) a halogen atom,
(x3) $C_{1-6}$ alkoxy, or
(x4) $C_{1-6}$ alkylcarbonyloxy);
(y) a 5- or 6-membered monocyclic heteroarylcarbonylamino group (wherein the group is optionally substituted with $C_{1-6}$ alkyl);
(z) a 4- to 7-membered saturated heterocyclylcarbonylamino group (wherein the group is optionally substituted with $C_{1-6}$ alkyl optionally substituted with one to three fluorine atoms);
(aa) a mono- or di-$C_{1-6}$ alkylaminocarbonylamino group;
(ab) a 4- to 7-membered cyclic amino group (wherein the ring is optionally substituted with a group selected from the above-described (i41)-(i49)); and the like.

Examples of a substituent of "an optionally substituted $C_{1-6}$ alkenyl group", "an optionally substituted $C_{1-6}$ alkynyl group", "an optionally substituted $C_{1-6}$ alkoxy group", "an optionally substituted $C_{1-6}$ alkylcarbonyl group", "an optionally substituted $C_{1-6}$ alkylcarbonyloxy group", "an optionally substituted $C_{1-6}$ alkylcarbonylamino group", "an optionally substituted $C_{1-6}$ alkylthio group", "an optionally substituted $C_{1-6}$ alkylsulfinyl group", "an optionally substituted $C_{1-6}$ alkylsulfonyl group", "an optionally substituted $C_{1-6}$ alkoxycarbonyl group", "an optionally substituted $C_{1-6}$ alkylamino group", "an optionally substituted $C_{1-6}$ alkylaminocarbonyl group", "an optionally substituted $C_{1-6}$ alkylaminocarbonylamino group", and "an optionally substituted $C_{1-6}$ alkylaminocarbonylamino group" include: one group selected from the group consisting of the above-described (a) to (ab), which are examples of a substituent of the "optionally substituted $C_{1-6}$ alkyl group"; and the like.

Examples of a substituent of "an optionally substituted $C_{3-10}$ cycloalkyl group", "an optionally substituted $C_{3-10}$ cycloalkyloxy group", "an optionally substituted $C_{3-10}$ cycloalkylthio group", "an optionally substituted $C_{3-10}$ cycloalkylsulfinyl group", "an optionally substituted $C_{3-10}$ cycloalkylsulfonyl group", "an optionally substituted $C_{3-10}$ cycloalkyloxycarbonyl group", "an optionally substituted 3- to 8-membered heterocyclic group", "an optionally substituted 3- to 8-membered heterocyclyloxy group", "an optionally substituted 3- to 8-membered heterocyclyloxycarbonyl group", "an optionally substituted 3- to 8-membered heterocyclylsulfinyl group", "an optionally substituted 3- to 8-membered heterocyclylsulfonyl group", "3- to 8-membered cyclic amino group", "3- to 8-membered cyclic aminocarbonyl group", "3- to 8-membered cyclic aminosulfinyl group", and "3- to 8-membered cyclic aminosulfonyl group" include: one group selected from the group consisting of the above-described (a) to (ab), which are examples of a substituent of the "optionally substituted $C_{1-6}$ alkyl group", and $C_{1-4}$ alkyl; and the like. It is noted that a ring of the substituent (e.g., cycloalkyl, cyclic amino, and the like) is optionally substituted with oxo or thioxo.

Examples of a substituent of "an optionally substituted $C_{6-10}$ aryl group", "an optionally substituted $C_{6-10}$ aryloxy group", "an optionally substituted $C_{6-10}$ arylcarbonyl group", "an optionally substituted $C_{6-10}$ aryloxycarbonyl group", "an optionally substituted $C_{6-10}$ arylthio group", "an optionally substituted $C_{6-10}$ arylsulfinyl group", "an optionally substituted $C_{6-10}$ arylsulfonyl group", "an optionally substituted 5- or 6-membered monocyclic heteroaryl group", "an optionally substituted 5- or 6-membered monocyclic heteroaryloxy group", "an optionally substituted 5- or 6-membered monocyclic heteroarylcarbonyl group", "an optionally substituted 5- or 6-membered monocyclic heteroaryloxycarbonyl group", "an optionally substituted 5- or 6-membered monocyclic heteroarylthio group", "an optionally substituted 5- or 6-membered monocyclic heteroarylsulfinyl group", and "an optionally substituted 5- or 6-membered monocyclic heteroarylsulfonyl group" include:
(a2) a halogen atom;
(b2) a cyano group;
(c2) an optionally substituted $C_{1-6}$ alkyl group;
(d2) $C_{1-6}$ alkylsulfonyl group (wherein the group is optionally substituted with
(d21) a halogen atom,
(d22) hydroxy,
(d23) $C_{1-6}$ alkoxy,
(d24) $C_{3-10}$ cycloalkyl,
(d25) $C_{3-10}$ cycloalkyloxy,
(d26) di-$C_{1-6}$ alkylamino,
(d27) 4- to 7-membered cyclic amino, or
(d28) 4- to 7-membered saturated heterocycle);
(e2) an amino group (wherein the amino is optionally substituted with one or two groups that are identical or different and are selected from the group consisting of the above-described (h1) to (h9));
(f2) an aminosulfonyl group (wherein the amino is optionally substituted with one or two $C_{1-6}$ alkyl groups that are identical or different (wherein the alkyl is optionally substituted with a halogen atom, hydroxy, $C_{1-4}$ alkoxy, or di-$C_{1-6}$ alkylamino));
(g2) a 4- to 7-membered cyclic amino group (wherein the ring is optionally substituted with the above-described (i1) to (i12));
(h2) an aminocarbonyl group (wherein the amino group is optionally substituted with one or two groups that are identical or different and are selected from the group consisting of the (h1) to (h9));
(i2) a 4- to 7-membered saturated heterocycle (wherein the ring is optionally substituted with a group selected from the group consisting of the above-described (i1) to (i12));
(j2) a carboxy group;
(k2) a $C_{1-6}$ alkoxy group (wherein the group is optionally substituted with a group selected from the group consisting of the above-described (i1) to (i12));
(l2) $C_{3-10}$ cycloalkyloxy group;
(m2) a 4- to 7-membered saturated heterocyclyloxy group (wherein the ring is optionally substituted with a group selected from the group consisting of the above-described (i1) to (i12));
(n2) a $C_{7-14}$ aralkyloxy group;
(o2) a $C_{1-6}$ alkoxycarbonyl group (wherein the group is optionally substituted with a group selected from the group consisting of the above-described (i1) to (i12));
(p2) a $C_{1-6}$ alkylcarbonylamino group (wherein the amino is optionally substituted with $C_{1-6}$ alkyl, and the alkyl is optionally substituted with a group selected from the group consisting of the above-described (d21) to (d28);

(q2) a $C_{3-10}$ cycloalkylcarbonylamino group (wherein the amino is optionally substituted with $C_{1-6}$ alkyl);
(r2) a 5- or 6-membered monocyclic heteroarylcarbonylamino group (wherein the amino is optionally substituted with $C_{1-6}$ alkyl);
(s2) a 4- to 7-membered saturated heterocyclylcarbonylamino group (wherein the amino is optionally substituted with $C_{1-6}$ alkyl, and the ring is optionally substituted with a group selected from the group consisting of the above-described (i1) to (i12));
(t2) a mono- or di-$C_{1-6}$ alkylaminocarbonylamino group (wherein the amino is optionally substituted with $C_{1-6}$ alkyl);
(u2) $C_{1-6}$ alkoxycarbonylamino group (wherein the amino is optionally substituted with $C_{1-6}$ alkyl, and the alkoxy is optionally substituted with a group selected from the group consisting of the above-described (i1) to (i12));
(v2) a $C_{6-10}$ aryl group;
(w2) a 5- or 6-membered monocyclic heteroaryl group; and the like.

Preferred embodiments of the present invention are further described.

In the present specification, formula (1) is an isomer having a relationship with the following formula (1') between an oxidant and a reductant that can attain equilibrium. They can be considered as being synonymous.

[Chemical formula 20]

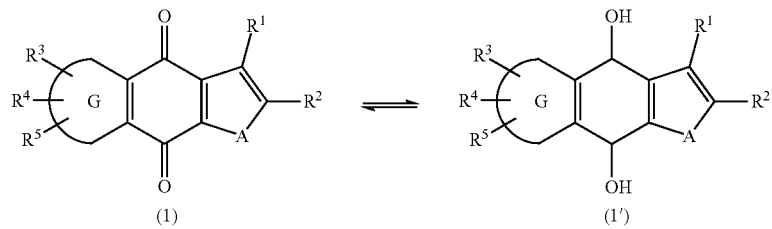

It is preferable that "A" is an oxygen atom or a sulfur atom.

It is preferable that "ring G" is the following formulas (a) to (h):

[Chemical formula 21]

(a)
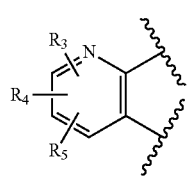

(b)
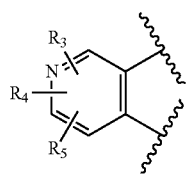

(c)
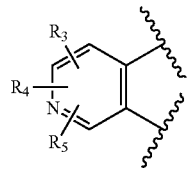

(d)
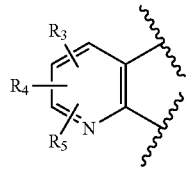

(e)
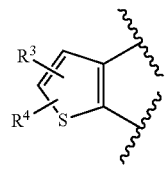

-continued (f)
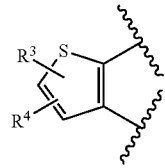

(g)
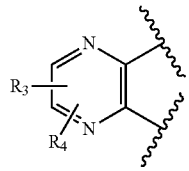

(h)
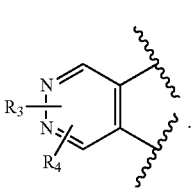

It is more preferable that "ring G" is the following formulas (a) to (f):

[Chemical formula 22]

(a)
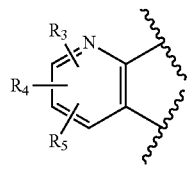

(b)
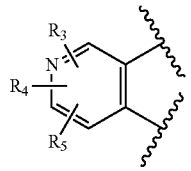

(c)
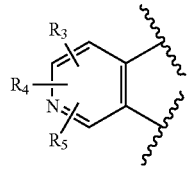

(d)
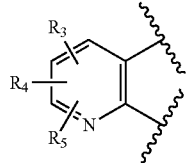

(e)
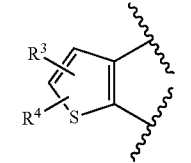

(f)
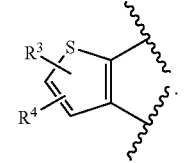

It is further preferable that "ring G" is the following formulas (a) to (d):

[Chemical formula 23]

(a)
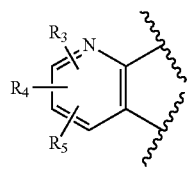

-continued (b)
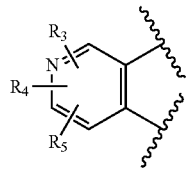

(c)
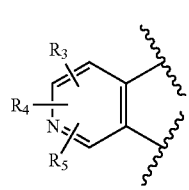

(d)
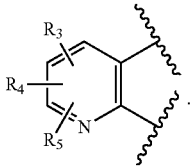

It is further preferable that "ring G" is the following formula (e) or (f):

[Chemical formula 24]

(e)
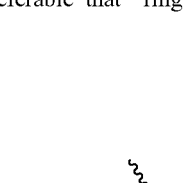

(f)
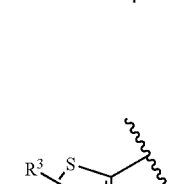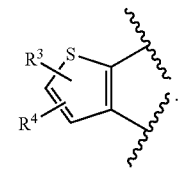

It is preferable that "$R^1$" is a hydrogen atom or a $C_{1-6}$ alkylcarbonyl group (wherein the alkyl is optionally substituted with 3- to 8-membered cyclic amino).

It is preferable that "$R^2$" is a hydrogen atom.

It is preferable that all of "$R^3$", "$R^4$", and "$R^5$" are hydrogen atoms.

It is preferable that "$R^6$" is a hydrogen atom.

Preferred embodiments of the present invention encompass compounds represented by the following formulas (1a) to (1p).

(1) A compound represented by the following formula (1a) or a pharmacologically acceptable salt thereof:

[Chemical formula 25]

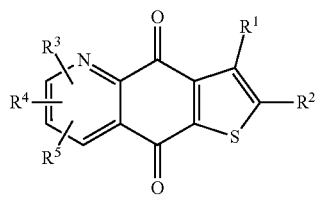

(1a)

[each symbol in the formula is defined the same as item 1]. Preferred embodiments of respective symbols in the compound represented by the above formula (1a) are the same as the preferred embodiments in the compound represented by formula (1)

(2) A compound represented by the following formula (1b) or a pharmacologically acceptable salt thereof:

[Chemical formula 26]

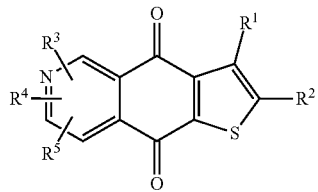

(1b)

[each symbol in the formula is defined the same as item 1]. Preferred embodiments of respective symbols in the compound represented by the above formula (1b) are the same as the preferred embodiments in the compound represented by formula (1).

(3) A compound represented by the following formula (1c) or a pharmacologically acceptable salt thereof:

[Chemical formula 27]

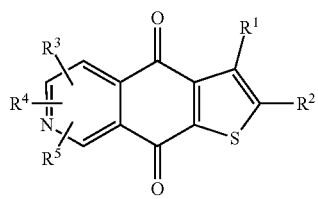

(1c)

[each symbol in the formula is defined the same as item 1]. Preferred embodiments of respective symbols in the compound represented by the above formula (1c) are the same as the preferred embodiments in the compound represented by formula (1).

(4) A compound represented by the following formula (1d) or a pharmacologically acceptable salt thereof:

[Chemical formula 28]

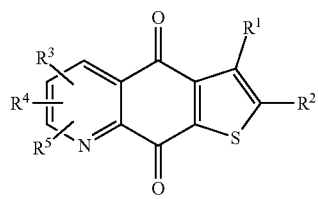

(1d)

[each symbol in the formula is defined the same as item 1]. Preferred embodiments of respective symbols in the compound represented by the above formula (1d) are the same as the preferred embodiments in the compound represented by formula (1).

(5) A compound represented by the following formula (1e) or a pharmacologically acceptable salt thereof:

[Chemical formula 29]

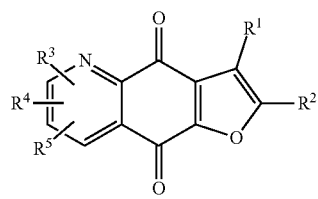

(1e)

[each symbol in the formula is defined the same as item 1]. Preferred embodiments of respective symbols in the compound represented by the above formula (1e) are the same as the preferred embodiments in the compound represented by formula (1).

(6) A compound represented by the following formula (1f) or a pharmacologically acceptable salt thereof:

[Chemical formula 30]

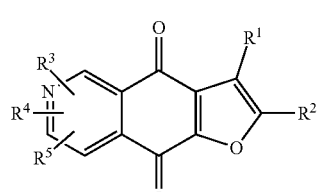

(1f)

[each symbol in the formula is defined the same as item 1]. Preferred embodiments of respective symbols in the compound represented by the above formula (1f) are the same as the preferred embodiments in the compound represented by formula (1).

(7) A compound represented by the following formula (1g) or a pharmacologically acceptable salt thereof:

[Chemical formula 31]

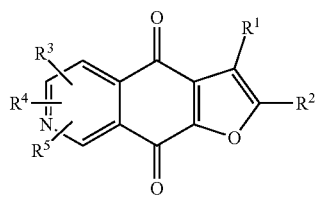

(1g)

[each symbol in the formula is defined the same as item 1]. Preferred embodiments of respective symbols in the compound represented by the above formula (1g) are the same as the preferred embodiments in the compound represented by formula (1).

(8) A compound represented by the following formula (1h) or a pharmacologically acceptable salt thereof:

[Chemical formula 32]

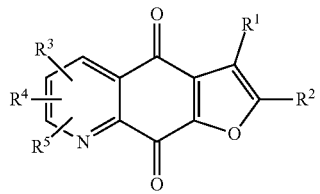

(1h)

[each symbol in the formula is defined the same as item 1]. Preferred embodiments of respective symbols in the compound represented by the above formula (1h) are the same as the preferred embodiments in the compound represented by formula (1).

(9) A compound represented by the following formula (1i) or a pharmacologically acceptable salt thereof:

[Chemical formula 33]

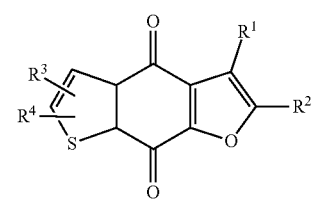

(1i)

[each symbol in the formula is defined the same as item 1]. Preferred embodiments of respective symbols in the compound represented by the above formula (1i) are the same as the preferred embodiments in the compound represented by formula (1).

(10) A compound represented by the following formula (1j) or a pharmacologically acceptable salt thereof:

[Chemical formula 34]

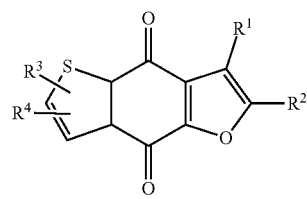

(1j)

[each symbol in the formula is defined the same as item 1]. Preferred embodiments of respective symbols in the compound represented by the above formula (1j) are the same as the preferred embodiments in the compound represented by formula (1).

(11) A compound represented by the following formula (1k) or a pharmacologically acceptable salt thereof:

[Chemical formula 35]

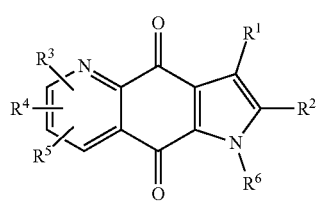

(1k)

[each symbol in the formula is defined the same as item 1]. Preferred embodiments of respective symbols in the compound represented by the above formula (1k) are the same as the preferred embodiments in the compound represented by formula (1).

(12) A compound represented by the following formula (1l) or a pharmacologically acceptable salt thereof:

[Chemical formula 36]

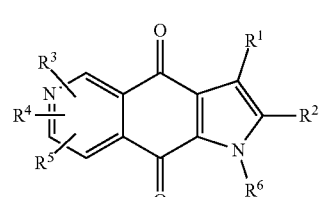

(1l)

[each symbol in the formula is defined the same as item 1]. Preferred embodiments of respective symbols in the compound represented by the above formula (1l) are the same as the preferred embodiments in the compound represented by formula (1).

(13) A compound represented by the following formula (1m) or a pharmacologically acceptable salt thereof:

[Chemical formula 37]

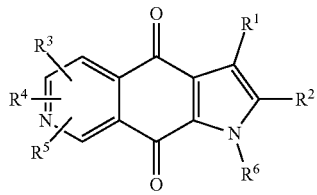

(1m)

[each symbol in the formula is defined the same as item 1]. Preferred embodiments of respective symbols in the compound represented by the above formula (1m) are the same as the preferred embodiments in the compound represented by formula (1).

(14) A compound represented by the following formula (1n) or a pharmacologically acceptable salt thereof:

[Chemical formula 38]

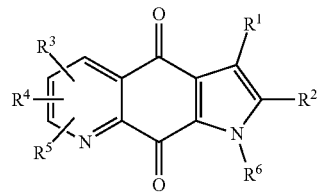

(1n)

[each symbol in the formula is defined the same as item 1]. Preferred embodiments of respective symbols in the compound represented by the above formula (1n) are the same as the preferred embodiments in the compound represented by formula (1).

(15) A compound represented by the following formula (1o) or a pharmacologically acceptable salt thereof:

[Chemical formula 39]

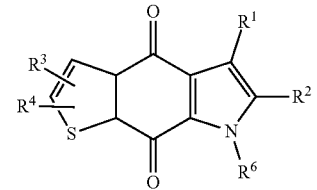

(1o)

[each symbol in the formula is defined the same as item 1]. Preferred embodiments of respective symbols in the compound represented by the above formula (1o) are the same as the preferred embodiments in the compound represented by formula (1).

(16) A compound represented by the following formula (1p) or a pharmacologically acceptable salt thereof:

[Chemical formula 40]

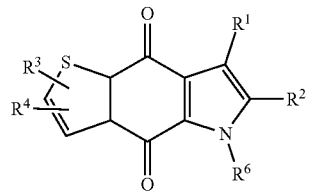

(1p)

[each symbol in the formula is defined the same as item 1]. Preferred embodiments of respective symbols in the compound represented by the above formula (1p) are the same as the preferred embodiments in the compound represented by formula (1).

A "pharmacologically acceptable salt" includes acid addition salts and base addition salts. Examples of acid addition salts include: inorganic acid salts such as hydrochlorides, hydrobromides, sulfates, hydroiodides, nitrates, phosphates, and the like; and organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate, camphorsulfonate, and the like; and examples of base addition salts include inorganic base salts such as sodium, potassium, calcium, magnesium, barium, and aluminum salts, and the like, organic base salts such as trimethylamine, triethylamine, pyridine, picoline, 2,6-lutidine, ethanolamine, diethanolamine, triethanolamine, tromethamine [tris(hydroxymethyl)methylamine], t-butylamine, cyclohexylamine, dicyclohexylamine, and N,N-dibenzylethylamine, and the like, and further salts of an amino acid such as basic and acidic amino acids including arginine, lysine, ornithine, aspartic acid, glutamic acid, and the like.

Suitable salts and pharmaceutically acceptable salts of starting compounds and target compounds are conventional nontoxic salts. They include acid addition salts such as organic acid salts (e.g., acetate, trifluoroacetate, maleate, fumarate, citrate, tartrate, methanesulfonate, benzenesulfonate, formate, p-toluenesulfonate, or the like) and inorganic acid salts (e.g., hydrochloride, hydrobromide, hydroiodide, sulfate, nitrate, phosphate, or the like), salts with an amino acid (e.g., arginine, aspartic acid, glutamic acid, or the like), metal salts such as alkali metal salts (e.g., sodium salt, potassium salt, or the like), alkali earth metal salts (e.g., calcium salt, magnesium salt, or the like), and the like, ammonium salts, organic base salts (e.g., trimethylamine salts, triethylamine salts, pyridine salts, picoline salts, dicyclohexylamine salts, N,N'-dibenzylethylene diamine salts, or the like), or the like, and additionally those skilled in the art can appropriately select them.

When it is desired to obtain a salt of the present compound, if the present compound is obtained in a salt form, it may be purified as it is, or if it is obtained in free form, it may be dissolved or suspended in a suitable organic solvent, and an acid or a base is added thereto to form a salt in accordance with a general method.

In addition, although the present compounds and pharmacologically acceptable salts thereof may exist in an adduct form with water or any kind of solvent, these adducts are also encompassed by the present invention.

In addition, the present invention encompasses compounds represented by formula (1) or prodrugs thereof, or pharmacologically acceptable salts thereof. It also encompasses hydrates or solvates (such as ethanol solvates and the like) thereof. Further, the present invention encompasses all tautomers and all present stereoisomers of the present compound (1) as well as those in all modes of crystal forms.

The term "a prodrug of a compound of formula (1)" in the present specification means a compound that is converted to a compound of formula (1) by reaction with an enzyme, gastric acid, or the like under physiological condition in vivo, for example, a compound that is converted to a compound of formula (1) by enzymatic oxidation, reduction, hydrolysis, or the like.

Among the present compounds (1), there are compounds that may exist as enantiomers based on an optically-active center, atropisomers based on axial or planar chirality caused by restriction of intramolecular rotation, other stereoisomers, tautomers, geometric isomer, and the like. However, all possible isomers and mixtures thereof, including these, are encompassed within the scope of the present invention.

In particular, an enantiomer and an atropisomer can be obtained as a racemic body, or an optically-active substance when an optically-active starting material or intermediate is used, respectively. If necessary, in an appropriate step of the above-described production method, a corresponding starting material, intermediate, or racemic body as a final product can be physically or chemically resolved into their optical enantiomers by a known separation method, such as a method using an optically active column, a fractional crystallization method, or the like. Specifically, for example, in a diastereomer method, two types of diastereomers are formed from a racemic body by reaction using an optical active resolving agent. Since these different diastereomers generally have different physical properties, they can be separated by a known method such as fractional crystallization and the like.

Hereinafter, production methods of compounds represented by formula (1) in the present invention are described. Compounds represented by formula (1) or pharmacologically acceptable salts thereof (hereinafter sometimes referred to as "the present compound(s)") are described with examples. However, the scope of present invention is certainly not limited to these examples.

A compound of the present invention represented by formula (1) or a salt thereof can be produced from a known compound, for example, the following production methods: Methods 1 to 14, and methods in accordance therewith, or by appropriately combining synthesis methods well-known to those skilled in the art.

It is noted that a compound in a reaction includes the case where it forms a salt, for example, salts similar to salts in compound (1) and the like are used as such a salt.

In addition, a compound obtained in each step can be used in a next reaction as a reaction solution or as a composition. However, it can be isolated from a reaction mixture in accordance with a routine method, and readily purified by a separation means such as recrystallization, distillation, chromatography, and the like.

Each symbol of compounds in the following reactions is defined the same as above, unless specifically indicated.

Production Method 1:

[Chemical formula 41]

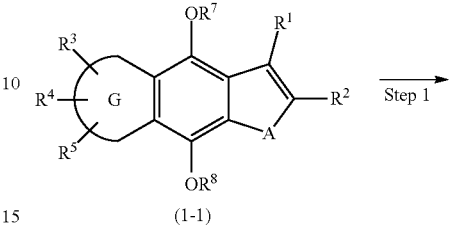

(1-1)

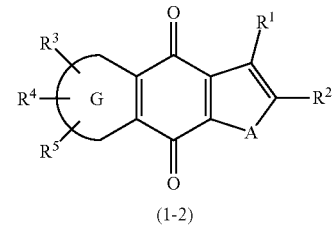

(1-2)

(In the formulas, A, $R^1$, $R^2$, $R^3$, $R^4$, $R^5$, $R^7$, $R^8$, and G are defined the same as the above-described item 21.)

To this step 1, a method described in literature [for example, European Journal of Organic Chemistry, 3876, vol. 20, (2010), Tetrahedron, 4213, vol. 57, (2001), Journal of Medicinal Chemistry, 7273, vol. 55, (2012, ACS Applied Materials & Interfaces, 3994, vol. 4, (2012), and the like] is applied, and Compound (1-2) can be produced from Compound (1-1).

It is noted that in the present invention, this method is applied to compound (1-1) where ring G is a saturated heterocycle, and however, until now, there has been no report that this method has been applied to the production of the heterocyclic compound (1-2).

Compound (1-2) can be produced by reacting it, in solvent in the presence of an oxidant, with (1-1) obtained by a known synthesis method or the following production method. Organic solvent includes aprotic solvent (N,N-dimethylformamide, N-methyl-2-pyrrolidone, dimethyl sulfoxide, acetonitrile, propionitrile, and the like), ether type solvent (tetrahydrofuran, 1,4-dioxane, and the like), halogenated hydrocarbons (dichloromethane, chloroform, 1,2-dichloroethane, chlorobenzene, and the like), hydrocarbons (toluene, benzene, and the like), water, mixed solvents thereof, and the like, and suitably a mixed solvent of acetonitrile and water. The following can be used as oxidants: metal type oxidants [osmium tetraoxide, potassium permanganate, silver(II) picolinate, ammonium hexanitratocerate(IV), benzeneseleninic acid, bis(4-methoxyphenyl) selenoxide, bis(tetrabutylammonium) dichromate, lead tetraacetate, phosphomolybdic acid hydrate, pyridinium chlorochromate, pyridinium dichromate, pyridinium fluorochromate, quinolinium dichromate, silver(II) pyridine-2-carboxylate, tetrapropylammonium perruthenate, and the like], hypervalent iodine oxidants [(2-iodoxybenzoic acid, Dess-Martin periodinane, 1-(tert-butylperoxy)-1,2-benziodoxol-3-(1H)-one, bis(pyridine)iodonium tetrafluoroborate, iodosobenzene, iodomesitylene diacetate, {hydroxy(tosyloxy)iodo}benzene, poly{4-(diacetoxyiodo)styrene}, (diacetoxyiodo)benzene, bis(trifluoroacetoxy)iodobenzene, {bis(trifluoroacetoxy)iodo}pentafluorobenzene, and the like], N-chlorosuccinimide, N-bromosuccinimide, N-iodosuccinimide, and the like, and suitably, ammonium hexanitratocerate(IV), (diacetoxyiodo)benzene, N-bromosuccinimide, and the like. The amount of an oxidant used is, generally, 2 to 10 mol, preferably, 2 to 3 mol per mol of compound (1-1). A reaction time is, generally, about 0.5 to about 48 hours, preferably, about 0.5 to about 12 hours. A reaction temperature is, generally, about −20 to about 180° C., preferably, about 0 to about 100° C.

Production Method 2:

[Chemical formula 42]

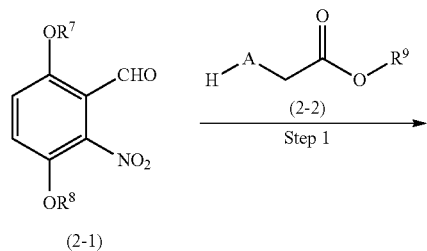

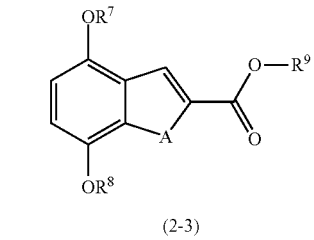

(In the formulas, A, $R^7$, and $R^8$ are defined the same as above. $R^9$ is $C_{1-6}$ alkyl.)

This step 1 can produce compound (2-3) from compound (2-1) in accordance with a similar method to methods and the like described in literature [for example, Heterocycles, 1913, vol. 75, (2008), Journal of Medicinal Chemistry, 1819, vol. 53, (2010), Journal of the Chilean Chemical Society, 14, vol. 54, (2009), Molecules, 1388, vol. 17, (2012), Bioorganic & Medicinal Chemistry Letters, 4961, vol. 15, (2005), Synlett, 670, vol. 5, (2001), and the like].

A solvent used in this step 1 may be any solvent as long as it is inactive in the reaction, and although it is not particularly limited, for example, THF, 1,4-dioxane, DME, benzene, toluene, xylene, DMF, DMA, NMP, and the like can be used alone or after mixing them. Among others, THF or DMF is preferred.

As a base, for example, basic salts such as sodium carbonate, potassium carbonate, cesium carbonate, sodium acetate, sodium hydride, calcium hydride, and the like, aromatic amines such as pyridine, lutidine, and the like, tertiary amines such as triethylamine, tripropylamine, tributylamine, cyclohexyldimethylamine, 4-dimethylaminopyridine, N,N-diisopropylethylamine, N,N-dimethylaniline, N-methylpiperidine, N-methylpyrrolidine, N-methylmorpholine, and the like can be used. Among others, potassium carbonate or sodium hydride is preferred.

A reaction is performed from at a temperature between room temperature and the boiling point of a solvent used, preferably, 0 to 80° C., generally, for 0.5 to 24 hours.

Production Method 3:

[Chemical formula 43]

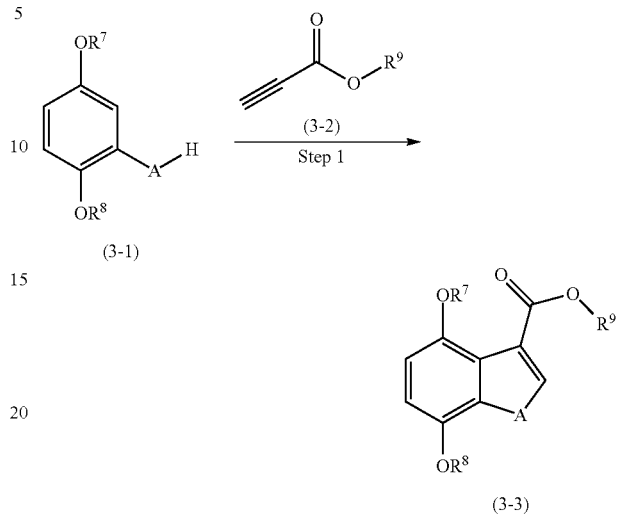

(In the formulas, A, $R^7$, $R^8$, and $R^9$ are defined the same as above.)

This step 1 can produce compound (3-3) from compound (3-1) in accordance with a similar method to methods and the like described in literature [for example, Tetrahedron, 12227, vol. 55, (1999), Journal of Organic Chemistry, 4692, vol. 76, (2011), Journal of Heterocyclic Chemistry, 683, vol. 49, (2012), and the like].

Production Method 4:

[Chemical formula 44]

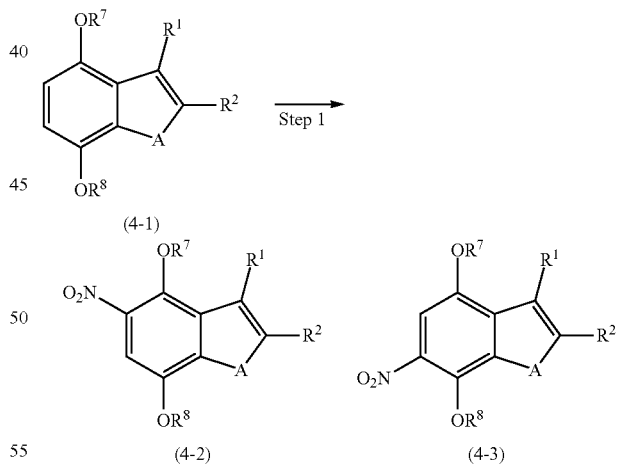

(In the formulas, $R^1$, $R^2$, $R^7$, $R^8$, and A are defined the same as above.)

This step 1 can produce compound (4-2) and compound (4-3) from compound (4-1) in accordance with a similar method to methods and the like described in literature [for example, Organic Letters, 2157, vol. 7, (2005), Journal of Medicinal Chemistry, 7574, vol. 56, (2013), Bioorganic & Medicinal Chemistry Letters, 138, vol. 22, (2012), Khimiya Geterotsiklicheskikh Soedinenii, 27, vol. 1, (1980), and the like].

Production Method 5:

[Chemical formula 45]

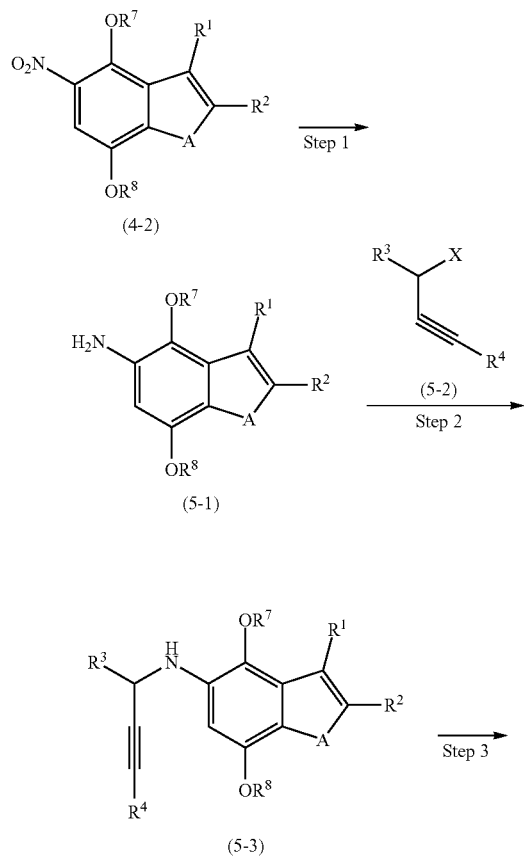

(In the formulas, $R^1$, $R^2$, $R^3$, $R^4$, $R^7$, $R^8$, and A are defined the same as above.)

These steps (1 to 3) can produce compound (5-4) from compound (4-2) in accordance with similar methods to methods and the like described in literature [for example, Bioorganic & Medicinal Chemistry Letters, 806, vol. 22, 2012 Journal of Medicinal Chemistry, 7574, vol. 56, (2013), Khimiya Geterotsiklicheskikh Soedinenii, 27, vol. 1, (1980), Synlett, 1781, vol. 11, (2009), Tetrahedron Letters, 5452, vol. 52, (2011), Bulletin of the Chemical Society of Japan, 891, vol. 70, (1997), Synlett, 116, vol. 1, (2011), Tetrahedron, 4612, vol. 69, (2013), Tetrahedron Letters, 5145, vol. 52, (2011), Chemistry Letters, 1422, vol. 36, (2007), European Journal of Organic Chemistry, 4039, vol. 19, (2004), Tetrahedron, 2755, vol. 64, (2008), and the like].

Production Method 6:

[Chemical formula 46]

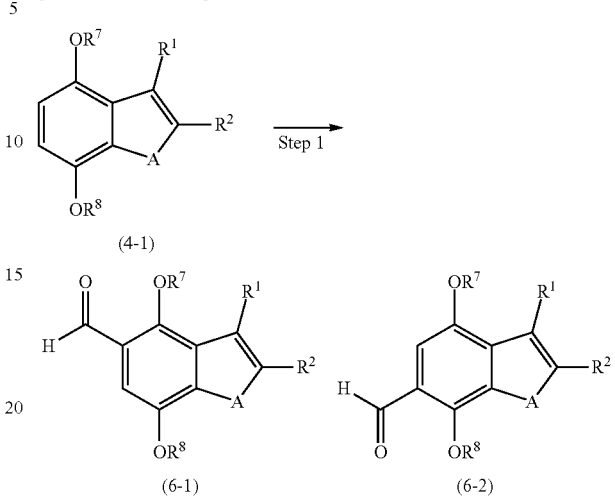

(In the formulas, $R^1$, $R^2$, $R^7$, $R^8$, and A are defined the same as above.)

This step can produce compound (6-1) and compound (6-2) from compound (4-1) in accordance with a similar method to methods and the like described in literature [for example, Physiological Zoology, 312, vol. 36, (1963), European Journal of Medicinal Chemistry, 4827, vol. 46, (2011), Synthetic Metals, 2491, vol. 159, (2009), Journal of the American Chemical Society, 4466, vol. 132, (2010), Bulletin of the Chemical Society of Japan, 4464, vol. 61, (1988), and the like].

Production Method 7:

[Chemical formula 47]

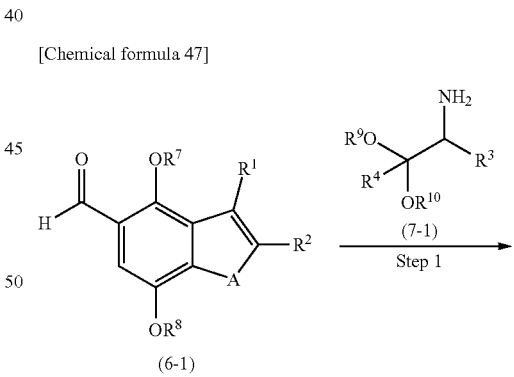

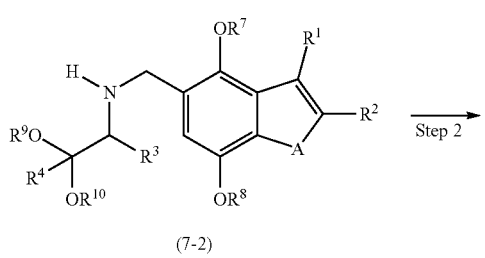

-continued

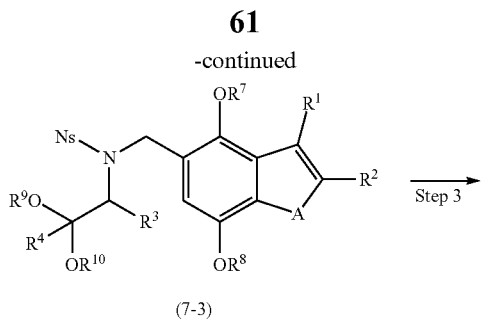

(7-3)

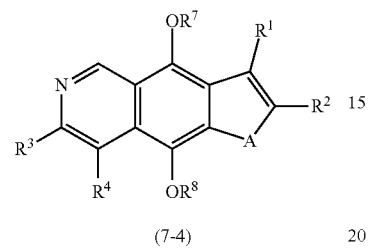

(7-4)

(In the formulas, $R^1$, $R^2$, $R^3$, $R^4$, $R^7$, $R^8$, $R^9$, and A are defined the same as above. $R^{10}$ is $C_{1-6}$ alkyl.)

These steps (1 to 3) can produce compound (7-4) from compound (6-1) in accordance with similar methods to methods and the like described in literature [for example, Journal of Organic Chemistry, 5026, vol. 78, (2013), Tetrahedron, 5787, vol. 62, (2006), Tetrahedron Letters, 8527, vol. 38, (1997), Indian Journal of Chemistry, Section B: Organic Chemistry Including Medicinal Chemistry, 72, vol. 25B, (1986), and the like].

Production Method 8

[Chemical formula 48]

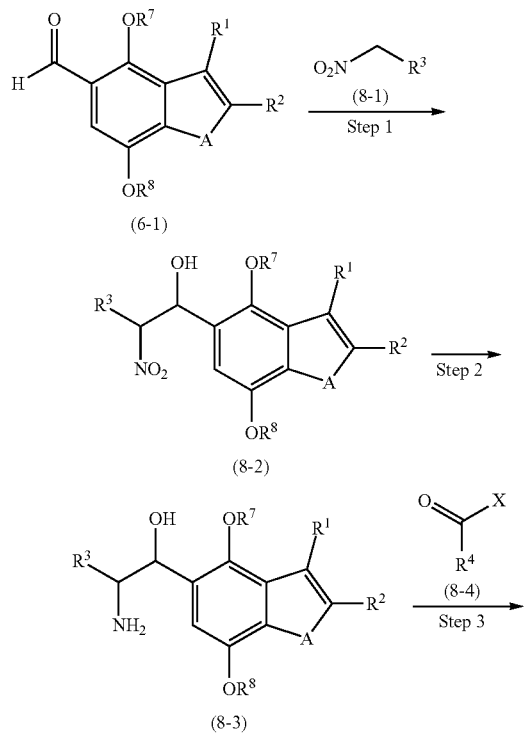

-continued

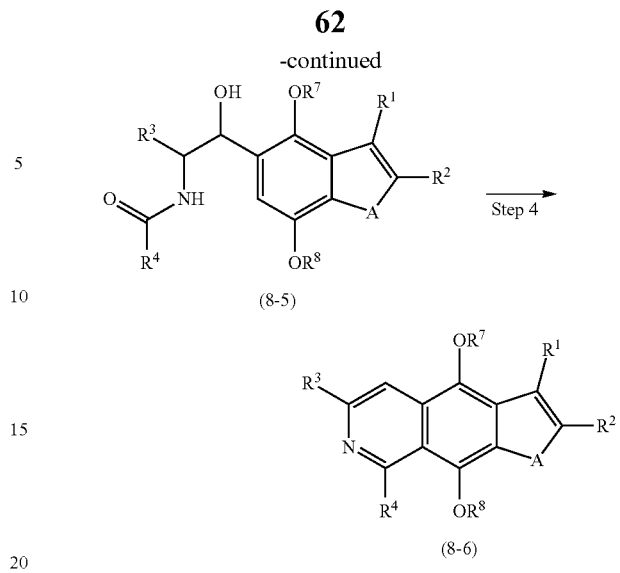

[In the formulas, $R^1$, $R^2$, $R^3$, $R^4$, $R^7$, $R^8$, and A are defined the same as above. X represents a leaving group (e.g., a chlorine atom, a bromine atom, an iodine atom, methoxy, ethoxy, propoxy, butoxy, imidazole, pyrrole, optionally substituted phenoxy, and the like).]

These steps (1 to 4) can produce compound (8-6) from compound (6-1) in accordance with similar methods to methods and the like described in literature [for example, Compt. Rend., 1265, vol. 120, (1895), Journal of Organic Chemistry, 1418, vol. 68, (2003), Journal of the American Chemical Society, 3554, vol. 77, (1955), Journal of Organic Chemistry, 2353, vol. 60, (1995), Journal of Organic Chemistry, 3742, vol. 46, (1981), Tetrahedron: Asymmetry, 1395, vol. 22, (2011), Journal of Medicinal Chemistry, 8287, vol. 53, (2010), Tetrahedron, 11020, vol. 64, (2008), Tetrahedron: Asymmetry, 2281, vol. 6, (1995), Journal of Organic Chemistry, 650, vol. 14, (1949), Polish Journal of Chemistry, 1317, vol. 75, (2001), and the like].

Production Method 9:

[Chemical formula 49]

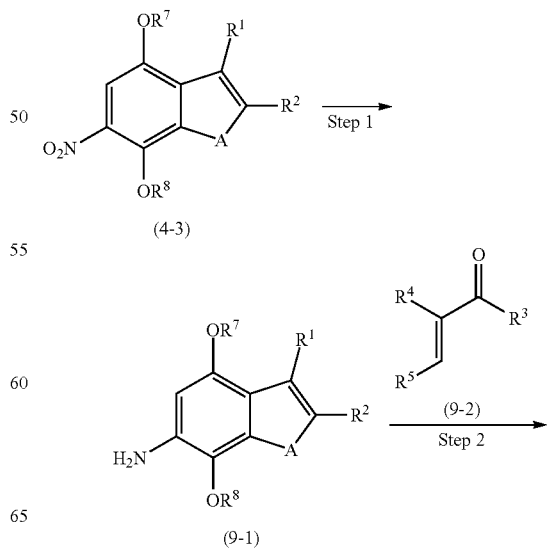

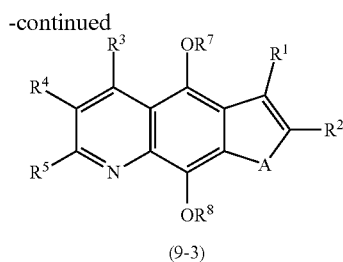

(9-3)

(In the formulas, $R^1$, $R^2$, $R^3$, $R^4$, $R^5$, $R^7$, $R^8$, and A are defined the same as above.)

These steps (1 to 2) can produce compound (9-3) from compound (4-3) in accordance with similar methods to methods and the like described in literature [for example, Bulletin of the Chemical Society of Japan, 891, vol. 70, (1997), Tetrahedron Letters, 1783, vol. 47, (2006), Tetrahedron, 1763, vol. 67, (2011), Tetrahedron Letters, 6869, vol. 50, (2009), Synlett, 449, vol. 3, (2004), Heterocycles, 2631, vol. 60, (2003), Tetrahedron, 3259, vol. 42, (1986), Journal of Medicinal Chemistry, 1832, vol. 28, (1985), and the like].

Production Method 10:

[Chemical formula 50]

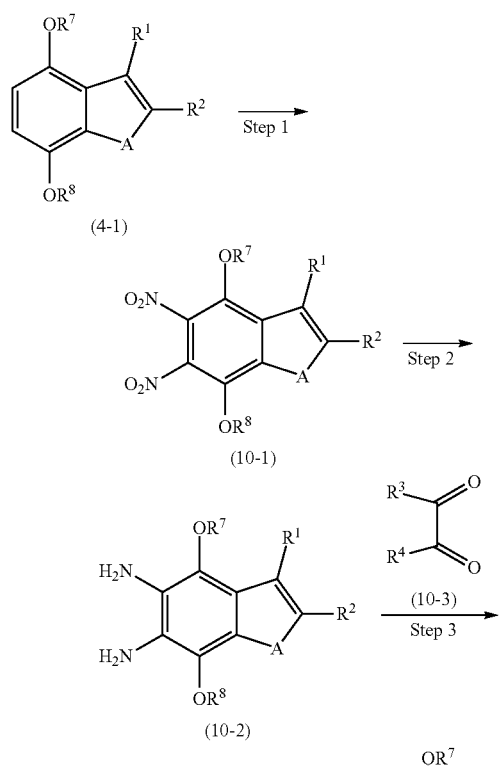

(In the formulas, $R^1$, $R^2$, $R^3$, $R^4$, $R^7$, $R^8$, and A are defined the same as above.)

These steps (1 to 3) can produce compound (10-4) from compound (4-1) in accordance with similar methods to methods and the like described in literature [for example, European Journal of Medicinal Chemistry, 611, vol. 24, (1989), Heterocycles, 1623, vol. 34, (1992), European Journal of Medicinal Chemistry, 611, vol. 24, (1989), Journal of Medicinal Chemistry, 614, vol. 33, (1990), Asian Journal of Chemistry, 5575, vol. 22, (2010), Journal of the American Chemical Society, 8227, vol. 135, (2013), Journal of Organic Chemistry, 2548, vol. 73, (2008), Journal of Organic Chemistry, 6599, vol. 72, (2007), Bioorganic & Medicinal Chemistry Letters, 3771, vol. 14, (2004), Russian Chemical Bulletin, 414, vol. 58, (2010), Collection of Czechoslovak Chemical Communications, 285, vol. 49, (1984), and the like].

Production Method 11:

[Chemical formula 51]

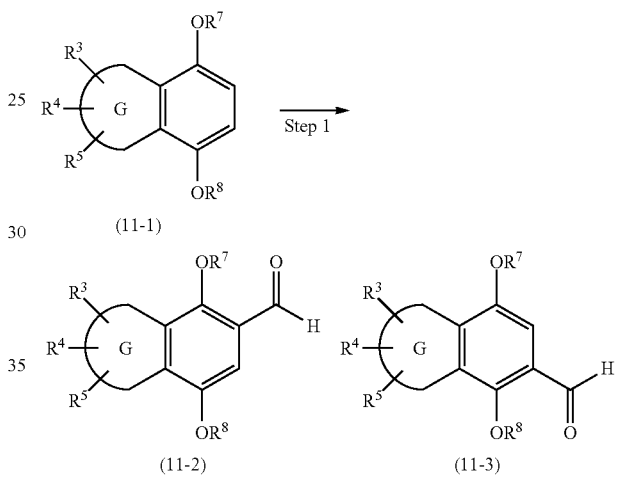

(In the formulas, $R^3$, $R^4$, $R^5$, $R^7$, $R^8$, A, and G are defined the same as above.)

This step can produce compounds (11-2) and (11-3) from compound (11-1) in accordance with a similar method to methods and the like described in literature [for example, Physiological Zoology, 312, vol. 36, (1963), European Journal of Medicinal Chemistry, 4827, vol. 46, (2011), Synthetic Metals, 2491, vol. 159, (2009), Journal of the American Chemical Society, 4466, vol. 132, (2010), Bulletin of the Chemical Society of Japan, 4464, vol. 61, (1988), and the like].

Production Method 12:

[Chemical formula 52]

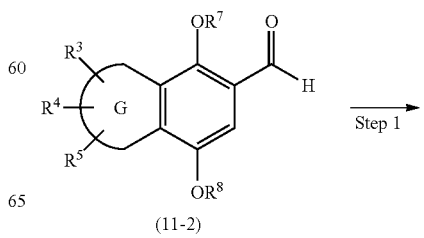

(11-2)

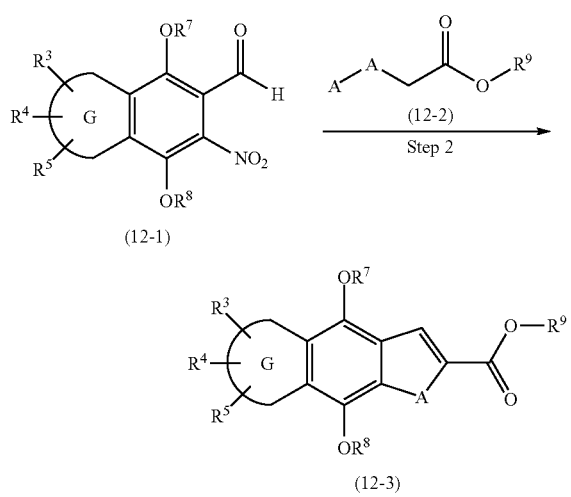

(In the formula, $R^3$, $R^4$, $R^5$, $R^7$, $R^8$, $R^9$, A, and G are defined the same as above.)

These steps (1 to 2) can produce compound (12-3) from compound (11-2) in accordance with similar methods to methods and the like described in literature [for example, Organic Letters, 2157, vol. 7, (2005), Journal of Medicinal Chemistry, 7574, vol. 56, (2013), Bioorganic & Medicinal Chemistry Letters, 138, vol. 22, (2012), Khimiya Geterotsiklicheskikh Soedinenii, 27, vol. 1, (1980), Heterocycles, 1913, vol. 75, (2008), Journal of Medicinal Chemistry, 1819, vol. 53, (2010), Journal of the Chilean Chemical Society, 14, vol. 54, (2009), Molecules, 1388, vol. 17, (2012), Bioorganic & Medicinal Chemistry Letters, 4961, vol. 15, (2005), Synlett, 670, vol. 5, (2001), and the like].

Production Method 13:

[Chemical formula 53]

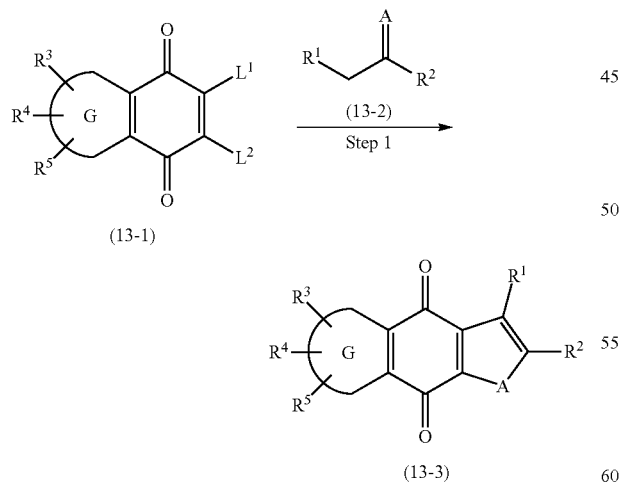

[In the formulas, $R^1$, $R^2$, $R^3$, $R^4$, $R^5$, A, and G are defined the same as above. $L^1$ and $L^2$ represent hydrogen, a hydroxyl group, or a leaving group (e.g., a chlorine atom, a bromine atom, an iodine atom, methanesulfonyloxy, trifluoromethanesulfonyloxy, p-toluenesulfonyloxy, or the like).]

Step 1

In this step 1, compound (10-3) can be produced by reacting, in an organic solvent in the presence of a base, (13-1) obtained as a commercially available product or in accordance with a known method [for example, Journal of Medicinal Chemistry, 1329, vol. 29, (1986), European Journal of Medicinal Chemistry, 3938, vol. 45, (2010), Bioorganic & Medicinal Chemistry Letters, 952, vol. 21, (2011), European Journal of Organic Chemistry, 4201, vol. 18, (2006), Journal of Organic Chemistry, 5026, vol. 78, (2013), and the like], with (13-2) obtained as a commercially available product or in accordance with a known synthesis method [for example, Bioorganic & Medicinal Chemistry, 5705, vol. 20, (2012), Journal of American Chemical Society, 3460, vol. 103, (1981), Journal of Medicinal Chemistry, 1347, vol. 40, (1997), Journal of Medicinal Chemistry, 5233, vol. 45, (2002), Organic Letters, 2856, vol. 11, (2009), and the like]. Organic solvent includes aprotic solvent such as N,N-dimethylformamide, N-methyl-2-pyrrolidone, dimethyl sulfoxide, and the like, ether type solvent such as tetrahydrofuran, 1,4-dioxane, and the like, halogenated hydrocarbons such as dichloromethane, chloroform, 1,2-dichloroethane, chlorobenzene, and the like, hydrocarbons such as toluene, benzene, and the like, mixed solvents thereof, and the like, and suitably N,N-dimethylformamide, N-methyl-2-pyrrolidone, dimethyl sulfoxide, acetonitrile, and tetrahydrofuran. In addition, it can be produced in a two-layer system of organic solvent—water. Both of organic bases and inorganic bases can be used as a base. Organic bases include 1-hydroxybenzotriazole, N-methylmorpholine, triethylamine, diisopropylethylamine, tributylamine, 1,8-diazabicyclo[5.4.0]undec-7-ene, 1,5-diazabicyclo[4.3.0]non-5-ene, 1,4-diazabicyclo[5.4.0]undec-7-ene, pyridine, dimethylaminopyridine, picoline, and the like. Inorganic bases include alkali halides such as potassium fluoride and the like, alkali hydroxide such as sodium hydroxide, potassium hydroxide, and the like, alkali carbonate such as sodium carbonate, potassium carbonate, cesium carbonate, sodium hydrogen carbonate, and the like, alkali alkoxide such as sodium ethoxide, sodium tert-butoxide, potassium tert-butoxide, and the like, alkali metal such as n-butyl lithium, methyl lithium, isopropylmagnesium bromide, and the like. The amount of compound (9-2) used is generally 1 to 5 mol, preferably, 1.2 to 3 mol per mol of compound (9-1). The amount of a base used is generally 2 to 10 mol, preferably, 2 to 3 mol per mol of compound (1-1). A reaction time is generally about 0.5 to about 48 hours, preferably, about 0.5 to about 12 hours. A reaction temperature is generally about −20 to about 180° C., preferably, about 0 to about 150° C.

Production Method 14:

[Chemical formula 54]

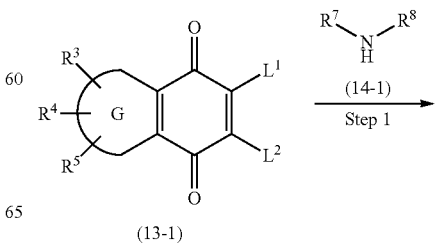

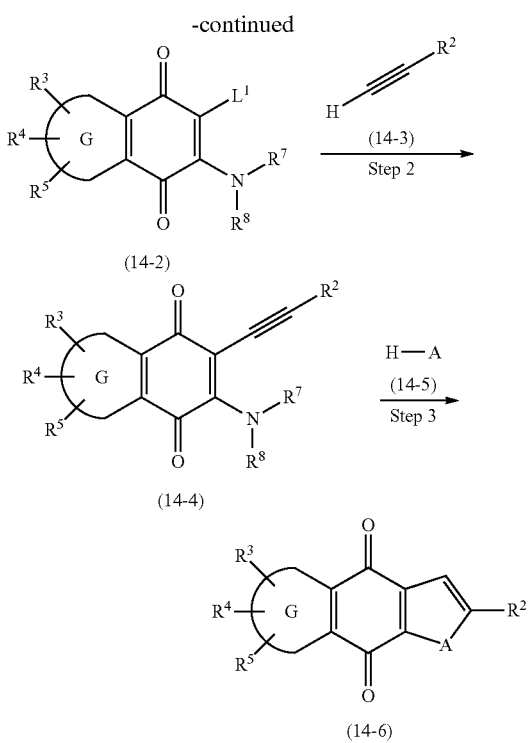

[In the formulas, $R^2$, $R^3$, $R^4$, $R^5$, $R^7$, $R^8$, $L^1$, $L^2$, A, and G are defined the same as above.]

These steps (1 to 3) can produce compound (14-6) from compound (13-1) in accordance with similar methods to methods and the like described in literature [for example, US2012/0077986A1 and the like].

In each reaction of the production methods described above, in a case other than the case where the use of a protecting group is specifically and explicitly indicated, if any functional group other than a reaction point is modified under a described reaction condition or is unsuitable for performing the described reaction method, a target compound can be obtained by protecting any point other than the reaction point as necessary, and unprotecting after the reaction is finished or a series of reactions are performed.

As a protecting group, a common protecting group such as those described in literature (e.g., Protective Groups in Organic Synthesis, 3$^{rd}$ ed., T. W. Greene, John Wiley & Sons Inc. (1999), and the like) can be used. Further specifically, examples of a protecting group for an amino group can include benzyloxycarbonyl, tert-butoxycarbonyl, acetyl, benzyl, and the like, and examples of a protecting group for a hydroxyl group include trialkylsilyl groups such as trimethylsilyl, tert-butyldimethylsilyl, and the like, acetyl, benzyl, and the like, respectively.

Introduction and removal of a protecting group can be performed by routine methods in synthetic organic chemistry (e.g., refer to Protective Groups in Organic Synthesis, described above) or methods in accordance therewith.

In addition, intermediates or final products in the above-described production methods can be derived to other compounds encompassed by the present invention by appropriately converting a functional group thereof, and in particular, extend any kind of side chain using an amino group, a hydroxyl group, a carbonyl group, a halogen group, or the like as an aid, and at this time, as necessary, performing the above-described protection and deprotection. Conversion of a functional group and extension of a side chain can be performed by a routine, general method (refer to, e.g., Comprehensive Organic Transformations, R. C. Larock, John Wiley & Sons Inc. (1999), and the like).

Intermediates and target compounds in the above-described respective production methods can be subjected to a routine purification method in synthetic organic chemistry, for example, neutralization, filtration, extraction, washing, drying, concentration, recrystallization, any kind of chromatography, and the like to isolate and purify it. In addition, the intermediates can be subjected to a next reaction without particular purification.

Among starting materials and intermediates in respective production methods described above, those of which production methods are not particularly and repeatedly described are commercially available compounds or can be synthesized from a commercially available compound by a known method to those skilled in the art or a method in accordance therewith.

The present compound is provided, for example, as an anticancer agent. Although the type of cancer to which it is applied is not limited, specific examples thereof include acute leukemia, chronic lymphocytic leukemia, chronic myelocytic leukemia, polycythemia vera, malignant lymphoma, brain tumor, head and neck cancer, esophageal cancer, thyroid cancer, small cell lung cancer, non-small-cell lung cancer, breast cancer, gastric cancer, gallbladder•bile duct cancer, hepatoma, pancreatic cancer, colon cancer, rectal cancer, chorioepithelioma, endometrial cancer, cervical cancer, urothelial cancer, renal cell cancer, testicular tumor, Wilms' tumor, skin cancer, malignant melanoma, neuroblastoma, osteosarcoma, Ewing's sarcoma, and soft tissue sarcoma. Hematological cancer in the present invention is a concept encompassing lymphoma and leukemia, and has an effect to reduce or annihilate carcinoma or to inhibit the growth of carcinoma for the purposes of preventing/or treating cancer. It is noted that in the present invention, "prevention (preventing)" is an action to administer an active ingredient of the present invention to a healthy human that does not develop a disease, and a purpose thereof is, for example, to prevent the onset of a disease. "Treatment (treating)" is an action to administer an active ingredient of the present invention to a person (patient) diagnosed as developing a disease by a medical doctor, and a purpose thereof is, for example, to alleviate the disease and symptoms, to inhibit the growth of carcinoma, or to return it to a state prior to the onset of the disease. In addition, even when the purpose of administration is to prevent a disease or symptoms from deteriorating or carcinoma from growing, if it is administered to a patient, it is an action for therapy.

When the present compound is administered, the amount of the compound used varies depending on symptoms, age, administration method, and the like. For example, in the case of oral administration, it is desirable to administer to an adult 0.01 mg as the lower limit (preferably 1 mg) and 5000 mg as the upper limit (preferably 500 mg) once or in several batches daily depending on the symptoms. In the case of intravenous injection, an effect is expected by administering to an adult 0.01 mg as the lower limit (preferably 0.1 mg) and 1000 mg as the upper limit (preferably 30 mg) once or in several batches daily depending on the symptoms. Examples of its administration schedule include single-dose administration, once a day administration for three days in a row, and the like. Further, each administration described above can be repeated at intervals of about 7 days to about 60 days.

The present compound can be administered orally or parenterally (e.g., intravenous, subdermal, or intramuscular injection, ocular administration, transrectally, percutaneously, transnasally, or the like). For oral administration, for example, tablets, capsules, pills, granules, powders, solutions, suspensions, and the like can be used. In addition, for parenteral administration, injections, eye drops, suppositories, patches, poultices, lotions, creams, and the like can be used. These preparations comprise the present compound and pharmacologically acceptable additives, and produced using conventional known techniques.

More specifically, depending on parenteral or oral administration, the present compound can be formed into a preparation using a suitable dosage form, and administrated. Examples of the dosage form include, but are not limited to, tablets, capsules, powders, granules, solutions, suspensions, injections, patches, poultices, and the like. The preparation is produced by a known method using a pharmaceutically acceptable additive.

As additives, excipients, disintegrants, binders, fluidizers, lubricants, coating agents, solvents, solubilizing agents, thickeners, dispersants, stabilizers, sweeteners, flavors, and the like can be used in accordance with a purpose. Specific examples thereof include lactose, mannitol, crystalline cellulose, low-substituted hydroxypropylcellulose, corn starch, partly pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide, talc, and the like.

It is possible to more effectively perform preventive treatment of cancer by combining one to three types selected from the group consisting of: (1) administering an effective amount of the present compound; and (2) (i) administering an effective amount of another anticancer agent, (ii) administering an effective amount of a hormonal therapeutic agent; and (iii) non-pharmacological therapy. Examples of non-pharmacological therapy include surgery, radiotherapy, gene therapy, thermotherapy, cryotherapy, laser cauterization therapy, and the like. Two or more types of these also can be combined.

The present compound can be used in combination with another drug for purpose of enhancing its effect. Specifically, the present compound can be used in combination with a drug such as a hormonal therapeutic agent, a chemotherapeutic agent, an immunotherapeutic agent, or a cell growth factor, a pharmaceutical agent to inhibit its receptor activity, and the like. Hereinafter, a drug that may be used in combination with the present compound is abbreviated to a combination drug.

The present compound, even when used as a single agent, exhibits excellent anticancer effect, and further the combination use with one or several of the above-described combination drugs (polypharmacy) can further enhance its effect or improve the QOL of a patient.

Examples of "hormonal therapeutic agents" include Fosfestrol, Diethylstilbestrol, Chlorotrianisene, Medroxyprogesterone acetate, Megestrol acetate, Chlormadinone acetate, Cyproterone acetate, Danazol, Dienogest, Asoprisnil, Allylestrenol, Gestrinone, Nomegestrol, Tadenan, Mepartricin, Raloxifene, Ormeloxifene, Levormeloxifene, antiestrogen (e.g., Tamoxifen citrate, Toremifene citrate, and the like), pill preparation, Mepitiostane, Testololactone, aminoglutethimide, LH-RH derivatives (LH-RH agonist (e.g., Goserelin acetate, Buserelin, Leuprorelin, and the like), LH-RH antagonist), Droloxifene, Epitiostanol, ethynyl estradiol sulfonate, aromatase inhibitor (e.g., Fadrozole hydrochloride, Anastrozole, Letrozole, exemestane, vorozole, formestane, and the like), anti-androgen (e.g., Flutamide, Bicalutamide, Nilutamide, and the like), adrenocortical hormone type pharmaceutical agent (e.g., Dexamethasone, Prednisolone, Betamethasone, Triamcinolone, and the like), androgen synthesis inhibitor (e.g., Abiraterone and the like), retinoid and a pharmaceutical agent to delay the metabolism of retinoid (e.g., Liarozole and the like), and the like.

As "chemotherapeutic agents", for example, alkylating agents, antimetabolites, anticancer antibiotics, plant-derived anticancer agents, other chemotherapeutic agents, and the like are used. Representative examples are described below.

Examples of "alkylating agents" include Nitrogen mustard, Nitrogen mustard N-oxide hydrochloride, Chlorambucil, Cyclophosphamide, Ifosfamide, Thiotepa, Carboquone, Improsulfan tosylate, Busulfan, Nimustine hydrochloride, Mitobronitol, Melphalan, Dacarbazine, Ranimustine, Estramustine phosphate sodium, Triethylenemelamine, Carmustine, Lomustine, Streptozocin, Pipobroman, Etoglucide, Carboplatin, Cisplatin, miriplatin, Nedaplatin, Oxaliplatin, Altretamine, Ambamustine, Dibrospidium chloride, Fotemustine, Prednimustine, Pumitepa, Ribomustin, Temozolomide, Treosulfan, Trofosfamide, Zinostatin stimalamer, Adozelesin, Cystemustine, Bizelesin, and DDS preparations thereof, and the like.

Examples of "antimetabolites" include Mercaptopurine, 6-Mercaptopurine riboside, Thioinosine, Methotrexate, Pemetrexed, Enocitabine, Cytarabine, Cytarabin ocfosfate, Ancitabine hydrochloride, 5-FU type pharmaceutical agent (e.g., Fluorouracil, Tegafur, UFT, Doxifluridine, Carmofur, Galocitabine, Emitefur, Capecitabine, and the like), Aminopterin, Nelarabine, Leucovorin calcium, tabloid, Butocin, calcium folinate, calcium levofolinate, Cladribine, Emitefur, Fludarabine, Gemcitabine, hydroxycarbamide, Pentostatin, Piritrexim, Idoxuridine, Mitoguazone, Tiazofurin, Ambamustine, Bendamustine, and DDS preparations thereof, and the like.

Examples of "anticancer antibiotics" include Actinomycin D, Actinomycin C, Mitomycin C, Chromomycin A3, Bleomycin hydrochloride, Bleomycin sulfate, Peplomycin sulfate, Daunorubicin hydrochloride, Doxorubicin hydrochloride, Aclarubicin hydrochloride, Pirarubicin hydrochloride, Epirubicin hydrochloride, Neocarzinostatin, Mithramycin, Sarkomycin, Carzinophilin, Mitotane, Zorubicin hydrochloride, Mitoxantrone hydrochloride, Idarubicin hydrochloride, and DDS preparations thereof, and the like.

Examples of "plant-derived anticancer agents" include Etoposide, Etoposide phosphate, Vinblastine sulfate, Vincristine sulfate, Vindesine sulfate, Teniposide, Paclitaxel, Docetaxel, DJ-927, Vinorelbine, Irinotecan, Topotecan, and DDS preparations thereof, and the like.

Examples of "other chemotherapeutic agents" include Sobuzoxane and the like.

Examples of "immunotherapeutic agents (BRM)" include Picibanil, Krestin, Sizofiran, Lentinan, Ubenimex, interferon, interleukin, macrophage colony stimulating factor, granulocyte-colony stimulating factor, Erythropoietin, Lymphotoxin, BCG vaccine, *Corynebacterium parvum*, Levamisole, polysaccharide K, Procodazole, anti-CTLA4 antibody, PD-1 antibody, Toll-like Receptors agonist (e.g., TLR7 agonist, TLR8 agonist, TLR9 agonist, and the like).

A cell growth factor and a cell growth factor in a pharmaceutical agent to inhibit the activity of its receptor may be any substance as long as it promotes cell growth. Generally, they include a factor that is a peptide having a molecular weight of 20,000 or less and exhibits an effect at a low concentration by binding with a receptor. Specifically, they include EGF (epidermal growth factor) or substances having substantially the same activity as it (e.g., TGFalpha and the like), insulin or substances having substantially the same activity as it (e.g., insulin, IGF (insulin-like growth factor)-1, IGF-2, and the like), FGF (fibroblast growth factor) or substances having substantially the same activity as it (e.g., acidic FGF, basic FGF, KGK (keratinocyte growth factor), FGF-10, and the like), and other cell growth factors (e.g., CSF (colony stimulating factor), EPO (erythropoietin), IL-2 (interleukin-2), NGF (nerve growth factor), PDGF (platelet-derived growth factor), TGF-beta (transforming growth factor beta), HGF (hepatocyte growth factor), VEGF (vascular endothelial growth factor), heregulin, angiopoietin, and the like).

The period of administration of the present compound and a combination pharmaceutical agent is not limited, and these may be administered concurrently or at intervals to a subject to be administered. In addition, a mixture of the present compound and a combination pharmaceutical agent may be made. The dosage of a combination pharmaceutical agent can be appropriately selected using clinically used dose as criteria. In addition, the mixing ratio of the present compound and a combination pharmaceutical agent can be appropriately selected depending on a subject to be administered, an administration route, target disease, symptoms, combinations, and the like. For example, when a subject to be administered is a human, 0.01 to 100 parts by weight of a combination pharmaceutical agent may be used relative to one part by weight of the present compound. In addition, for purpose of inhibiting its side effect, they can be used in combination with a pharmaceutical agent (a combination pharmaceutical agent) such as an antiemetic agent, a sleep-inducing agent, an anticonvulsant, and the like.

EXAMPLES

Hereinafter, the present invention is more specifically described with reference examples, examples, and test examples. However, the scope of the present invention is certainly not limited to these examples. It is noted that compound names shown in the following reference examples and examples do not always follow the IUPAC nomenclature. It is noted that although abbreviations are sometimes used to simplify a description, these abbreviations are defined the same as the above descriptions.

In the present specification, the following abbreviations are sometimes used.

In NMR and MS data of reference examples and examples, the following abbreviations are used.
Me: a methyl group
Et: an ethyl group
Ns: a 2-nitrobenzenesulfonyl group
Ts: a p-toluenesulfonyl group
tert: tertiary
Boc: a tert-butoxycarbonyl group
DMF: N,N-dimethylformamide
DMSO: dimethyl sulfoxide
HATU: O-(7-azabenzotriazol-1-yl)-N,N,N',N'-tetramethyl-uronium hexafluorophosphate
HOBt: 1-hydroxybenzotriazole
NMP: N-methylpyrrolidone
THF: tetrahydrofuran
WSC.HCl: 1-ethyl-3-(3-dimethylaminopropyl)carbodiimide hydrochloride
s: singlet
brs: broad singlet
d: doublet
dd: double doublet
t: triplet
q: quartet
m: multiplet
br: broad
J: coupling constant
Hz: Hertz
CDCl$_3$: deuterated chloroform
DMSO-d$_6$: deuterated dimethyl sulfoxide Analysis conditions for identification of a compound are as follow.
NMR: 400 MHz
MS: Kinetex, C18, 0.05% trifluoroacetic acid in water/0.05% trifluoroacetic acid in acetonitrile, acetonitrile 10-99% 3.0 min, 0.5 mL/min, or BEH, C18, 0.05% formic acid in water/acetonitrile, acetonitrile 2-96% 2.2 min, 0.8 mL/min.

Reference Example 1: methyl 4,7-dimethoxy-1-benzothiophene-2-carboxylate

[Chemical formula 55]

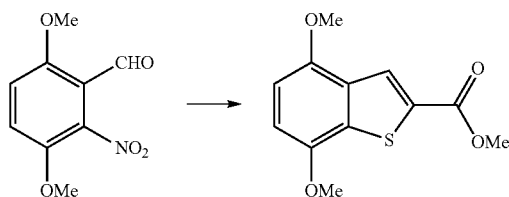

To a solution of 3,6-dimethoxy-2-nitrobenzaldehyde (70.0 g) in DMF (420 mL) was added dropwise methyl mercaptoacetate (33.4 mL) at room temperature. Subsequently, potassium carbonate (137 g) was added thereto in 10 parts, and then at unchanged constant temperature the reaction mixture was stirred for 1 hour. Methyl iodide (41.3 mL) was added dropwise thereto, followed by stirring for another 1 hour. The insoluble substance was removed through Celite, and then solvent was evaporated off. The resulting residue was dissolved in ethyl acetate (700 mL), washed with water (2×700 mL) and saturated brine (700 mL), and then dried over sodium sulfate. The solvent was then evaporated off to yield a standard compound as a flesh-colored powder (81.1 g).

$^1$H-NMR (CDCl$_3$, δppm): 8.04 (1H, s), 7.04 (1H, d, J=8.4 Hz), 6.90 (1H, d, J=8.4 Hz), 3.92 (3H, s), 3.89 (3H, s), 3.88 (3H, s).
MS (ESI+) 253 (M$^+$+1)

Reference Example 2: methyl 5-amino-4,7-dimethoxy-1-benzothiophene-2-carboxylate (2A)

Reference Example 3: methyl 6-amino-4,7-dimethoxy-1-benzothiophene-2-carboxylate (2B)

[Chemical formula 56]

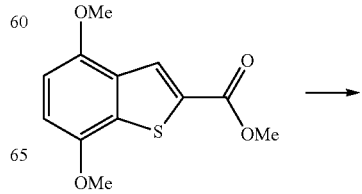

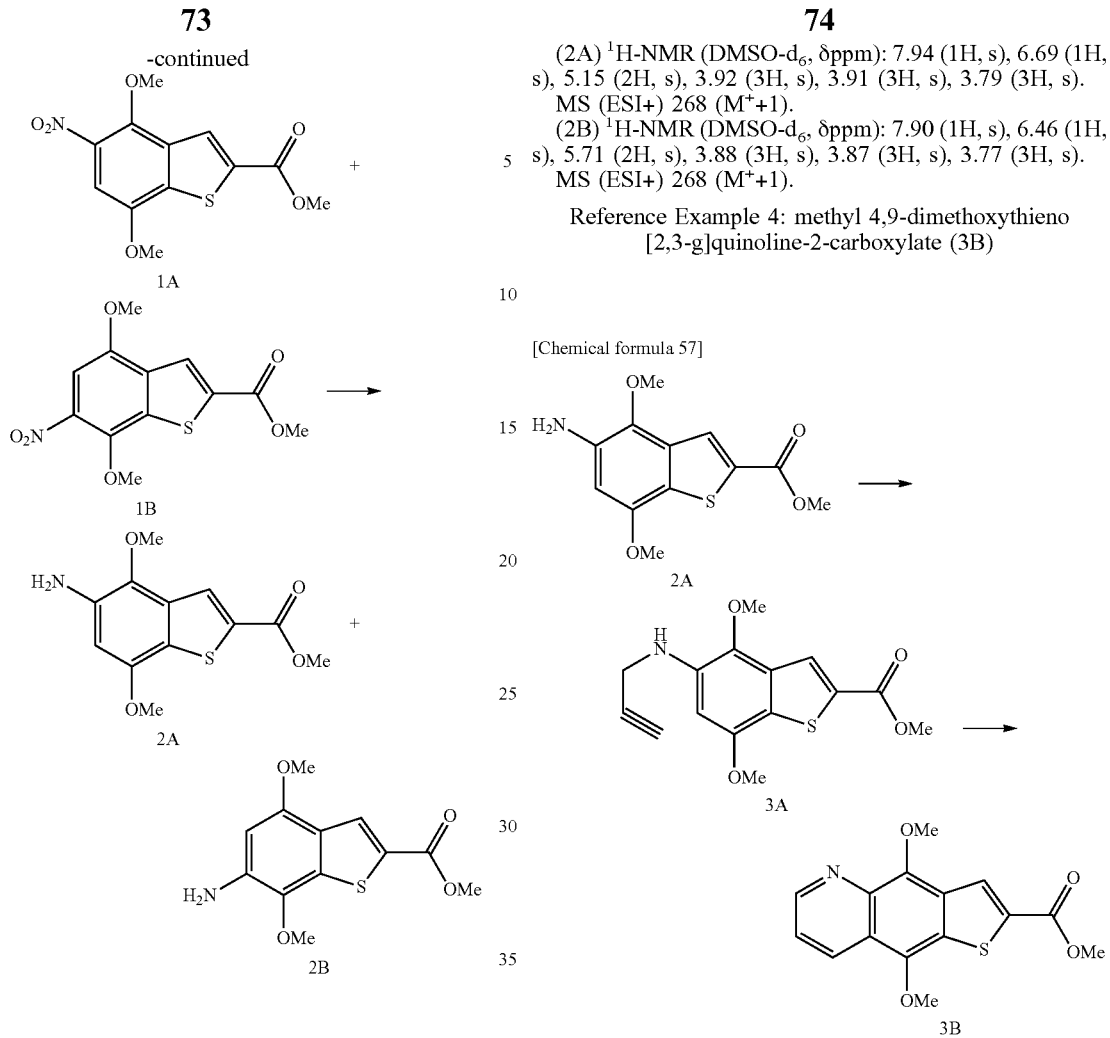

To a solution of methyl 4,7-dimethoxy-1-benzothiophene-2-carboxylate (2.04 g) (which was obtained in Reference example 1) in acetic acid (102 mL) was added dropwise 70% aqueous nitric acid solution (512 µL), and then the reaction mixture was stirred at 70° C. for 1 hour. After it was returned to room temperature, the reaction solution was poured into iced water, and then extracted with chloroform two times. The resulting organic layer was washed with saturated brine, and then dried over sodium sulfate. The solvent was then evaporated off to yield a mixture of 1A and 1B (2.57 g). This was used in the next reaction without further purification.

To a suspension of 90% reduced iron (2.68 g) and ammonium chloride (555 mg) in methanol/water (57.6 mL/28.8 mL), which had been heated and stirred at 75° C., was added dropwise a suspension of the obtained mixture of 1A and 1B (2.57 g) in methanol (8.65 mL), and then the reaction mixture was stirred at 75° C. for 2 hours. After the reaction solution was cooled to room temperature, it was filtered through Celite, and then the solvent of the resulting filtrate was evaporated off. The resulting residue was dissolved in ethyl acetate, washed with aqueous saturated sodium bicarbonate and saturated brine, and then dried over sodium sulfate. The solvent was evaporated off, and then the resulting residue was purified by silica gel column chromatography (ethyl acetate/hexane) to yield Compound 2A as a brown solid (1.74 g), and Compound 2B as a flesh-colored solid (474 mg).

(2A) $^1$H-NMR (DMSO-$d_6$, δppm): 7.94 (1H, s), 6.69 (1H, s), 5.15 (2H, s), 3.92 (3H, s), 3.91 (3H, s), 3.79 (3H, s). MS (ESI+) 268 (M$^+$+1).

(2B) $^1$H-NMR (DMSO-$d_6$, δppm): 7.90 (1H, s), 6.46 (1H, s), 5.71 (2H, s), 3.88 (3H, s), 3.87 (3H, s), 3.77 (3H, s). MS (ESI+) 268 (M$^+$+1).

Reference Example 4: methyl 4,9-dimethoxythieno[2,3-g]quinoline-2-carboxylate (3B)

[Chemical formula 57]

(a) 4,7-Dimethoxy-5-(prop-2-yn-1-ylamino)-1-benzothiophene-2-carboxylate (3A)

To a solution of methyl 5-amino-4,7-dimethoxy-1-benzothiophene-2-carboxylate (274 mg) (which was obtained in Reference example 2) in acetonitrile (3.1 mL) were added potassium carbonate (213 mg) and 3-bromopropyne (117 µL), and then the reaction mixture was heated and stirred at 70° C. for 6 hours. The reaction solution was returned to room temperature, and then the solvent was evaporated off. The resulting residue was dissolved in ethyl acetate, washed with water and saturated brine, and then dried over sodium sulfate. The solvent was evaporated off, and then the resulting residue was purified by silica gel column chromatography (ethyl acetate/hexane) to yield Compound 3A as a yellow solid (142 mg).

(b) Methyl 4,9-dimethoxythieno[2,3-g]quinoline-2-carboxylate (3B)

To a solution of Compound 3A (90.2 mg) (which was obtained above) in DMSO (6 mL) was added silver hexafluoroantimonate (10.2 mg), and then the reaction mixture was heated and stirred at 110° C. for 3 hours. The reaction solution was returned to room temperature, ethyl acetate and water were added thereto, followed by stirring for 5 minutes. The resulting organic layer was washed with aqueous saturated sodium bicarbonate and saturated brine, and then dried over sodium sulfate. The solvent was evaporated off, and then the resulting residue was purified by silica gel column chromatography (ethyl acetate/hexane) to yield Compound 3B as a yellow solid (20.4 mg).

(3A) $^1$H-NMR (CDCl$_3$, δppm): 8.04 (1H, s), 7.26 (1H, s), 6.54 (2H, s), 4.49 (1H, brs), 4.05 (2H, s), 3.98 (3H, s), 3.94 (3H, s), 3.87 (3H, s), 2.23 (1H, s).

MS (ESI+) 306 (M$^+$+1).

(3B) $^1$H-NMR (CDCl$_3$, δppm): 8.97 (1H, dd, J=1.6, 4.0 Hz), 8.55 (1H, dd, J=1.6, 8.8 Hz), 8.42 (1H, s), 7.46 (1H, dd, J=4.0, 8.8 Hz), 4.34 (3H, s), 4.16 (3H, s), 3.99 (3H, s).

MS (ESI+) 304 (M$^+$+1).

Reference Example 5: 4,9-dimethoxythieno[2,3-g]quinoline-2-carboxylic Acid

[Chemical formula 58]

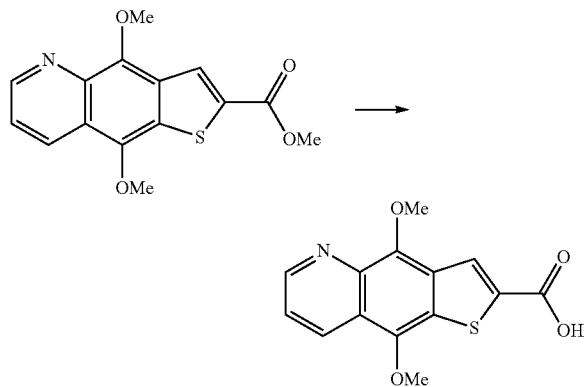

To a solution of methyl 4,9-dimethoxythieno[2,3-g]quinoline-2-carboxylate (70.0 mg) (which was obtained in Reference example 4) in THF/ethanol (346 μL/346 μL) was added 1 N aqueous sodium hydroxide solution (692 μL), and then the reaction mixture was stirred at room temperature for 2 hours. After the solvent was evaporated off, water was added thereto, and then the liquid property was made acidic (pH=2 to 3) with 2 N aqueous hydrochloric acid solution. The reaction mixture was extracted with Ethyl acetate three times, and then the resulting organic layer was washed with saturated brine. The organic layer was dried over sodium sulfate, and then the solvent was evaporated off to yield the title compound as a brown solid (65.2 mg).

$^1$H-NMR (DMSO-d$_6$, δppm): 8.99 (1H, dd, J=1.2, 4.4 Hz), 8.59 (1H, dd, J=1.2, 8.4 Hz), 8.20 (1H, s), 7.63 (1H, dd, J=4.4, 8.4 Hz), 4.27 (3H, s), 4.10 (3H, s).

MS (ESI+) 290 (M$^+$+1)

Reference Example 6: 1-(4,9-dimethoxythieno[2,3-g]quinolin-2-yl)ethanone (4B)

[Chemical formula 59]

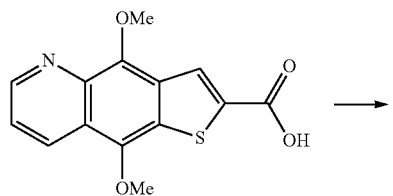

(a) (4,9-Dimethoxythieno[2,3-g]quinolin-2-yl) (morpholin-4-yl)methanone (4A)

To a solution of 4,9-dimethoxythieno[2,3-g]quinoline-2-carboxylic acid (35.2 mg) (which was obtained in Reference example 5) in DMF (1.2 mL) were added morpholine (21.2 μL), HATU (92.6 mg), and Hunig's base (128 μL), and then the reaction mixture was stirred at room temperature for 1.5 hours. The reaction solution was poured into water, and then extracted with ethyl acetate three times. The resulting organic layer was washed with saturated brine, and then dried over sodium sulfate. The solvent was then evaporated off to yield Compound 4A as a yellow solid (41.0 mg).

(b) 1-(4,9-Dimethoxythieno[2,3-g]quinolin-2-yl)ethanone (4B)

To a solution of Compound 4A (which was obtained above) in THF (1.14 mL), under ice-cooling, was added dropwise methylmagnesium bromide (114 μL), and then the reaction mixture was stirred at room temperature for 3.5 hours. The reaction solution was poured into water, and then extracted with ethyl acetate two times. The resulting organic layer was washed with saturated brine, and then dried over sodium sulfate. The solvent was then evaporated off to yield Compound 4B as a brown solid (36.0 mg).

(4A) MS (ESI+) 359 (M$^+$+1).

(4B) $^1$H-NMR (CDCl$_3$, δppm): 8.97 (1H, dd, J=1.6, 4.0 Hz), 8.56 (1H, dd, J=1.6, 8.8 Hz), 8.30 (1H, s), 7.47 (1H, dd, J=4.0, 8.8 Hz), 4.39 (3H, s), 4.16 (3H, s), 2.74 (3H, s).

MS (ESI+) 288 (M$^+$+1).

Example 1: 2-acetylthieno[2,3-g]quinoline-4,9-dione

[Chemical formula 60]

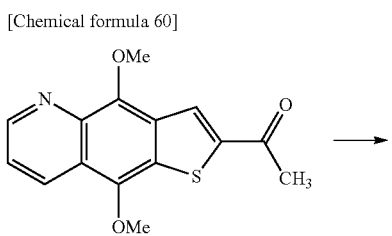

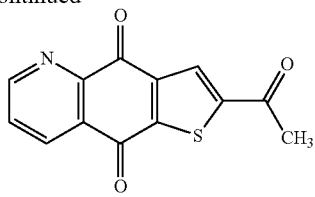

To a mixture solution of 1-(4,9-dimethoxythieno[2,3-g]quinolin-2-yl)ethanone (4.0 mg) (which was obtained in Reference example 6) in acetonitrile (1 mL) and water (1 mL) was added Ammonium Cerium Nitrate (16 mg) at 0° C., and then the reaction mixture was stirred for 1 hour. Aqueous saturated sodium hydrogen carbonate solution was added to the reaction solution, which was then extracted with ethyl acetate. The organic layer was dried over anhydrous sodium sulfate, filtered, and then concentrated under reduced pressure. The residue was purified by silica gel column chromatography (hexane/ethyl acetate) to yield the title compound as a yellow solid (1.8 mg)

MS (ESI+) 258 (M$^+$+1).

Example 2: 2-(1-hydroxyethyl)thieno[2,3-g]quinoline-4,9-dione (5B)

[Chemical formula 61]

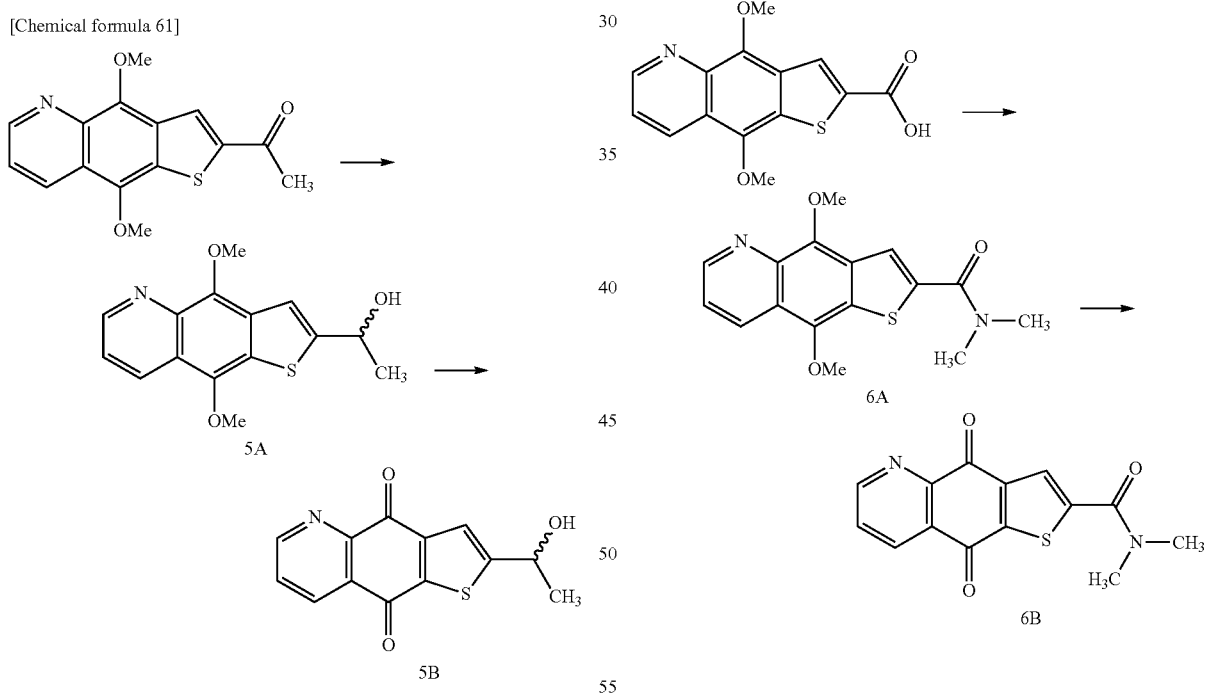

(a) 1-(4,9-dimethoxythieno[2,3-g]quinolin-2-yl)ethanol (5A)

To a solution of 1-(4,9-dimethoxythieno[2,3-g]quinolin-2-yl)ethanone (34.9 mg) (which was obtained in Reference example 6) in THF (1.2 mL), under ice-cooling, was added sodium borohydride (10.0 mg), and then the reaction mixture was stirred at room temperature for 2 hours. Aqueous saturated ammonium chloride solution was added thereto, and then extraction with ethyl acetate was performed two times. The resulting organic layer was washed with saturated brine, and then dried over sodium sulfate. The solvent was then evaporated off to yield Compound 5A as a brown solid (33.3 mg).

(b) 2-(1-Hydroxyethyl)thieno[2,3-g]quinoline-4,9-dione (5B)

Using Compound 5A (32.1 mg) obtained above and according to the same method as Example 1, Compound 5B was obtained as a yellow solid (10.4 mg).

(5A) $^1$H-NMR (CDCl$_3$, δppm): 8.95 (1H, dd, J=2.0, 3.6 Hz), 8.53 (1H, dd, J=2.0, 8.8 Hz), 7.53 (1H, s), 7.41 (1H, dd, J=3.6, 8.8 Hz), 5.29-5.21 (1H, m), 4.26 (3H, s), 4.14 (3H, s), 1.72 (3H, d, J=6.0 Hz).

MS (ESI+) 290 (M$^+$+1)

(5B) $^1$H-NMR (DMSO-d$_6$, δppm): 9.02 (1H, dd, J=2.0, 4.4 Hz), 8.47 (1H, dd, J=2.0, 8.0 Hz), 7.85 (1H, dd, J=4.4, 8.0 Hz), 7.57 (1H, s), 6.14 (1H, d, J=5.2 Hz), 5.18-4.98 (1H, m), 1.50 (3H, d, J=6.0 Hz).

MS (ESI+) 260 (M$^+$+1).

Example 3: N,N-dimethyl-4,9-dioxo-4,9-dihydrothieno[2,3-g]quinoline-2-carboxamide (6B)

[Chemical formula 62]

(a) 4,9-Dimethoxy-N,N-dimethylthieno[2,3-g]quinoline-2-carboxamide (6A)

To a solution of 4,9-dimethoxythieno[2,3-g]quinoline-2-carboxylic acid (25.9 mg) (which was obtained in Reference example 5) in DMF (1.0 mL) were added dimethylamine hydrochloride (8.8 mg), WSC.HCl (25.8 mg), HOBt (18.2 mg), and Hunig's base (57.9 μL), and then the reaction mixture was stirred at room temperature for 1.5 hours. The reaction solution was poured into water, and then extracted with ethyl acetate two times. The resulting organic layer was washed with saturated brine, and then dried over sodium sulfate. The solvent was then evaporated off to yield Compound 6A as a yellow solid (17.3 mg).

(b) N,N-dimethyl-4,9-dioxo-4,9-dihydrothieno[2,3-g]quinoline-2-carboxamide (6B)

Using Compound 6A (17.3 mg) obtained above and according to the same method as Example 1, the title compound 68B was obtained as a pale green solid (5.5 mg).
(6A) MS (ESI+) 317 (M⁺+1).
(6B) MS (ESI+) 287 (M⁺+1).

Reference Example 7: 2-(chloromethyl)-4,9-dimethoxythieno[2,3-g]quinoline (7A)

[Chemical formula 63]

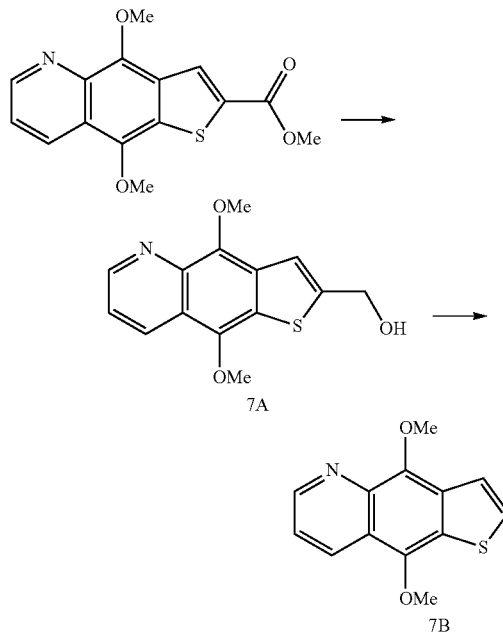

(a) (4,9-Dimethoxythieno[2,3-g]quinolin-2-yl)methanol (7A)

To a solution of methyl 4,9-dimethoxythieno[2,3-g]quinoline-2-carboxylate (27.8 mg) (which was obtained in Reference example 4) in dichloromethane (1.0 mL), under ice-cooling, was added lithium aluminum hydride (73.6 mg), and then the reaction mixture was stirred at room temperature overnight. Under ice-cooling, aqueous saturated Rochelle salt solution was added thereto, and then extraction with ethyl acetate was performed two times. The resulting organic layer was washed with saturated brine, and then dried over sodium sulfate. The solvent was then evaporated off to yield Compound 7A as a yellow oil (22.7 mg).

(b) 2-(Chloromethyl)-4,9-dimethoxythieno[2,3-g]quinoline (7B)

To a solution of Compound 7A (22.7 mg) (which was obtained above) in dichloromethane (1.0 mL), under ice-cooling, was added thionyl chloride (7.6 µL), and then the reaction mixture was stirred at room temperature for 2 hours. The solvent was evaporated off, and then azeotropy of the resulting residue with toluene yields Compound 7B as a brown oil (23.7 mg).
(7A) MS (ESI+) 276 (M⁺+1).
(7B) MS (ESI+) 294 (M⁺+1).

Reference Example 8: 4,9-dimethoxy-2-(morpholin-4-ylmethyl)thieno[2,3-g]quinoline

[Chemical formula 64]

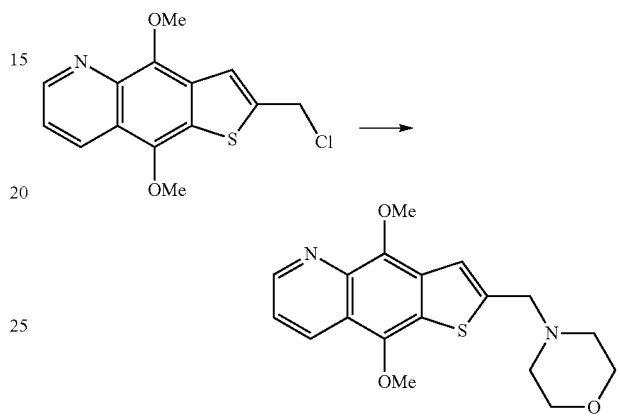

To a solution of 2-(chloromethyl)-4,9-dimethoxythieno[2,3-g]quinoline (which was obtained in Reference example 7) in acetonitrile (1.0 mL) were added Hunig's base (28.8 µL), morpholine (7.9 µL), and sodium iodide (a catalytic amount), and then the reaction mixture was stirred at room temperature overnight. The solvent was evaporated off, and then the resulting residue was purified by silica gel column chromatography (ethyl acetate/hexane→chloroform/methanol) to yield the title compound as a yellow solid (19.1 mg).
MS (ESI+) 345 (M⁺+1).

Example 4: 2-(morpholin-4-ylmethyl)thieno[2,3-g]quinoline-4,9-dione

[Chemical formula 65]

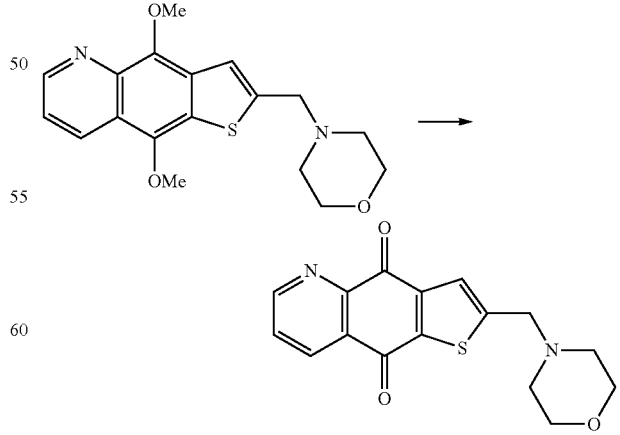

Using 4,9-dimethoxy-2-(morpholin-4-ylmethyl)thieno[2,3-g]quinoline (19.1 mg) obtained in Reference example 8 and according to the same method as Example 1, the title compound was obtained as a pale green solid (13.3 mg).
MS (ESI+) 315 (M⁺+1).

Example 5: 2-{[cyclohexyl(ethyl)amino]methyl}thieno[2,3-g]quinoline-4,9-dione (8B)

[Chemical formula 66]

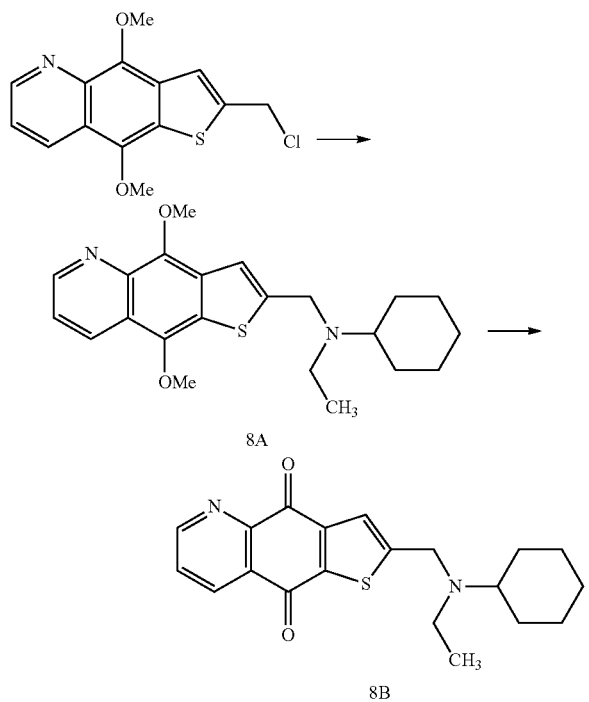

(a) N-[(4,9-dimethoxythieno[2,3-g]quinolin-2-yl)methyl]-N-ethylcyclohexanamine (8A)

Using cyclohexylethylamine (16.8 μL) and according to the same method as Reference example 8, Compound 8A was obtained as a yellow oil (13.5 mg).

(b) 2-{[Cyclohexyl(ethyl)amino]methyl}thieno[2,3-g]quinoline-4,9-dione (8B)

Using Compound 8A (13.5 mg) obtained above and according to the same method as Example 1, the title compound 8B was obtained as a brown solid (7.9 mg).
(8A) MS (ESI+) 385 (M⁺+1).
(8B) MS (ESI+) 355 (M⁺+1).

Example 6: 2-{[ethyl(2-methoxyethyl)amino]methyl}thieno[2,3-g]quinoline-4,9-dione (9B)

[Chemical formula 67]

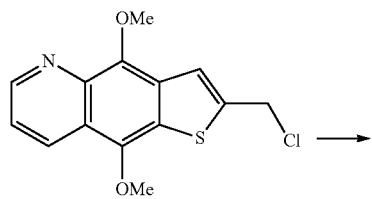

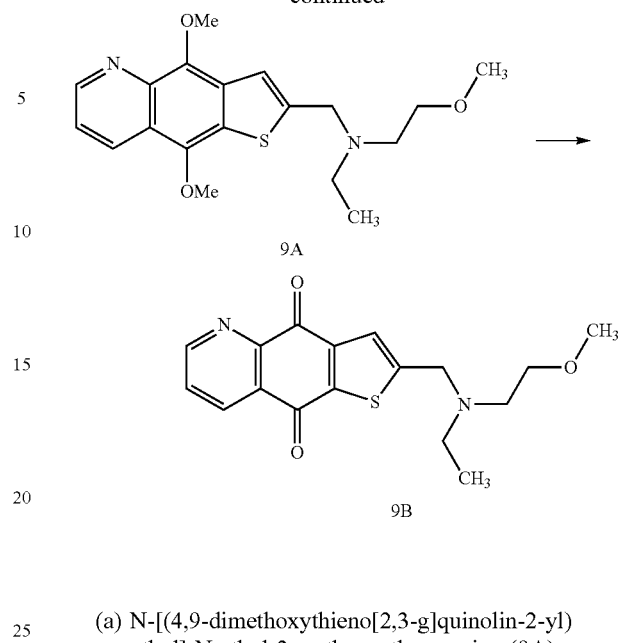

(a) N-[(4,9-dimethoxythieno[2,3-g]quinolin-2-yl)methyl]-N-ethyl-2-methoxyethaneamine (9A)

Using 2-methoxyethylethylamine (14.9 μL) and according to the same method as Reference example 8, Compound 9A was obtained as a yellow oil (13.3 mg).

(b) 2-{[Ethyl(2-methoxyethyl)amino]methyl}thieno[2,3-g]quinoline-4,9-dione (9B)

Using Compound 9A (13.3 mg) obtained above and according to the same method as Example 1, the title compound 9B was obtained as a brown solid (11.5 mg).
(9A) MS (ESI+) 361 (M⁺+1).
(9B) MS (ESI+) 331 (M⁺+1).

Example 7: 2-{[ethyl(pyridin-4-ylmethyl)amino]methyl}thieno[2,3-g]quinoline-4,9-dione (10B)

[Chemical formula 68]

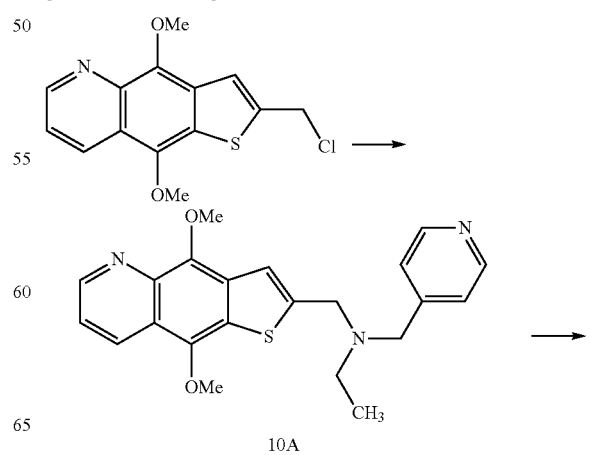

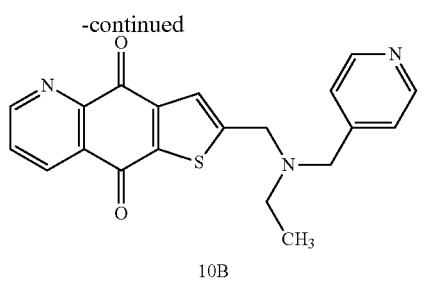

10B (a) N-[(4,9-dimethoxythieno[2,3-g]quinolin-2-yl)methyl]-N-(pyridin-4-ylmethyl)ethaneamine (10A)

Using N-ethyl-4-picolylamine (26.4 mg) and according to the same method as Reference example 8, Compound 10A was obtained as a brown solid (18.0 mg).

(b) 2-{[Ethyl(pyridin-4-ylmethyl)amino]methyl}thieno[2,3-g]quinoline-4,9-dione (10B)

Using Compound 10A (18.0 mg) obtained above and according to the same method as Example 1, the title compound 10B was obtained as a brown solid (10.3 mg).

(10A) MS (ESI+) 394 ($M^+$+1).
(10B) MS (ESI+) 364 ($M^+$+1).

Example 8: 2-{[ethyl(pyridin-4-ylmethyl)amino]methyl}thieno[2,3-g]quinoline-4,9-dione (11B)

[Chemical formula 69]

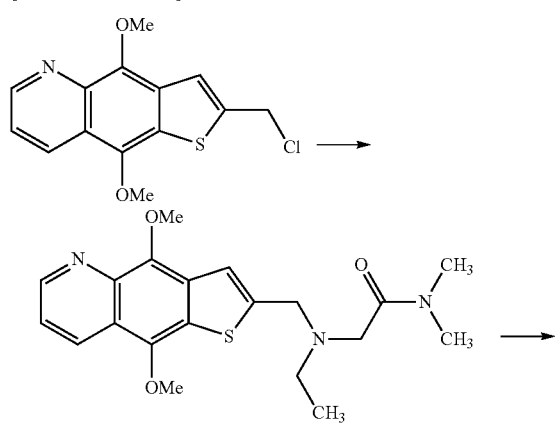

11A

11B (a) N'2'-[(4,9-dimethoxythieno[2,3-g]quinolin-2-yl)methyl]-N'2'-ethyl-N,N-dimethylglycinamide (11A)

Using 2-ethylamino-N,N-dimethylacetamide (25.2 mg) and according to the same method as Reference example 8, Compound 11A was obtained as a brown solid (28.0 mg).

(b) 2-{[Ethyl(pyridin-4-ylmethyl)amino]methyl}thieno[2,3-g]quinoline-4,9-dione (11B)

Using Compound 11A (28.0 mg) obtained above and according to the same method as Example 1, the title compound 11B was obtained as a brown oil (16.0 mg).

(11A) MS (ESI+) 388 ($M^+$+1).
(11B) MS (ESI+) 358 ($M^+$+1).

Reference Example 9: N-[(4,9-dimethoxyfuro[2,3-g]quinolin-2-yl)methyl]ethaneamine

[Chemical formula 70]

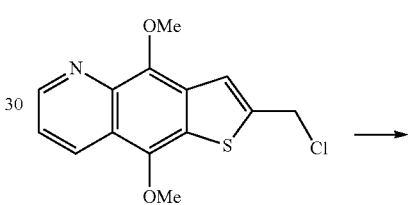

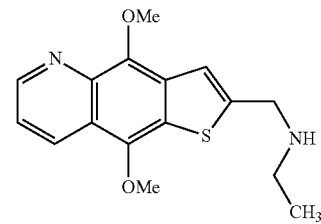

Using ethylamine and according to the same method as Reference example 8, the title compound was obtained as a brown oil (127 mg).

MS (ESI+) 303 ($M^+$+1).

Example 9: N-[(4,9-dioxo-4,9-dihydrofuro[2,3-g]quinolin-2-yl)methyl]-N-ethyl-3-methylbutanamide (12B)

[Chemical formula 71]

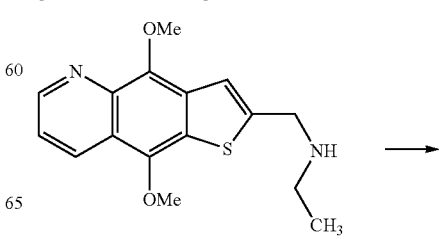

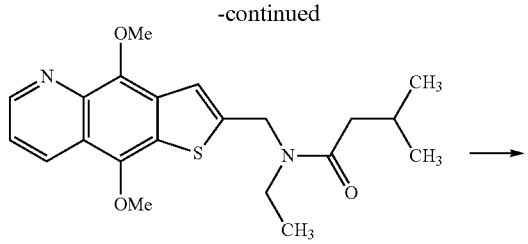

12A

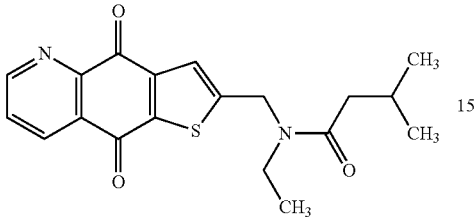

12B

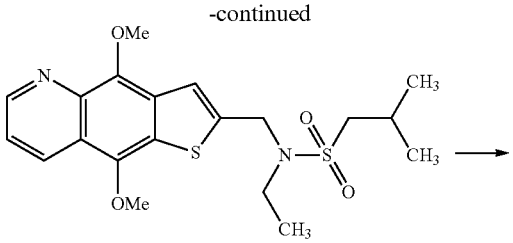

13A

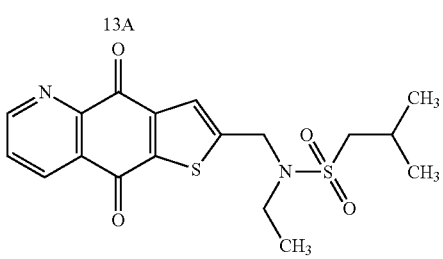

13B (a) N-[(4,9-dimethoxyfuro[2,3-g]quinolin-2-yl)methyl]-N-ethyl-3-methylbutanamide (12A)

To a solution of N-[(4,9-dimethoxyfuro[2,3-g]quinolin-2-yl)methyl]ethaneamine (40.0 mg) (which was obtained in Reference example 9) in THF (1 mL), under ice-cooling, were added dropwise isovaleryl chloride (19.4 μL) and triethylamine (27.7 μL), and then the reaction mixture was stirred at room temperature for 1 hour. Aqueous saturated sodium bicarbonate was added thereto, and then extraction with ethyl acetate was performed. The resulting organic layer was washed with saturated brine, and then dried over sodium sulfate. The solvent was then evaporated off. The resulting residue was purified by silica gel column chromatography (ethyl acetate/hexane) to yield Compound 12A as a yellow solid (26.1 mg).

(b) N-[(4,9-dioxo-4,9-dihydrofuro[2,3-g]quinolin-2-yl)methyl]-N-ethyl-3-methylbutanamide (12B)

Using Compound 12A (28.0 mg) obtained above and according to the same method as Example 1, the title compound 12B was obtained as a yellow powder (17.7 mg).
(12A) MS (ESI+) 387 (M$^+$+1)
(12B) $^1$H-NMR (DMSO-d$_6$, δppm): 9.02 (1H, d, J=2.8 Hz), 8.46 (1H, dd, J=1.6, 8.0 Hz), 7.84 (1H, dd, J=4.4, 8.0 Hz), 7.70-7.64 (1H, m), 4.92-4.75 (2H, m), 3.48-3.36 (2H, m), 2.26 (2H, d, J=6.8 Hz), 2.15-2.02 (1H, m), 1.17-1.01 (3H, m), 0.96-0.84 (6H, m).
MS (ESI+) 357 (M$^+$+1).

Example 10: N-[(4,9-dioxo-4,9-dihydrofuro[2,3-g]quinolin-2-yl)methyl]-N-ethyl-2-methylpropane-1-sulfonamide (13B)

(a) N-[(4,9-dimethoxyfuro[2,3-g]quinolin-2-yl)methyl]-N-ethyl-2-methylpropane-1-sulfonamide (13A)

Using N-[(4,9-dimethoxyfuro[2,3-g]quinolin-2-yl)methyl]ethaneamine (40.0 mg) (which was obtained in Reference example 9) and isobutanesulfonyl chloride (20.7 μL) and according to the same method as Example 9a, Compound 13A was obtained as a yellow solid (21.2 mg).

(b) N-[(4,9-dioxo-4,9-dihydrofuro[2,3-g]quinolin-2-yl)methyl]-N-ethyl-2-methylpropane-1-sulfonamide (13B)

Using Compound 13A (20.5 mg) obtained above and according to the same method as Example 1, the title compound 13B was obtained as a yellow powder (16.8 mg).
(13A) MS (ESI+) 423 (M$^+$+1).
(13B) $^1$H-NMR (DMSO-d$_6$, δppm): 9.03 (1H, dd, J=2.0, 4.4 Hz), 8.48 (1H, dd, J=2.0, 8.0 Hz), 7.86 (1H, dd, J=4.8, 8.0 Hz), 7.70-7.64 (1H, m), 4.72-4.65 (2H, m), 3.36-3.22 (2H, m), 3.08 (2H, d, J=6.4 Hz), 2.19-2.08 (1H, m), 1.15-1.08 (3H, m), 1.08-1.02 (6H, m).
MS (ESI+) 393 (M$^+$+1).

Example 11: ethyl [(4,9-dioxo-4,9-dihydrofuro[2,3-g]quinolin-2-yl)methyl]ethylcarbamate (14B)

[Chemical formula 72]

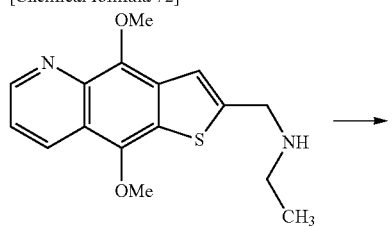

[Chemical formula 73]

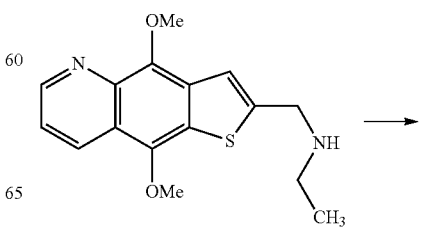

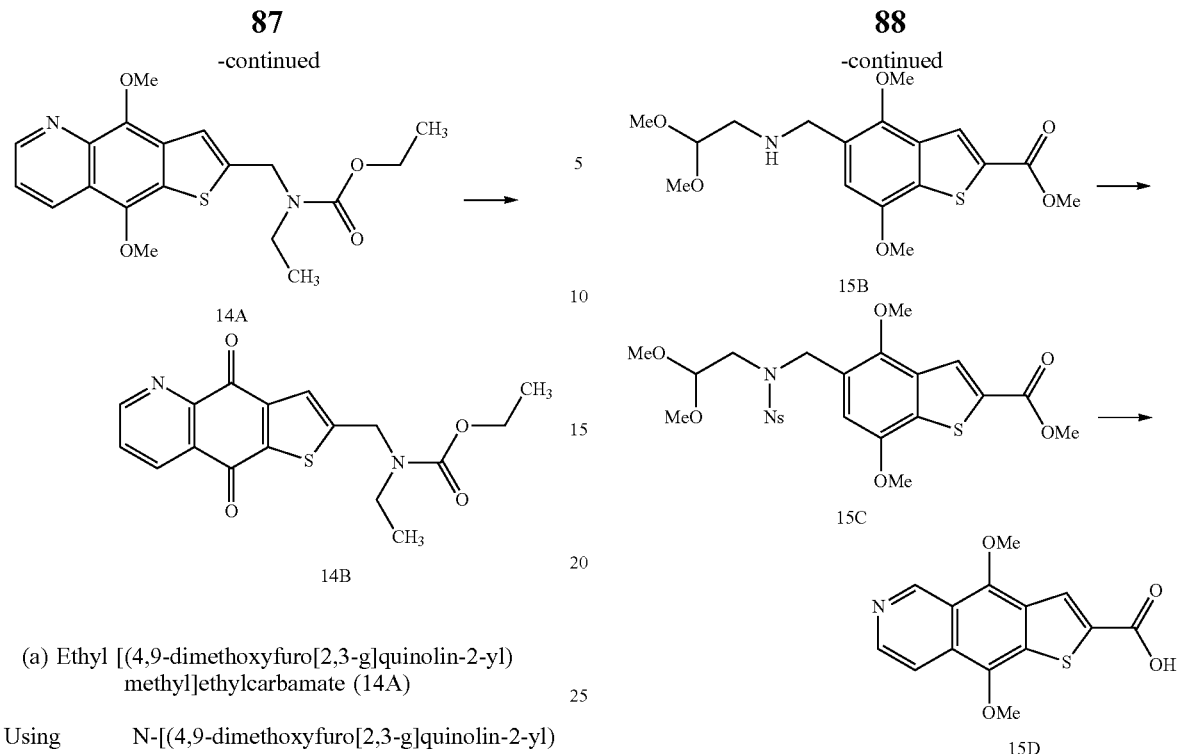

(a) Ethyl [(4,9-dimethoxyfuro[2,3-g]quinolin-2-yl)methyl]ethylcarbamate (14A)

Using N-[(4,9-dimethoxyfuro[2,3-g]quinolin-2-yl)methyl]ethaneamine (40.0 mg) (which was obtained in Reference example 9) and ethyl chloroformate (15.1 μL) and according to the same method as Example 9a, Compound 14A was obtained as a yellow solid (21.9 mg).

(b) Ethyl [(4,9-dioxo-4,9-dihydrofuro[2,3-g]quinolin-2-yl)methyl]ethylcarbamate (14B)

Using Compound 14A (21.5 mg) obtained above and according to the same method as Example 1, the title compound 14B was obtained as a yellow powder (16.2 mg).
(14A) MS (ESI+) 375 (M$^+$+1).
(14B) $^1$H-NMR (DMSO-d$_6$, δppm): 9.03 (1H, d, J=4.8 Hz), 8.47 (1H, d, J=7.2 Hz), 7.89-7.82 (1H, m), 7.69 (1H, s), 4.72 (2H, s), 4.13 (2H, q, J=6.8), 3.32 (2H, q, J=6.8 Hz), 1.22 (3H, t, J=6.8 Hz), 1.08 (3H, t, J=6.8 Hz).
MS (ESI+) 345 (M$^+$+1).

Reference Example 10: 4,9-dimethoxythieno[2,3-g]isoquinoline-2-carboxylic acid (15D)

[Chemical formula 74]

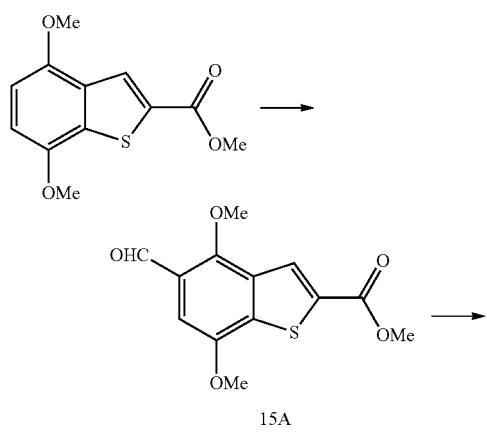

(a) Methyl 5-formyl-4,7-dimethoxy-1-benzothiophene-2-carboxylate (15A)

Under nitrogen atmosphere, to a solution of methyl 4,7-dimethoxy-1-benzothiophene-2-carboxylate (10 g) (which was obtained in Reference example 1) in dichloromethane (250 mL) was added dropwise titanium tetrachloride (9.9 mL) at 0° C., and then the reaction mixture was stirred for 30 minutes. 1,1-Dichloromethyl methyl ether (4.6 mL) was added dropwise thereto, and then the reaction mixture was stirred at 0° C. for 2 hours followed by at room temperature for 1 hour. The reaction solution was poured into iced water, and then extracted with chloroform. The organic layer was dried over anhydrous sodium sulfate, filtered, and then concentrated under reduced pressure. The resulting residue was recrystallized from ethyl acetate to yield Compound 15A (10.2 g).

(b) Methyl 5-{[(2,2-dimethoxyethyl)amino]methyl}-4,7-dimethoxy-1-benzothiophene-2-carboxylate (15B)

A solution of Compound 15A (31.8 g) (which was obtained above), aminoacetaldehyde dimethyl acetal (25 mL), and trimethyl orthoformate (5 mL) in toluene (500 mL) was heated at reflux for 2 hours using Dean-Stark apparatus. The residue resulting from the concentration of the reaction solution under reduced pressure was dissolved in methanol (300 mL), and then sodium borohydride (4.3 g) was added at 0° C. thereto, followed by stirring for 30 minutes. Water (300 mL) was added to the residue resulting from the concentration of the reaction solution under reduced pressure, and then extraction with ethyl acetate was performed. The organic layer was dried over anhydrous sodium sulfate, filtered, and then concentrated under reduced pressure. The resulting residue was recrystallized at −78° C. using a mixed solvent of diethyl ether and hexane to yield Compound 15B (32.6 g).

(c) Methyl 5-({(2,2-dimethoxyethyl) [(2-nitrophenyl)sulfonyl]amino}methyl)-4,7-dimethoxy-1-benzothiophene-2-carboxylate (15C)

To a solution of Compound 15B (25 g) (which was obtained above) in chloroform (300 mL) was added aqueous saturated sodium hydrogen carbonate solution (200 mL) and 2-nitrobenzenesulfonyl chloride (15 g), and then the reaction mixture was stirred at room temperature for 4 hours. The reaction solution was extracted with chloroform. The organic layer was dried over anhydrous sodium sulfate, filtered, and then concentrated under reduced pressure. The resulting residue was recrystallized from diethyl ether to yield Compound 15C (35.6 g).

(d) 4,9-Dimethoxythieno[2,3-g]isoquinoline-2-carboxylic Acid (15D)

To a solution of Compound 15C (1 g) (which was obtained above) in 1,4-dioxane (10 mL) was added 35% hydrochloric acid (10 mL), and then the reaction mixture was heated at reflux for 5 hours. The reaction solution was poured into iced water, and then the precipitated solid was collected by filtration and dried. The resulting residue was dissolved in methanol (10 mL), and then activated carbon (200 mg) was added thereto. After stirring for 30 minutes, it was filtered, and then concentrated under reduced pressure. The resulting residue was washed with ethyl acetate, and then collected by filtration to yield Compound 15D (330 mg).

(15A) $^1$H-NMR (DMSO-$d_6$, δppm): 10.36 (1H, s), 8.27 (1H, s), 7.22 (1H, s), 4.09 (3H, s), 3.99 (3H, s), 3.91 (3H, s).
MS (ESI+) 281 (M$^+$+1).

(15B) $^1$H-NMR (DMSO-$d_6$, δppm): 8.06 (1H, s), 7.17 (1H, s), 4.41 (1H, t, J=5.2 Hz), 3.93 (3H, s), 3.88 (3H, s), 3.85 (3H, s), 3.81 (2H, s), 2.59 (2H, d, J=5.5 Hz).
MS (ESI+) 370 (M$^+$+1).

(15C) $^1$H-NMR (DMSO-$d_6$, δppm): 8.10 (1H, s), 8.05 (1H, d, J=7.3 Hz), 7.99 (1H, d, J=7.3 Hz), 7.85 (1H, t, J=7.6 Hz), 7.75 (1H, t, J=7.6 Hz), 6.75 (1H, s), 4.73 (2H, s), 4.38 (1H, t, J=5.2 Hz), 3.89 (3H, s), 3.87 (3H, s), 3.75 (3H, s), 3.39-3.34 (2H, m), 3.16 (6H, s).
MS (ESI+) 555 (M$^+$+1).

(15D) $^1$H-NMR (DMSO-$d_6$, δppm): 9.85 (1H, s), 8.57 (1H, d, J=6.7 Hz), 8.45 (1H, s), 8.27 (1H, d, J=6.7 Hz), 4.35 (3H, s), 4.11 (3H, s).
MS (ESI+) 290 (M$^+$+1).

Reference Example 11: 1-(4,9-dimethoxythieno[2,3-g]isoquinolin-2-yl)ethanone (16B)

[Chemical formula 75]

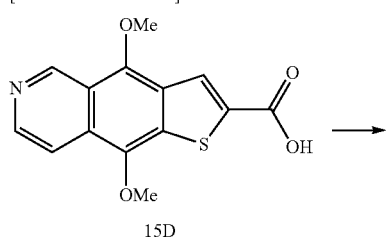

15D

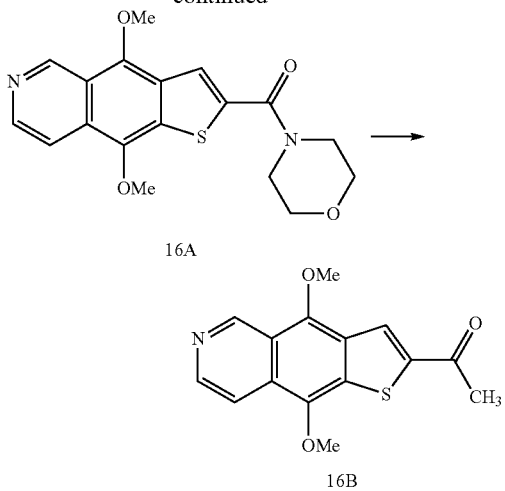

16A

16B (a) (4,9-Dimethoxythieno[2,3-g]isoquinolin-2-yl)(morpholin-4-yl)methanone (16A)

Using 4,9-dimethoxythieno[2,3-g]isoquinoline-2-carboxylic acid (286.0 mg) obtained in Reference example 10 and according to the same method as Reference example 6a, the title compound 16A was obtained as a yellow powder (132 mg).

(b) 1-(4,9-Dimethoxythieno[2,3-g]isoquinolin-2-yl)ethanone (16B)

Using Compound 16A (132.0 mg) obtained above and according to the same method as Reference example 6b, the title compound 16B was obtained as a yellow powder (46 mg).

(16A) MS (ESI+) 359 (M$^+$+1)
(16B) MS (ESI+) 288 (M$^+$+1)

Example 12: 2-acetylthieno[2,3-g]isoquinoline-4,9-dione

[Chemical formula 76]

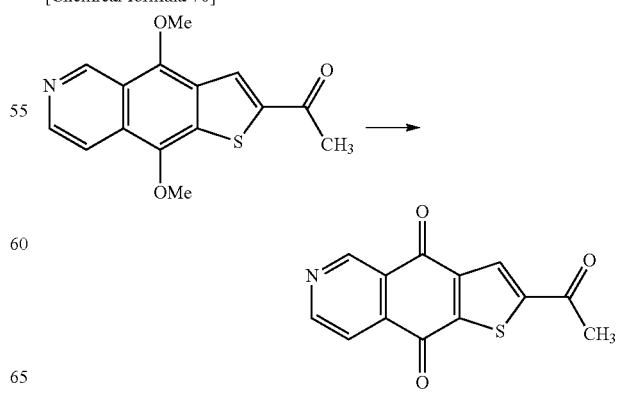

Using 1-(4,9-dimethoxythieno[2,3-g]isoquinolin-2-yl)ethanone (46.0 mg) obtained in Reference example 11 and according to the same method as Example 1, the title compound was obtained as a yellow powder (19 mg).

MS (ESI+) 258 (M$^+$+1).

Example 13: 2-(1-hydroxyethyl)thieno[2,3-g]isoquinoline-4,9-dione (17B)

[Chemical formula 77]

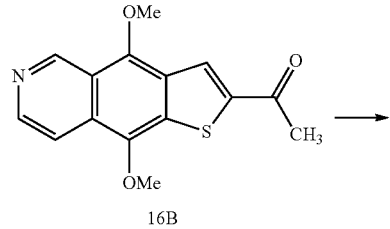

16B

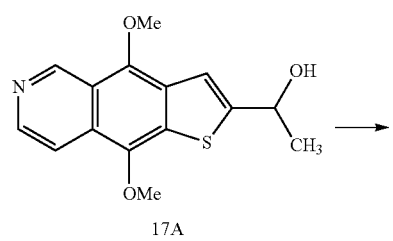

17A

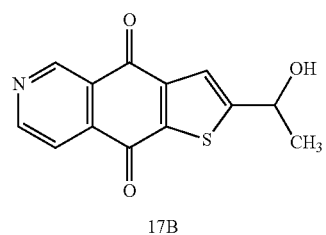

17B (a) 1-(4,9-Dimethoxythieno[2,3-g]isoquinolin-2-yl)ethanol (17A)

Using 1-(4,9-dimethoxythieno[2,3-g]isoquinolin-2-yl)ethanone (52.0 mg) obtained in Reference example 11 and according to the same method as Example 2a, Compound 17A was obtained as a yellow powder (44.0 mg).

(b) 2-(1-Hydroxyethyl)thieno[2,3-g]isoquinoline-4,9-dione (17B)

Using Compound 17A (44.0 mg) obtained above and according to the same method as Example 1, the title compound 17B was obtained as a yellow powder (29.0 mg).

(17A) MS (ESI+) 290 (M$^+$+1).
(17B) MS (ESI+) 260 (M$^+$+1).

Reference Example 12: (4,9-dimethoxythieno[2,3-g]isoquinolin-2-yl)methanol

[Chemical formula 78]

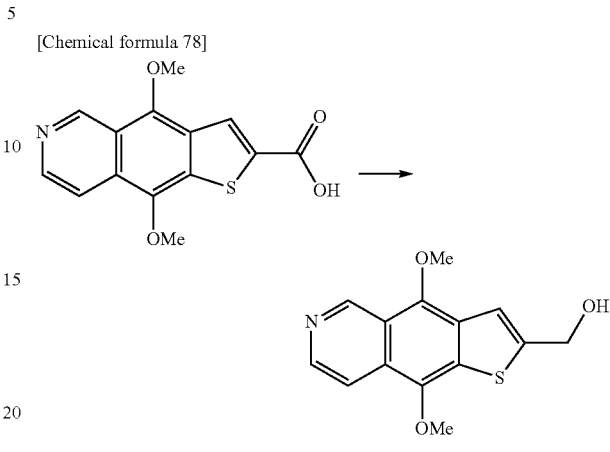

To a solution of 4,9-dimethoxythieno[2,3-g]isoquinoline-2-carboxylic acid (100 mg) (which was obtained in Reference example 10) and N-methylmorpholine (411 µL) in dimethoxyethane (5.0 mL), under ice-cooling, was added isobutyl chloroformate (270 µL), and then the reaction mixture was stirred for 20 minutes. After Celite filtration, under ice-cooling, an aqueous solution of sodium borohydride (257 mg) was added to the filtrate. After stirring for 2 hours, 2.0 mol/L aqueous sodium hydroxide solution was added thereto, and then the mixture was stirred for 24 hours. After the reaction solution was extracted with ethyl acetate, the resulting organic layer was washed with water and saturated brine, and then dried over sodium sulfate. The solvent was then evaporated off. The resulting residue was purified by silica gel column chromatography (chloroform/methanol) to yield the title compound (41 mg).

MS (ESI+) 276 (M$^+$+1).

Example 14: 2-(1-hydroxymethyl)thieno[2,3-g]isoquinoline-4,9-dione

[Chemical formula 79]

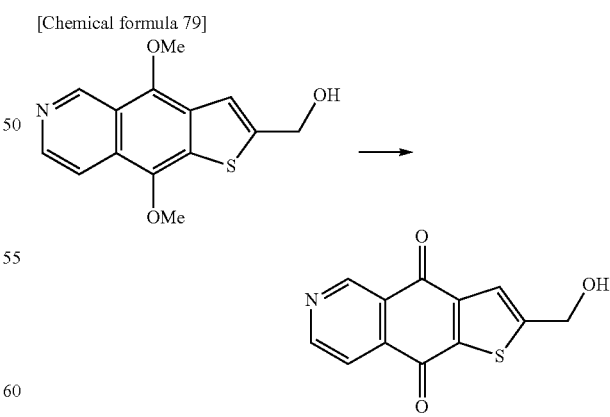

Using (4,9-dimethoxythieno[2,3-g]isoquinolin-2-yl)methanol (20 mg) obtained in Reference example 12 and according to the same method as Example 1, the title compound was obtained as a yellow powder (9.0 mg).

MS (ESI+) 246 (M$^+$+1).

Example 15: 2-(2-hydroxypropan-2-yl)thieno[2,3-g]isoquinoline-4,9-dione (18B)

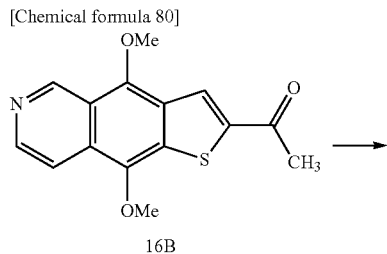

16B

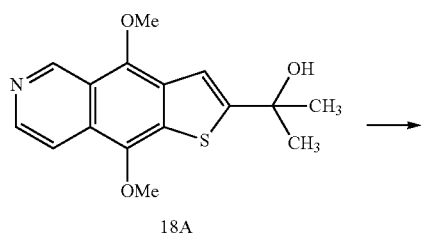

18A

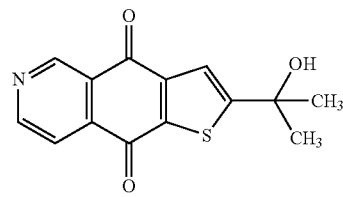

18B

(a) 2-(4,9-Dimethoxythieno[2,3-g]isoquinolin-2-yl)propan-2-ol (18A)

To a solution of 1-(4,9-dimethoxythieno[2,3-g]isoquinolin-2-yl)ethanone (33 mg) (which was obtained in Reference example 11) in THF (1.0 mL), under ice-cooling, was added dropwise 3 N methylmagnesium bromide (1.0 mL), and then the reaction mixture was stirred for 1 hour. Methanol was added to the reaction solution, and then aqueous saturated ammonium chloride solution was added. After extraction with ethyl acetate two times, the resulting organic layer was washed with water and saturated brine, and then dried over sodium sulfate. The solvent was then evaporated off. The resulting residue was purified by silica gel column chromatography (chloroform/methanol) to yield Compound 18A (23 mg).

(b) 2-(2-Hydroxypropan-2-yl)thieno[2,3-g]isoquinoline-4,9-dione (18B)

Using Compound 18A (23 mg) obtained above and according to the same method as Example 1, the title compound 18B was obtained as a yellow powder (9.0 mg).

(18A) MS (ESI+) 304 (M$^+$+1).

(18B) MS (ESI+) 274 (M$^+$+1)

Reference Example 13: 2-[cyclopropyl(ethoxy)methyl]-4,9-dimethoxythieno[2,3-g]isoquinoline (19C)

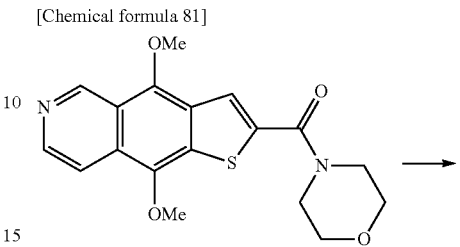

16A

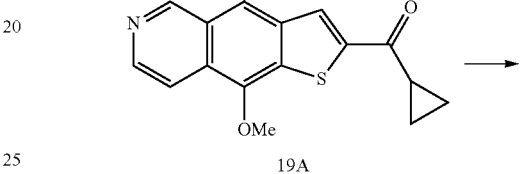

19A

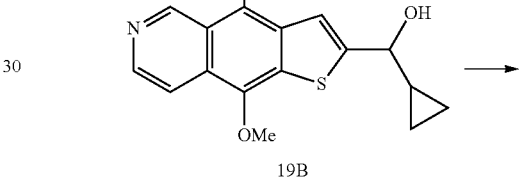

19B

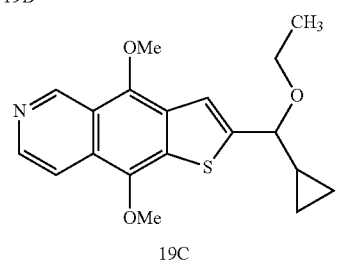

19C

(a) Cyclopropyl(4,9-dimethoxythieno[2,3-g]isoquinolin-2-yl)methanone (19A)

Using (4,9-dimethoxythieno[2,3-g]isoquinolin-2-yl)(morpholin-4-yl)methanone (100 mg) (which was obtained in Reference example 11a) and cyclopropylmagnesium bromide (1.95 mL) and according to the same method as Reference example 6b, Compound 19A was obtained (23 mg).

(b) Cyclopropyl(4,9-dimethoxythieno[2,3-g]isoquinolin-2-yl)methanol (19B)

Using Compound 19A (52 mg) obtained above and according to the same method as Example 2a, Compound 19B was obtained (17 mg).

(c) 2-[Cyclopropyl(ethoxy)methyl]-4,9-dimethoxythieno[2,3-g]isoquinoline (19C)

To a solution of Compound 19B (28 mg) (which obtained above) in THF (1.0 mL), under ice-cooling, was added sodium hydride (6.0 mg), and then the reaction mixture was stirred for 10 minutes. Subsequently, ethyl iodide (28 µL) was added dropwise. After that, dimethylformamide (1.0 mL) was added, and then the reaction mixture was stirred at room temperature for 1 hour. Water was added, and then extracted with ethyl acetate. The resulting organic layer was washed with saturated brine, and then dried over sodium sulfate. The solvent was then evaporated off. The resulting residue was purified by silica gel column chromatography (hexane/ethyl acetate) to yield the title compound 19C (8.0 mg).

(19A) MS (ESI+) 314 (M$^+$+1).
(19B) MS (ESI+) 316 (M$^+$+1).
(19C) MS (ESI+) 344 (M$^+$+1).

Example 16: 2-[cyclopropyl(hydroxy)methyl]thieno[2,3-g]isoquinoline-4,9-dione

[Chemical formula 82]

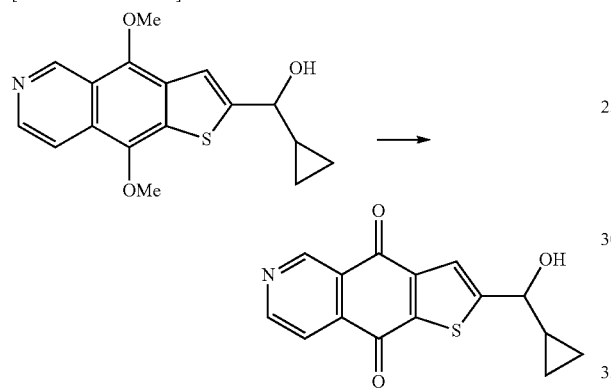

Using cyclopropyl(4,9-dimethoxythieno[2,3-g]isoquinolin-2-yl)methanol (17 mg) obtained in Reference example 13b and according to the same method as Example 1, the title compound was obtained as a yellow powder (9.0 mg).
MS (ESI+) 286 (M$^+$+1).

Example 17: 2-[cyclopropyl(ethoxy)methyl]thieno[2,3-g]isoquinoline-4,9-dione

[Chemical formula 83]

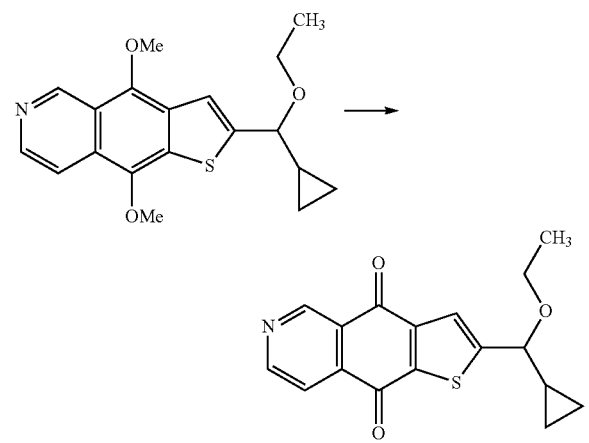

Using 2-[cyclopropyl(ethoxy)methyl]-4,9-dimethoxythieno[2,3-g]isoquinoline (8.0 mg) obtained in Reference example 13c and according to the same method as Example 1, the title compound was obtained as a yellow powder (9.0 mg).
MS (ESI+) 314 (M$^+$+1).

Example 18: 2-[(benzyloxy)methyl]thieno[2,3-g]isoquinoline-4,9-dione (20B)

[Chemical formula 84]

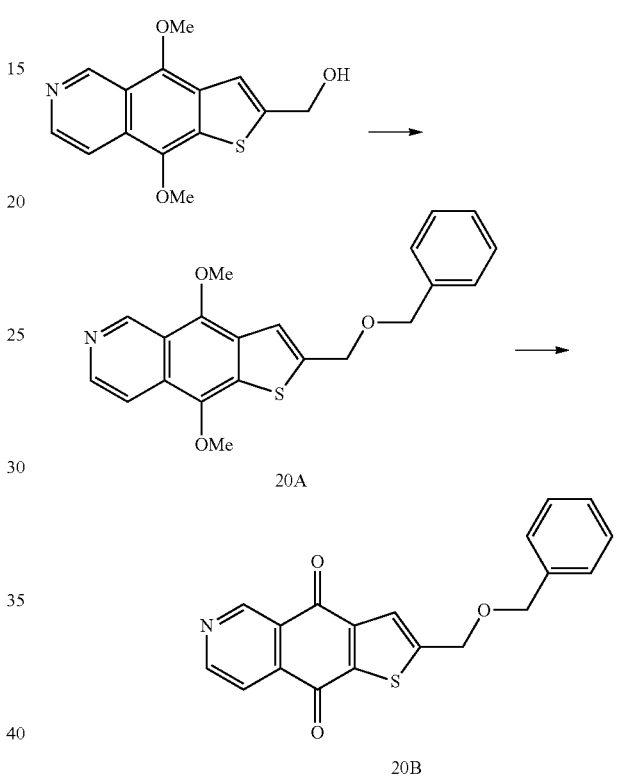

(a) 2-[(Benzyloxy)methyl]-4,9-dimethoxythieno[2,3-g]isoquinoline (20A)

To a solution of (4,9-dimethoxythieno[2,3-g]isoquinolin-2-yl)methanol (20 mg) (which was obtained in Reference example 12), phenol (10 mg), and triphenylphosphine (29 mg) in toluene (2 mL) was added dropwise diisopropyl azodicarboxylate (22 µL), and then the reaction mixture was stirred at room temperature for 2 hours. The reaction solution was purified by silica gel column chromatography (hexane:ethyl acetate=100:0 to 0:100) to yield a mixture comprising Compound 20A.

(b) 2-[(Benzyloxy)methyl]thieno[2,3-g]isoquinoline-4,9-dione (20B)

Using a mixture comprising 20A obtained above and according to the same method as Example 1, the title compound 20B (1.8 mg) was obtained.
(20A) MS (ESI+) 352 (M$^+$+1).
(20B) $^1$H-NMR (DMSO-d$_6$, δppm): 9.36 (1H, br s), 9.20 (1H, br s), 8.03 (1H, br s), 7.88 (1H, s), 7.40 (2H, t, J=7.9 Hz), 7.15 (2H, d, J=7.9 Hz), 7.06 (1H, t, J=7.3 Hz), 5.59 (2H, br s).
MS (ESI+) 323 (M$^+$+1).

Reference Example 14: methyl 4,9-dioxo-4,9-dihydrothieno[2,3-g]isoquinoline-2-carboxylate (21B)

[Chemical formula 85]

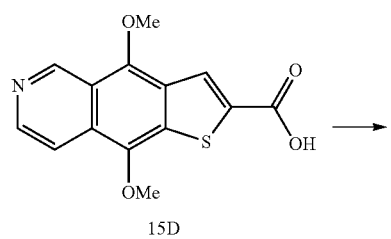

15D

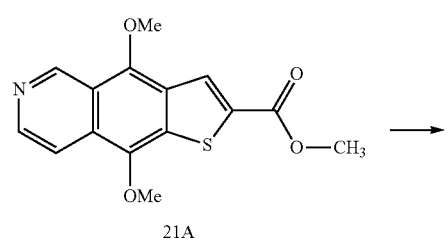

21A

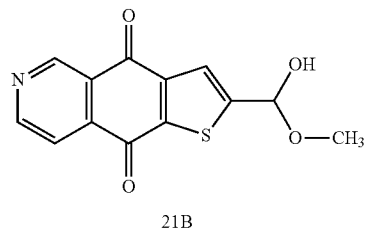

21B (a) Methyl 4,9-dimethoxythieno[2,3-g]isoquinoline-2-carboxylate (21A)

To a solution of 4,9-dimethoxythieno[2,3-g]isoquinoline-2-carboxylic acid (55.0 mg) (which was obtained in Reference example 10) in DMF (10 mL) were added potassium carbonate (50 g) and methyl iodide (10 μL) at room temperature, and then the reaction mixture was stirred for 1 hour. The insoluble was removed by Celite, and then the solvent was evaporated off. The resulting residue was purified by silica gel column chromatography (chloroform/ethyl acetate) to yield Compound 21A (52 mg).

(b) Methyl 4,9-dioxo-4,9-dihydrothieno[2,3-g]isoquinoline-2-carboxylate (21B)

Using Compound 21A (52 mg) obtained above and according to the same method as Example 1, the title compound 21B was obtained as a yellow powder (29 mg).

(21A) MS (ESI+) 304 (M$^+$+1).

(21B) MS (ESI+) 274 (M$^+$+1).

Example 19: N,N-dimethyl-4,9-dioxo-4,9-dihydrothieno[2,3-g]isoquinoline-2-carboxamide (22B)

[Chemical formula 86]

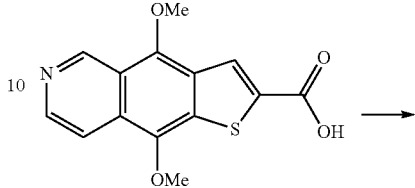

15D

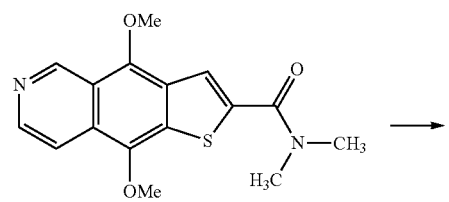

22A

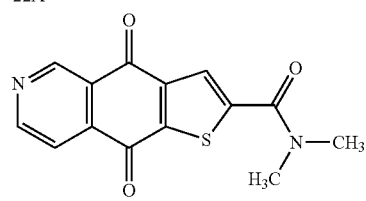

22B (a) 4,9-Dimethoxy-N,N-dimethylthieno[2,3-g]isoquinoline-2-carboxyamide (22A)

Using 4,9-dimethoxythieno[2,3-g]isoquinoline-2-carboxylic acid (99.0 mg) (which was obtained in Reference example 10) and dimethylamine hydrochloride and according to the same method as Reference example 6a, Compound 22A was obtained as a yellow solid (46 mg).

(b) N,N-dimethyl-4,9-dioxo-4,9-dihydrothieno[2,3-g]isoquinoline-2-carboxamide (22B)

Using Compound 22A (46.0 mg) obtained above and according to the same method as Example 1, the title compound 22B was obtained as a pale yellow solid (18.0 mg).

(22A) MS (ESI+) 317 (M$^+$+1).

(22B) MS (ESI+) 287 (M$^+$+1).

Example 20: 2-(morpholin-4-ylcarbonyl)thieno[2,3-g]isoquinoline-4,9-dione

[Chemical formula 87]

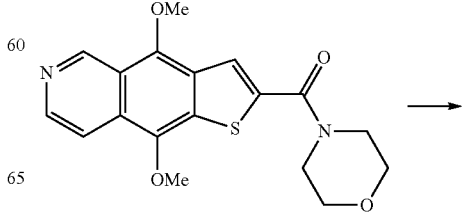

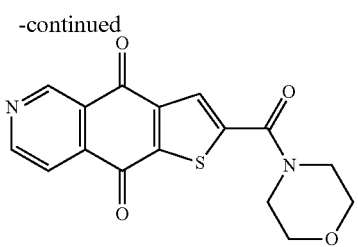

Using Compound 16A (50 mg) obtained in Reference example 11a and according to the same method as Example 1, the title compound was obtained as a pale yellow solid (18.0 mg).

MS (ESI+) 329 (M⁺+1).

Example 21: N-(2,2-difluoroethyl)-4,9-dioxo-4,9-dihydrothieno[2,3-g]isoquinoline-2-carboxyamide (23B)

[Chemical formula 88]

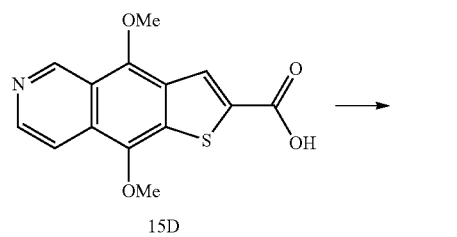

15D

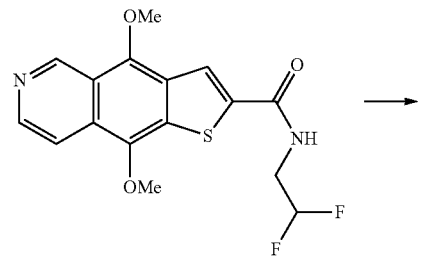

23A

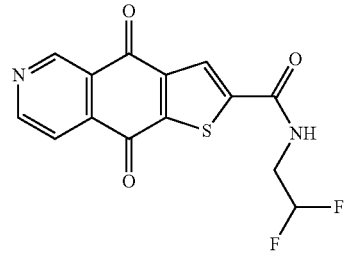

23B (a) N-(2,2-difluoroethyl)-4,9-dimethoxythieno[2,3-g]isoquinoline-2-carboxyamide (23A)

Using 4,9-dimethoxythieno[2,3-g]isoquinoline-2-carboxylic acid (30 mg) (which was obtained in Reference example 10) and 2,2-difluoroethylamine (20 μL) and according to the same method as Reference example 6a, Compound 23A was obtained.

(b) N-(2,2-difluoroethyl)-4,9-dioxo-4,9-dihydrothieno[2,3-g]isoquinoline-2-carboxyamide (23B)

Using Compound 23A obtained above and according to the same method as Example 1, the title compound 23B was obtained as a pale yellow solid (6.1 mg).

(23A) MS (ESI+) 353 (M⁺+1).

(23B) MS (ESI+) 323 (M⁺+1).

Example 22: 3-(morpholin-4-ylcarbonyl)thieno[2,3-g]isoquinoline-4,9-dione (24G)

[Chemical formula 89]

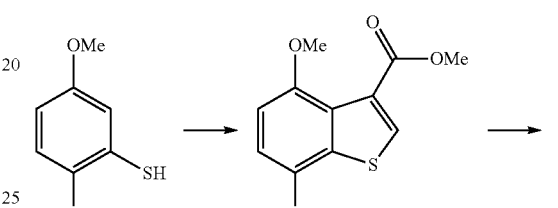

24A

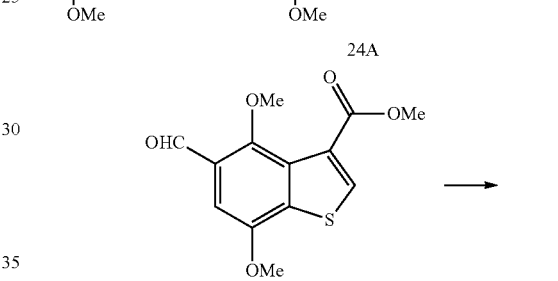

24B

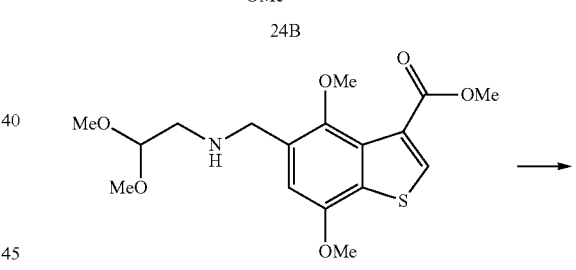

24C

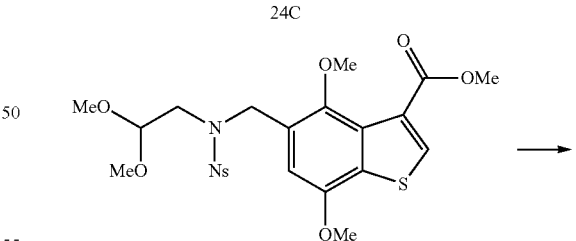

24D

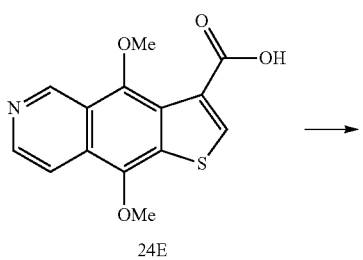

24E

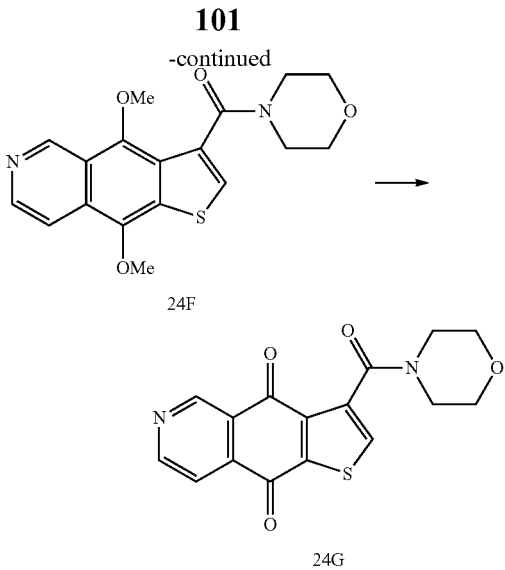

24F

24G (a) Methyl 4,7-dimethoxy-1-benzothiophene-3-carboxylate (24A)

A solution of 2,5-dimethoxythiophenol (1 g), azobisisobutyronitrile (19 mg), and methyl propiolate (0.53 mL) in trifluorotoluene (5 mL) was stirred at 90° C. for 2 hours. The residue resulting from the concentration of the reaction solution under reduced pressure was purified by silica gel column chromatography (hexane:ethyl acetate=100:0 to 70:30) to yield Compound 24A (130 mg).

(b) Methyl 5-formyl-4,7-dimethoxy-1-benzothiophene-3-carboxylate (24B)

Using Compound 24A (130 mg) obtained above and according to the same procedure as Reference example 10a, Compound 24B (96 mg) was obtained.

(c) Methyl 5-{[(2,2-dimethoxyethyl)amino]methyl}-4,7-dimethoxy-1-benzothiophene-3-carboxylate (24C)

Using Compound 24B (96 mg) obtained above and according to the same method as Reference example 10b, Compound 24C was obtained as a crude product. The whole amount thereof was used in the next reaction without further purification.

(d) Methyl 5-({(2,2-dimethoxyethyl) [(2-nitrophenyl)sulfonyl]amino}methyl)-4,7-dimethoxy-1-benzothiophene-3-carboxylate (24D)

Using the crude product of Compound 24C obtained above and according to the same procedure as Reference example 10c, Compound 24D (174 mg) was obtained.

(e) 4,9-Dimethoxythieno[2,3-g]isoquinoline-3-carboxylic Acid (24E)

To a solution of Compound 24D (174 mg) (which was obtained above) in 1,4-dioxane (1 mL) was added 35% hydrochloric acid (1 mL), and then the reaction mixture was heated at reflux for 5 hours. The reaction solution was poured into iced water, and then the precipitated solid was removed by Celite filtration. The filtrate was neutralized with 28% ammonia water, and then extracted with ethyl acetate. The organic layer was dried over anhydrous sodium sulfate, filtered, and then concentrated under reduced pressure. The resulting residue was recrystallized from a mixed solution of ethyl acetate and hexane to yield Compound 24E (7 mg).

(f) (4,9-Dimethoxythieno[2,3-g]isoquinolin-3-yl)(morpholin-4-yl)methanone (24F)

Using the above-described Compound 24E (7 mg) and according to the same procedure as Reference example 6a, Compound 24F (8 mg) was obtained.

(g) 3-(Morpholin-4-ylcarbonyl)thieno[2,3-g]isoquinoline-4,9-dione (24G)

Using the above-described Compound 24F (8 mg) and according to the same method as Example 1, the title compound 24G (2.8 mg) was obtained.

(24A) $^1$H-NMR (DMSO-d$_6$, δppm): 8.04 (1H, s), 6.93 (2H, d, J=8.5 Hz), 6.89 (2H, d, J=8.5 Hz), 3.90 (3H, s), 3.82 (3H, s), 3.80 (3H, s).
MS (ESI+) 253 (M$^+$+1).
(24B) $^1$H-NMR (DMSO-d$_6$, δppm): 10.36 (1H, s), 8.38 (1H, s), 7.14 (1H, s), 4.08 (3H, s), 3.89 (3H, s), 3.84 (3H, s).
MS (ESI+) 281 (M$^+$+1).
(24C) MS (ESI+) 370 (M$^+$+1).
(24D) $^1$H-NMR (DMSO-d$_6$, δppm): 8.10-8.07 (2H, m), 8.00 (1H, d, J=7.3 Hz), 7.87 (1H, td, J=7.9, 1.2 Hz), 7.78 (1H, td, J=7.6, 1.2 Hz), 6.63 (1H, s), 4.75 (2H, s), 4.37 (1H, t, J=5.2 Hz), 3.85 (3H, s), 3.81 (3H, s), 3.63 (3H, s), 3.34 (2H, d, J=4.9 Hz).
MS (ESI+) 555 (M$^+$+1).
(24E) $^1$H-NMR (DMSO-d$_6$, δppm): 13.40 (1H, br s), 9.58 (1H, s), 8.53 (1H, d, J=6.1 Hz), 8.26 (1H, s), 8.01 (1H, d, J=6.1 Hz), 4.16 (3H, s), 3.94 (3H, s).
MS (ESI+) 290 (M$^+$+1).
(24F) MS (ESI+) 359 (M$^+$+1).
(24G) $^1$H-NMR (DMSO-d$_6$, δppm): 9.29 (1H, s), 9.13 (1H, br s), 8.26 (1H, br s), 7.98 (1H, br s), 3.80-3.56 (4H, m), 3.49-3.40 (2H, m), 3.22-3.04 (2H, m).
MS (ESI+) 329 (M$^+$+1)

Example 23: 2-[1-(morpholin-4-yl)ethyl]thieno[2,3-g]isoquinoline-4,9-dione (25C)

[Chemical formula 90]

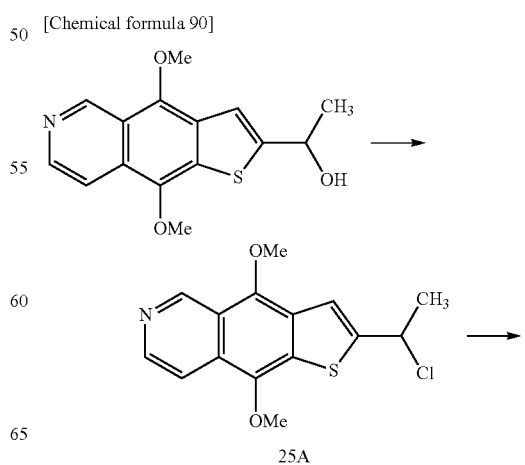

25A

-continued

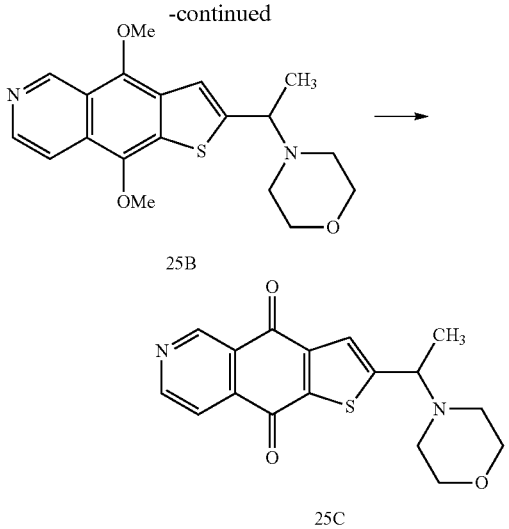

(a) 2-(1-Chloroethyl)-4,9-dimethoxythieno[2,3-g]isoquinoline (25A)

Using 1-(4,9-dimethoxythieno[2,3-g]isoquinolin-2-yl)ethanol (36.5 mg) obtained in Example 13a and according to the same method as Reference example 7b, Compound 25A was obtained as a yellow solid.

(b) 4,9-Dimethoxy-2-[1-(morpholin-4-yl)ethyl]thieno[2,3-g]isoquinoline (25B)

Using Compound 25A (which was obtained above) and morpholine and according to the same method as Reference example 8, Compound 25B was obtained (5.9 mg).

(c) 2-[1-(Morpholin-4-yl)ethyl]thieno[2,3-g]isoquinoline-4,9-dione (25C)

Using Compound 25B (5.7 mg) obtained above and according to the same method as Example 1, the title compound 25C was obtained as a yellow solid (5.0 mg).

(25A) MS (ESI+) 308 (M$^+$+1).
(25B) MS (ESI+) 359 (M$^+$+1).
(25C) MS (ESI+) 329 (M$^+$+1).

Reference Example 15: 2-(chloromethyl)-4,9-dimethoxythieno[2,3-g]isoquinoline

[Chemical formula 91]

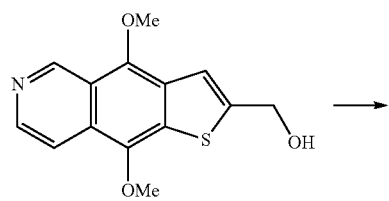

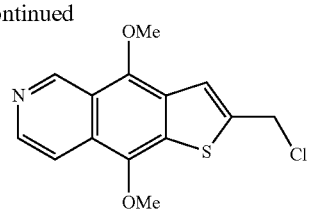

Using (4,9-dimethoxythieno[2,3-g]isoquinolin-2-yl)methanol (190 mg) obtained in Reference example 12 and according to the same method as Reference example 7b, the title compound was obtained as a crude product (265 mg). This was used in the next reaction without further purification.

MS (ESI+) 294 (M$^+$+1)

Example 24: 2-{[ethyl(2-methoxyethyl)amino]methyl}thieno[2,3-g]isoquinoline-4,9-dione (26A)

[Chemical formula 92]

(a) N-[(4,9-dimethoxythieno[2,3-g]isoquinolin-2-yl)methyl]-N-ethyl-2-methoxyethaneamine (26A)

Using 2-(chloromethyl)-4,9-dimethoxythieno[2,3-g]isoquinoline (which was obtained in Reference example 15) in acetonitrile (1.0 mL) and N-ethyl-2-methoxyethaneamine (14 μL) and according to the same method as Reference example 8, Compound 26A was obtained (20 mg).

(b) 2-{[Ethyl(2-methoxyethyl)amino]methyl}thieno[2,3-g]isoquinoline-4,9-dione (26B)

Using N-[(4,9-dimethoxythieno[2,3-g]isoquinolin-2-yl)methyl]-N-ethyl-2-methoxyethaneamine (20 mg) obtained above and according to the same method as Example 1, the title compound 26B was obtained as a yellow solid (13.2 mg).

(26A) MS (ESI+) 361 (M⁺+1)
(26B) MS (ESI+) 331 (M⁺+1)

Example 25: cyclohexyl(ethyl)amino]methyl}thieno[2,3-g]isoquinoline-4,9-dione (27B)

[Chemical formula 93]

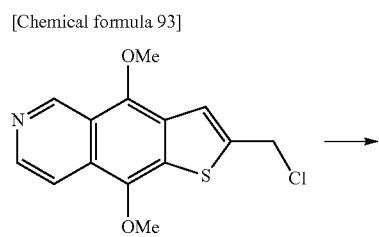

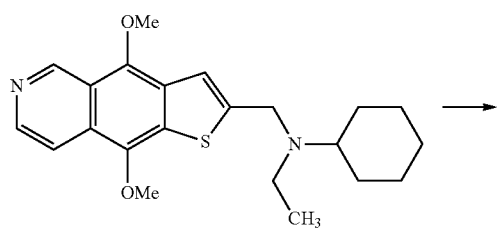

27A

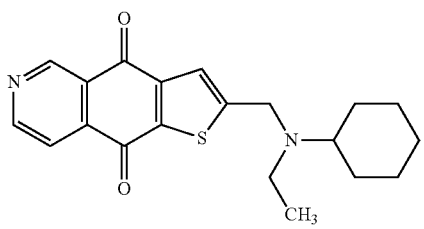

27B (a) N-[(4,9-dimethoxythieno[2,3-g]isoquinolin-2-yl)methyl]-N-ethylcyclohexylamine (27A)

Using 2-(chloromethyl)-4,9-dimethoxythieno[2,3-g]isoquinoline (30 mg) (which was obtained in Reference example 15) and N-ethylcyclohexylamine (17 μL) and according to the same method as Reference example 8, Compound 27A was obtained (16 mg).

(b) 2-{[Cyclohexyl(ethyl)amino]methyl}thieno[2,3-g]isoquinoline-4,9-dione (27B)

Using N-[(4,9-dimethoxythieno[2,3-g]isoquinolin-2-yl)methyl]-N-ethylcyclohexylamine (16.0 mg) obtained above and according to the same method as Example 1, the title compound 27B was obtained as a yellow solid (13.2 mg).

(27A) MS (ESI+) 385 (M⁺+1).
(27B) MS (ESI+) 355 (M⁺+1).

Example 26: 2-{[(2,2-difluoroethyl)amino]methyl}thieno[2,3-g]isoquinoline-4,9-dione (28B)

[Chemical formula 94]

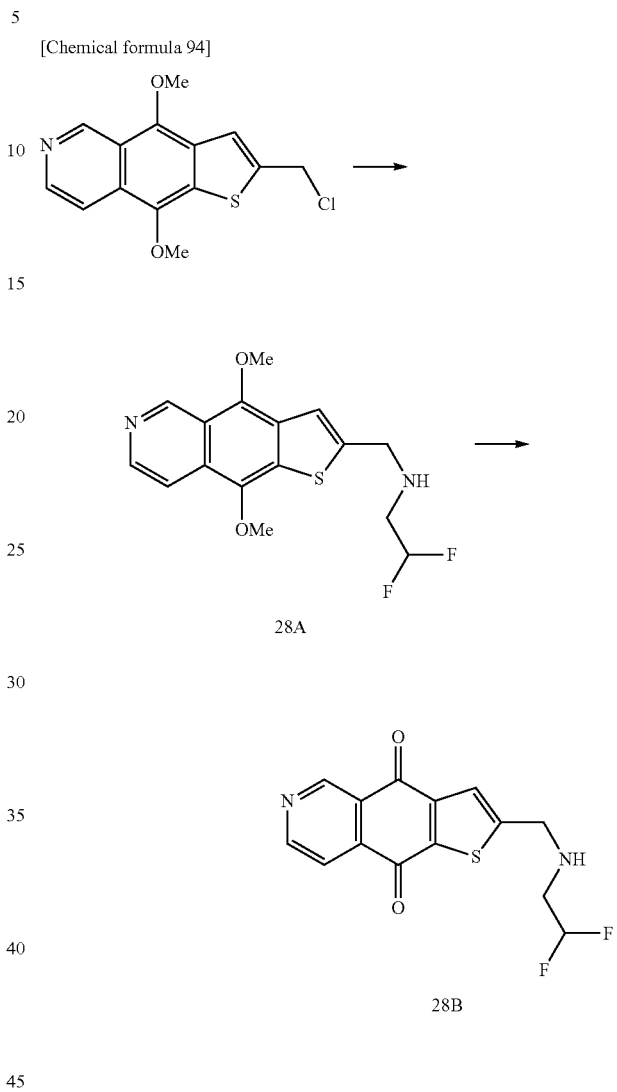

(a) N-[(4,9-dimethoxythieno[2,3-g]isoquinolin-2-yl)methyl]-2,2-difluoroethaneamine (28A)

Using 2-(chloromethyl)-4,9-dimethoxythieno[2,3-g]isoquinoline (30 mg) (which was obtained in Reference example 15) and 2,2-difluoroethylamine (70 μL) and according to the same method as Reference example 8, Compound 28A was obtained (21 mg).

(b) 2-{[(2,2-Difluoroethyl)amino]methyl}thieno[2,3-g]isoquinoline-4,9-dione (28B)

Using N-[(4,9-dimethoxythieno[2,3-g]isoquinolin-2-yl)methyl]-2,2-difluoroethaneamine (21 mg) obtained above and according to the same method as Example 1, the title compound 28B was obtained as a yellow solid (13.2 mg).

(28A) MS (ESI+) 385 (M⁺+1).
(28B) MS (ESI+) 309 (M⁺+1)

Example 27: 2-[(4-acetylpiperazin-1-yl)methyl]thieno[2,3-g]isoquinoline-4,9-dione (29B)

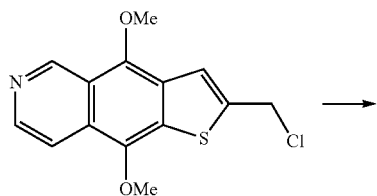

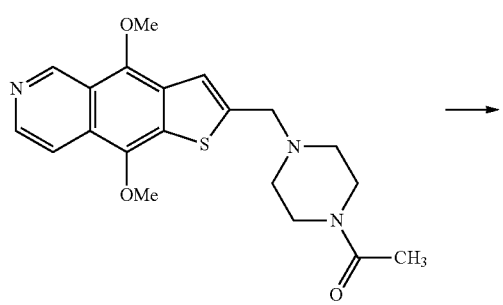

(a) 1-{4-[(4,9-Dimethoxythieno[2,3-g]isoquinolin-2-yl)methyl]piperazin-1-yl}ethanone (29A)

Using 2-(chloromethyl)-4,9-dimethoxythieno[2,3-g]isoquinoline (30 mg) (which was obtained in Reference example 15) and 1-acetylpiperazine (14 mg) and according to the same method as Reference example 8, Compound 29A was obtained (21 mg).

(b) 2-[(4-Acetylpiperazin-1-yl)methyl]thieno[2,3-g]isoquinoline-4,9-dione (29B)

Using 1-{4-[(4,9-dimethoxythieno[2,3-g]isoquinolin-2-yl)methyl]piperazin-1-yl}ethanone (9.7 mg) obtained above and according to the same method as Example 1, the title compound 29B was obtained as a yellow solid (2.6 mg).

(29A) MS (ESI+) 386 (M$^+$+1)

(29B) MS (ESI+) 356 (M$^+$+1)

Example 28: N-(2,2-difluoroethyl)-N-((4,9-dioxo-4,9-dihydrothieno[2,3-g]isoquinolin-2-yl)methyl)cyclohexanecarboxamide (30B)

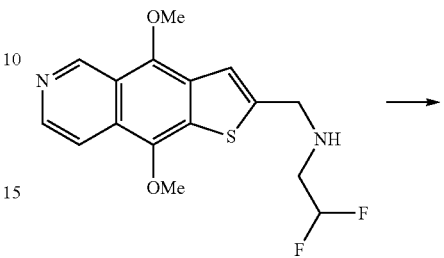

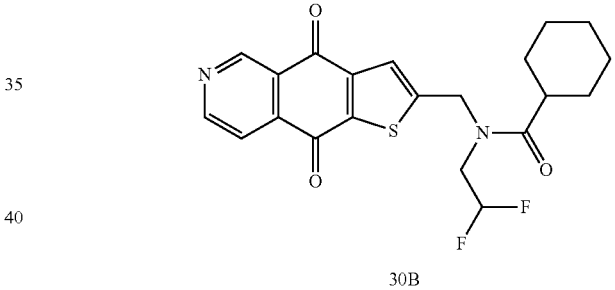

(a) N-(2,2-difluoroethyl)-N-[(4,9-dimethoxythieno[2,3-g]isoquinolin-2-yl)methyl]cyclohexanecarboxyamide (30A)

Using N-[(4,9-dimethoxythieno[2,3-g]isoquinolin-2-yl)methyl]-2,2-difluoroethaneamine (36 mg) (which was obtained in Example 26a) and cyclohexanecarbonyl chloride (16 μL) and according to the same method as Example 9a, Compound 30A was obtained (48 mg).

(b) N-(2,2-Difluoroethyl)-N-[(4,9-dihydrothieno[2,3-g]isoquinolin-2-yl)methyl]cyclohexanecarboxyamide (30B)

Using Compound 30A (48 mg) obtained above and according to the same method as Example 1, the title compound 30B was obtained as a yellow solid (1.2 mg).

(30A) MS (ESI+) 449 (M$^+$+1).

(30B) MS (ESI+) 419 (M$^+$+1).

Example 29: 4,9-dioxo-4,9-dihydrothieno[2,3-g]isoquinoline-2-carbonitrile (31D)

[Chemical formula 97]

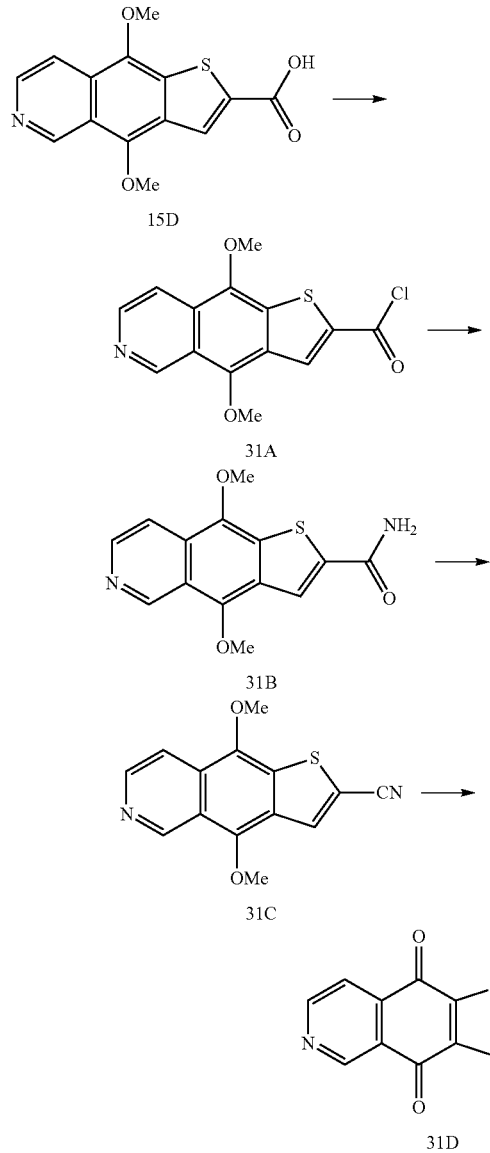

(a) 4,9-Dimethoxythieno[2,3-g]isoquinoline-2-carbonyl Chloride (31A)

To 4,9-dimethoxythieno[2,3-g]isoquinoline-2-carboxylic acid (50 mg) (which was obtained in Reference example 10) was added thionyl chloride (2.0 mL), and the reaction mixture was heated at reflux for 1 hour. After the solvent was evaporated off, the resulting residue was suspended in diethyl ether, and then collected by filtration to yield Compound 31A (37 mg).

(b) 4,9-Dimethoxythieno[2,3-g]isoquinoline-2-carboxyamide (31B)

To Compound 31A (33 mg) (which was obtained above) was added 28% aqueous ammonia solution (2.0 mL), and then the reaction mixture was stirred for 1 hour. From the reaction solution, the solid was collected by filtration to yield Compound 31B (20.0 mg).

(c) 4,9-Dimethoxythieno[2,3-g]isoquinoline-2-carbonitrile (31C)

To Compound 31B (20.0 mg) (which was obtained above) was added phosphoryl chloride (1.0 mL), and then the reaction mixture was heated at reflux for 1 hour. After the solvent was evaporated off, chloroform followed by aqueous saturated sodium hydrogen carbonate solution were added. After extraction with ethyl acetate two times, the resulting organic layer was washed with water and saturated brine, and then dried over sodium sulfate. The solvent was then evaporated off. The resulting residue was purified by silica gel column chromatography (chloroform/methanol) to yield Compound 31C (24 mg).

(d) 4,9-Dioxo-4,9-dihydrothieno[2,3-g]isoquinoline-2-carbonitrile (31D)

Using Compound 31C (24 mg) obtained above and according to the same method as Example 1, the title compound 31D was obtained as a yellow solid (1.2 mg).

(31B) MS (ESI+) 289 ($M^+$+1).
(31C) MS (ESI+) 304 ($M^+$+1).
(31D) MS (ESI+) 241 ($M^+$+1).

Example 30: 2-(1-fluoroethyl)thieno[2,3-g]isoquinoline-4,9-dione (32B)

[Chemical formula 98]

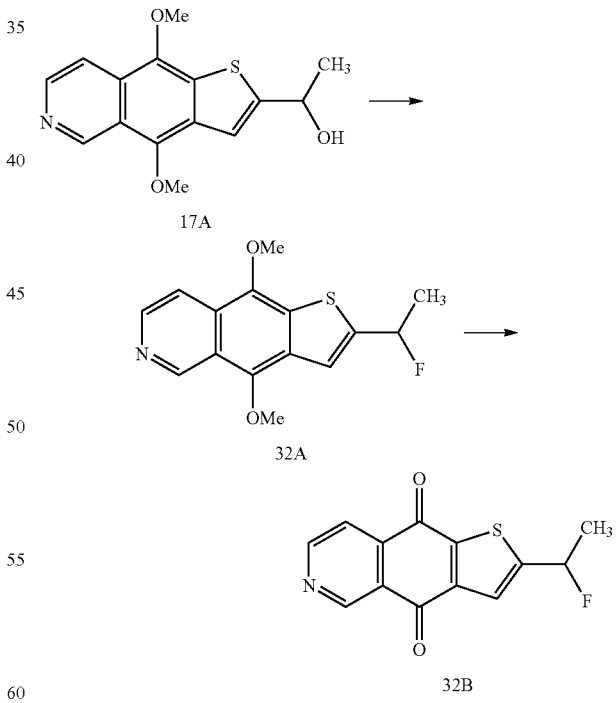

(a) 2-(1-Fluoroethyl)-4,9-dimethoxythieno[2,3-g]isoquinoline (32A)

To a solution of 1-(4,9-dimethoxythieno[2,3-g]isoquinolin-2-yl)ethanol (46 mg) (which was obtained in Example 13a) in dichloromethane (1.0 mL), under ice-cooling, was added FLUOLEAD™ (66 mg), and then the reaction mixture was stirred for 1 hour. Aqueous sodium hydroxide solution (2 N) was added thereto. After extraction with ethyl acetate, the resulting organic layer was washed with water and saturated brine, and then dried over sodium sulfate. The solvent was then evaporated off. The resulting residue was purified by silica gel column chromatography (chloroform/methanol) to yield Compound 32A (24 mg).

(b) 2-(1-Fluoroethyl)thieno[2,3-g]isoquinoline-4,9-dione (32B)

Using Compound 32A (24 mg) obtained above and according to the same method as Example 1, the title compound 32B was obtained as a yellow solid (1.2 mg).
(32A) MS (ESI+) 292 (M$^+$+1).
(32B) MS (ESI+) 262 (M$^+$+1).

Example 31: 2-(3-ethyl-1,2,4-oxadiazol-5-yl)thieno[2,3-g]isoquinoline-4,9-dione (33B)

[Chemical formula 99]

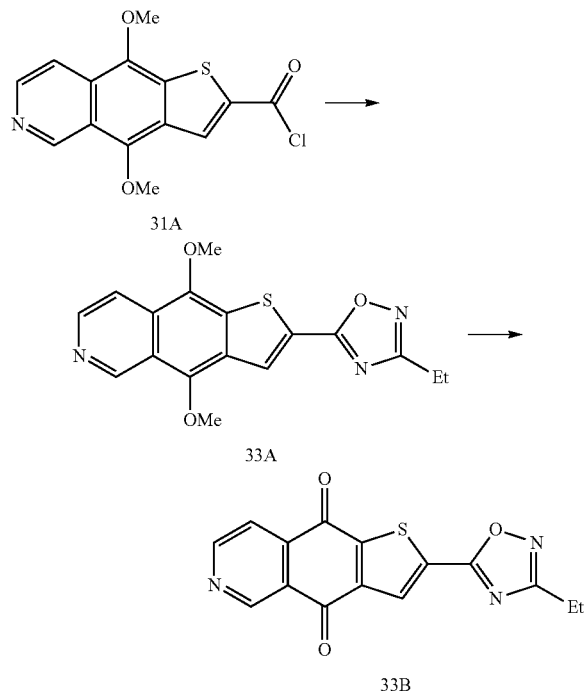

(a) 2-(3-Ethyl-1,2,4-oxadiazol-5-yl)-4,9-dimethoxythieno[2,3-g]isoquinoline (33A)

To a solution of 4,9-dimethoxythieno[2,3-g]isoquinoline-2-carbonyl chloride (960 mg) (which was obtained in Example 29a) in chloroform (40 mL) were added N-hydroxypropionamidine (288 mg) and Hunig's base (1.6 mL), and then the reaction mixture was stirred at room temperature for 1 hour. Aqueous saturated sodium hydrogen carbonate solution was added to the reaction solution, and then extraction with ethyl acetate was performed. The resulting organic layer was washed with saturated brine, and then dried over sodium sulfate. The solvent was then evaporated off. To the solution of the resulting residue in THF (20 mL), tetra-N-butylammonium fluoride (2.5 mL) was added, followed by heating at reflux for 1 hour. The reaction solution was returned to room temperature, aqueous saturated sodium hydrogen carbonate solution was added thereto, and then extraction with ethyl acetate was performed. The resulting organic layer was washed with saturated brine, and then dried over sodium sulfate. The solvent was then evaporated off. The resulting residue was suspended in methanol and collected by filtration to yield Compound 33A (285 mg).

(b) 2-(3-Ethyl-1,2,4-oxadiazol-5-yl)thieno[2,3-g]isoquinoline-4,9-dione (33B)

Using Compound 33A (50 mg) obtained above and according to the same method as Example 1, the title compound 33B was obtained as a yellow solid (32 mg).
(33A) MS (ESI+) 342 (M$^+$+1).
(33B) MS (ESI+) 312 (M$^+$+1)

Example 32: 2-(morpholin-4-yl)thieno[2,3-g]isoquinoline-4,9-dione (34D)

[Chemical formula 100]

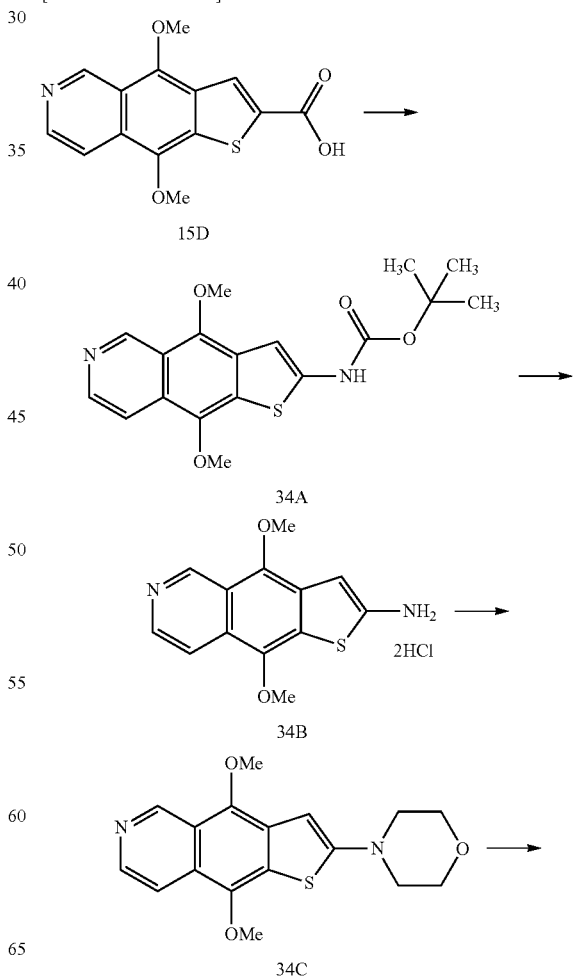

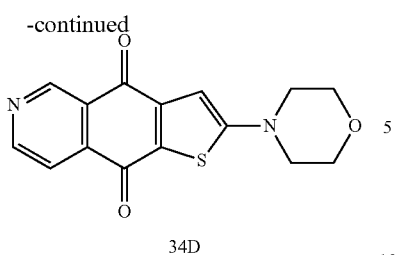

34D (a) Tert-butyl (4,9-dimethoxythieno[2,3-g]isoquinolin-2-yl)carbamate (34A)

A solution of 4,9-dimethoxythieno[2,3-g]isoquinoline-2-carboxylic acid (200 mg) (which was obtained in Reference example 10), diisopropylethylamine (120 μL), diphenylphosphoryl azide (310 μL), and tert-butyl alcohol (1 mL) in NMP (1 mL) was stirred at room temperature for 30 minutes, and then heated at reflux for 2 hours. The reaction solution was purified by silica gel column chromatography (hexane:ethyl acetate=50:50 to 0:100) to yield Compound 34A (140 mg).

(b) 4,9-Dimethoxythieno[2,3-g]isoquinoline-2-amine.dihydrochloride (34B)

To Compound 34A (140 mg) obtained above was added 4 mol/L solution (3 mL) of hydrogen chloride in 1,4-dioxane, and then the reaction mixture was stirred at room temperature for 1 hour. The reaction solution was concentrated under reduced pressure to yield Compound 34B (110 mg).

(c) 4,9-Dimethoxy-2-(morpholin-4-yl)thieno[2,3-g]isoquinoline (34C)

A solution of Compound 34B (50 mg) (which was obtained above), diisopropylethylamine (260 μL), and bis-bromoethyl ether (94 μL) in DMF (1.5 mL) was stirred at 90° C. for 2 hours. Cesium carbonate (100 mg) was added to the reaction solution, which was then stirred at 120° C. for another 3 hours. Water (5 mL) was added to the reaction solution, which was then extracted with ethyl acetate. The organic layer was dried over anhydrous sodium sulfate, filtered, and then concentrated under reduced pressure. The resulting residue was purified by silica gel column chromatography (hexane:ethyl acetate=100:0 to 0:100) to yield a mixture comprising Compound 34C.

(d) 2-(Morpholin-4-yl)thieno[2,3-g]isoquinoline-4,9-dione (34D)

Using a mixture comprising Compound 34C obtained above and according to the same method as Example 1, the title compound 34D was obtained (1.3 mg).

(34A) MS (ESI+) 361 (M$^+$+1).
(34B) MS (ESI+) 261 (M$^+$+1).
(34C) MS (ESI+) 331 (M$^+$+1).
(34D) MS (ESI+) 301 (M$^+$+1)

Reference Example 16: 4,9-dimethoxythieno[3,2-g]isoquinoline-2-carboxylic Acid (35E)

[Chemical formula 101]

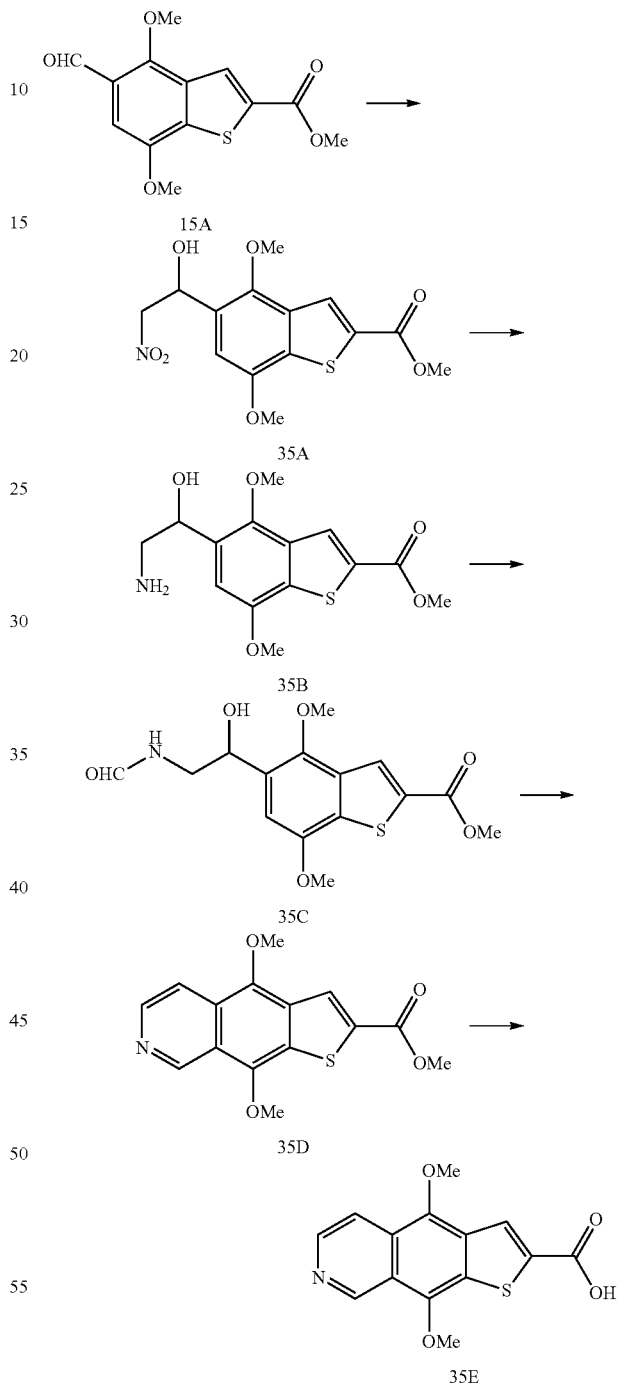

(a) Methyl 5-(1-hydroxy-2-nitroethyl)-4,7-dimethoxy-1-benzothiophene-2-carboxylate (35A)

A solution of methyl 5-formyl-4,7-dimethoxy-1-benzothiophene-2-carboxylate (10 g) (which was obtained in Reference example 10a) and diisopropylethylamine (40 mL) in nitromethane (200 mL) was stirred at room temperature for 4 hours. Thirty percent aqueous sodium hydrogen sulfite solution (200 mL) was added to the reaction solution, it was stirred for 30 minutes, and then extraction with ethyl acetate was performed. The organic layer was washed with saturated sodium hydrogen carbonate, dried over anhydrous sodium sulfate, filtered, and then concentrated under reduced pressure to yield Compound 35A. This product was used in the next reaction without further purification.

(b) Methyl 5-(2-amino-1-hydroxyethyl)-4,7-dimethoxy-1-benzothiophene-2-carboxylate (35B)

To a solution of Compound 35A (which was obtained above) and nickel chloride hexahydrate (33.9 g) in methanol (300 mL), under ice-cooling, was added portionwise sodium borohydride (5.4 g) over a period of 30 or more minutes, and then the reaction mixture was stirred for another hour. Water (200 mL) was added to the reaction solution, and then the precipitated solid was removed through Celite filtration. After methanol was evaporated off under reduced pressure, the aqueous layer was extracted with ethyl acetate, and then the organic layer was washed with 28% ammonium water. The organic layer was dried over anhydrous sodium sulfate, filtered, and then concentrated under reduced pressure. The resulting residue was purified by silica gel column chromatography (hexane:ethyl acetate=20:80 to 0:100, then chloroform:methanol=100:0 to 90:10) to yield Compound 35B (9 g).

(c) Methyl 5-[2-(formylamino)-1-hydroxyethyl]-4,7-dimethoxy-1-benzothiophene-2-carboxylate (35C)

A solution of Compound 35B (9 g) (which was obtained above) and acetic anhydride (450 µL) in formic acid (100 mL) was heated at reflux for 3 hours. To the residue resulting from the concentration of the reaction solution under reduced pressure, saturated potassium carbonate/methanol solution (100 mL) was added, and then the reaction mixture was stirred at room temperature for 2 hours. The reaction solution was filtered through Celite, and then the filtrate was concentrated under reduced pressure. Water (100 mL) was added to the resulting residue, and then it was extracted with ethyl acetate. The organic layer was dried over anhydrous sodium sulfate, filtered, and then concentrated under reduced pressure. The resulting residue recrystallized from mixed solution of ethyl acetate and hexane to yield Compound 35C (8 g).

(d) Methyl 4,9-dimethoxythieno[3,2-g]isoquinoline-2-carboxylate (35D)

A solution of Compound 35C (1.7 g) (which was obtained above) and phosphorus oxychloride (1.4 mL) in acetonitrile (5 mL) was heated at reflux for 3 hours. The residue resulting from the concentration of the reaction solution under reduced pressure was neutralized with aqueous saturated sodium hydrogen carbonate solution. The aqueous layer was extracted with ethyl acetate. The organic layer was dried over anhydrous sodium sulfate, filtered, and then concentrated under reduced pressure. The resulting residue was purified by silica gel column chromatography (hexane:ethyl acetate=100:0 to 50:50) to Compound 35D to yield (320 mg).

(e) 4,9-Dimethoxythieno[3,2-g]isoquinoline-2-carboxylic Acid (35E)

Using Compound 35D (320 mg) obtained above and according to the same method as Reference example 5, the title compound 35E was obtained (297 mg).

(35A) $^1$H-NMR (DMSO-$d_6$, δppm): 8.13 (1H, s), 7.20 (1H, s), 6.19 (1H, d, J=5.5 Hz), 5.71-5.65 (1H, m), 4.81-4.6 (2H, m), 3.97 (3H, s), 3.94 (3H, s), 3.89 (3H, s).

MS (ESI+) 342 (M$^+$+1).

(35B) MS (ESI+) 312 (M$^+$+1).

(35C) $^1$H-NMR (DMSO-$d_6$, δppm): 8.21 (1H, s), 8.09 (1H, s), 6.97 (1H, s), 6.05-5.94 (1H, m), 5.27-5.19 (1H, m), 3.97 (3H, s), 3.95 (3H, s), 3.93 (3H, s), 3.80-3.72 (1H, m), 3.58-3.49 (1H, m).

MS (ESI+) 340 (M$^+$+1).

(35D) $^1$H-NMR (DMSO-$d_6$, δppm): 9.61 (1H, s), 8.55 (1H, d, J=6.1 Hz), 8.36 (1H, s), 8.04 (1H, d, J=6.1 Hz), 4.19 (3H, s), 4.14 (3H, s), 3.94 (3H, s).

MS (ESI+) 304 (M$^+$+1).

(35E) $^1$H-NMR (DMSO-$d_6$, δppm): 14.03 (1H, br s), 9.58 (1H, s), 8.53 (1H, s), 8.17 (1H, s), 8.02 (1H, s), 4.18 (3H, s), 4.12 (3H, s).

MS (ESI+) 290 (M$^+$+1).

Reference Example 17: 1-(4,9-dimethoxythieno[3,2-g]isoquinolin-2-yl)ethanone (36B)

[Chemical formula 102]

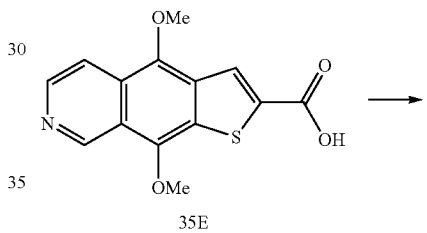

35E

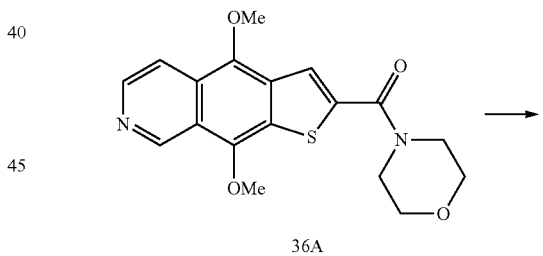

36A

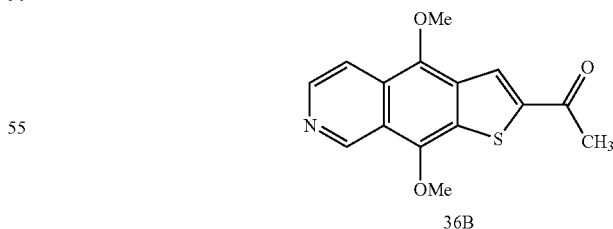

36B

Using 4,9-dimethoxythieno[3,2-g]isoquinoline-2-carboxylic acid (29 mg) obtained in Reference example 16 and according to the same method as Reference example 6, the title compound 36B was obtained.

(36A) MS (ESI+) 359 (M$^+$+1).

(36B) MS (ESI+) 288 (M$^+$+1).

Example 33: 2-acetylthieno[3,2-g]isoquinoline-4,9-dione

[Chemical formula 103]

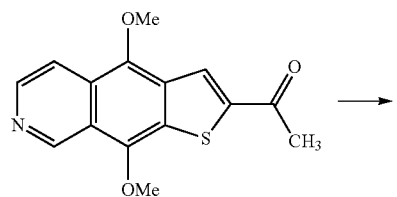

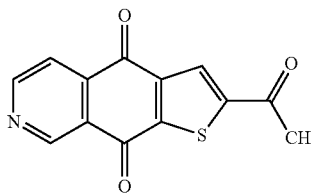

Using 1-(4,9-dimethoxythieno[3,2-g]isoquinolin-2-yl)ethanone obtained in Reference example 17 and according to the same method as Example 1, synthesis was carried out to yield the title compound (5.5 mg).

$^1$H-NMR (DMSO-d$_6$, δppm): 9.26 (1H, s), 9.10 (1H, br s), 7.96 (1H, br s), 7.55 (1H, s), 6.15 (1H, d, J=4.9 Hz), 5.09 (1H, br s), 1.48 (3H, d, J=6.1 Hz).

MS (ESI+) 258 (M$^+$+1).

Example 34: 1-(4,9-dimethoxythieno[3,2-g]isoquinolin-2-yl)ethanol (37B)

[Chemical formula 104]

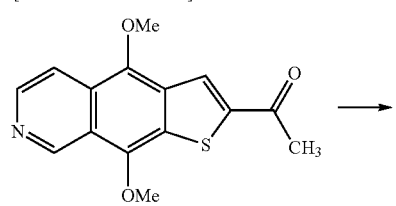

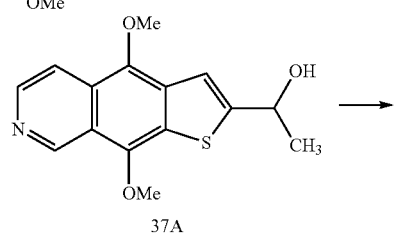

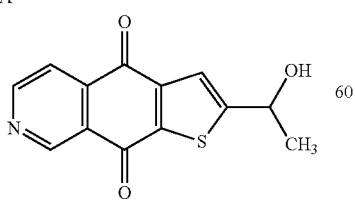

Using 1-(4,9-dimethoxythieno[3,2-g]isoquinolin-2-yl)ethanone (40 mg) obtained in Reference example 17 and according to the same method as Example 2, synthesis was carried out to yield the title compound 37B (12 mg).

(37A) MS (ESI+) 290 (M$^+$+1).

(37B) $^1$H-NMR (DMSO-d$_6$, δppm): 9.26 (1H, s), 9.10 (1H, br s), 7.96 (1H, br s), 7.55 (1H, s), 6.15 (1H, d, J=4.9 Hz), 5.09 (1H, br s), 1.48 (3H, d, J=6.1 Hz).

MS (ESI+) 260 (M$^+$+1).

Example 35: N-[(4,9-dimethoxythieno[3,2-g]isoquinolin-2-yl)methyl]-2,2-difluoroethaneamine (38E)

[Chemical formula 105]

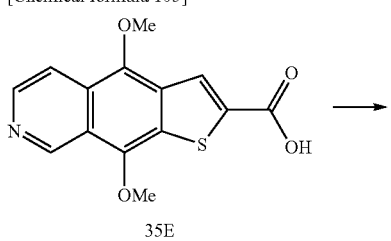

35E

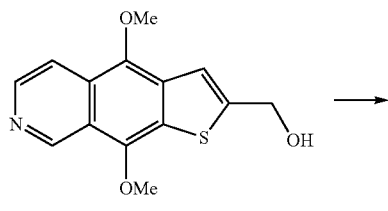

38A

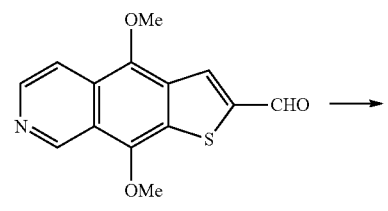

38B

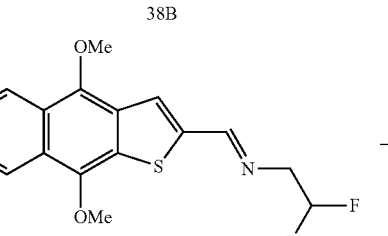

38C

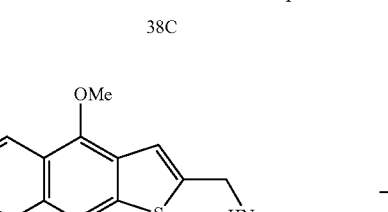

38D

-continued

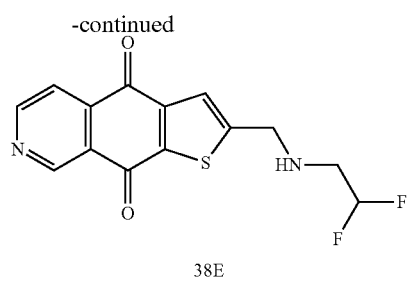

38E

(a) (4,9-Dimethoxythieno[3,2-g]isoquinolin-2-yl) methanol (38A)

Using 4,9-dimethoxythieno[3,2-g]isoquinoline-2-carboxylic acid (60 mg) obtained in Reference example 16 and according to the same method as Reference example 12, synthesis was carried out to yield Compound 38A (37 mg).

(b) 4,9-Dimethoxythieno[3,2-g]isoquinoline-2-carbaldehyde (38B)

A suspension of Compound 38A (37 mg) (which was obtained above) and manganese dioxide (240 mg) in chloroform (2 mL) was stirred at room temperature for 3 hours. The reaction solution was filtered through Celite, and then the filtrate was concentrated under reduced pressure to yield a crude product of Compound 38B (36 mg). The whole amount of this product was used in the next reaction without further purification.

(c) (E)-N-(2,2-difluoroethyl)-1-(4,9-dimethoxythieno[3,2-g]isoquinolin-2-yl)methanimine (38C)

To a solution of the crude product 38B (36 mg) (which was obtained above), difluoroethylamine (19 μL), and acetic acid (23 μL) in THF (2 mL) was added sodium triacetoxyborohydride (57 mg), and then the reaction mixture was stirred at room temperature for 1 hour. Aqueous saturated sodium hydrogen carbonate solution (2 mL) was added to the reaction solution, which was then extracted with ethyl acetate. The organic layer was dried over anhydrous sodium sulfate, filtered, and then concentrated under reduced pressure to yield Compound 38C as a crude product. The whole amount of this product was used in the next reaction without further purification.

(d) N-[(4,9-dimethoxythieno[3,2-g]isoquinolin-2-yl) methyl]-2,2-difluoroethaneamine (38D)

To a solution of the crude product 38C in THF (2 mL) was added sodium borohydride (15 mg), and then the reaction mixture was stirred at room temperature for 2 hours. After that, methanol (0.2 mL) was added to the reaction solution, and then stirred for another 10 minutes.

Water was added to the reaction solution. After extraction with ethyl acetate, the organic layer was dried over anhydrous sodium sulfate, filtered, and then concentrated under reduced pressure to yield Compound 38D as a crude product. The whole amount of this product was used in the next reaction without further purification.

(e) 2-{[(2,2-Difluoroethyl)amino]methyl}thieno[3,2-g]isoquinoline-4,9-dione (38E)

Using the crude product 38D obtained above and according to the same method as Example 1, the title compound 38E was obtained (2.3 mg).

(38A) MS (ESI+) 276 (M$^+$+1).
(38B) MS (ESI+) 274 (M$^+$+1).
(38C) MS (ESI+) 337 (M$^+$+1).
(38D) MS (ESI+) 339 (M$^+$+1).
(38E) MS (ESI+) 309 (M$^+$+1).

Reference Example 18: 1-(4,9-dimethoxythieno[3,2-g]quinolin-2-yl) ethanol (39E)

[Chemical formula 106]

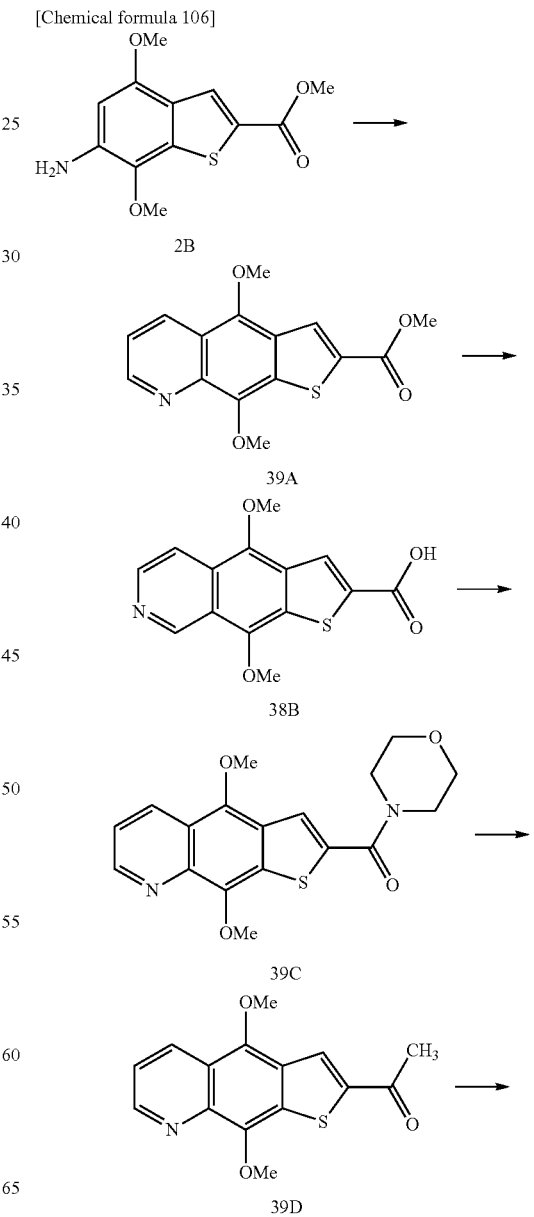

121

-continued

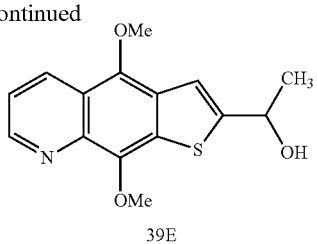

39E (a) Methyl 4,9-dimethoxy-[3,2-g]quinoline-2-carboxylate (39A)

To a solution of methyl 6-amino-4,7-dimethoxy-1-benzothiophene-2-carboxylate (1.2 g) (which was obtained in Reference example 3) in acetic acid (4.0 mL) were added aqueous hydrogen bromide solution (4.0 mL) and 2-propenal (670 μL), and then the reaction mixture was stirred at 70° C. for 3 hours. After it was returned to room temperature, the solvent was evaporated off to yield Compound 39A as a crude product. This was used in the next reaction without further purification.

(b) 4,9-Dimethoxythieno[3,2-g]quinoline-2-carboxylic Acid (39B)

Using Compound 39A obtained above and according to the same method as Reference example 5, Compound 39B was obtained as a crude product. This was used in the next reaction without further purification.

(c) (4,9-Dimethoxythieno[3,2-g]quinolin-2-yl) (morpholin-4-yl)methanone (39C)

Using Compound 39B obtained above and according to the same method as Reference example 6a, Compound 39C was obtained (110 mg).

(d) 1-(4,9-Dimethoxythieno[3,2-g]quinolin-2-yl)ethanone (39D)

Using Compound 39C (110 mg) obtained above and according to the same method as Reference example 6b, Compound 39D was obtained as a crude product. This was used in the next reaction without further purification.

(e) 1-(4,9-Dimethoxythieno[3,2-g]quinolin-2-yl)ethanol (39E)

Using Compound 39D obtained above and according to the same method as Example 2a, the title compound 39E was obtained as a crude product (90 mg). This was used in the next reaction without further purification.

(39A) MS (ESI+) 304 (M$^+$+1).
(39B) MS (ESI+) 290 (M$^+$+1).
(39C) MS (ESI+) 359 (M$^+$+1).
(39D) MS (ESI+) 288 (M$^+$+1).
(39E) MS (ESI+) 290 (M$^+$+1)

Example 36: 2-acetylthieno[3,2-g]quinoline-4,9-dione

[Chemical formula 107]

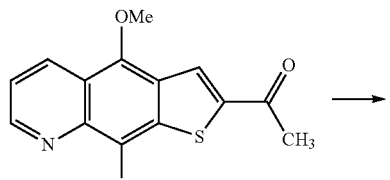

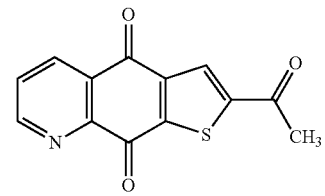

Using 1-(4,9-dimethoxythieno[3,2-g]quinolin-2-yl)ethanone (17 mg) obtained in Reference example 18d and according to the same method as Example 1, the title compound was obtained (9.3 mg).

MS (ESI+) 258 (M$^+$+1)

Example 37: 2-(1-hydroxyethyl)thieno[3,2-g]quinoline-4,9-dione

[Chemical formula 108]

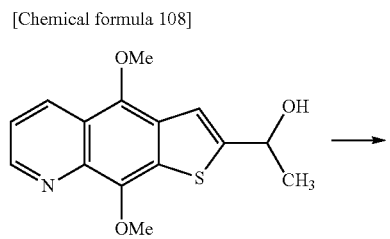

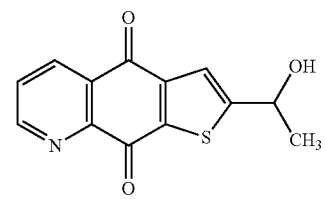

Using 1-(4,9-dimethoxythieno[3,2-g]quinolin-2-yl)ethanol obtained in Reference example 18 and according to the same method as Example 1, the title compound was obtained (1.9 mg).

$^1$H-NMR (DMSO-d$_6$, δppm): 9.01 (1H, d, J=3.1 Hz), 8.46 (1H, dd, J=7.9, 1.8 Hz), 7.85 (1H, dd, J=7.9, 4.9 Hz), 7.53 (1H, s), 6.13 (1H, s), 5.07 (1H, d, J=6.1 Hz), 1.48 (3H, d, J=7.3 Hz).

MS (ESI+) 260 (M$^+$+1)

Example 38: 2-(1-methoxyethyl)thieno[3,2-g]quinoline-4,9-dione (40B)

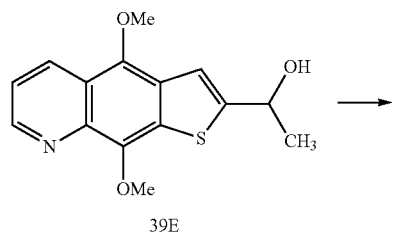

39E

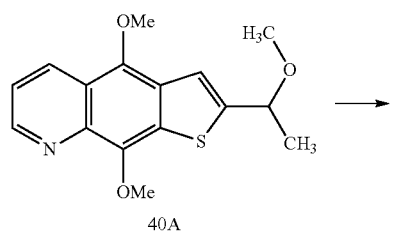

40A

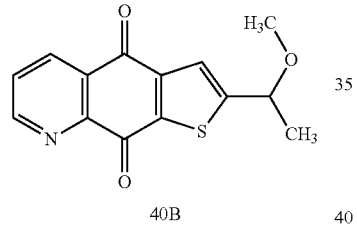

40B (a) (4,9-Dimethoxythieno-2-(1-methoxyethyl)thieno[3,2-g]quinoline (40A)

Using 1-(4,9-dimethoxythieno[3,2-g]quinolin-2-yl)ethanol (90 mg) (which was obtained in Reference example 18e) and methyl iodide (80 μL) and according to the same method as Reference example 13c, Compound 40A was obtained (95 mg).

(b) 2-(1-Methoxyethyl)thieno[3,2-g]quinoline-4,9-dione (40B)

Using Compound 40A (95 mg) obtained above and according to the same method as Example 1, the title compound 40B was obtained (24.8 mg).

(40A) MS (ESI+) 304 (M$^+$+1).
(40B) $^1$H-NMR (DMSO-d$_6$, δppm): 9.02 (1H, dd, J=4.6, 1.5 Hz), 8.47 (1H, dd, J=7.9, 1.2 Hz), 7.86 (1H, dd, J=7.9, 4.3 Hz), 7.65 (1H, s), 4.80 (1H, q, J=6.3 Hz), 3.31 (3H, s), 1.50 (3H, d, J=6.1 Hz).
MS (ESI+) 274 (M$^+$+1).

Example 39: 2-[(3,5-dimethylpiperidin-5-yl)carbonyl]thieno[3,2-g]quinoline-4,9-dione (41B)

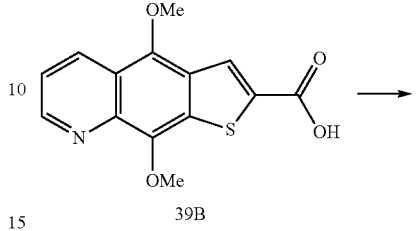

39B

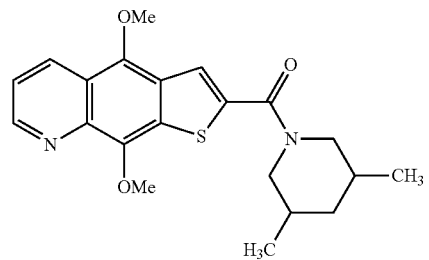

41A

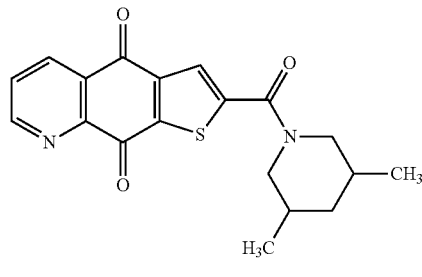

41B (a) (4,9-Dimethoxythieno[3,2-g]quinolin-2-yl) (3,5-dimethylpiperidin-5-yl)methanone (41A)

Using 4,9-dimethoxythieno[3,2-g]quinoline-2-carboxylic acid (89 mg) (which was obtained in Reference example 18b) and 3,5-dimethylpiperidine (83 μL) and according to the same method as Reference example 6a, Compound 41A was obtained (18 mg).

(b) 2-[(3,5-Dimethylpiperidin-5-yl)carbonyl]thieno[3,2-g]quinoline-4,9-dione (41B)

Using Compound 41A (18 mg) obtained above and according to the same method as Example 1, the title compound 41B was obtained (10.5 mg).

(41A) MS (ESI+) 385 (M$^+$+1).
(41B) MS (ESI+) 355 (M$^+$+1).

Example 40: N-(2,2-difluoroethyl)-4,9-dioxo-4,9-dihydroxythieno[3,2-g]quinoline-2-carboxamide (42B)

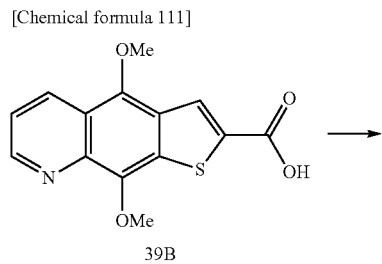

39B

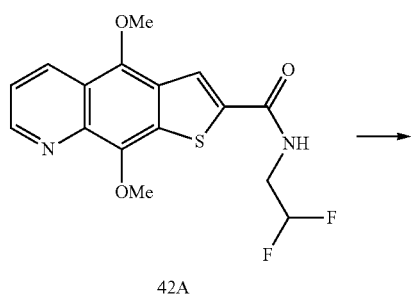

42A

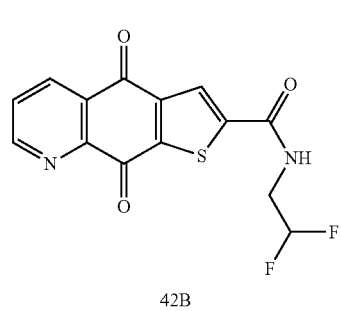

42B (a) N-(2,2-Difluoroethyl)-4,9-dimethoxythieno[3,2-g]quinoline-2-carboxamide (42A)

Using 4,9-dimethoxythieno[3,2-g]quinoline-2-carboxylic acid (73 mg) obtained in Reference example 18b and according to the same method as Example 21a, Compound 42A was obtained (30 mg).

(b) N-(2,2-Difluoroethyl)-4,9-dioxo-4,9-dihydroxythieno[3,2-g]quinoline-2-carboxamide (42B)

Using Compound 42A (30 mg) obtained above and according to the same method as Example 1, the title compound 42B was obtained (21.9 mg).

(42A) MS (ESI+) 353 ($M^+ +1$).
(42B) MS (ESI+) 323 ($M^+ +1$).

Example 41: tert-butyl (4,9-dioxo-4,9-dihydrothieno[3,2-g]quinolin-2-yl)methylcarbamate (43C)

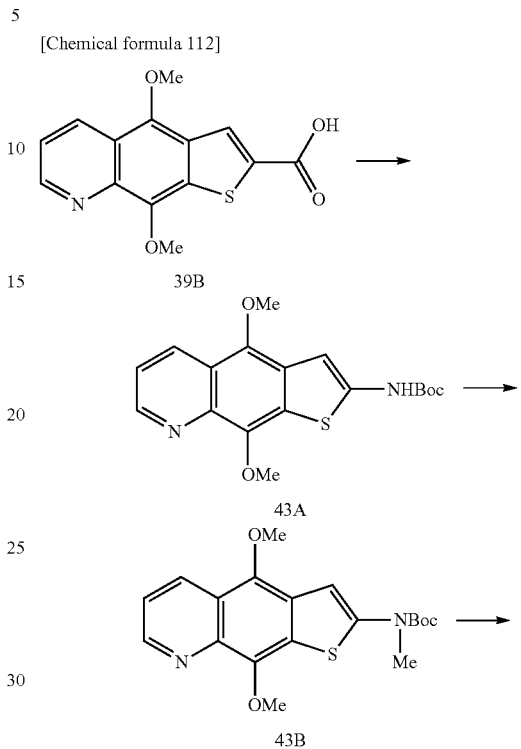

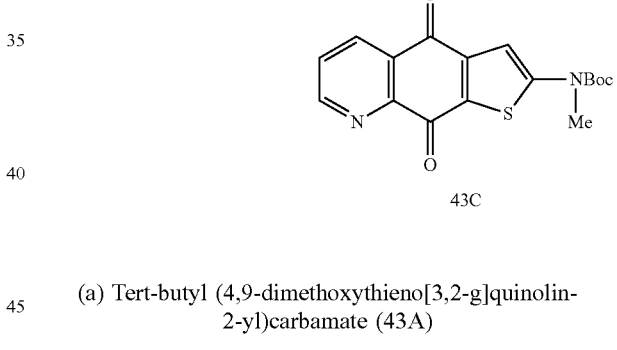

43C (a) Tert-butyl (4,9-dimethoxythieno[3,2-g]quinolin-2-yl)carbamate (43A)

To a solution of 4,9-dimethoxythieno[3,2-g]quinoline-2-carboxylic acid (22 mg) (which was obtained in Reference example 18b) in tert-butanol (1.0 mL) were added triethylamine (42 μL) and diphenylphosphoryl azide (24 μL), and then the reaction mixture was stirred for 12 hours. Water was added thereto, and then extracted with ethyl acetate. The resulting organic layer was washed with saturated brine, and then dried over sodium sulfate. The solvent was then evaporated off. The resulting residue was purified by silica gel column chromatography (hexane/ethyl acetate) to yield Compound 43A (7.0 mg).

(b) Tert-butyl (4,9-dimethoxythieno[3,2-g]quinolin-2-yl)methylcarbamate (43B)

To a solution of Compound 43A (7.0 mg) (which was obtained above) in dimethylformamide (500 μL), under ice-cooling, was added sodium hydride (1.0 mg), and then the reaction mixture was stirred at room temperature for 20 minutes. Subsequently, methyl iodide (3.0 μL) was added thereto, and then the reaction mixture was stirred for 1 hour. After that, aqueous saturated ammonium chloride solution was added thereto, and then extraction with ethyl acetate was performed. The resulting organic layer was washed with water and saturated brine, and then dried over sodium sulfate. The solvent was then evaporated off. The resulting residue was purified by silica gel column chromatography (hexane/ethyl acetate) to yield Compound 43B (3.7 mg).

(c) Tert-butyl (4,9-dioxo-4,9-dihydrothieno[3,2-g] quinolin-2-yl)methylcarbamate (43C)

Using Compound 43B (3.7 mg) obtained above and according to the same method as Example 1, the title compound 43C was obtained (3.8 mg).
(43A) MS (ESI+) 361 (M$^+$+1).
(43B) MS (ESI+) 375 (M$^+$+1).
(43C) MS (ESI+) 345 (M$^+$+1)

Reference Example 19: methyl 4,7-dimethoxy-1-benzofuran-2-carboxylate

[Chemical formula 113]

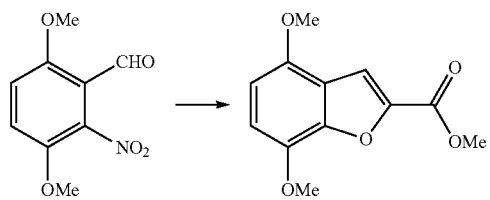

To a solution of methyl glycolate (25.0 g) in THF (400 mL), under ice-cooling, sodium hydride (13.1 g) was added in 10 parts, and the reaction mixture was stirred at room temperature for 1 hour. To the reaction solution ice-cooled again, 3,6-dimethoxy-2-nitrobenzaldehyde (48.8 g) was added in 10 parts, and the reaction mixture was heated and stirred at 60° C. for 6 hours. The reaction solution was cooled to room temperature, aqueous saturated sodium bicarbonate (500 mL) was added thereto, and then extraction with chloroform (2×500 mL) was performed. The resulting organic layer was washed with saturated brine, dried over sodium sulfate, and then purified by amino-silica gel chromatography (chloroform). The resulting crude product was suspended in methanol, stirred at room temperature for 1 hour, filtered, and then dried to yield the title compound as an opaque white solid (7.7 g).

$^1$H-NMR (DMSO-d$_6$, δppm): 7.63 (1H, s), 7.03 (1H, d, J=8.4 Hz), 6.74 (1H, d, J=8.4 Hz), 3.90 (3H, s), 3.88 (3H, s), 3.87 (3H, s).

Reference Example 20: methyl 5-amino-4,7-dimethoxy-1-benzofuran-2-carboxylate (45A)

Reference Example 21: methyl 6-amino-4,7-dimethoxy-1-benzofuran-2-carboxylate (45B)

[Chemical formula 114]

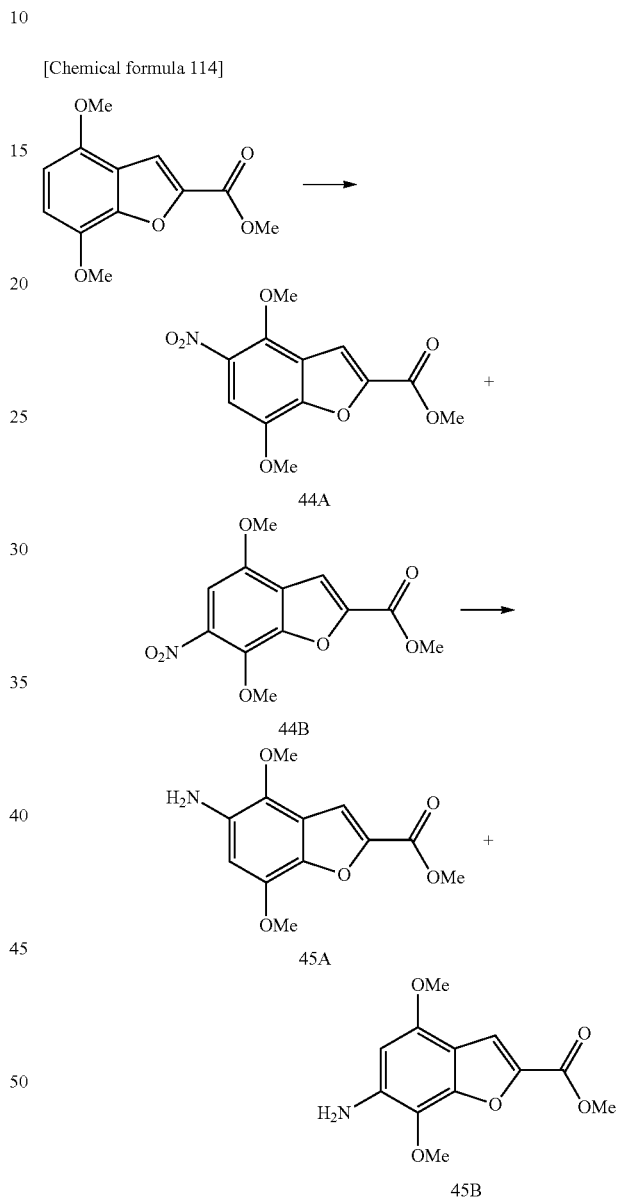

Using methyl 4,7-dimethoxy-1-benzofuran-2-carboxylate (5.00 g) obtained in Reference example 19 and according to the same methods as Reference examples 2 and 3, Compound 45A was obtained as a brown powder (1.38 g) and Compound 45B was obtained as an opaque white solid (707 mg).

(45A) $^1$H-NMR (DMSO-d$_6$, δppm): 7.63 (1H, s), 6.60 (1H, s), 4.76 (2H, s), 3.87 (3H, s), 3.84 (3H, s), 3.79 (3H, s).

(45B) $^1$H-NMR (DMSO-d$_6$, δppm): 7.46 (1H, s), 6.28 (1H, s), 5.48 (2H, s), 3.83 (3H, s), 3.79 (3H, s), 3.79 (3H, s).

Reference Example 22: methyl 4,9-dimethoxyfuro[2,3-g]quinoline-2-carboxylate (46B)

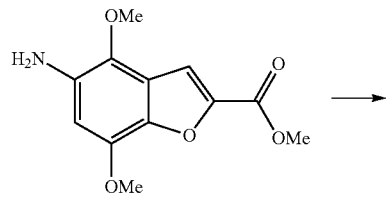

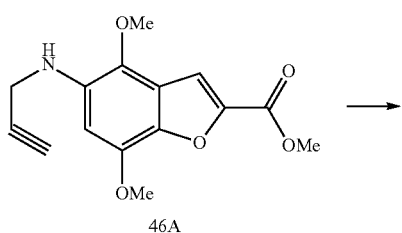
46A

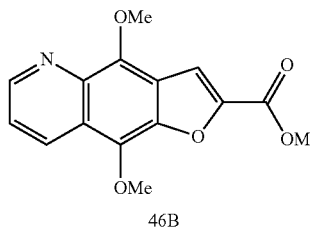
46B (a) Methyl 4,7-dimethoxy-5-(prop-2-yn-1-ylamino)-1-benzofuran-2-carboxylate (46A)

Using Compound 45A (920 mg) obtained in Reference example 20 and according to the same method as Reference example 4a, Compound 46A was obtained as a yellow powder (477 mg).

(b) Methyl 4,9-dimethoxyfuro[2,3-g]quinoline-2-carboxylate (46B)

Using Compound 46A (440 mg) and according to the same method as Reference example 4b, Compound 46B was obtained as a yellow solid (112 mg).

(46A) $^1$H-NMR (DMSO-d$_6$, δppm): 7.70 (1H, s), 6.70 (1H, s), 5.31 (1H, s), 4.00 (2H, brs), 3.91 (3H, s), 3.88 (3H, s), 3.82 (3H, s), 3.03 (1H, s).

MS (ESI+) 290 (M$^+$+1).

(46B) $^1$H-NMR (DMSO-d$_6$, δppm): 8.90 (1H, d, J=4.0 Hz), 8.61 (1H, d, J=8.4 Hz), 7.94 (1H, s), 7.53 (1H, dd, J=4.0, 8.4 Hz), 4.31 (3H, s), 4.27 (3H, s), 3.97 (3H, s).

MS (ESI+) 288 (M$^+$+1).

Reference Example 23: 4,9-dimethoxyfuro[2,3-g]quinoline-2-carboxylic Acid

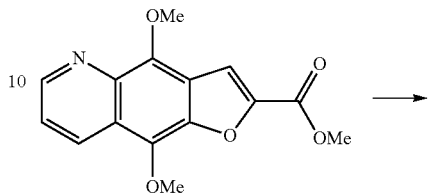

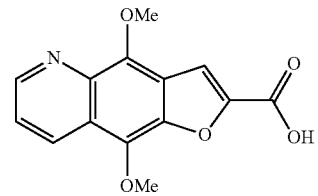

Using Compound 46B (110 mg) obtained in Reference example 22 and according to the same method as Reference example 5, the title compound was obtained as a brown solid (100 mg).

MS (ESI+) 274 (M$^+$+1).

Reference Example 24: 1-(4,9-dimethoxyfuro[2,3-g]quinolin-2-yl)ethanone (47B)

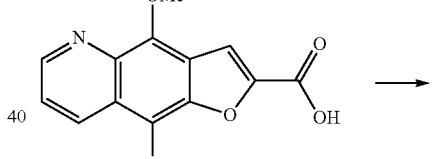

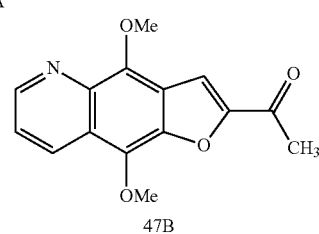
47A

47B (a) (4,9-Dimethoxyfuro[2,3-g]quinolin-2-yl)(morpholin-4-yl)methanone (47A)

Using 4,9-dimethoxyfuro[2,3-g]quinoline-2-carboxylic acid (100 mg) obtained in Reference example 23 and according to the same method as Reference example 6a, Compound 47A was obtained as a brown solid (90.1 mg).

(b) 1-(4,9-Dimethoxyfuro[2,3-g]quinolin-2-yl)ethanone (47B)

Using Compound 47A (89.0 mg) obtained above and according to the same method as Reference example 6b, Compound 47B was obtained as a yellow solid (67.0 mg).

(47A) $^1$H-NMR (DMSO-d$_6$, δppm): 8.89 (1H, dd, J=1.6, 4.0 Hz), 8.61 (1H, dd, J=1.6, 8.4 Hz), 7.70 (1H, s), 7.54 (1H, dd, J=4.0, 8.4 Hz), 4.25 (3H, s), 4.23 (3H, s), 3.98-3.90 (8H, m).

MS (ESI+) 343 (M$^+$+1).

(47B) $^1$H-NMR (DMSO-d$_6$, δppm): 8.90 (1H, d, J=4.0 Hz), 8.61 (1H, d, J=8.4 Hz), 8.29 (1H, s), 7.57 (1H, dd, J=4.0, 8.4 Hz), 4.31 (3H, s), 4.24 (3H, s), 2.65 (3H, s).

MS (ESI+) 272 (M$^+$+1).

Example 42: 2-acetylfuro[2,3-g]quinoline-4,9-dione

[Chemical formula 118]

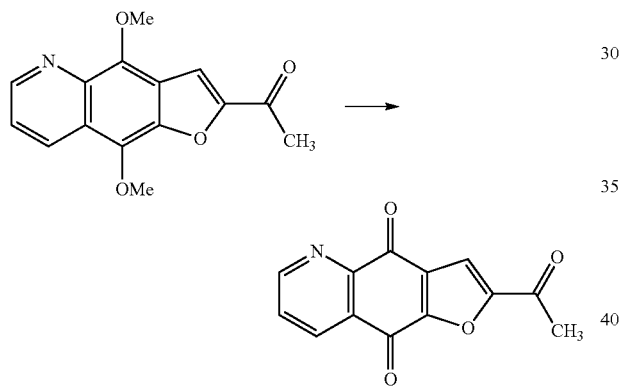

Using 1-(4,9-dimethoxyfuro[2,3-g]quinolin-2-yl)ethanone (24.0 mg) obtained in Reference example 24 and according to the same method as Example 1, the title compound was obtained as a yellow powder (15.7 mg).

MS (ESI+) 242 (M$^+$+1).

Example 43: 2-(1-hydroxyethyl)furo[2,3-g]quinoline-4,9-dione (48B)

[Chemical formula 119]

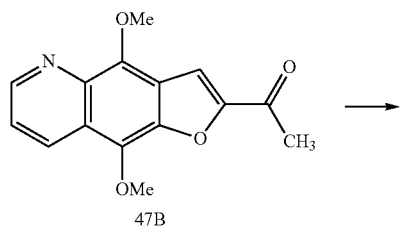

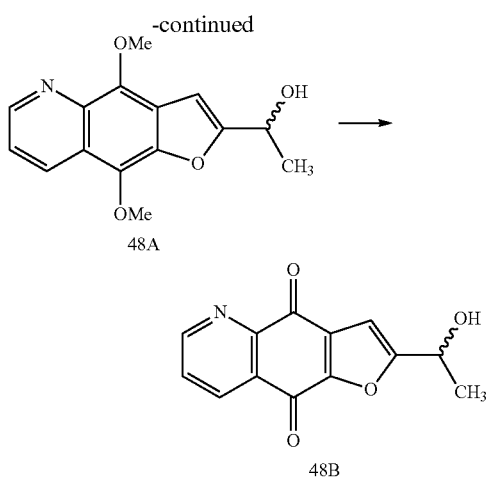

(a) 1-(4,9-Dimethoxyfuro[2,3-g]quinolin-2-yl)ethanol (48A)

Using 1-(4,9-dimethoxyfuro[2,3-g]quinolin-2-yl)ethanone (42.2 mg) obtained in Reference example 24 and according to the same method as Example 2a, Compound 48A was obtained as a yellow solid (38.3 mg).

(b) 2-(1-Hydroxyethyl)furo[2,3-g]quinoline-4,9-dione (48B)

Using Compound 48A and according to the same method as Example 1, the title compound 48B was obtained as a yellow powder (29.2 mg).

(48A) MS (ESI+) 274 (M$^+$+1).
(48B) MS (ESI+) 244 (M$^+$+1).

Reference Example 25: methyl 5-formyl-4,7-dimethoxy-1-benzofuran-2-carboxylate (49A)

Reference Example 26: methyl 6-formyl-4,7-dimethoxy-1-benzofuran-2-carboxylate (49B)

[Chemical formula 120]

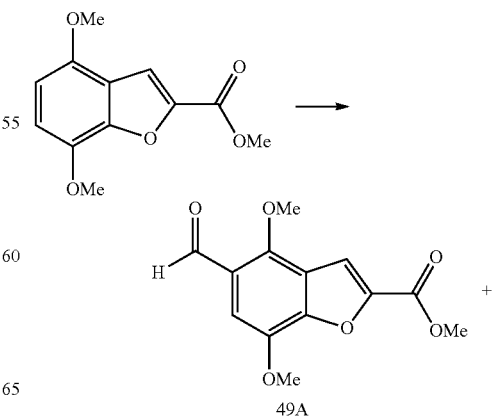

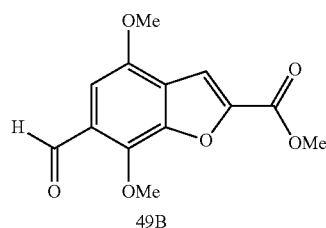

49B

Under nitrogen atmosphere, to a solution of methyl 4,7-dimethoxy-1-benzofuran-2-carboxylate (9.00 mg) (which was obtained in Reference example 19) in dichloromethane (200 mL) was added dropwise titanium tetrachloride (12.3 mL) at 0° C., and then the reaction mixture was stirred for 30 minutes. 1,1-Dichloromethylmethyl ether (4.50 mL) was added dropwise, stirred at 0° C. for 1 hour, and then stirred at room temperature for 3 hours. The reaction solution was poured into iced water, and then extracted with chloroform. The organic layer was dried over anhydrous sodium sulfate, filtered, and then concentrated under reduced pressure. The resulting residue was purified by silica gel chromatography (ethyl acetate/chloroform) to yield Compound 49A (6.20 g) and Compound 49B (0.68 g) as a yellow solid, respectively.

(49A) MS (ESI+) 265 (M$^+$+1).
(49B) MS (ESI+) 265 (M$^+$+1).

Reference Example 27: 4,9-dimethoxyfuro[2,3-g]isoquinoline-2-carboxylic Acid (50D)

[Chemical formula 121]

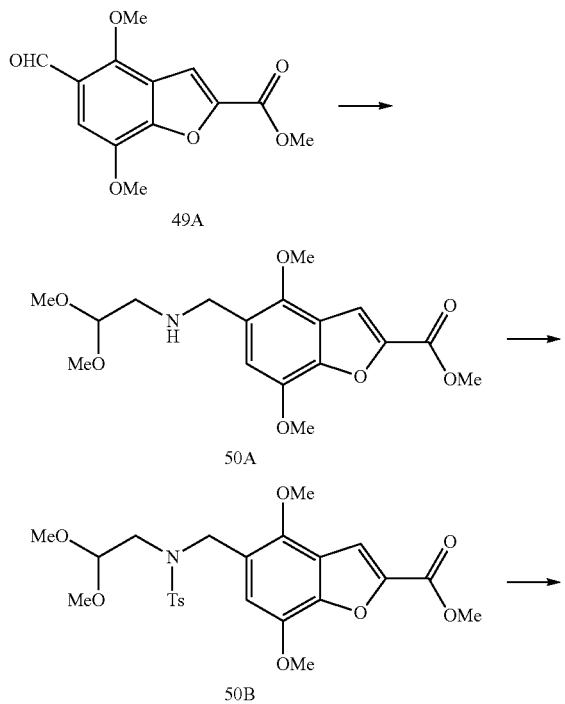

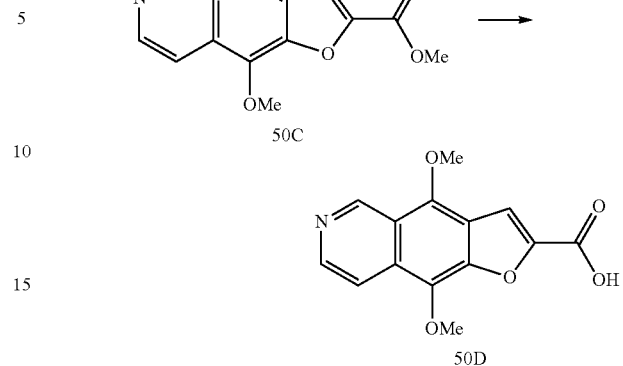

50C

50D (a) Methyl 5-{[(2,2-dimethoxyethyl)amino]methyl}-4,7-dimethoxy-1-benzofuran-2-carboxylate (50A)

Using methyl 5-formyl-4,7-dimethoxy-1-benzofuran-2-carboxylate (1.30 g) obtained in Reference example 25 and according to the same method as Reference example 10b, Compound 50A (1.50 g) was obtained.

(b) Methyl 5-({(2,2-dimethoxyethyl) [(4-methylphenyl)sulfonyl]amino}methyl)-4,7-dimethoxy-1-benzofuran-2-carboxylate (50B)

To a solution of Compound 50A (1.50 g) (which was obtained above) in chloroform (50 mL) were added aqueous saturated sodium hydrogen carbonate solution (200 mL) and p-toluenesulfonyl chloride (1.88 g), and then the reaction mixture was stirred at room temperature for 2 hours. Aqueous saturated sodium hydrogen carbonate solution (50 mL) was added to the reaction solution, which was then extracted with chloroform. The organic layer was dried over anhydrous sodium sulfate, filtered, and then concentrated under reduced pressure. The resulting residue was purified by silica gel chromatography (methanol/chloroform) to yield Compound 50B (1.67 g).

(c) Methyl 4,9-dimethoxyfuro[2,3-g]isoquinoline-2-carboxylate (50C)

Under nitrogen atmosphere, to a solution of Compound 50B (1.67 g) (which was obtained above) in methylene chloride (50 mL) was added titanium tetrachloride (1.62 mL) at 0° C., and then the reaction mixture was stirred at room temperature for 6 hours. The reaction solution was poured into iced water, neutralized with sodium hydrogen carbonate (pH=7-8), and then extracted with chloroform. The organic layer was dried over anhydrous sodium sulfate, filtered, and then concentrated under reduced pressure. The resulting residue was purified by silica gel chromatography (ethyl acetate/chloroform) to yield Compound 50C (0.28 g).

(d) 4,9-Dimethoxyfuro[2,3-g]isoquinoline-2-carboxylic Acid (50D)

Using Compound 50C (0.28 g) obtained above and according to the same method as Reference example 5, Compound 50D (0.23 g) was obtained.

(50A) MS (ESI+) 354 (M⁺+1).
(50B) MS (ESI+) 508 (M⁺+1).
(50C) MS (ESI+) 288 (M⁺+1).
(50D) MS (ESI+) 273 (M⁺+1).

Reference Example 28: 1-(4,9-dimethoxyfuro[2,3-g]isoquinolin-2-yl)ethanone (51B)

[Chemical formula 122]

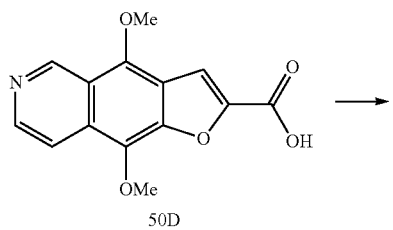

50D

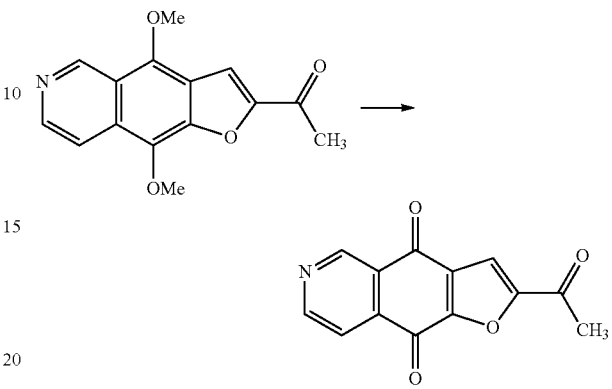

51A

51B (a) (4,9-Dimethoxyfuro[2,3-g]isoquinolin-2-yl)(morpholin-4-yl)methanone (51A)

Using 4,9-dimethoxyfuro[2,3-g]isoquinoline-2-carboxylic acid (0.23 g) obtained in Reference example 27 and according to the same method as Reference example 6a, Compound 51A was obtained as a yellow powder (0.24 g).

(b) 1-(4,9-Dimethoxyfuro[2,3-g]isoquinolin-2-yl)ethanone (51B)

Using Compound 51A (0.24 g) obtained above and according to the same method as Reference example 6b, Compound 51B was obtained as a yellow powder (0.18 g).

(51A) MS (ESI+) 343 (M⁺+1).
(51B) MS (ESI+) 272 (M⁺+1).

Example 44: 2-acetylfuro[2,3-g]isoquinoline-4,9-dione

[Chemical formula 123]

Using 1-(4,9-dimethoxyfuro[2,3-g]isoquinolin-2-yl)ethanone (70 mg) obtained in Reference example 28 and according to the same method as Example 1, the title compound was obtained as a yellow powder (38 mg).
MS (ESI+) 242 (M⁺+1).

Example 45: 2-(1-hydroxyethyl)furo[2,3-g]isoquinoline-4,9-dione (52B)

[Chemical formula 124]

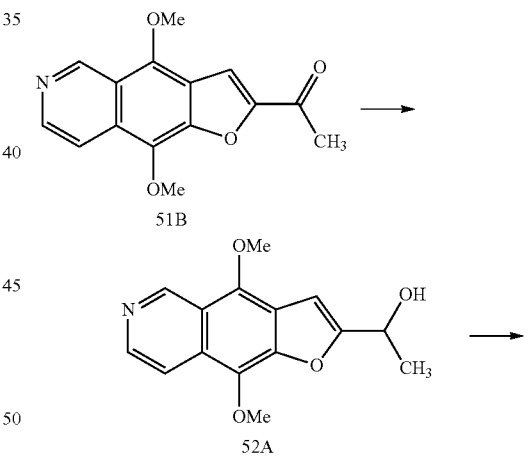

(a) 1-(4,9-Dimethoxyfuro[2,3-g]isoquinolin-2-yl)ethanol (52A)

Using 1-(4,9-dimethoxyfuro[2,3-g]isoquinolin-2-yl)ethanone (52.0 mg) obtained in Reference example 28 and according to the same method as Example 2a, Compound 52A was obtained as a yellow powder (44.0 mg).

(b) 2-(1-Hydroxyethyl)furo[2,3-g]isoquinoline-4,9-dione (52B)

Using Compound 52A (44.0 mg) obtained above and according to the same method as Example 1, Compound 52B was obtained as a yellow powder (29.0 mg).
(52A) MS (ESI+) 274 (M⁺+1).
(52B) MS (ESI+) 244 (M⁺+1).

Example 46: N-(2,2-difluoroethyl)-4,9-dioxo-4,9-dihydrofuro[2,3-g]isoquinoline-2-carboxamide (53B)

[Chemical formula 125]

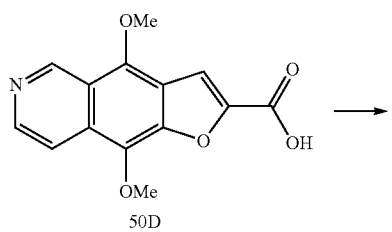

50D

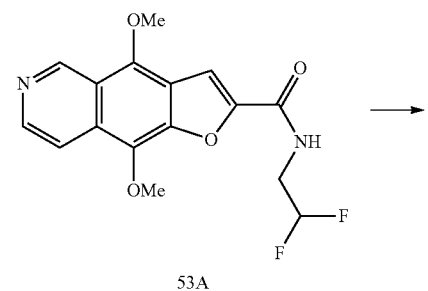

53A

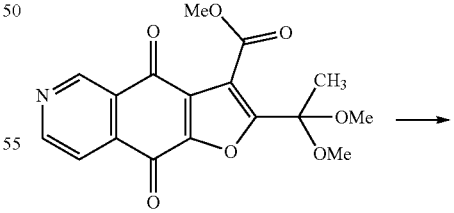

53B (a) N-(2,2-Difluoroethyl)-4,9-dimethoxyfuro[2,3-g]isoquinoline-2-carboxamide (53A)

Using 4,9-dimethoxyfuro[2,3-g]isoquinoline-2-carboxylic acid (7.9 mg) obtained in Reference example 27 and according to the same method as Example 21a, Compound 53A (3.9 mg) was obtained.

(b) N-(2,2-Difluoroethyl)-4,9-dioxo-4,9-dihydrofuro[2,3-g]isoquinoline-2-carboxamide (53B)

Using Compound 53A (3.9 mg) obtained above and according to the same method as Example 1, the title compound 53B was obtained (2.4 mg).
(53A) MS (ESI+) 337 (M⁺+1).
(53B) MS (ESI+) 307 (M⁺+1).

Reference Example 29: methyl 2-(1,1-dimethoxyethyl)-4,9-dioxo-4,9-dihydrofuro[2,3-g]isoquinoline-3-carboxylate

[Chemical formula 126]

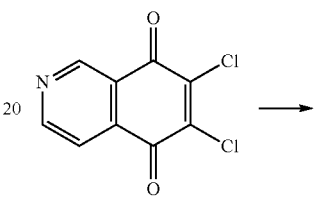

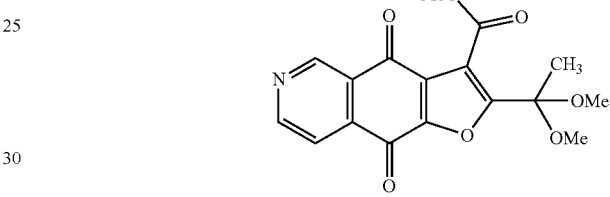

A solution of 6,7-dichloroisoquinoline-5,8-dione (1.14 g), methyl 4,4-dimethoxy-3-oxovalerate (1.05 g), and potassium carbonate (1.73 g) in acetonitrile (50 mL) was heated and stirred at 90° C. for 5 hours. After the heating was finished, the precipitated solid was filtered through Celite with ethyl acetate. After the filtrate was concentrated under reduced pressure, the resulting residue was purified by silica gel column chromatography (chloroform) to yield the title compound as a yellow solid (1.15 g).
MS (ESI+) 346 (M⁺+1).

Reference Example 30: methyl 2-acetyl-4,9-dioxo-4,9-dihydrofuro[2,3-g]isoquinoline-3-carboxylate

[Chemical formula 127]

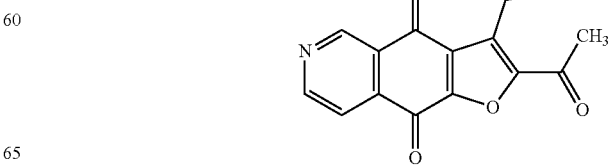

A solution of Compound (1.15 g) (which was obtained in Reference example 29) in formic acid (10 mL) was stirred at 25° C. for 4 hours. After the reaction solution was concentrated under reduced pressure, the resulting residue was purified by silica gel column chromatography (chloroform) to yield the title compound as a yellow solid (0.87 g).
MS (ESI+) 300 (M⁺+1).

Example 47: 2-acetyl-3-(morpholin-4-carbonyl)furo[2,3-g]isoquinoline-4,9-dione

[Chemical formula 128]

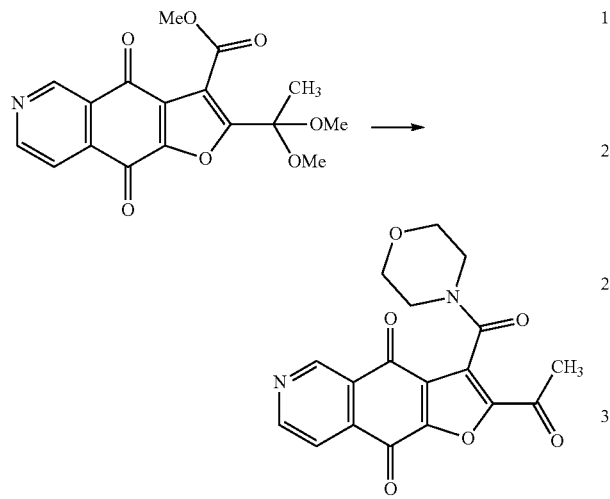

A solution of the compound (0.5 g) (which was obtained in Reference example 29) in a mixture of 4 N hydrochloric acid in 1,4-dioxane (10 mL) and concentrated hydrochloric acid (4 mL) was stirred at 120° C. for 9 hours. The reaction solution was concentrated under reduced pressure, and then a solution of DMF (10 mg) in toluene (5 mL) was added thereto. Subsequently, thionyl chloride (143 mg) was added dropwise, and then heated and stirred at 90° C. for 4 hours. After the heating was finished, concentration under reduced pressure was performed. To the residue, THF (5 mL) was added, and then morpholine (0.5 mL) was added dropwise at 0° C. After stirring at 25° C. for 1 hour, concentration under reduced pressure was performed. The resulting residue was purified by silica gel column chromatography (chloroform) to yield the title compound as a yellow solid (70 mg).
MS (ESI+) 355 (M⁺+1).

Reference Example 31: 4,9-dimethoxyfuro[2,3-g]isoquinoline-3-carboxylic Acid (54C)

[Chemical formula 129]

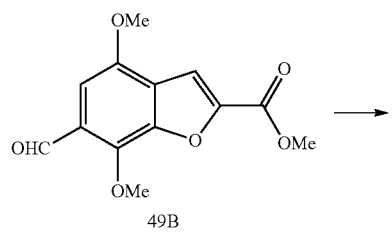

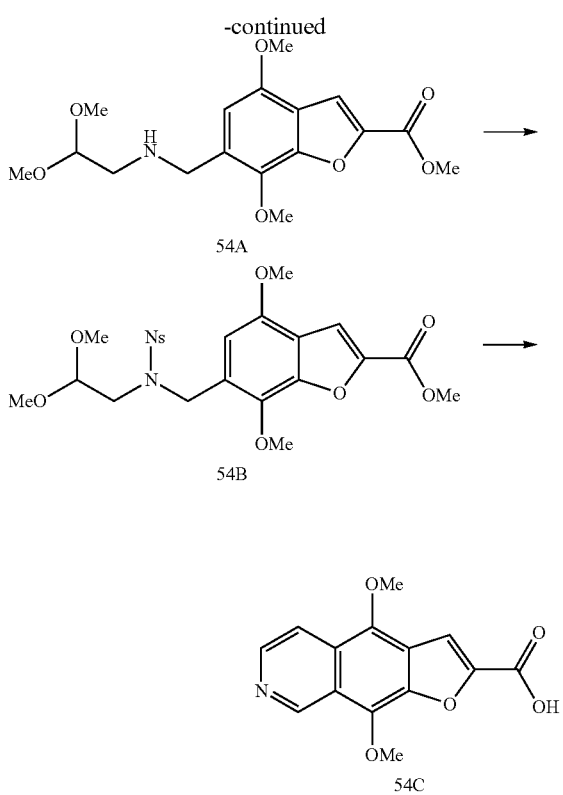

(a) Methyl 6-{[(2,2-dimethoxyethyl)amino]methyl}-4,7-dimethoxy-1-benzofuran-2-carboxylate (54A)

Using Compound 49B (605 mg) obtained in Reference example 26 and according to the same method as Reference example 10b, Compound 54A was obtained as a crude product. The whole amount of this product was used in the next reaction.

(b) Methyl 6-({(2,2-dimethoxyethyl) [(2-nitrophenyl)sulfonyl]amino}methyl)-4,7-dimethoxy-1-benzofuran-2-carboxylate (54B)

Using the above-described crude product 54A and according to the same method as Reference example 10c, Compound 54B (1.10 g) was obtained.

(c) 4,9-Dimethoxyfuro[2,3-g]isoquinoline-3-carboxylic Acid (54C)

Using Compound 54B (500 mg) obtained above and according to the same method as Reference example 10d, the title compound 54C was obtained (126 mg).

(54A) MS (ESI+) 354 (M⁺+1).

(54B) ¹H-NMR (DMSO-d₆, δppm): 8.02 (2H, d, J=7.9 Hz), 7.98 (2H, d, J=7.9 Hz), 7.85 (1H, t, J=7.6 Hz), 7.76 (1H, t, J=7.6 Hz), 7.62 (1H, s), 6.52 (1H, s), 4.71 (2H, s), 4.38 (1H, t, J=4.9 Hz), 3.96 (3H, s), 3.88 (3H, s), 3.70 (3H, s), 3.35 (2H, d, J=5.5 Hz), 3.17 (6H, s).
MS (ESI+) 539 (M⁺+1).

(54C) $^1$H-NMR (DMSO-d$_6$, δppm): 14.05 (1H, br s), 9.57 (1H, s), 8.44 (1H, d, J=6.1 Hz), 8.08 (1H, s), 7.97 (1H, d, J=6.1 Hz), 4.27 (6H, s).

MS (ESI+) 274 (M$^+$+1).

Reference Example 32: 1-(4,9-dimethoxyfuro[3,2-g]isoquinolin-2-yl)ethanone (55B)

[Chemical formula 130]

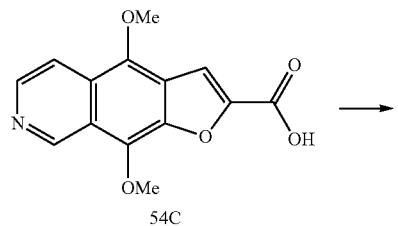

54C

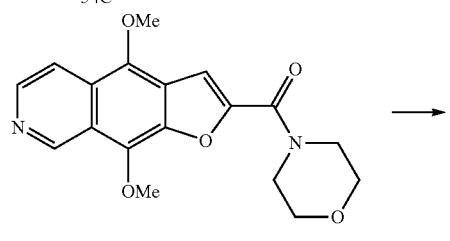

55A

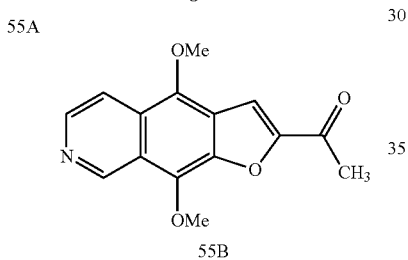

55B (a) (4,9-Dimethoxyfuro[3,2-g]isoquinolin-2-yl)(morpholin-4-yl)methanone (55A)

Using 4,9-dimethoxyfuro[2,3-g]isoquinoline-3-carboxylic acid obtained in Reference example 31 and according to the same method as Reference example 6a, Compound 55A was obtained (80.0 mg).

(b) 1-(4,9-Dimethoxyfuro[3,2-g]isoquinolin-2-yl)ethanone (55B)

Using Compound 55A (80.0 mg) obtained above and according to the same method as Reference example 6b, the title compound 55B was obtained (27.0 mg).

(55A) $^1$H-NMR (DMSO-d$_6$, δppm): 9.56 (1H, s), 8.44 (1H, d, J=6.1 Hz), 7.95 (1H, d, J=6.1 Hz), 7.84 (1H, s), 4.29 (3H, s), 4.22 (3H, s), 3.87-3.57 (8H, m).

MS (ESI+) 343 (M$^+$+1).

(55B) $^1$H-NMR (DMSO-d$_6$, δppm): 9.61 (1H, s), 8.55 (1H, d, J=6.1 Hz), 8.36 (1H, s), 8.04 (1H, d, J=6.1 Hz), 4.19 (3H, s), 4.14 (3H, s), 3.94 (3H, s).

MS (ESI+) 272 (M$^+$+1).

Example 48: 2-acetylfuro[3,2-g]isoquinoline-4,9-dione

[Chemical formula 131]

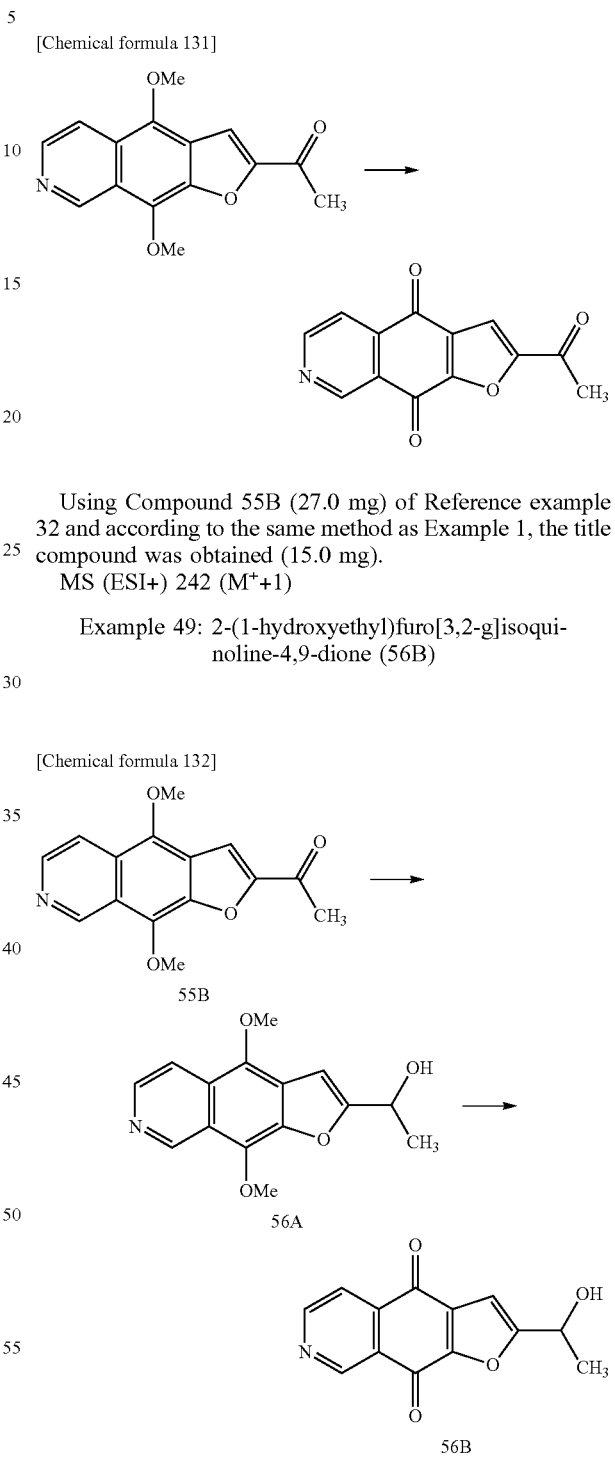

Using Compound 55B (27.0 mg) of Reference example 32 and according to the same method as Example 1, the title compound was obtained (15.0 mg).

MS (ESI+) 242 (M$^+$+1)

Example 49: 2-(1-hydroxyethyl)furo[3,2-g]isoquinoline-4,9-dione (56B)

[Chemical formula 132]

(a) 1-(4,9-Dimethoxyfuro[3,2-g]isoquinolin-2-yl)ethanol (56A)

Using Compound 55B (60.0 mg) of Reference example 32 and according to the same method as Reference example 2a, Compound 56A was obtained (24.0 mg).

(b) 2-(1-Hydroxyethyl)furo[3,2-g]isoquinoline-4,9-dione (56B)

Using Compound 56A (24.0 mg) obtained above and according to the same method as Example 2b, the title compound 56B was obtained (15.0 mg).

(56A) MS (ESI+) 242 (M$^+$+1)

(56B) $^1$H-NMR (DMSO-d$_6$, δppm): 9.24 (1H, s), 9.10 (1H, br s), 7.92 (1H, br s), 6.95 (1H, br s), 5.83 (1H, d, J=5.5 Hz), 4.92-4.85 (1H, m), 1.46 (3H, d, J=6.7 Hz).

MS (ESI+) 244 (M$^+$+1).

Reference Example 33: 1-(4,9-dimethoxyfuro[3,2-g]quinolin-2-yl)ethanol (57E)

[Chemical formula 133]

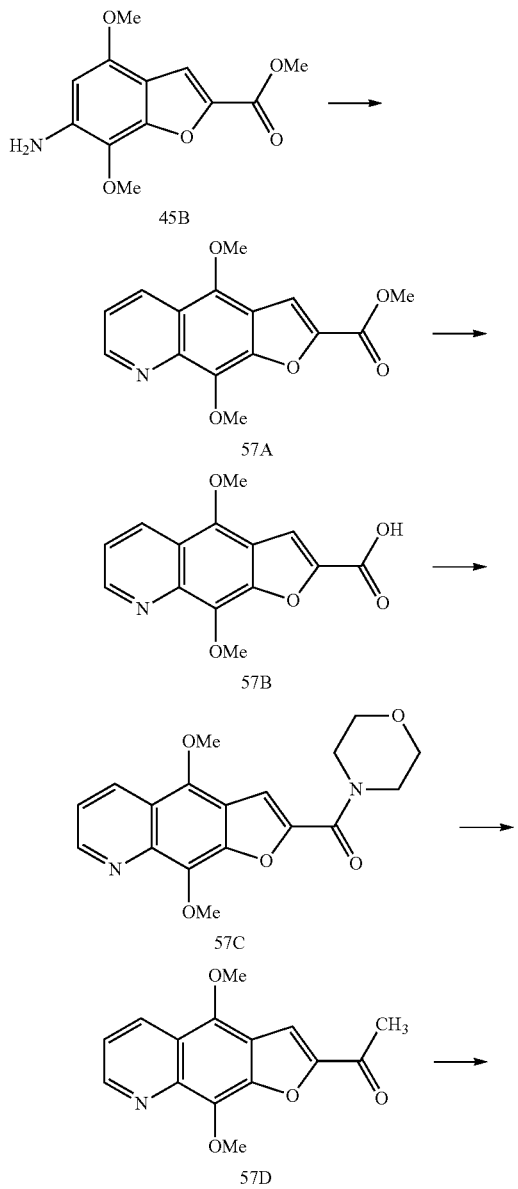

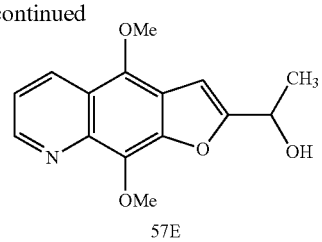

(a) Methyl 4,9-dimethoxyfuro[3,2-g]quinoline-2-carboxylate (57A)

To a solution of methyl 6-amino-4,7-dimethoxybenzofuran-2-carboxylate (100 mg) (which was obtained in Reference example 21) in methanol (0.9 mL) were added in concentrated hydrochloric acid (0.4 mL), and 2-propenal (60 μL), and then the reaction mixture was stirred at 70° C. for 2 hours. After it was returned to room temperature, the solvent was evaporated off to yield Compound 57A. The obtained compound was used in the next reaction without purification.

(b) 4,9-Dimethoxyfuro[3,2-g]quinoline-2-carboxylic Acid (57B)

Methyl 4,9-dimethoxyfuro[3,2-g]quinoline-2-carboxylate (which was obtained above) was added to concentrated hydrochloric acid (1.0 mL), and then the reaction mixture was heated at reflux for 1 hour. After it was returned to room temperature, the solvent was evaporated off to yield Compound 57B. The obtained compound was used in the next reaction without purification.

(c) (4,9-Dimethoxyfuro[3,2-g]quinolin-2-yl) (morpholin-4-yl)methanone (57C)

Using 4,9-dimethoxyfuro[3,2-g]quinoline-2-carboxylic acid obtained above and according to the same method as Reference example 6a, Compound 57C was obtained (53.0 mg).

(d) 1-(4,9-Dimethoxyfuro[3,2-g]quinolin-2-yl)ethanone (57D)

Using (4,9-dimethoxyfuro[3,2-g]quinolin-2-yl) (morpholin-4-yl)methanone (53 mg) obtained above and according to the same method as Reference example 6b, Compound 57D was obtained.

(e) 1-(4,9-Dimethoxyfuro[3,2-g]quinolin-2-yl)ethanol (57E)

Using 1-(4,9-dimethoxyfuro[3,2-g]quinolin-2-yl)ethanone (10 mg) obtained above and according to the same method as Example 2a, the title compound 57E was obtained.

(57A) MS (ESI+) 288 (M$^+$+1).
(57B) MS (ESI+) 274 (M$^+$+1).
(57C) MS (ESI+) 343 (M$^+$+1).
(57D) MS (ESI+) 272 (M$^+$+1).
(57E) MS (ESI+) 274 (M$^+$+1).

Example 50: 2-acetylfuro[3,2-g]quinoline-4,9-dione

[Chemical formula 134]

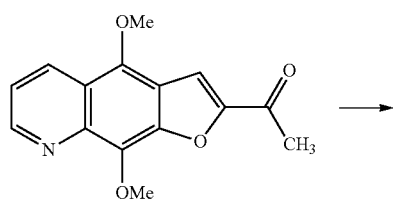

Using 1-(4,9-dimethoxyfuro[3,2-g]quinolin-2-yl)etha-none (35 mg) obtained in Reference example 33 and according to the same method as Example 1, the title compound was obtained (7.1 mg).
MS (ESI+) 242 (M$^+$+1).

Example 51: 2-(1-hydroxyethyl)furo[3,2-g]quino-line-4,9-dione

[Chemical formula 135]

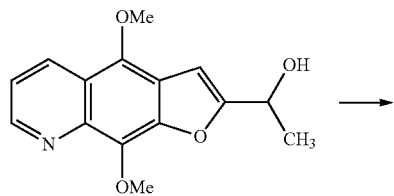

Using 1-(4,9-dimethoxyfuro[3,2-g]quinolin-2-yl)ethanol obtained in Reference example 33 and according to the same method as Example 1, the title compound was obtained (3.7 mg).
MS (ESI+) 244 (M$^+$+1).

Reference Example 34: (4,7-dimethoxy-1-benzo-furan-2-yl) (morpholin-4-yl)methanone (58B)

[Chemical formula 136]

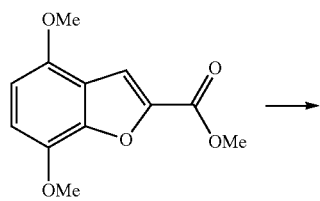

(a) 4,7-Dimethoxy-1-benzofuran-2-carboxylic Acid (58A)

Using methyl 4,7-dimethoxy-1-benzofuran-2-carboxylate (16.0 g) obtained in Reference example 19 and according to the same method as Reference example 5, Compound 58A (7.2 g) was obtained.

(b) (4,7-Dimethoxy-1-benzofuran-2-yl) (morpholin-4-yl)methanone (58B)

Using Compound 58A (7.2 g) obtained above and according to the same method as Reference example 6a, the title compound 58B was obtained as a yellow powder (9.8 g).
(58A) MS (ESI+) 223 (M$^+$+1).
(58B) MS (ESI+) 292 (M$^+$+1)

Reference Example 35: 4,7-dimethoxy-2-(morpho-lin-4-ylcarbonyl)-1-benzofuran-5-carbaldehyde (59A)

Reference Example 36: 4,7-dimethoxy-2-(morpho-lin-4-ylcarbonyl)-1-benzofuran-6-carbaldehyde (59B)

[Chemical formula 137]

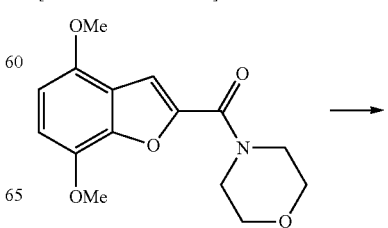

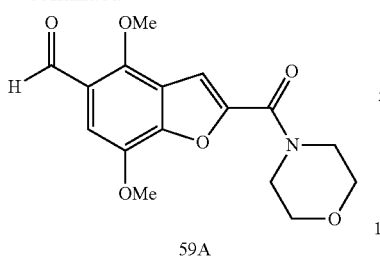

59A

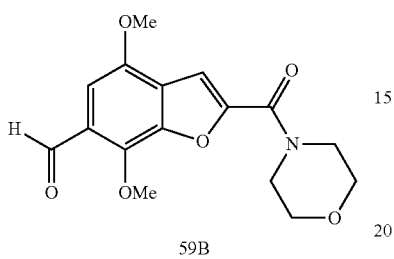

59B

Using (4,7-dimethoxy-1-benzofuran-2-yl) (morpholin-4-yl)methanone (9.8 g) under nitrogen atmosphere and according to the same methods as Reference examples 25 and 26, Compound 59A (8.8 g) and Compound 59B (0.88 g) were obtained as yellow solids, respectively.

(59A) MS (ESI+) 320 (M$^+$+1)

(59B) MS (ESI+) 320 (M$^+$+1).

Reference Example 37: 1-(4,8-dimethoxythieno[3,2-f][1]benzofuran-2-yl)ethanone (60E)

[Chemical formula 138]

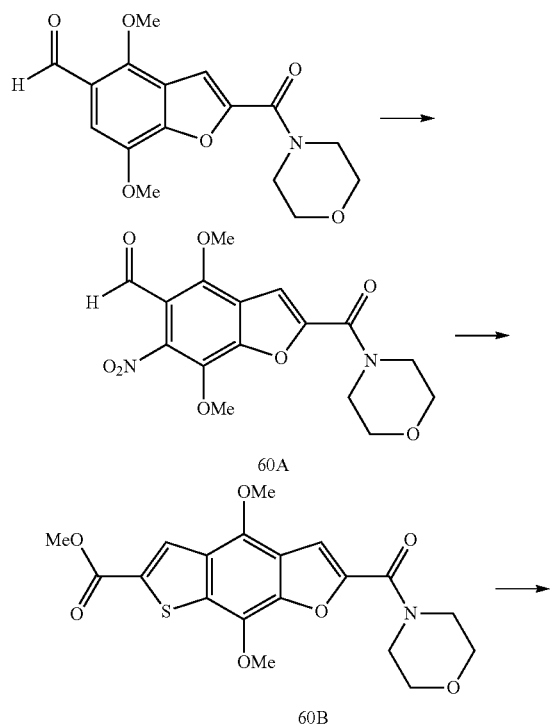

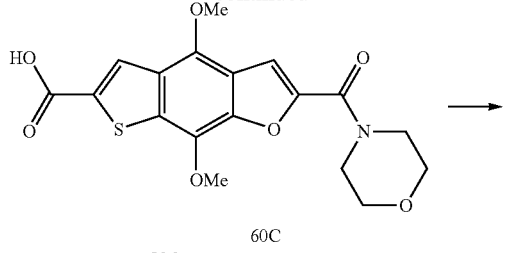

60C

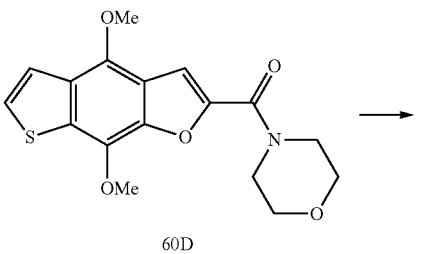

60D

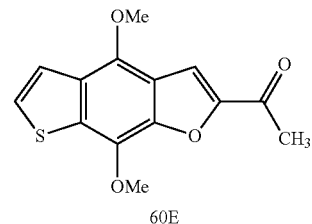

60E (a) 4,7-Dimethoxy-2-(morpholin-4-ylcarbonyl)-6-nitro-1-benzofuran-5-carbaldehyde (60A)

To a solution of 4,7-dimethoxy-2-(morpholin-4-ylcarbonyl)-1-benzofuran-5-carbaldehyde (8.8 g) (which was obtained in Reference example 35) in acetic acid (50 mL) was added dropwise 70% aqueous nitric acid solution (12.3 mL), and then the reaction mixture was heated and stirred at 70° C. for 1.5 hours. After the reaction solution was cooled to room temperature, it was poured into iced water, and then extracted with ethyl acetate two times. The resulting organic layer was washed with water and saturated brine, and then dried over sodium sulfate. The solvent was then evaporated off. The resulting residue was purified by silica gel chromatography (ethyl acetate/chloroform) to yield Compound 60A (7.09 g) as a yellow solid.

(b) Methyl 4,8-dimethoxy-2-(morpholin-4-ylcarbonyl)thieno[3,2-f][1]benzofuran-6-carboxylate (60B)

Using Compound 60A (7.09 g) obtained above and according to the same method as Reference example 1, Compound 60B (4.06 g) was obtained as a yellow solid.

(c) 4,8-Dimethoxy-2-(morpholin-4-ylcarbonyl)thieno[3,2-f][1]benzofuran-6-carboxylic Acid (60C)

Using Compound 60B (4.06 g) obtained above and according to the same method as Reference example 5, Compound 60C (3.5 g) was obtained.

(d) (4,8-Dimethoxythieno[3,2-f][1]benzofuran-2-yl)(morpholin-4-yl)methanone (60D)

To a solution of Compound 60C (3.50 g) (which was obtained above) in quinoline (10 mL) was added copper (3.40 g), and then the reaction mixture was stirred at 190° C. for 5 hours. After the reaction solution was cooled to room temperature, it was poured into iced water, neutralized to pH=3-5 with 1 N aqueous hydrochloric acid solution, and then extracted with ethyl acetate. The resulting organic layer was washed with water and saturated brine, and then dried over sodium sulfate. The solvent was then evaporated off. The resulting residue was purified by silica gel chromatography (ethyl acetate/chloroform) to yield Compound 60D (670 mg) as a yellow solid.

(e) 1-(4,8-Dimethoxythieno[3,2-f][1]benzofuran-2-yl)ethanone (60E)

Using Compound 60D (580 mg) obtained above and according to the same method as Reference example 6b, the title compound 60E was obtained as a yellow powder (350 mg).

(60A) MS (ESI+) 365 (M$^+$+1).
(60B) MS (ESI+) 406 (M$^+$+1).
(60C) MS (ESI+) 392 (M$^+$+1).
(60D) MS (ESI+) 348 (M$^+$+1).
(60E) MS (ESI+) 277 (M$^+$+1).

Example 52: 2-acetylthieno[3,2-f][1]benzofuran-4,8-dione

[Chemical formula 139]

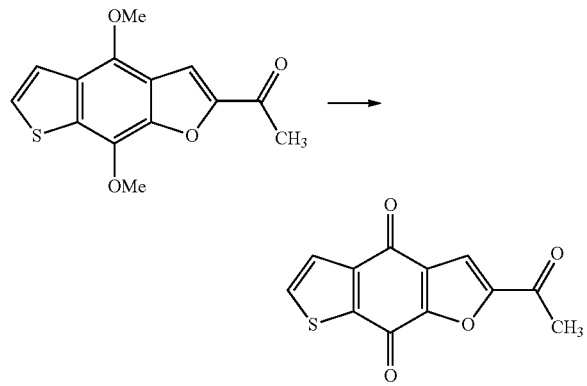

Using 1-(4,8-dimethoxythieno[3,2-f][1]benzofuran-2-yl)ethanone (300 mg) obtained in Reference example 37 and according to the same method as Example 1, the title compound was obtained as a yellow powder (260 mg).
MS (ESI+) 247 (M$^+$+1).

Example 53: 2-(1-hydroxyethyl)thieno[3,2-f][1]benzofuran-4,8-dione (61B)

[Chemical formula 140]

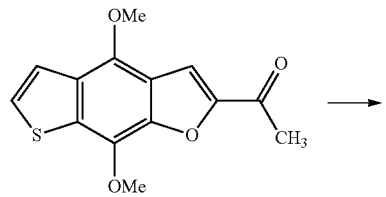

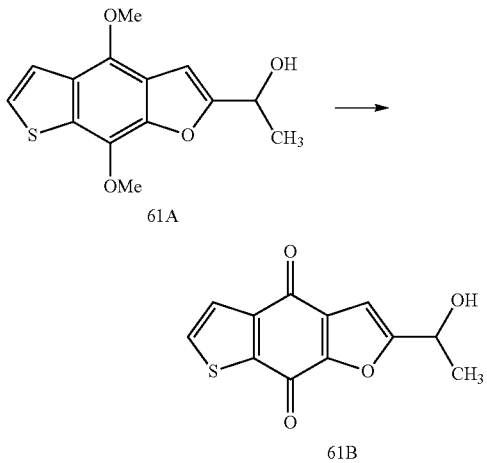

(a) 1-(4,8-Dimethoxythieno[3,2-f][1]benzofuran-2-yl)ethanol (61A)

Using 1-(4,8-dimethoxythieno[3,2-f][1]benzofuran-2-yl)ethanone (50 mg) obtained in Reference example 37 and according to the same method as Example 2a, Compound 61A was obtained as a yellow solid (50 mg).

(b) 2-(1-Hydroxyethyl)thieno[3,2-f][1]benzofuran-4,8-dione (61B)

Using Compound 61A (50 mg) obtained above and according to the same method as Example 1, the title compound 61B was obtained as a yellow powder (33 mg).

(61A) MS (ESI+) 279 (M$^+$+1).
(61B) MS (ESI+) 249 (M$^+$+1)

Example 54: 2-(2-hydroxypropan-2-yl)thieno[3,2-f][1]benzofuran-4,8-dione (62B)

[Chemical formula 141]

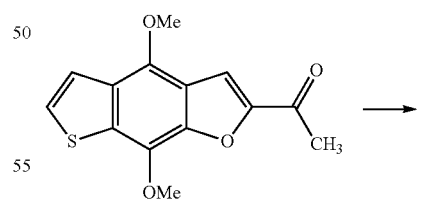

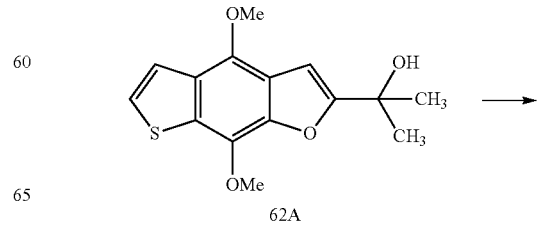

151
-continued

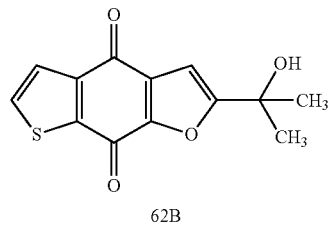

62B (a) 2-(4,8-Dimethoxythieno[3,2-f][1]benzofuran-2-yl)propan-2-ol (62A)

Using 1-(4,8-dimethoxythieno[3,2-f][1]benzofuran-2-yl)ethanone (50 mg) obtained in Reference example 37 and according to the same method as Example 15a, Compound 62A was obtained as a yellow solid (49 mg).

(b) 2-(2-Hydroxypropan-2-yl)thieno[3,2-f][1]benzofuran-4,8-dione (62B)

Using Compound 62A (50 mg) obtained above and according to the same method as Example 1, the title compound 62B was obtained as a yellow powder (33 mg).

(62A) MS (ESI+) 293 (M⁺+1).
(62B) MS (ESI+) 263 (M⁺+1)

Example 55: 2-(morpholin-4-ylcarbonyl)thieno[3,2-f][1]benzofuran-4,8-dione

[Chemical formula 142]

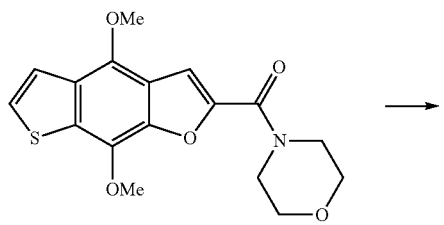

Using (4,8-dimethoxythieno[3,2-f][1]benzofuran-2-yl)(morpholin-4-yl)methanone (84 mg) obtained in Reference example 37d and according to the same method as Example 1, the title compound was obtained as a yellow powder (66 mg).

MS (ESI+) 318 (M⁺+1)

152

Example 56: 2-acetylthieno[2,3-f][1]benzofuran-4,8-dione (63F)

[Chemical formula 143]

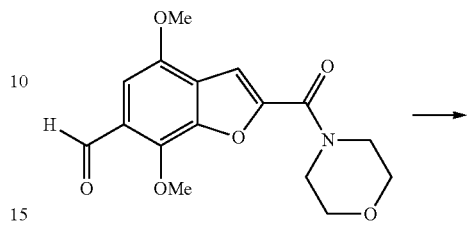

63A

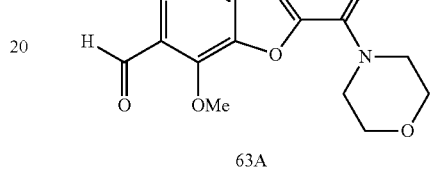

63B

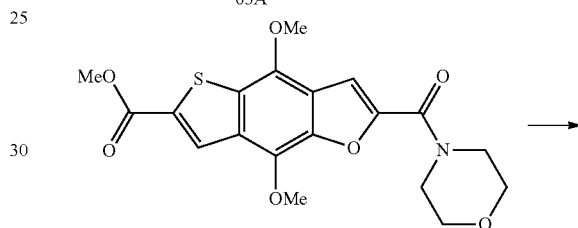

63C

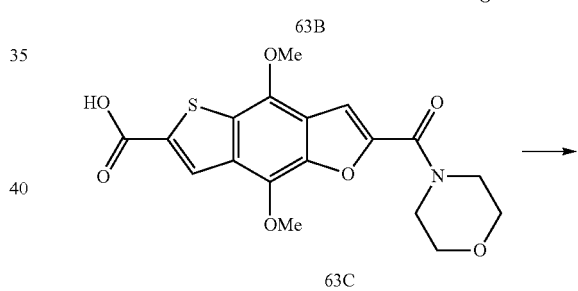

63D

63E

153
-continued

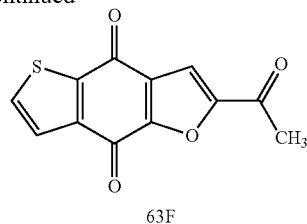
63F (a) 4,7-Dimethoxy-2-(morpholin-4-ylcarbonyl)-5-nitro-1-benzofuran-6-carbaldehyde (63A)

Using 4,7-dimethoxy-2-(morpholin-4-ylcarbonyl)-1-benzofuran-6-carbaldehyde (880 mg) obtained in Reference example 36 and according to the same method as Reference example 37a, Compound 63A was obtained as a yellow powder (840 mg).

(b) Methyl 4,8-dimethoxy-2-(morpholin-4-ylcarbonyl)thieno[2,3-f][1]benzofuran-6-carboxylate (63B)

Using Compound 63A (840 mg) obtained above and according to the same method as Reference example 37b, Compound 63B was obtained as a yellow powder (460 mg).

(c) 4,8-Dimethoxy-2-(morpholin-4-ylcarbonyl)thieno[2,3-f][1]benzofuran-6-carboxylic Acid (63C)

Using Compound 63B (460 mg) obtained above and according to the same method as Reference example 37c, Compound 63C was obtained as a yellow powder (190 mg).

(d) (4,8-Dimethoxythieno[2,3-f][1]benzofuran-2-yl)(morpholin-4-yl)methanone (63D)

Using Compound 63C (190 mg) obtained above and according to the same method as Reference example 37d, Compound 63D was obtained as a yellow powder (80 mg).

(e) 1-(4,8-Dimethoxythieno[2,3-f][1]benzofuran-2-yl)ethanone (63E)

Using Compound 63D (80 mg) obtained above and according to the same method as Reference example 37e, Compound 63E was obtained as a yellow powder (47 mg).

(f) 2-Acetylthieno[2,3-f][1]benzofuran-4,8-dione (63F)

Using Compound 63E (47 mg) obtained above and according to the same method as Example 1, the title compound 63F was obtained as a yellow powder (19 mg).

(63A) MS (ESI+) 365 (M$^+$+1).
(63B) MS (ESI+) 406 (M$^+$+1).
(63C) MS (ESI+) 392 (M$^+$+1).
(63D) MS (ESI+) 348 (M$^+$+1).
(63E) MS (ESI+) 277 (M$^+$+1).
(63F) MS (ESI+) 247 (M$^+$+1).

154
Reference Example 38: dimethyl 4,8-dioxo-4,8-dihydrothieno[3,2-f][1]benzofuran-2,6-dicarboxylate (64C)

[Chemical formula 144]

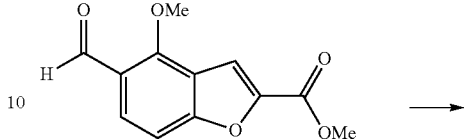

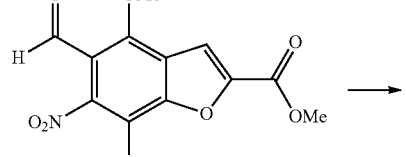
64A

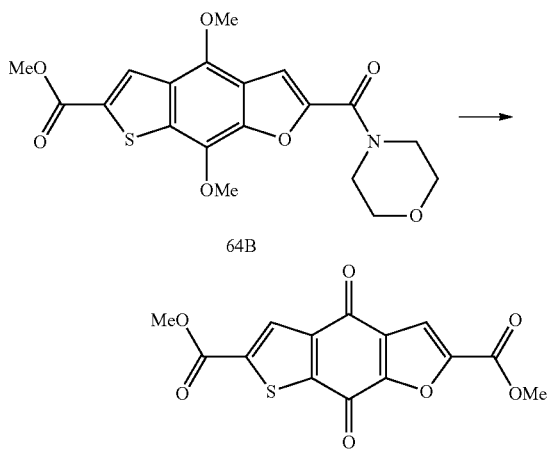
64B

64C (a) Methyl 5-formyl-4,7-dimethoxy-6-nitro-1-benzofuran-2-carboxylate (64A)

Using methyl 5-formyl-4,7-dimethoxy-1-benzofuran-2-carboxylate (33 mg) obtained in Reference example 25 and according to the same method as Reference example 37a, Compound 64A was obtained as a yellow powder (21 mg).

(b) Dimethyl 4,8-dimethoxythieno[3,2-f][1]benzofuran-2,6-dicarboxylate (64B)

Using Compound 64A (21 mg) obtained above and according to the same method as Reference example 37b, Compound 64B was obtained as a yellow powder (11 mg).

(c) Dimethyl 4,8-dioxo-4,8-dihydrothieno[3,2-f][1]benzofuran-2,6-dicarboxylate (64C)

Using Compound 64B (11 mg) obtained above and according to the same method as Example 1, the title compound 64C was obtained as a yellow powder (4 mg).
(64A) MS (ESI+) 310 (M$^+$+1)
(64B) MS (ESI+) 351 (M$^+$+1)
(64C) MS (ESI+) 321 (M$^+$+1).

Reference Example 39: 5,9-dimethoxythieno[2,3-g]quinoxaline-7-carboxylic Acid (65D)

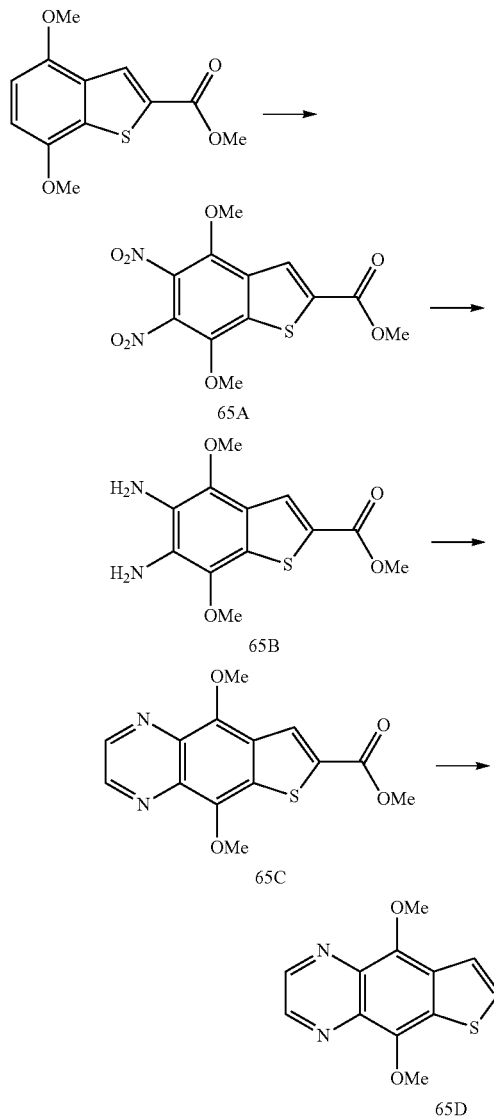

[Chemical formula 145]

(a) Methyl 4,7-dimethoxy-5,6-dinitro-1-benzothiophene-2-carboxylate (65A)

A solution of methyl 4,7-dimethoxy-1-benzothiophene-2-carboxylate (3.70 g) (which was obtained in Reference example 1) in aqueous nitric acid solution (37 mL) was stirred for 1.5 hours under heating at reflux. After it was returned to room temperature, the reaction solution was poured into iced water, and then extracted with ethyl acetate two times. The resulting organic layer was washed with aqueous saturated sodium bicarbonate and saturated brine, and then dried over sodium sulfate. The solvent was then evaporated off to yield Compound 65A as a yellow powder (5.05 g).

(b) Methyl 5,6-diamino-4,7-dimethoxy-1-benzothiophene-2-carboxylate (65B)

To a solution of Compound 65A (5.05 g) (which was obtained above) in methanol (50 mL), under ice-cooling, were slowly added nickel chloride (1.90 g), sodium borohydride (2.77 g), and then the reaction mixture was stirred at 0° C. for 1.5 hours. The reaction solution was returned to room temperature, and then filtered through Celite. The solvent of the filtrate was then evaporated off. The resulting residue was dissolved in ethyl acetate, washed with aqueous saturated sodium bicarbonate and saturated brine, and then dried over sodium sulfate. The solvent was then evaporated off to yield Compound 65B as a brown solid (0.64 g).

(c) Methyl 5,9-dimethoxythieno[2,3-g]quinoxaline-7-carboxylate (65C)

To a solution of Compound 65B (640 mg) (which was obtained above) in THF (68.0 mL) was added 40% aqueous glyoxal solution (2.27 mL), and then the reaction mixture was stirred for 1 hour under heating at reflux. The reaction solution was returned to room temperature, and then the solvent was evaporated off. The resulting residue was dissolved in chloroform, washed with water and saturated brine, and then dried over sodium sulfate. The solvent was then evaporated off to yield Compound 65C as a yellow powder (679 mg).

(d) 5,9-Dimethoxythieno[2,3-g]quinoxaline-7-carboxylic Acid (65D)

Using Compound 65C (679 mg) obtained above and according to the same method as Reference example 5, the title compound 65D was obtained as a yellow solid.

(65A) $^1$H-NMR (DMSO-$d_6$, δppm): 8.51 (1H, s), 4.16 (3H, s), 4.15 (3H, s), 3.97 (3H, s).
(65B) $^1$H-NMR (CDCl$_3$, δppm): 8.04 (1H, s), 3.94 (3H, s), 3.93 (3H, s), 3.92 (3H, s).
MS (ESI+) 283 (M$^+$+1).
(65C) $^1$H-NMR (DMSO-$d_6$, δppm): 9.01-8.99 (2H, m), 8.33 (1H, s), 4.30 (3H, s), 4.27 (3H, s), 3.94 (3H, s).
MS (ESI+) 305 (M$^+$+1).
(65D) MS (ESI+) 291 (M$^+$+1)

Example 57: 7-(morpholin-4-ylcarbonyl)thieno[2,3-g]quinoxaline-5,9-dione (66B)

[Chemical formula 146]

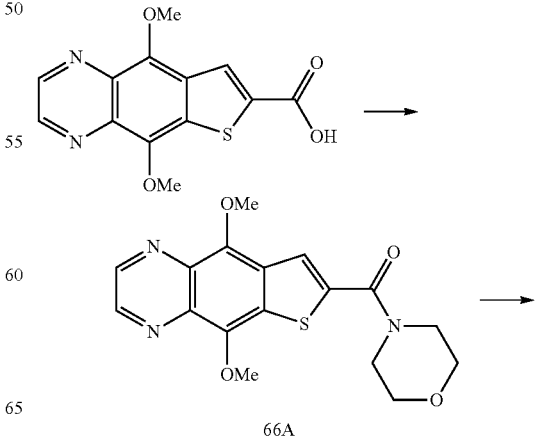

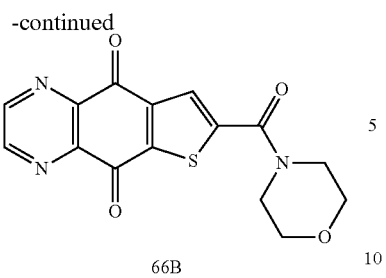

66B

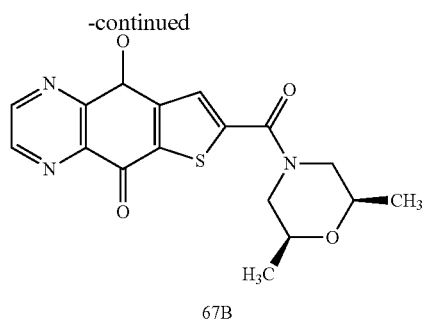

67B (a) 5,9-Dimethoxythieno[2,3-g]quinoxalin-7-yl(morpholin-4-yl)methanone (66A)

Using 5,9-dimethoxythieno[2,3-g]quinoxaline-7-carboxylic acid (64.7 mg) obtained in Reference example 39 and according to the same method as Reference example 6a, Compound 66A was obtained as a brown solid (98.7 mg).

(b) 7-(Morpholin-4-ylcarbonyl)thieno[2,3-g]quinoxaline-5,9-dione (66B)

Using Compound 66A (15.0 mg) obtained above and according to the same method as Example 1, the title compound 66B was obtained as a yellow solid (2.5 mg).

(66A) $^1$H-NMR (DMSO-d$_6$, δppm): 8.98 (2H, s), 7.92 (1H, s), 4.26 (3H, s), 4.25 (3H, s), 3.80-3.63 (8H, m).

MS (ESI+) 360 (M$^+$+1).

(66B) MS (ESI+) 330 (M$^+$+1).

Example 58: 7-{[(2R,6S)-2,6-dimethylmorpholin-4-yl]carbonyl}thieno[2,3-g]quinoxaline-5,9-dione (67B)

[Chemical formula 147]

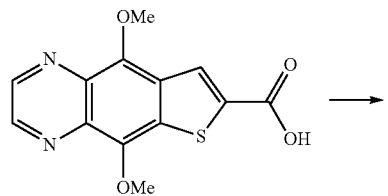

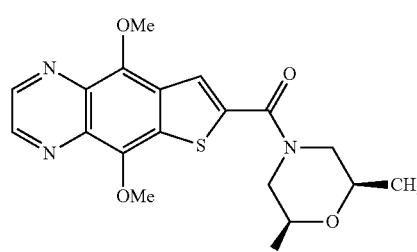

67A (a) 5,9-Dimethoxythieno[2,3-g]quinoxalin-7-yl)[(2R,6S)-2,6-dimethylmorpholin-4-yl]methanone (67A)

Using 5,9-dimethoxythieno[2,3-g]quinoxaline-7-carboxylic acid (which was obtained in Reference example 39) and (2S,6R)-2,6-dimethylmorpholine (51.4 mg) and according to the same method as Reference example 6a, Compound 67A was obtained as a brown solid (82.4 mg).

(b) 7-{[(2R,6S)-2,6-dimethylmorpholin-4-yl]carbonyl}thieno[2,3-g]quinoxaline-5,9-dione (67B)

Using Compound 67A (16.5 mg) obtained above and according to the same method as Example 1, the title compound 67B was obtained as a yellow solid (9.7 mg).

(67A) MS (ESI+) 388 (M$^+$+1)

(67B) MS (ESI+) 358 (M$^+$+1)

Reference Example 40: 5,9-dimethoxy-7-(morpholin-4-ylmethyl)thieno[2,3-g]quinoxaline (68C)

[Chemical formula 148]

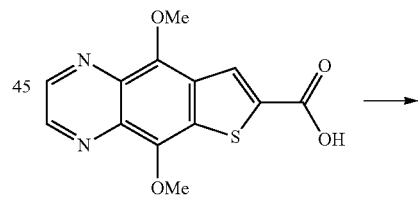

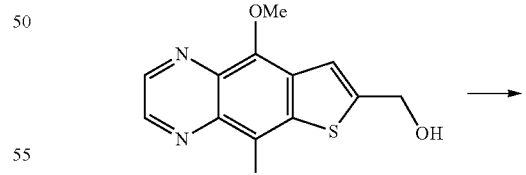

68A

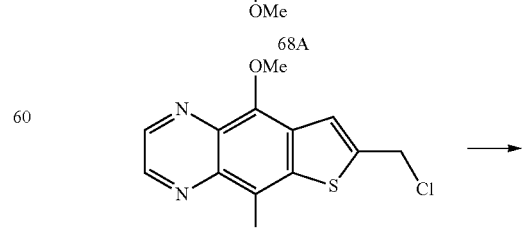

68B

-continued

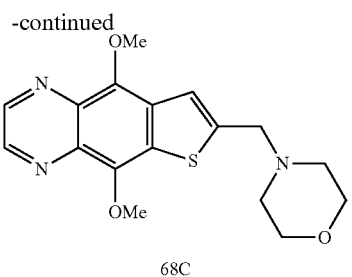

68C (a) (5,9-Dimethoxythieno[2,3-g]quinoxalin-7-yl)methanol (68A)

Using 5,9-dimethoxythieno[2,3-g]quinoxaline-7-carboxylic acid (31.4 mg) obtained in Reference example 39 and according to the same method as Reference example 12, Compound 68A was obtained as a yellow powder (9.0 mg).

(b) 7-(Chloromethyl)-5,9-dimethoxythieno[2,3-g]quinoxaline (68B)

Using Compound 68A (7.0 mg) obtained above and according to the same method as Reference example 7b, Compound 68B was obtained as a yellow solid.

(c) 5,9-Dimethoxy-7-(morpholin-4-ylmethyl) thieno[2,3-g]quinoxaline (68C)

Using Compound 68B obtained above and according to the same method as Reference example 8, the title compound 68C was obtained as a yellow powder (4.4 mg).

(68A) $^1$H-NMR (DMSO-d$_6$, δppm): 8.95-8.92 (2H, m), 7.54 (1H, s), 5.84 (1H, t, J=6.0 Hz), 4.81 (2H, d, J=6.0 Hz), 4.23 (3H, s), 4.18 (3H, s).
MS (ESI+) 277 (M$^+$+1).
(68B) $^1$H-NMR (DMSO-d$_6$, δppm): 9.00-8.91 (2H, m), 7.82 (1H, s), 5.21 (2H, s), 4.22 (3H, s), 4.18 (3H, s).
MS (ESI+) 295 (M$^+$+1).
(68C) MS (ESI+) 346 (M$^+$+1).

Example 59: 7-(morpholin-4-ylmethyl)thieno[2,3-g]quinoxaline-5,9-dione

[Chemical formula 149]

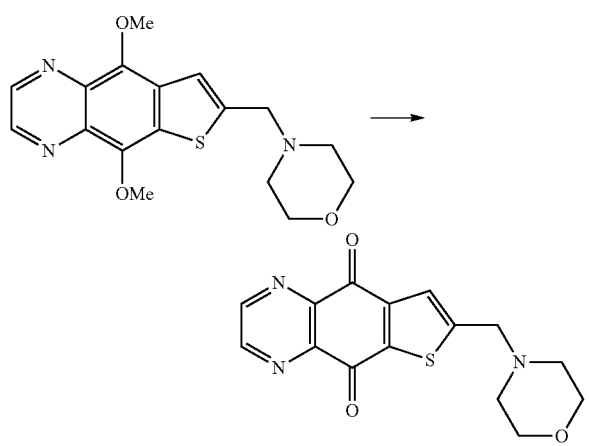

Using 5,9-dimethoxy-7-(morpholin-4-ylmethyl)thieno[2,3-g]quinoxaline (4.0 mg) obtained in Reference example 40 and according to the same method as Example 1, the title compound was obtained as a yellow solid (0.6 mg).
$^1$H-NMR (CDCl$_3$, δppm): 8.98-8.96 (2H, m), 7.59 (1H, s), 3.90-3.50 (6H, m), 2.70-2.40 (4H, m).
MS (ESI+) 316 (M$^+$+1).

Reference Example 41: methyl 2-(1,1-dimethoxyethyl)-4,9-dioxo-4,9-dihydrofuro[2,3-g]phthalazine-3-carboxylate

[Chemical formula 150]

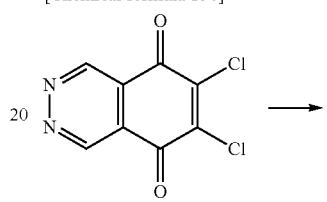

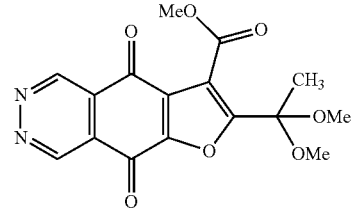

Using 6,7-dichlorophthalazine-5,8-dione (1.14 g) and according to the same method as Reference example 29, the title compound was obtained as a yellow solid (0.1 g).
MS (ESI+) 341 (M$^+$+1).

Reference Example 42: methyl 2-acetyl-4,9-dioxo-4,9-dihydrofuro[2,3-g]phthalazine-3-carboxylate

[Chemical formula 151]

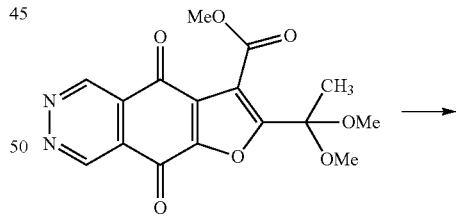

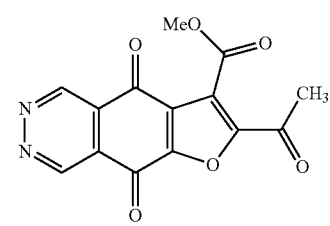

Using the compound (0.1 g) obtained in Reference example 41 and according to the same method as Reference example 30, the title compound was obtained as a yellow solid (0.03 g).
MS (ESI+) 301 (M$^+$+1).

Reference Example 43: 4,9-dimethoxythieno[2,3-g]isoquinoline-2-carbaldehyde

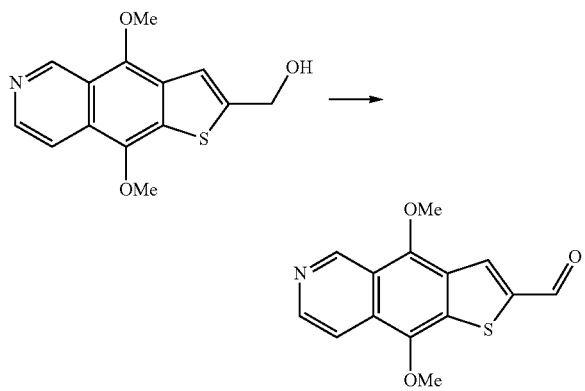

To a solution of (4,9-dimethoxythieno[2,3-g]isoquinolin-2-yl)methanol (315 mg) (which was obtained in Reference example 12) in dichloromethane (30 mL) was added manganese dioxide (1.6 g) under room temperature, and then the reaction mixture was stirred for 12 hours. The reaction solution was filtered through Celite, and then the solvent of the filtrate was evaporated off. The resulting residue was purified by silica gel column chromatography (chloroform/methanol) to yield the title compound (169 mg).

LC-MS: $[M+H]^+/Rt(min)=274/0.39$.

Reference Example 44: ethyl (E)-3-(4,9-dimethoxythieno[2,3-g]isoquinolin-2-yl)acrylate

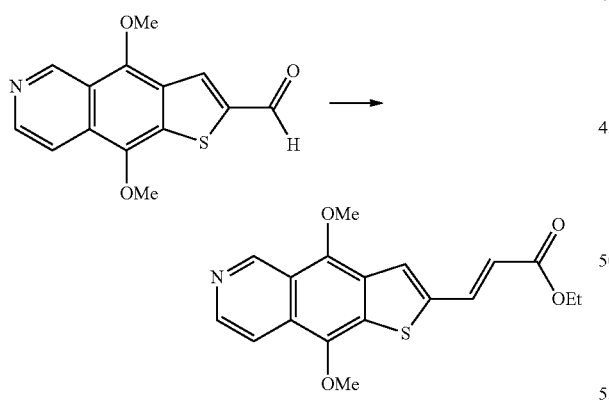

To a solution of 4,9-dimethoxythieno[2,3-g]isoquinoline-2-carbaldehyde (86 mg) (which was obtained in Reference example 43) in toluene (30 mL) was added (carbethoxymethylene)triphenylphosphorane (164 mg) under room temperature, and then the reaction mixture was stirred at 80° C. for 2 hours. The reaction solution was cooled to room temperature, and then the solvent of the filtrate was evaporated off. The resulting residue was purified by silica gel column chromatography (chloroform/ethyl acetate) to yield the title compound (68 mg).

LC-MS: $[M+H]/Rt(min)=344/0.87$.

Example 60: ethyl (E)-3-(4,9-dioxo-4,9-dihydrothieno[2,3-g]isoquinolin-2-yl)acrylate

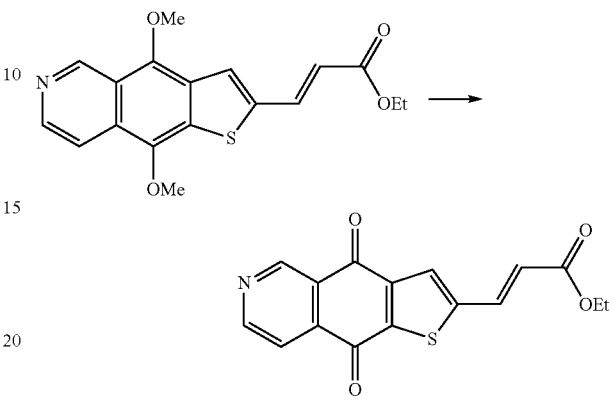

Using ethyl (E)-3-(4,9-dimethoxythieno[2,3-g]isoquinolin-2-yl)acrylate (68 mg) obtained in Reference example 44 and according to the same method as Example 1, the title compound was obtained as a yellow powder (24 mg).

LC-MS: $[M+H]^+/Rt(min)=314/0.97$.

Reference Example 45: 2-ethynyl-4,9-dimethoxythieno[2,3-g]isoquinoline

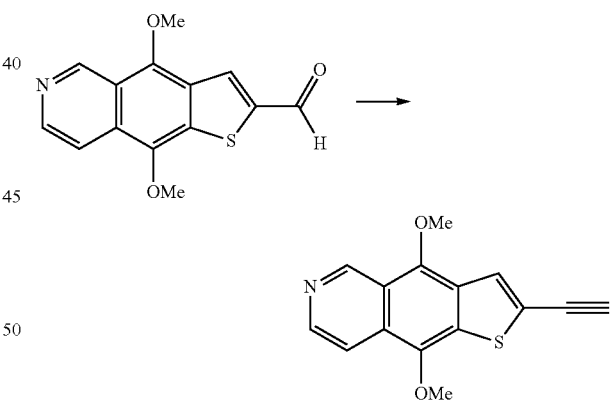

To a solution of 4,9-dimethoxythieno[2,3-g]isoquinoline-2-carbaldehyde (83 mg) (which was obtained in Reference example 43) in methanol (30 mL) was added potassium carbonate (126 mg) and dimethyl(1-diazo-2-oxopropyl)phosphonate (88 mg) under room temperature, and then the reaction mixture was stirred at 0° C. for 5 hours. The reaction solution was returned to room temperature, and then filtrated through Celite. The solvent of the filtrate was then evaporated off. The resulting residue was purified by silica gel column chromatography (chloroform/ethyl acetate) to yield the title compound (32 mg).

LC-MS: $[M+H]^+/Rt(min)=270/0.76$.

Example 61: 2-ethynylthieno[2,3-g]isoquinoline-4,9-dione

[Chemical formula 156]

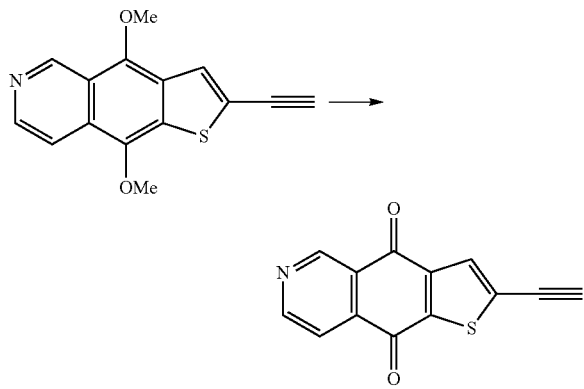

Using 2-ethynyl-4,9-dimethoxythieno[2,3-g]isoquinoline (32 mg) obtained in Reference example 45 and according to the same method as Example 1, the title compound was obtained as a yellow powder (9 mg).

LC-MS: [M+H]$^+$/Rt(min)=240/0.87.

Reference Example 46: ethyl 2-(difluoromethyl)-4,9-dioxo-4,9-dihydrofuro[2,3-g]isoquinoline-3-carboxylate

[Chemical formula 157]

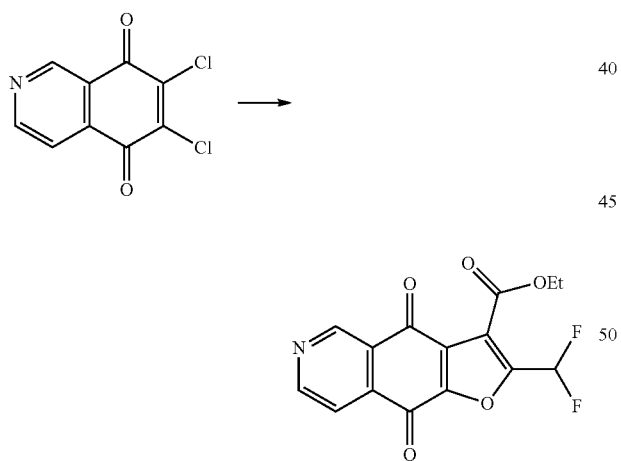

A solution of 6,7-dichloroisoquinoline-5,8-dione (355 mg), ethyl 4,4-difluoroacetoacetate (288 µL), potassium carbonate (507 mg) in acetonitrile (15 mL) was stirred for 5 hours under heating at reflux. The reaction solution was cooled to room temperature. The insoluble substance was filtered and then the filtrate was concentrated under reduced pressure. The resulting residue was purified by silica gel column chromatography (hexane/ethyl acetate) to yield the title compound as a yellow solid (225 mg)

MS (ESI+) 322 (M$^+$+1)

Reference Example 47: 2-(difluoromethyl)-4,9-dioxo-4,9-dihydrofuro[2,3-g]isoquinoline-3-carboxylic Acid

[Chemical formula 158]

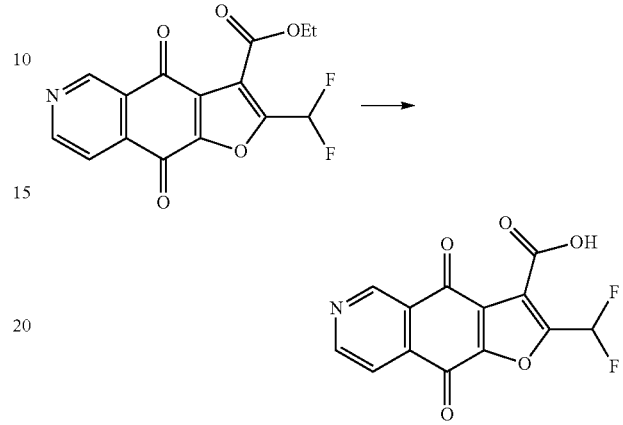

A solution of ethyl 2-(difluoromethyl)-4,9-dioxo-4,9-dihydrofuro[2,3-g]isoquinoline-3-carboxylate (190 mg) (which was obtained in Reference example 46) in concentrated hydrochloric acid (20 mL) was stirred for 2 hours under heating at reflux. The reaction solution was cooled to room temperature and then concentrated under reduced pressure to yield a crude product of the title compound (176 mg).

MS (ESI+) 294 (M$^+$+1).

Example 62: 2-(difluoromethyl)-3-(morpholine-4-carbonyl)furo[2,3-g]isoquinoline-4,9-dione

[Chemical formula 159]

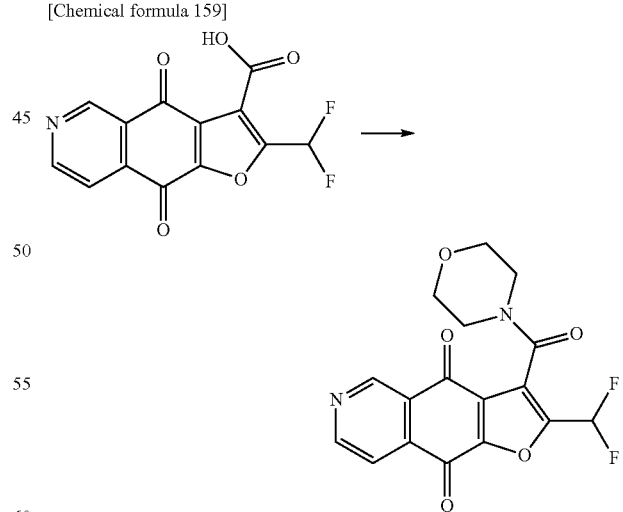

DMF (10 µL) was added to a solution of 2-(difluoromethyl)-4,9-dioxo-4,9-dihydrofuro[2,3-g]isoquinoline-3-carboxylic acid (158 mg) (which was obtained in Reference example 47) in thionyl chloride (5 mL), and then the reaction mixture was stirred at 100° C. for 5 hours. The reaction solution was cooled to room temperature and then concentrated under reduced pressure. The resulting residue was then dissolved in THF (5 mL) and cooled to 0° C. Subsequently, morpholine (94 µL) was added dropwise, and then the reaction solution was stirred at room temperature for 15 minutes. The reaction solution was concentrated under reduced pressure, and then water and chloroform were added to the residue, followed by extraction with chloroform. The organic layer was dried over anhydrous sodium sulfate and then filtered. The filtrate was concentrated under reduced pressure, and then the resulting residue was purified by silica gel column chromatography (hexane/ethyl acetate) to yield the title compound as a yellow solid (41 mg).

MS (ESI+) 363 (M$^+$+1).

Example 63: 2-(difluoromethyl)furo[2,3-g]isoquinoline-4,9-dione

[Chemical formula 160]

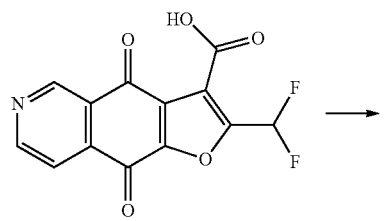

To a solution of 2-(difluoromethyl)-4,9-dioxo-4,9-dihydrofuro[2,3-g]isoquinoline-3-carboxylic acid (211 mg) (which was obtained in Reference example 47) in quinoline (3 mL) was added cupper powder (133 mg), and then the reaction mixture was stirred at 150° C. for 1 hour. The reaction solution was cooled to room temperature, poured into iced water, and then extracted with chloroform. The organic layer was dried over anhydrous sodium sulfate, filtered, and then concentrated under reduced pressure. The organic layer was dried over anhydrous sodium sulfate, and then filtered. The filtrate was concentrated under reduced pressure, and then the resulting residue was purified by silica gel column chromatography (hexane/ethyl acetate) to yield the title compound as a yellow solid (72 mg).

LC-MS: [M+H]$^+$/Rt(min)=250/0.75.

Test Example 1: Proliferation Inhibition Assay of Cancer Cells

HCT-116 cells (derived from human colon adenocarcinoma), HT-29 cells (derived from human colon cancer), and FaDu cells (derived from human hypopharynx cancer) were obtained from American Type Culture Collection (ATCC). HCT-116 cells and HT-29 cells were cultured using McCoy's 5a medium containing 10% fetal bovine serum (FBS) and 1% penicillin/streptomycin, and FaDu cells were cultured using MEM medium containing 10% FBS, 1% non-essential amino acid, 1% sodium pyruvate, and 1% penicillin/streptomycin, respectively, at 37° C. in the presence of 5% $CO_2$. After cells were seeded at 300-600 cells/well onto black µClear-plate 384 well (Greiner bio-one Cat. No. 781091), a test substance was added such that the final concentration of DMSO is 0.1%, and cultured for 4 days. The number of living cells was then counted using Cell Titer-Glo (Registered trademark) Luminescent Cell Viability Assay (Promega) to calculate a concentration for 50% inhibition of cell proliferation of respective test substances (Bulk IC50 value; µM).

A test shown in Test example 1 was carried out for compounds obtained in the Examples.

The concentrations for 50% inhibition of cell proliferation of respective test substances (Bulk IC50 value; µM) are shown in Table 1.

TABLE 1

| Example | IC$_{50}$ (µM) | | |
| --- | --- | --- | --- |
| | HCT | FaDu | HT |
| 1 | 0.01 | 0.01 | 0.57 |
| 2 | 0.08 | 0.10 | 0.86 |
| 3 | 0.06 | 0.07 | 0.56 |
| 4 | 0.57 | 0.46 | 0.68 |
| 5 | 0.45 | 0.54 | 0.92 |
| 6 | 0.39 | 0.41 | 0.93 |
| 7 | 0.40 | 0.40 | 2.64 |
| 8 | 0.38 | 0.37 | 0.83 |
| 9 | 0.53 | 0.60 | >10 |
| 10 | 0.50 | 0.50 | 6.14 |
| 11 | 0.49 | 0.45 | 3.85 |
| 12 | 0.05 | <0.01 | 0.18 |
| 13 | 0.06 | 0.02 | 0.37 |
| 14 | 0.06 | 0.03 | 0.48 |
| 15 | 0.34 | 0.04 | 0.61 |
| 16 | 0.06 | <0.01 | 0.58 |
| 17 | 0.41 | 0.84 | 0.87 |
| 18 | 1.00 | 0.57 | >10 |
| 19 | 0.07 | <0.01 | 0.10 |
| 20 | 0.05 | <0.01 | 0.09 |
| 21 | 0.06 | <0.01 | 0.07 |
| 22 | 0.48 | 0.44 | 0.81 |
| 23 | 0.10 | 0.03 | 0.58 |
| 24 | 0.34 | 0.03 | 0.65 |
| 25 | 0.69 | 0.46 | 0.96 |
| 26 | 0.09 | 0.02 | 0.45 |
| 27 | 0.50 | 0.03 | 0.40 |
| 28 | 0.47 | 0.08 | 0.63 |
| 29 | 0.04 | <0.01 | 0.32 |
| 30 | <0.01 | <0.01 | 0.05 |
| 31 | 0.04 | <0.01 | 0.31 |
| 32 | 6.56 | 2.15 | >10 |
| 33 | <0.01 | <0.01 | 0.09 |
| 34 | 0.07 | 0.04 | 0.64 |
| 35 | 0.08 | 0.05 | 0.60 |
| 36 | 0.10 | 0.09 | 0.73 |
| 37 | 0.06 | 0.08 | 0.62 |
| 38 | 0.55 | 0.44 | 0.66 |
| 39 | 0.38 | 0.09 | 3.71 |
| 40 | 0.07 | 0.05 | 0.55 |
| 41 | 0.70 | 0.78 | 4.52 |
| 42 | 0.54 | 0.47 | 0.72 |
| 43 | 0.62 | 0.66 | 5.62 |
| 44 | 0.06 | 0.03 | 0.51 |
| 45 | 0.06 | 0.03 | 0.52 |
| 46 | <0.01 | <0.01 | 0.05 |
| 47 | 0.36 | 0.05 | 0.41 |
| 48 | 0.07 | 0.06 | 0.62 |
| 49 | 0.04 | <0.01 | 0.08 |
| 50 | 0.47 | 0.47 | 0.59 |
| 51 | 0.39 | 0.49 | 0.84 |
| 52 | 0.07 | 0.43 | 0.64 |
| 53 | 0.55 | 0.64 | 0.68 |
| 54 | 0.61 | 0.67 | 2.47 |
| 55 | 0.05 | 0.06 | 0.58 |
| 56 | 0.09 | 0.56 | 0.62 |
| 57 | 5.71 | 8.21 | >10 |
| 58 | 0.64 | 3.71 | 7.06 |

TABLE 1-continued

| Example | IC$_{50}$ (μM) | | |
|---|---|---|---|
| | HCT | FaDu | HT |
| 59 | 0.28 | 0.36 | 0.84 |
| 60 | 2.71 | 0.75 | >10 |
| 61 | 0.19 | 0.05 | 0.54 |
| 62 | 0.06 | 0.04 | 0.57 |
| 63 | 0.05 | 0.05 | 0.54 |

As shown in Table 1, the compounds of the present invention exhibited strong inhibitory effects on the proliferation of cancer cells in the proliferation inhibition test of cancer cells. The compounds of Examples 1, 12, 16, 19, 20, 21, 29, 30, 31, 33, 46, 49, 62, and 63 exhibited a particularly strong effect on the inhibition of the proliferation of cancer cells.

Test Example 2: Inhibition Assay of Cancer Cell Sphere-Forming Ability

HCT-116 cells (derived from human colon adenocarcinoma), HT-29 cells (derived from human colon cancer), FaDu cells (derived from human hypopharynx cancer) were obtained from American Type Culture Collection (ATCC). HCT-116 cells and HT-29 cells were cultured using McCoy's 5a medium containing 10% fetal bovine serum (FBS) and 1% penicillin/streptomycin, and FaDu cells were cultured using MEM medium containing 10% FBS, 1% non-essential amino acid, 1% sodium pyruvate, and 1% penicillin/streptomycin, respectively, at 37° C. in the presence of 5% $CO_2$. HCT-116 cells, HT-29 cells, and FaDu cells were seeded onto 384 Well Black Clear Bottom Ultra-Low Attachment Microplate (Corning Cat. No. 3827) using DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), and 1% penicillin/streptomycin to be 350-800 cells/well. A test substance was added so that the final concentration of DMSO is 0.1%, and then cultured for 4 days. The number of living cells was then counted using Cell Titer-Glo (registered trademark) Luminescent Cell Viability Assay (Promega) to calculate the concentration for 50% inhibition of cell proliferation of respective test substances (Sphere IC50 value; μM).

A test shown in Test example 2 was carried out for compounds obtained in the Examples.

The concentrations for 50% inhibition of cell proliferation of respective test substances (Sphere IC50 value; UM) are shown in Table 2.

TABLE 2

| Example | IC$_{50}$ (μM) | | |
|---|---|---|---|
| | HCT | FaDu | HT |
| 1 | 0.02 | 0.02 | 0.07 |
| 2 | 0.23 | 0.12 | 0.55 |
| 3 | 0.05 | 0.05 | 0.43 |
| 4 | 0.55 | 0.34 | 0.63 |
| 5 | 0.39 | 0.50 | 0.57 |
| 6 | 0.20 | 0.33 | 0.63 |
| 7 | 0.51 | 0.36 | 3.04 |
| 8 | 0.41 | 0.32 | 0.60 |
| 9 | 0.28 | 0.10 | 0.61 |
| 10 | 0.38 | 0.09 | 0.53 |
| 11 | 0.46 | 0.28 | 0.71 |
| 12 | 0.04 | <0.01 | 0.03 |
| 13 | 0.05 | <0.01 | 0.06 |
| 14 | 0.09 | 0.02 | 0.09 |
| 15 | 0.40 | <0.01 | 0.46 |
| 16 | 0.22 | <0.01 | 0.15 |
| 17 | 0.55 | 0.05 | 0.54 |
| 18 | 5.71 | 0.63 | >10 |
| 19 | 0.05 | <0.01 | 0.04 |
| 20 | 0.06 | <0.01 | 0.06 |
| 21 | 0.05 | <0.01 | 0.06 |
| 22 | 0.50 | 0.31 | 0.16 |
| 23 | 0.31 | 0.04 | 0.48 |
| 24 | 0.43 | <0.01 | 0.18 |
| 25 | 0.80 | 0.06 | <0.01 |
| 26 | 0.17 | <0.01 | 0.07 |
| 27 | 0.47 | <0.01 | 0.06 |
| 28 | 0.57 | 0.09 | 0.59 |
| 29 | 0.05 | <0.01 | 0.05 |
| 30 | <0.01 | <0.01 | <0.01 |
| 31 | 0.03 | <0.01 | <0.01 |
| 32 | 7.70 | 1.25 | >10 |
| 33 | 0.02 | <0.01 | 0.07 |
| 34 | 0.24 | 0.04 | 0.50 |
| 35 | 0.27 | 0.04 | 0.39 |
| 36 | 0.07 | 0.05 | 0.25 |
| 37 | 0.06 | 0.06 | 0.49 |
| 38 | 0.55 | 0.28 | 0.59 |
| 39 | 0.35 | 0.45 | 0.55 |
| 40 | 0.08 | 0.05 | 0.51 |
| 41 | 0.83 | 0.46 | 3.82 |
| 42 | 0.31 | 0.08 | 0.59 |
| 43 | 0.51 | 0.33 | 0.60 |
| 44 | 0.06 | 0.04 | 0.08 |
| 45 | 0.06 | 0.03 | 0.08 |
| 46 | 0.04 | <0.01 | 0.05 |
| 47 | 0.26 | 0.05 | 0.17 |
| 48 | 0.07 | 0.05 | 0.55 |
| 49 | 0.04 | <0.01 | 0.06 |
| 50 | 0.26 | 0.17 | 0.58 |
| 51 | 0.09 | 0.08 | 0.43 |
| 52 | 0.05 | 0.06 | 0.08 |
| 53 | 0.56 | 0.45 | 0.59 |
| 54 | 0.60 | 0.59 | 0.77 |
| 55 | 0.04 | 0.01 | 0.04 |
| 56 | 0.06 | 0.08 | 0.58 |
| 57 | 4.97 | 5.65 | >10 |
| 58 | 0.56 | 0.76 | 5.97 |
| 59 | 0.05 | 0.06 | 0.63 |
| 60 | 7.41 | 0.83 | 8.98 |
| 61 | 0.28 | 0.05 | 0.24 |
| 62 | 0.05 | <0.01 | 0.04 |
| 63 | 0.06 | 0.04 | 0.24 |

As shown in Table 2, the compounds of the present invention exhibited strong effect to inhibit cancer cell sphere-forming ability in the inhibition test of cancer cell sphere-forming ability. The compounds of Examples 12, 13, 15, 16, 19, 20, 21, 24, 26, 27, 29, 30, 31, 33, 46, 49, 55, 62, and 63 exhibited a particularly strong effect to inhibit cancer cell sphere-forming ability.

As described above, the present invention is illustrated by preferable embodiments of the present invention. However, it will be understood that the scope of the present invention should be interpreted only by the claims. It will be understood that the contents of patents, patent applications, and literatures cited in the present specification should be incorporated by reference to the present specification as if their contents per se are specifically described in the present specification. The present application claims priority to Japanese Patent Application No. 2014-72398 (filed on Mar. 31, 2014) and its contents are incorporated in the present application by reference in its entirety.

INDUSTRIAL APPLICABILITY

The present invention provides novel tricyclic quinone derivatives, or pharmacologically acceptable salts thereof, production methods and uses thereof. The tricyclic quinone derivatives of the present invention have strong inhibitory effect on the proliferation of cancer cells and cancer cell sphere-forming ability, and are useful in the prevention, treatment, and/or the like of a disease such as cancer and the like.

The invention claimed is:

1. A compound or a pharmacologically acceptable salt thereof, wherein the compound is selected from the group consisting of:

| Example | Name | Structure |
|---|---|---|
| 1 | 2-acetylthieno[2,3-g]quinoline-4,9-dione | 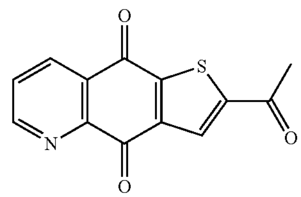 [SMILES: CC(=O)c1cc2c(s1)C(=O)c1cccnc1C2=O] |
| 2 | 2-(1-hydroxyethyl)thieno[2,3-g]quinoline-4,9-dione | 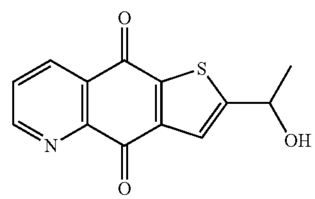 [SMILES: CC(O)c1cc2c(s1)C(=O)c1cccnc1C2=O] |
| 3 | N,N-dimethyl-4,9-dioxo-4,9-dihydrothieno[2,3-g]quinoline-2-carboxamide | 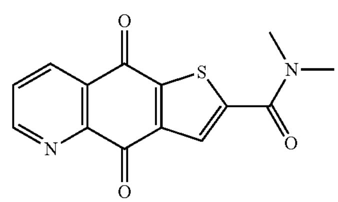 [SMILES: CN(C)C(=O)c1cc2c(s1)C(=O)c1cccnc1C2=O] |
| 4 | 2-(morpholin-4-ylmethyl)thieno[2,3-g]quinoline-4,9-dione | 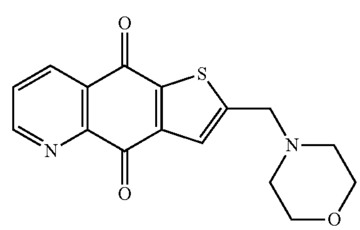 [SMILES: O=C1c2cc(CN3CCOCC3)sc2C(=O)c2cccnc21] |
| 5 | 2-{[cyclohexyl(ethyl)amino]methyl}thieno[2,3-g]quinoline-4,9-dione | 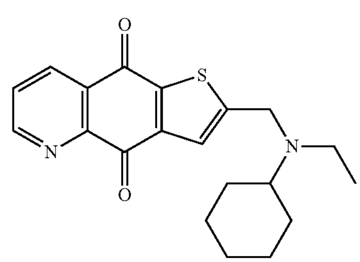 [SMILES: CCN(Cc1cc2c(s1)C(=O)c1cccnc1C2=O)C1CCCCC1] |
| 6 | 2-{[ethyl(2-methoxyethyl)amino]methyl}thieno[2,3-g]quinoline-4,9-dione | 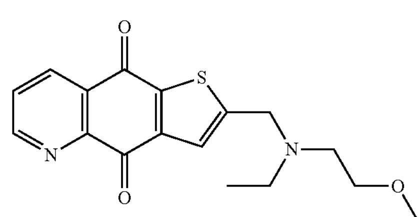 |

-continued

| Example | Name | Structure |
|---|---|---|
| 7 | 2-{[ethyl(pyridin-4-ylmethyl)amino]methyl}thieno[2,3-g]quinoline-4,9-dione | 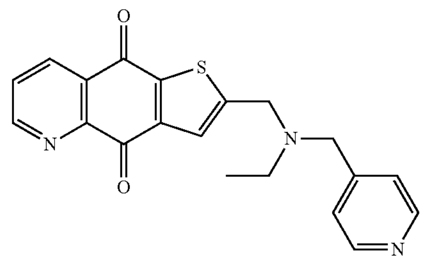 [SMILES: CCN(Cc1ccncc1)Cc1cc2c(s1)C(=O)c1cccnc1C2=O] |
| 8 | 2-(((4,9-dioxo-4,9-dihydrothieno[2,3-g]quinolin-2-yl)methyl)(ethyl)amino)-N,N-dimethylacetamide | 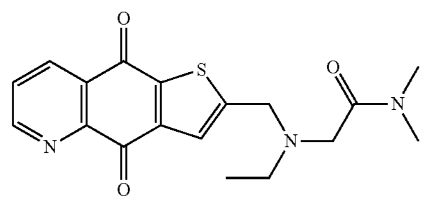 [SMILES: CCN(CC(=O)N(C)C)Cc1cc2c(s1)C(=O)c1cccnc1C2=O] |
| 12 | 2-acetylthieno[2,3-g]isoquinoline-4,9-dione | 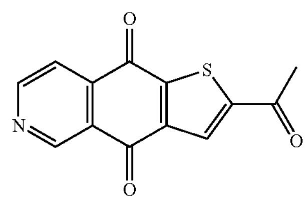 [SMILES: CC(=O)c1cc2c(s1)C(=O)c1ccncc1C2=O] |
| 13 | 2-(1-hydroxyethyl)thieno[2,3-g]isoquinoline-4,9-dione | 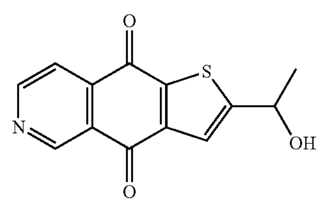 [SMILES: CC(O)c1cc2c(s1)C(=O)c1ccncc1C2=O] |
| 14 | 2-(1-hydroxymethyl)thieno[2,3-g]isoquinoline-4,9-dione | 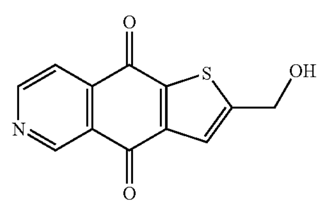 [SMILES: O=C1c2cnccc2C(=O)c2sc(CO)cc21] |
| 15 | 2-(2-hydroxypropan-2-yl)thieno[2,3-g]isoquinoline-4,9-dione | 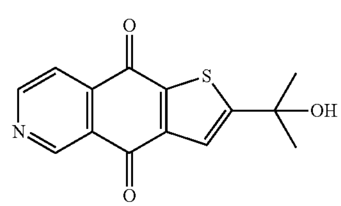 [SMILES: CC(C)(O)c1cc2c(s1)C(=O)c1ccncc1C2=O] |
| 16 | 2-[cyclopropyl(hydroxy)methyl]thieno[2,3-g]isoquinoline-4,9-dione | 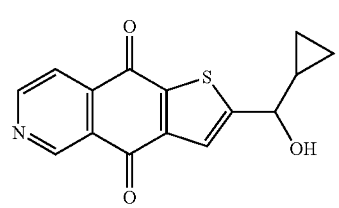 [SMILES: O=C1c2cnccc2C(=O)c2sc(C(O)C3CC3)cc21] |

| Example | Name | Structure |
|---|---|---|
| 17 | 2-[cyclopropl(ethoxy)methyl]thieno[2,3-g]isoquinoline-4,9-dione | 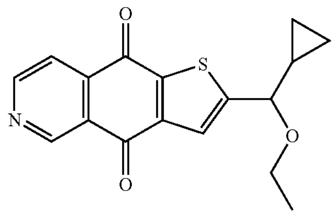 [SMILES: CCOC(c1cc2c(s1)C(=O)c1ccncc1C2=O)C1CC1] |
| 18 | 2-[(benzyloxy)methyl]thieno[2,3-g]isoquinoline-4,9-dione | 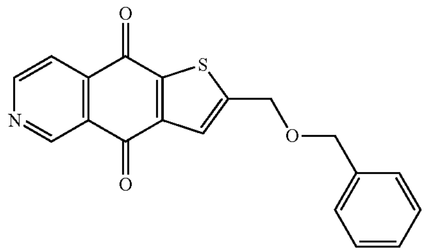 [SMILES: O=C1c2cnccc2C(=O)c2sc(COCc3ccccc3)cc21] |
| 19 | N,N-dimethyl-4,9-dioxo-4,9-dihydrothieno[2,3-g]isoquinoline-2-carboxamide | 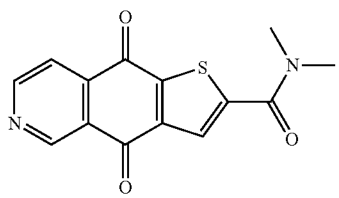 [SMILES: CN(C)C(=O)c1cc2c(s1)C(=O)c1ccncc1C2=O] |
| 20 | 2-(morpholin-4-ylcarbonyl)thieno[2,3-g]isoquinoline-4,9-dione | 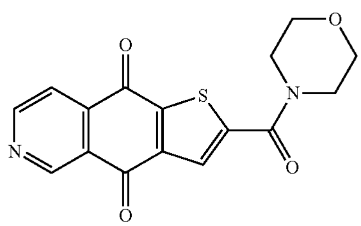 [SMILES: O=C1c2cnccc2C(=O)c2sc(C(=O)N3CCOCC3)cc21] |
| 21 | N-(2,2-difluoroethyl)-4,9-dioxo-4,9-dihydrothieno[2,3-g]isoquinoline-2-carboxamide | 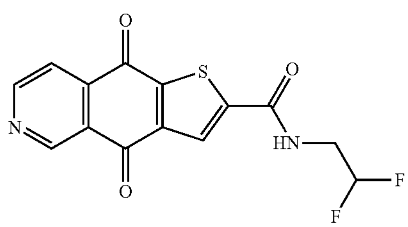 [SMILES: O=C(NCC(F)F)c1cc2c(s1)C(=O)c1ccncc1C2=O] |
| 23 | 2-[1-(morpholin-4-yl)ethyl]thieno[2,3-g]isoquinoline-4,9-dione | 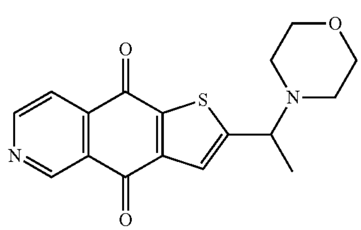 [SMILES: CC(c1cc2c(s1)C(=O)c1ccncc1C2=O)N1CCOCC1] |
| 24 | 2-{[ethyl(2-methoxyethyl)amino]methyl}thieno[2,3-g]isoquinoline-4,9-dione | 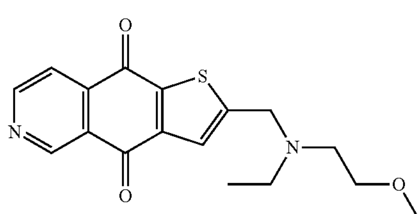 |

-continued

| Example | Name |
|---|---|
| 25 | 2-((cyclohexyl(ethyl)amino)methyl)thieno[2,3-g]isoquinoline-4,9-dione |
| 26 | 2-{[(2,2-difluoroethyl)amino]methyl}thieno[2,3-g]isoquinoline-4,9-dione |
| 27 | 2-[(4-acetylpiperazin-1-yl)methyl]thieno[2,3-g]isoquinoline-4,9-dione |
| 28 | N-(2,2-difloroethyl)-N-((4,9-dioxo-4,9-dihydrothieno[2,3-g]isoquinolin-2-yl)methyl)cyclohexanecarboxamide |
| 29 | 4,9-dioxo-4,9-dihydrothieno[2,3-g]isoquinoline-2-carbonitrile |
| 30 | 2-(1-fluoroethyl)thieno[2,3-g]isoquinoline-4,9-dione |
| 31 | 2-(3-ethyl-1,2,4-oxadiazol-5-yl)thieno[2,3-g]isoquinoline-4,9-dione |

| Example | Name | Structure |
|---|---|---|
| 32 | 2-(morpholin-4-yl)thieno[2,3-g]isoquinoline-4,9-dione | 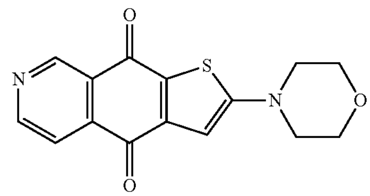 [SMILES: O=C1c2ccncc2C(=O)c2sc(N3CCOCC3)cc21] |
| 33 | 2-acetylthieno[3,2-g]isoquinoline-4,9-dione | 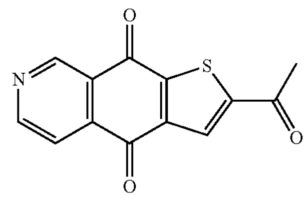 [SMILES: CC(=O)c1cc2c(s1)C(=O)c1cnccc1C2=O] |
| 36 | 2-acetylthieno[3,2-g]quinoline-4,9-dione | 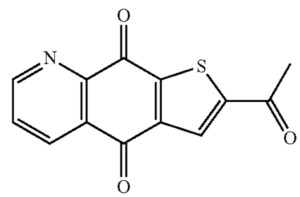 [SMILES: CC(=O)c1cc2c(s1)C(=O)c1ncccc1C2=O] |
| 37 | 2-(1-hydroxyethyl)thieno[3,2-g]quinoline-4,9-dione | 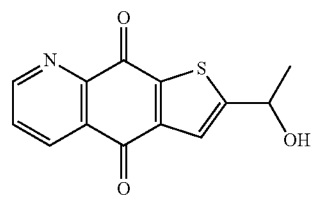 [SMILES: CC(O)c1cc2c(s1)C(=O)c1ncccc1C2=O] |
| 38 | 2-(1-methoxyethyl)thieno[3,2-g]quinoline-4,9-dione | 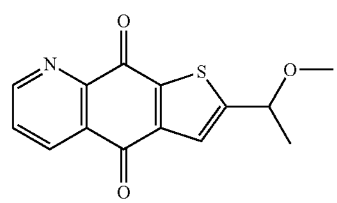 [SMILES: COC(C)c1cc2c(s1)C(=O)c1ncccc1C2=O] |
| 39 | 2-(3,5-dimethylpiperidine-1-carbonyl)thieno[3,2-g]quinoline-4,9-dione | 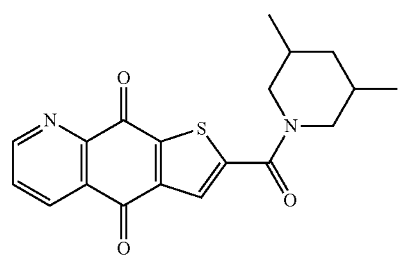 [SMILES: CC1CC(C)CN(C(=O)c2cc3c(s2)C(=O)c2ncccc2C3=O)C1] |
| 40 | N-(2,2-difluoroethyl)-4,9-dioxo-4,9-dihydrothieno[3,2-g]quinoline-2-carboxamide | 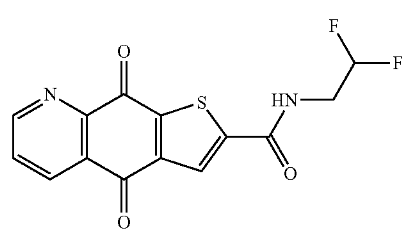 [SMILES: O=C(NCC(F)F)c1cc2c(s1)C(=O)c1ncccc1C2=O] |

-continued

| Example | Name | Structure |
|---|---|---|
| 41 | tert-butyl (4,9-dioxo-4,9-dihydrothieno[3,2-g]quinolin-2-yl)(methyl)carbamate | 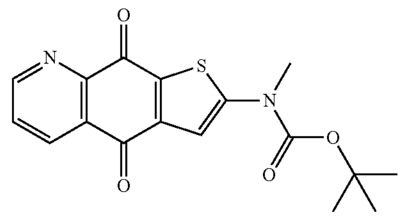 [SMILES: CN(C(=O)OC(C)(C)C)c1cc2c(s1)C(=O)c1ncccc1C2=O] |
| 60 | ethyl (E)-3-(4,9-dioxo-4,9-dihydrothieno[2,3-g]isoquinolin-2-yl)acrylate | 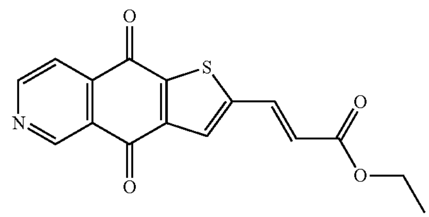 [SMILES: CCOC(=O)/C=C/c1cc2c(s1)C(=O)c1ccncc1C2=O] |
| 61 | 2-ethynylthieno[2,3-g]isoquinoline-4,9-dione | 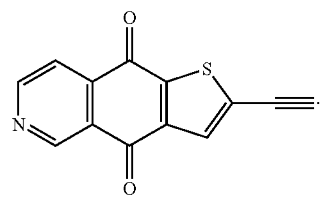 |

\* \* \* \* \*